(12) United States Patent
Zhao

(10) Patent No.: US 12,414,753 B2
(45) Date of Patent: Sep. 16, 2025

(54) APPARATUS AND METHODS FOR X-RAY IMAGING

(71) Applicant: XenseLab LLC, Irvine, CA (US)

(72) Inventor: Ying Zhao, Irvine, CA (US)

(73) Assignee: XENSELAB LLC, Irvine, CA (US)

( * ) Notice: Subject to any disclaimer, the term of this patent is extended or adjusted under 35 U.S.C. 154(b) by 775 days.

(21) Appl. No.: 17/159,779

(22) Filed: Jan. 27, 2021

(65) Prior Publication Data

US 2021/0244374 A1  Aug. 12, 2021

Related U.S. Application Data

(63) Continuation of application No. PCT/US2019/044226, filed on Jul. 30, 2019.
(Continued)

(51) Int. Cl.
*A61B 6/00*   (2024.01)
*A61B 6/06*   (2006.01)
(Continued)

(52) U.S. Cl.
CPC .............. *A61B 6/5282* (2013.01); *A61B 6/06* (2013.01); *A61B 6/4085* (2013.01);
(Continued)

(58) Field of Classification Search
CPC ........... A61B 6/025; A61B 6/032; A61B 6/06; A61B 6/4007; A61B 6/4071;
(Continued)

(56) References Cited

U.S. PATENT DOCUMENTS 4,809,308 A   2/1989 Adams et al.
5,020,086 A   5/1991 Peugeot
(Continued)

FOREIGN PATENT DOCUMENTS

EP         3129957 B1    6/2019
WO   WO 2009/012453 A1   1/2009
(Continued)

OTHER PUBLICATIONS

Alvarez, Robert E. et al., "Energy-selective Reconstructions in X-ray Computerized Tomography," Physics in Medicine & Biology, vol. 21, No. 5, 1976, pp. 733-744.
(Continued)

*Primary Examiner* — Dani Fox
(74) *Attorney, Agent, or Firm* — Procopio, Cory, Hargreaves & Savitch, LLP

(57) ABSTRACT

An x-ray apparatus and method can improve x-ray imaging in a variety of ways. For example, the improve x-ray apparatus can reduce scatter from x-ray images acquired by two-dimensional detectors. An improved 2D x-ray apparatus can provide 3D imaging for medical and/or industrial applications. An improved 2D x-ray apparatus and method can produce separate material imaging, and composition analysis for characterization and correlation of image, densitometry, and composition information of individual component or individual material within a single subject. Non-rotational 3D microscopy, combining 2D or 3D full field x-ray imaging and high resolution 2D or 3D x-ray microscopy or spectral absorptiometry and spectroscopy can achieve a higher resolution and wider field of view in x-ray imaging and quantitative analysis in 3D and real time. The x-ray apparatus can improve tracking and/or surgical guidance in time and/or space.

22 Claims, 44 Drawing Sheets

Related U.S. Application Data

(60) Provisional application No. 62/853,050, filed on May 26, 2019, provisional application No. 62/803,613, filed on Feb. 11, 2019, provisional application No. 62/755,425, filed on Nov. 3, 2018, provisional application No. 62/745,369, filed on Oct. 14, 2018, provisional application No. 62/729,433, filed on Sep. 11, 2018, provisional application No. 62/713,554, filed on Aug. 2, 2018, provisional application No. 62/712,058, filed on Jul. 30, 2018.

(51) Int. Cl.
*A61B 6/40* (2024.01)
*A61B 6/42* (2024.01)

(52) U.S. Cl.
CPC .......... *A61B 6/4241* (2013.01); *A61B 6/4266* (2013.01); *A61B 6/4452* (2013.01); *A61B 6/481* (2013.01); *A61B 6/482* (2013.01); *A61B 6/486* (2013.01)

(58) Field of Classification Search
CPC ... A61B 6/4078; A61B 6/4085; A61B 6/4241; A61B 6/4266; A61B 6/4452; A61B 6/481; A61B 6/482; A61B 6/483; A61B 6/486; A61B 6/5282

See application file for complete search history.

(56) References Cited

U.S. PATENT DOCUMENTS

| | | | |
|---|---|---|---|
| 5,097,492 A | | 3/1992 | Baker et al. |
| 5,594,770 A | | 1/1997 | Bowles et al. |
| 5,771,269 A | | 6/1998 | Chao |
| 6,570,955 B1 | | 5/2003 | Siffert et al. |
| 6,816,564 B2 | | 11/2004 | Charles, Jr. et al. |
| 9,036,879 B2 | | 5/2015 | Mendonca et al. |
| 9,579,526 B2 | | 2/2017 | Kunz et al. |
| 2009/0022264 A1* | | 1/2009 | Zhou ..................... A61B 6/025 378/5 |
| 2013/0307923 A1 | | 11/2013 | Inglese et al. |
| 2014/0133729 A1 | | 5/2014 | Goshen |
| 2015/0287193 A1 | | 10/2015 | Kato et al. |
| 2016/0095562 A1 | | 4/2016 | Baturin et al. |
| 2016/0187269 A1* | | 6/2016 | Brady .............. G01N 23/20008 378/87 |
| 2018/0067061 A1 | | 3/2018 | Butani et al. |

FOREIGN PATENT DOCUMENTS

| | | |
|---|---|---|
| WO | WO 2011/156526 A2 | 12/2011 |
| WO | WO 2017/144474 A1 | 8/2017 |
| WO | WO 2017/205612 A1 | 11/2017 |
| WO | WO 2019/144065 A1 | 7/2019 |
| WO | WO 2019/183002 A2 | 9/2019 |
| WO | WO 2020/028422 A1 | 2/2020 |

OTHER PUBLICATIONS

Gaudreault, David et al., "Comparative Study of Image Quality in Time-Correlated Single Photon Counting Computed Tomography," Journal of Latex Class Files, vol. 14, No. 8, Aug. 2015, in 7 pages.

Gordon, Richard, "A Tutorial on Art." IEEE Transactions on Nuclear Science, vol. NS-21, Jun. 1974, in 16 pages.

Mason, Jonathan H., "Quantative cone-beam CT reconstruction with polyenergetic scatter model fusion," Physics in Medicine & Biology, vol. 63, No. 22, Nov. 7, 2018.

McCollough, Cynthia H et al., Dual- and Multi-Energy CT: Principles, Technical Approaches, and Clinical Applications, Radiology, vol. 276, No. Sep. 3, 2015, pp. 637-653.

Sisniega, A. et al. "High-fidelity artifact correction for cone-beam CT imaging of the brain," Physics in Medicine & Biology, vol. 60, published Jan. 22, 2015, pp. 1415-1439.

Invitation to Pay Additional Fees in corresponding International Patent Application No. PCT/US2019/044226, dated Nov. 8, 2019, in 11 pages.

International Search Report and Written Opinion in corresponding International Patent Application No. PCT/US2019/044226, dated Jan. 16, 2020, in 16 pages.

International Preliminary Report on Patentability in corresponding International Patent Application No. PCT/US2019/044226, dated Feb. 11, 2021, in 11 pages.

* cited by examiner (a) Illuminate subject with X-rays of energy H (b) Acquire image $D_h(x, y)$ from the detector, $D_{hl}(x(i), y(j))$ is the image file from primary x ray long the projected line.

(c) Illuminate the subject with X-ray thin beams of energy H, there are spacings from adjacent thin beams (d) Acquire image $D_{lc}(x(i), y(j))$ from the detector (e) Obtain images $D_{sl}(x(i), y(j))$ from subtraction
$D_{sl}(x(i), y(j)) = D_{hl}(x(i), y(j)) - D_{lc}(x(i), y(j))$ Interpolate low resolution image $D_{sl}(x(i), y(j))$ to the rest of the detector to derive $D_{sh}(x, y)$ (f) Obtain high resolution primary image $D_{hp}(x, y) = D_h(x, y) - D_{sh}(x, y)$

FIG. 4

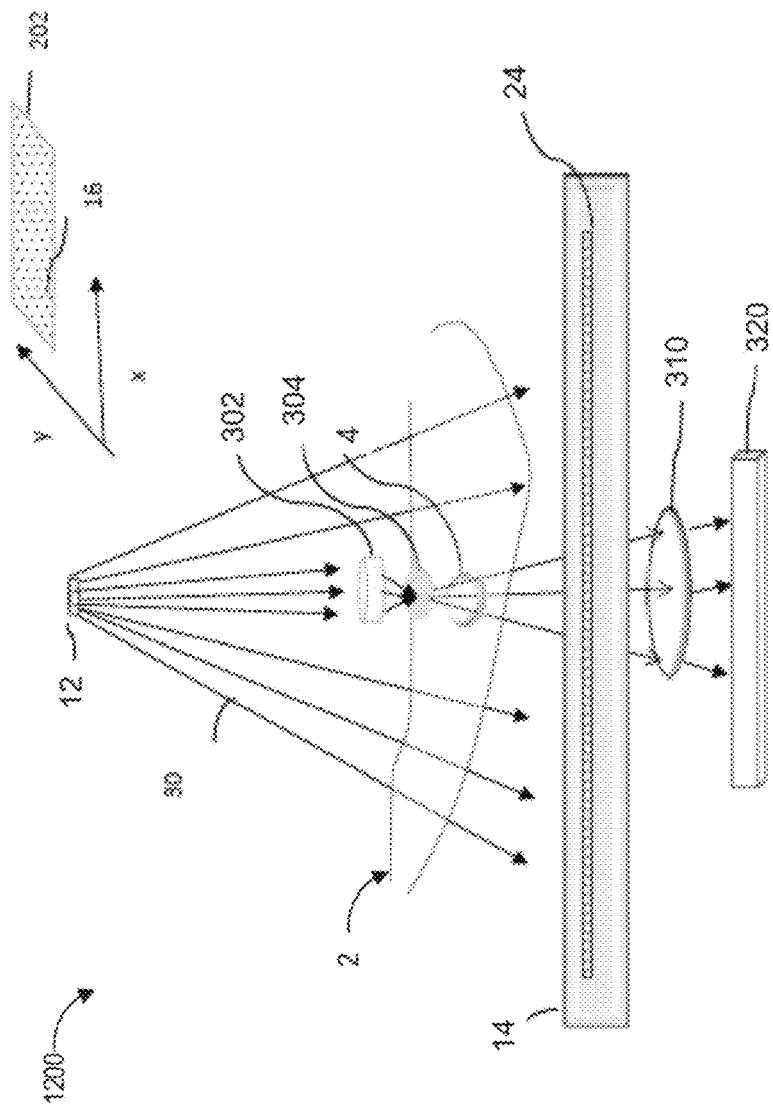

2D Primary and Scatter Image Separation

For Each Position X Ray Source Emitting from, Primary and Scatter X Ray Images are Separated, Examples of Various Embodiments

I.
Single or Dual Energy Scatter Removal

Space Domain: Dual Detector Assembly Static Or Adjustable Beam Selector or Focal Position Adjustable Beam Selector or 2 or 3D Position Adjustable Beam Selector Between the Detectors

II.
Space Domain: 1D to 3D Matrix Programmable X Ray Transmission System- Beam Selector - Between Front and Back Detector- Selective Transmission of Only Primary Beam
  a. Mem Based
  b. Crystal Based
  c. Modulated Crystal, via acoustic Modulator
  d. Liquid Crystal
  e. X Ray Optics for Diffraction or Refraction
  f. X Ray Optics for Internal Reflection Such as Polycapillary

III.
Time Domain: Time of Flight X Ray Source, Single Detector Scattered X Ray are Delayed Compared to Primary X Ray in the Time Domain

IV.
Frequency Domain: Primary Modulator - High Spatial Frequency Pattern of Attention Blocker, Modulates Separate, Primary X Ray, from Scattered X Ray of a Different Frequency

V.
Scatter Algorithms Single Energy X Ray Source and Single X Ray Detector

FIG. 15G

I.
Dual or Multiple Energy

For Each Position X Ray Source Emitting from,

1) Dual or Multiple Energy Method is Used to Seperate Components in the Imaged Object
2) Density Measurement for Separated Components in the Imaged Object
3) Dynamic Movement of Components or Region of Interest or Imaged Object or Tracking of Location of a Foreign Object(s) in 2D
4) Flow Dynamics
5) Contrast Agents Assisted Quantification and Visualization Measurements
6) AI Assisted Measurements and Analysis

II.
Interferometer a. Interference Image of Primary X Ray Obsorption Imaging
b. Dark Field Imaging (Scattered X Ray)
c. Phase Contrast Imaging Tabl Iou Interferometer Mem Based Crystal Based Multiple Emitting Points in One X Ray Source Pixelated X Ray Source

2D Functional Imaging

III.
Energy Sensitive Photon Counting Detector

Single Detector Used with Time of Fight X Ray Source

Or Energy Sensitive Photon Counting Detector May be the Front or Rear or Both Detectors in the Dual Detector Assembly.

Energy Dispersive Element Combined with Spatial Position Sensitive Detector

IV.
1D-3D Structure Technique for Measure Thickness and Composition of Components and Region of Interest a. Densitometry and Component Separation and Characteristics by Putting a 3D Microstructure in between the Imaging Object and the Front Detector and Calibration Method b. Densitometry and Component Separation and Characteristics by Putting a Physical 3D Microstructure in Between the Front and Back Detector c. 3D Microstructured Generated by Modulation for Example Acoustic Modulator.

d. Hardware Element such as Beam Selector 24 or Beam Plates such as P 1-4 or Beam Absorbing Particle Plate 105 may be Used for Densitometer or Low Spatial Resolution but Energy Sensitive Measurements, Especially when Combined with Energy Filter Means Such as K-edge filters Downstream of the Transmissive Regions of each of the Hardware Element.

FIG. 15H

1. Existing quantitative 2d and multiple dimensional x ray imaging and material decomposed image database combined with images from other modalities — MRI, PET, Optical imaging / analysis/spectroscopy, photoacoustic, ultrasound, magnetic particle based imaging modalities All stored as first measurements of static positions and 3D and 6D tracking data sets sufficient to characterize dynamic movements for the region of interest

2. Live measurements of x ray, along with any other imaging methods

3. colocation based on either co-location of dyes, or first, secondary, tertiary or more order dyes, each for a different modality or, common dyes, for two or more modalities, or; colocation based on component images differentiable based on measurable properties, or relative spatial locations or visibilities of specific component; or colocation based on images for each material type or distinct spatial structure or physical property, or matching of measurements of dynamic movement characteristics for components or target or regions of interest, or ; colocation of imaging modalities based on the means for combination from all of the above

4. Match live measurements of all modalities with first measurements database, determine 3D positioning, 4D and 6D tracking of components, targets, the region of interest.

FIG. 25

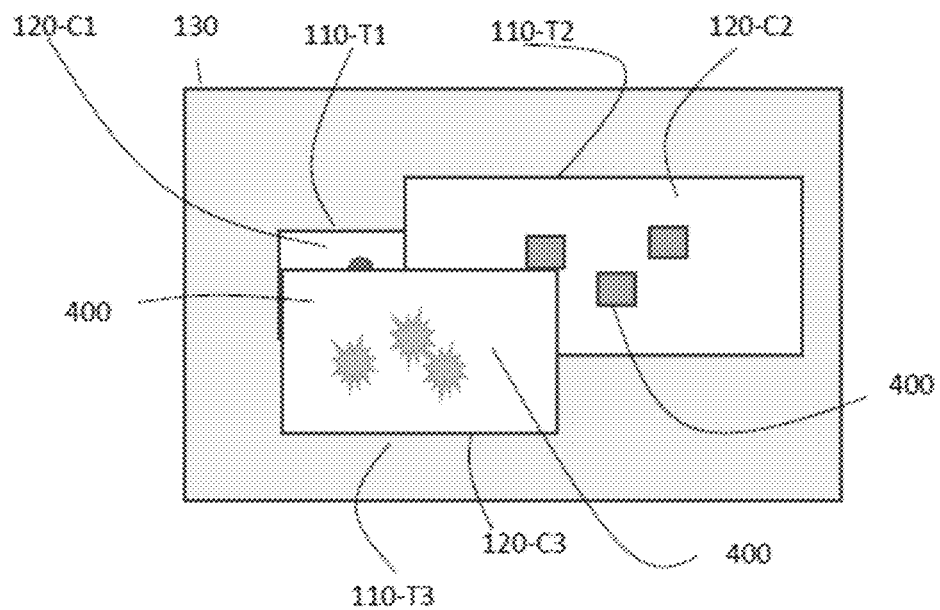
FIG. 26
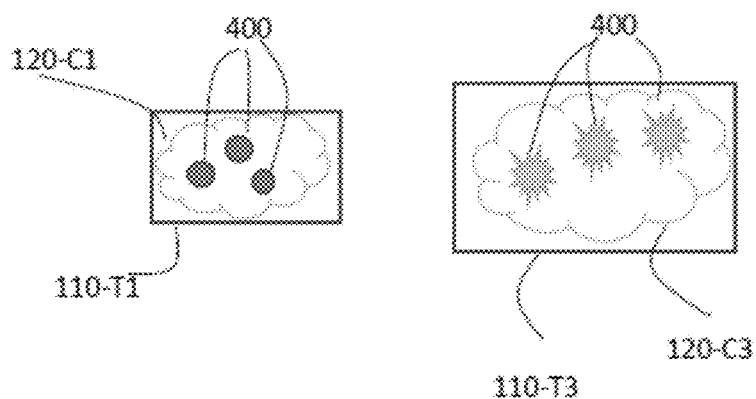
FIG. 27A   FIG. 27B
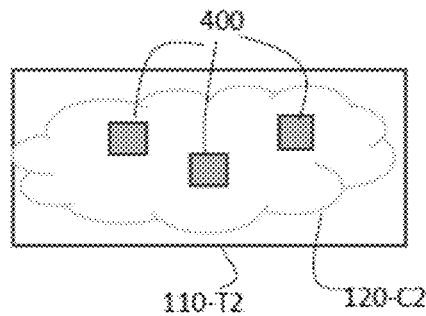
FIG. 27C

```
┌─────────────────────────────────────────────────────────────────────┐
│             Existing 3D Complete Imaging Data for Region of Interest │
│        Including the Dataset with Triple Energy or Dual Energy First Measurements │
│    Source: 2D Flat Panel Based Multiple Dimension Imaging Database, or CT Scanner │
│        or MRI, or PET or other Light Based Quantitative Analysis and Imaging System. │
└─────────────────────────────────────────────────────────────────────┘

┌─────────────────────────────────────────────────────────────────────┐
│    Calibrate X Ray Source and Detector Relative Distance and Position, and Beam │
│                              Selector Position                       │
└─────────────────────────────────────────────────────────────────────┘

┌─────────────────────────────────────────────────────────────────────┐
│     One or More 2D Images of Region of Interest are Sampled with Different X Ray │
│        Source Emitting Positions to Locate the Region of Interest, its Component and │
│         Targets of Static Position at the Start of the First Measurements for Dynamic │
│                    Movement Characterization Multiple                │
└─────────────────────────────────────────────────────────────────────┘

┌─────────────────────────────────────────────────────────────────────┐
│     First Measurements at Various Energy Levels are Sampled, for Example, Each Time │
│      Using One or More Data Regions Projected by X Ray Nanobeam or 2D Imaging of │
│       Region of Interest at One Energy Level, for Instance, High Energy Level, and using │
│          One or More Selected Nanobeam at a Different Energy Level, for Instance, Low │
│            Energy Level, at Various Times through out the Dynamic Movement Process │
└─────────────────────────────────────────────────────────────────────┘

┌─────────────────────────────────────────────────────────────────────┐
│    Extract Energy Decomposed Images of Distinct Substances, Materials and Components │
│        and Targets in the Region of Interest, and Selected Data Region, 2D, 3D, and 6D │
│     Presentations of Component, Targets and Region of Interest at Distinct Energy Levels, │
│      are Synthesized to Complete the Database to Characterize the Dynamic Movement of │
│        Component, Target and Region of Interest During the Dynamic Movement Process │
└─────────────────────────────────────────────────────────────────────┘

┌─────────────────────────────────────────────────────────────────────┐
│   Live Measurements Necessary for the Tracking of Components and Targets and Region │
│            of Interest, Throughout the Treatment or Tracking Process, Each Time: │
│       Sample One or More Data Regions Projected by X Ray Nanobeam or 2D Imaging of │
│            Region of Interest at One Energy Level, for Instance, High Energy Level, and │
│       Optionally, Based on Application Requirement, One or More Selected Nanobeam │
│      Projected Data Point Measurement at a Different Energy Level, for Instance, Low Energy │
│                         Level, or Medium Energy Level                 │
└─────────────────────────────────────────────────────────────────────┘
```

FIG. 28

Optional: For Each Live Measurement, Selected Different Regions of the Component and Region of Interest to be Illuminated by X Ray Nanobeam to Reduce Radiation Dosage Optional: Means to Select and Define Subsequent Regions to be Illuminated by X Ray Nanobeams to be so that Looking up of Location of the Such Regions are Relatively Easy to Track Look up in the Position Database, for Example, When the Illuminated Region is Right Next to the One Before to Limit the Number of Datasets Needed to Position the New Measurement Data.

With Each Live Measurement, Matching Live Measurements or Extracted Data Based on Live Measurements or Synthesized Data from Live Measurements and Extracted Data to those from First Measurement for the Corresponding Time Interval and Selected X Ray Illuminated Position, of the Component, Target and Region of Interest 1D, 2D, 3D, 4D and 6D Images of Component and Targets and Region of Interest are Extracted for Each Time Live Measurements Take Place to Track and Position Components, Target and Region of Interest.

FIG. 28 (CONT'D)

| Primary NanoXgen 1 binds Epitope 30 on Object of Interest 10 |
| --- |
| 1 |

| Conformation of Primary NanoXgen changes, result in Primary NanoXgen with a different 3D confirmation 11 |
| --- |
| 2 |

| Conformation of Primary NanoXgen changes, result in Primary NanoXgen with a different 3D Conformation , producing an new epitope 31 |
| --- |
| 3 |

| new epitope 31 of primary NanoXgen 11 binds to secondary nanoXgen 2, induces conformation change, creating secondary NanoXgen with new confirmation, 12 |
| --- |
| 4 |

| Complex 200 formed by primary NanoXgen 11 binding of the target 10 and of secondary NanoXgen with new conformation 12, creates a third epitope 33 involving all three parts, 10, 11, 12, which then binds to a tertiary NanoXgen 3. |
| --- |
| 5 |

| Labeling agents 100 on all three nanoXgen will thereby amplify the imaging contrast carried by primary nanoXgen by 3x |
| --- |
| 6 |

FIG. 30

APPARATUS AND METHODS FOR X-RAY IMAGING

INCORPORATION BY REFERENCE TO ANY PRIORITY APPLICATIONS

This application claims the benefit under 35 U.S.C. § 120 and 35 U.S.C. § 365 (c) as a continuation of International Application No. PCT/US2019/044226, designating the United States, with an international filing date of Jul. 30, 2019, titled "APPARATUS AND METHODS FOR X-RAY IMAGING," which claims priority benefit of U.S. Provisional Patent Application No. 62/713,554, filed on Aug. 2, 2018, U.S. Provisional Patent Application No. 62/803,613, filed on Feb. 11, 2019; U.S. Provisional Patent Application No. 62/853,050, filed on May 26, 2019; U.S. Provisional Patent Application No. 62/712,058, filed on Jul. 30, 2018: U.S. Provisional Patent Application No. 62/745,369, filed on Oct. 14, 2018: U.S. Provisional Patent Application No. 62/729,433, filed on Sep. 11, 2018: U.S. and U.S. Provisional Patent Application No. 62/755,425, filed on Nov. 3, 2018, the entire disclosure of each of which is hereby incorporated by reference and made part of this specification.

Any and all applications for which a foreign or domestic priority claim is identified in the Application Data Sheet as filed with the present application are hereby incorporated by reference under 37 CFR 1.57.

The application is related to International Patent Application No. PCT/US19/14391, filed on Jan. 20, 2019, International Patent Application No. PCT/US2019/022820, filed on Mar. 18, 2019, and U.S. Pat. Nos. 5,648,997, 5,771,269, 6052433A, 6134297A, and 6173034B1, the entire disclosure of each of which is hereby incorporated by reference and made part of this specification.

BACKGROUND

Field

The present disclosure relates generally to digital x-ray imaging.

Description of the Related Art

When a beam of x-rays (photons) penetrate a subject being imaged, photons of the beam can (1) penetrate the subject in a straight line (called the primary beam) and collected by an imaging detector, which produces the darker parts of an x-ray two-dimensional (2D) image: (2) be absorbed by the subject, producing the lighter parts of the image (for example, bones appearing white whereas air filled lungs appearing black): or (3) scatter within the subject but still leave the subject and collected by the imaging detector. It is difficult to correlate the scattered signal collected by the detector quantitatively with different densities of the content present internal to the subject, and the measurement of scatter is not easily correlated to a precise 3D spatial location of the internal content of the subject which generates the scatter signal, and can reduce clarity of the image formed by primary x-ray measurements. As the amount of scatter radiation increases, the image becomes less clear and the image contrast can be degraded.

The Scatter to Primary Beam Ratio (SPR) is the energy of the scattered radiation divided by the energy of the primary beam striking the same point on the imaging apparatus. For most imaging systems using two-dimensional detectors for human body imaging, the SPR may be as high as between 50% and 100%. Randomly scattered x-rays tend to reduce image contrast, produce blurring, and reduce the signal-to-noise ratio.

For diagnostics, inspection, image guidance, and tracking, security applications, quantitative imaging data may be needed. Rotational computed tomography (CT) can provide quantitative imaging data, but can be time consuming, generally not portable, requiring high radiation, and/or generally having a low molar sensitivity, in the order of Oct. 1, 2010-3 molar. Non-rotational CT and 2D imaging are cheaper, faster, and/or requiring lower radiation compared to rotational CT, but is typically not quantitative.

In clinical x-ray imaging, to diagnose illness including but not limited to stress fracture of bone, pulmonary embolism, and other diseases, correlation of image of fracture and densitometer at region of interest for bone or tissues are done separately in densitometer and an x-ray imaging system.

Three-dimensional (3D) x-ray microscopy images are generated using methods used in conventional rotational CT, where either the subject or the source and the detector rotates about an axis. Multiple images need to be taken of the entire subject in 180° to reconstruct a 3D image of the subject. As a result, the process is time-consuming. X-ray microscopy, which may reach a single digit nanometer (nm) resolution or a even higher resolution with advancement of objective lens, however, is often done for subject with a small form factor, such as in a 1 mm range.

Generally, without the addition of scanning and motion capabilities, photon counting detectors, energy sensitive detectors, silicon drift detectors, spectrometers and/or spectral absorptiometry systems are only capable of measuring subjects of small dimensions.

Due to high radiation level of conventional 3D CT scanners, the frequency of such imaging method, especially in diagnostic and therapeutic processes, is limited.

Clinical x-ray imaging often involves cases in connection with broken bones where the patient has to wear a plaster cast support. Current x-ray imaging technology does not have the capability of obtaining a clear two-dimensional projection x-ray image of a human body and internal organs due to the overlapping image of the plaster cast. Because the chemical composition of the plaster cast or fiberglass is close to that of the bone material and because of the thickness and irregular structure of the casts, practically no image information can be obtained regarding the status of the injured bone or tissue inside the cast. Consequently, the cast needs to be removed before each x-ray images can be taken to monitor the recovery and the patient's treatment and/or post operation care cannot be more timely personalized or administered.

Individual cells or small particles, molecules and/or organisms may need to be visualized, quantified, and/or tracked during diagnosis, screening, therapeutic monitoring in vivo or ex vivo for clinical and/or scientific purposes. However, current imaging modalities, such as x-ray imaging, have not been able to achieve the sensitivity needed.

In industrial and security x-ray imaging, hazardous, explosives and security threat (for example, at the airports) need to be analyzed, and materials and components in an imaged subject may need to be characterized and identified. These tasks can be performed with the advances of the present disclosure.

SUMMARY

X-ray imaging apparatuses and methods can improve x-ray imaging in a variety of ways.

In some configurations, an x-ray measurement system can comprise an x-ray source configured to emit one or more x-ray beams directed to an imaging subject; and a two-dimensional (2D) x-ray detector downstream of the imaging subject, wherein a controller of the system can be configured to obtain multiple dimension and/or three-dimensional (3D) images of the subject by moving or steering x-ray emitting positions or the x-ray source in at least two axes of 3D space, the 3D space including positions in x-y-z axis, and obtaining 2D x-ray measurements.

In some configurations, the detector can be configured to make first measurements and/or live or second measurements for diagnostics, inspection, tracking and/or monitoring of the subject. The x-ray source can be configured to emit x-ray beams with controllable energies. The x-ray source can be configured to emit a single cone beam or multiple thin beams. The system can comprise a beam selector or beam absorption plates configured to selectively allow certain beams to reach predetermined locations of the x-ray detector. The processor can be configured to remove scatter in the x-ray measurements. The system can comprise a second 2D x-ray detector. The 2D x-ray detector can be the only x-ray detector in the system. A distance between adjacent x-ray emitting position can be a dimension of the resolution needed in a third axis, and/or the minimum distance needed so that the two positions generate a set of x-ray beams, each set illuminating different voxel paths in the region of interest. A distance between adjacent x-ray emitting positions can be 1 pixel pitch, integer multiples of a pixel pitch, or less than 1 pixel pitch. A total number of emitting positions, or a total number of 2D images taken to construct the 3D image can be a depth of the third axis divided by the resolution of the third axis. When moving in x and y dimensions, a total movement angle from emitting positions that are furthest apart can be less than 0.1 degree or 0.1 degree, or between 0.1 to 1 degree. When moving in x, y, and z axes, a total movement angle from emitting positions that are furthest apart long each of the axis can be less than 0.0008 degrees, or 0.0008 degree, or between 0.0008 to 0.5 degrees, or between 0.5 degrees to 1 degree.

In some configurations, a method of monitoring an x-rayed subject in real time using two-dimensional x-ray detectors can comprise: obtaining a plurality of first x-ray measurements of the subject at a first time point: obtaining a plurality of second x-ray measurements of the subject at a second time point later than the first time point, the subject or a portion thereof having or not having moved between the first and second time points: matching the plurality of second x-ray measurements to the plurality of first x-ray measurements; and outputting 6D positioning of at least one target, component, and/or region of interest of the subject between the first and second time points.

In some configurations, the method can further comprise emitting x-ray's using an x-ray source, the x-ray being emitted in single pulses, each pulse at a different energy or wavelength. The method can further comprise emitting x-rays using an x-ray source, the x-ray being emitted in one or multiple pulses at different energy levels or wavelengths. The first and/or second measurements can comprise point, 1D, and/or 2D x-ray measurements and/or 3D and/or 4D imaging. The second x-ray measurement can comprise a live measurement. The method can further comprise determining a 6D relative position of the component to the target, region of interest, subject and other components in the region of interest. The first and/or second measurements can comprise quantitative images. Scatter can be removed from the first and/or second measurements in 1D and/or 2D. X-rays emitted to obtain the first and/or second measurement can be configured to pass a collimator. The collimator can be movable or rotatable to produce different transmission regions on an x-ray detector used for obtaining the first and/or second measurements. The method can further comprise emitting a plurality of x-ray thin beams to obtain the first and/or second measurements. The method can comprise sampling the first and/or second measurements more than once during dynamic movements. The method can comprise sampling the first and second measurements at a same frequency or different frequencies. The first measurements can further comprise simulated or synthesized data and/or predetermined data. Matching can comprise matching based on spatial structure, dimension, form factor, anatomic markers, flow properties, relative distance between components, and/or relative spatial positions, 3D volume, 6D orientation, composition, and/or density of the components. The subject can comprise a surgical tool, catheter, biopsy tip, robotic probe, and/or implant in a patient's body. The method can be applied in a robotic-assisted surgery including tracking components of a robotic surgical tool, or guidance probe or fiducial marker. The method can further comprise obtaining additional imaging data from other imaging modalities. The other imaging modalities can comprise detectors of different frame rate, detectors of different spectral resolution or different number of energy sensitive detector cells, single detector arrays or linear detector arrays or multiple detecting channels, spectral measurements, absorptiometry, x-ray microcopy, interferometry, spectroscopy, and/or non-x-ray based imaging modalities. The other imaging modalities can be configured to collocate or measure synchronously with or at a different time frame from x-ray measurements. The method can further comprise performing colocation of the first and second x-ray measurements and the additional imaging data based on component images differentiable based on measurable properties, and/or relative spatial locations and/or visibilities of any specific component. The subject or a portion thereof can have been moved between the first and second time points in multiple dimensions. The multiple dimensions can comprise up to six degrees of freedom and/or with time reference. The method can further comprise calibrating relative distances and positions among an x-ray source, an x-ray detector, and/or a beam selector. The method can further comprise sampling the first measurements at various energy levels and extracting energy decomposed images of distinct substances, materials and components and targets in the region of interest, and selected point data region, 2D, 3D, 4D, 5D, 6D, and 7D presentations of component, targets and region of interest at distinct energy levels.

In some configurations, an x-ray imaging system configured to produce images of a subject including two or more materials can comprise: an x-ray source configured to emit one or more x-ray beams having a plurality of energy levels and directed to the subject: an x-ray detector or detector assembly downstream of the imaging subject, the detector comprising spectral sensitive detectors: a filter; and a collimator configured to selectively allow or prohibit passage of preselected beams, wherein a processor of the system can be configured to three-dimensionally image a region of interest in the subject based on one dimensional and/or two-dimensional data received at the x-ray detector or detector assembly.

In some configurations, the filter can comprise a coded aperture. The coded aperture can comprise a K-edge coded aperture. The coded aperture can be located between the subject and the detector or detector assembly, or between the x-ray source and the subject. The collimator can be located between the filter and x-ray source. The detector or detector assembly can comprise a flat panel detector and a spectral measurement detector or a detector of varied frame rate or detection assembly behind the flat panel detector. The detector or detector assembly can comprise a flat panel detector and a smaller 2D detector or 1D or point detector behind the flat panel detector. The filter can improve a speed of energy and/or spectral sensitive measurements by the system.

In some configurations, an x-ray imaging system with improved scatter removal and/or reduced radiation level can comprise: an x-ray source configured to emit one or more x-ray beams directed to an imaging subject: a first two-dimensional x-ray detector downstream of the imaging subject; and a spectral measurements, x-ray microscopy, absorptiometry assembly, or fast frame rate detector, wherein a processor of the system can be configured to receive and process a full view x-ray signal of the imaging subject from the x-ray detector and a higher spatial or spectral resolution signal of a region of interest within the imaging subject from the microscopy spectroscopy, or absorptiometry assembly.

In some configurations, the x-ray source can be configured to emit x-ray beams with controllable energies. The x-ray source can be configured to emit at least two consecutive x-ray pulses with controllable energies for each imaging operation, the two consecutive x-ray a high-energy pulse followed by a low-energy pulse, or emit a broad band x-ray spectrum having none, one, or more energy peaks. The x-ray source can be monochromatic. The x-ray source can be configured to emit a single cone beam or fan beam or multiple beams. The x-ray source can comprise a beam steering device to control emitting locations of multiple beams. Movements of the multiple beams can comprise integer multiples or a fraction of a pixel pitch of the x-ray detector. The x-ray source can comprise a diffractive component that splits and diffracts the x-ray beam into multiple x-ray beams of different energies or wavelengths. The microscopy or absorptiometry or spectral x-ray measurements, or fast imaging assembly can comprise spectrally sensitive detectors, or silicon shift detectors, or photon counting detectors, or photodiode, or photo multiplier tubes, and fast frame rate 2D detectors. The system can comprise a beam selector configured to selectively allow certain beams to reach predetermined locations of the x-ray detector. The beam selector can comprise a 2D array. Holes on the beam selector can be separated by integer multiples of a pixel pitch of the x-ray detector. The x-ray detector can comprise regions configured to receive only primary images and regions configured to receive only scatter images, and wherein the processor is configured to remove scatter based on signals received on the x-ray detector. The processor can be configured to remove scatter at each energy level for a multiple energy system.

In some configurations, an x-ray imaging system with improved scatter removal and/or reduced radiation level can comprise: an x-ray source configured to emit a plurality of x-ray beams spaced from each other by a distance, wherein certain x-ray beams that pass through an imaging subject can comprise primary beams and scatter beams: a two-dimensional x-ray detector downstream of the imaging subject; and a beam selector configured to selectively allow the primary beams to reach predetermined locations of the detector so that certain other locations of the detector are devoid of primary beams, wherein a processor of the system can be configured to obtain a high resolution primary signal by interpolating a high resolution scatter signal from signals in the certain other locations of the detector.

In some configurations, the distance can comprise one pixel on the detector. The beam selector can be configured such that the predetermined locations and the certain other locations of the detector form a checker board pattern. The beam selector can comprise a plurality of beam absorbing particles. The x-ray source can be configured to emit single-, dual-, or spectral-energy x-ray beams. The detector can comprise spectrally sensitive detectors. The processor can be configured to remove scatter at each energy level for a multiple energy system. The processor can be configured to output material decomposition analysis of the imaging subject having two or more materials. The material decomposition analysis can be based at least in part on a database of x-ray measurement properties of different materials.

In some configurations, an x-ray imaging system with improved scatter removal and/or reduced radiation level can comprise: an x-ray source configured to emit one or more x-ray beams, wherein the one or more x-ray beams that pass through an imaging subject can comprise primary beams and scatter beams: a front two-dimensional x-ray detector downstream of the imaging subject: a beam selector configured to selectively allow certain beams to reach predetermined locations of the detector; and a rear two-dimensional x-ray detector, the beam selector located between the front and rear detectors, wherein a processor of the system can be configured to determine a high resolution scatter signal based in part on an x-ray signal received by the rear detector and output a high resolution primary signal by subtracting the high solution scatter signal from a high resolution signal received at the front detector.

In some configurations, the x-ray source can be configured to emit single-, dual-, or spectral-energy x-ray beams. The beam selector can comprise a plurality of stacked plates. Holes in the plurality of stacked plates can align to form illuminating paths. A size of holes can be increasingly bigger from a plate closer to the front detector toward a plate closer to the rear detector. The beam selector can be moveable in one or more dimensions and/or focal points. The detector can comprise spectrally sensitive detectors. The processor can be configured to remove scatter at each energy level for a multiple energy system. The processor can be configured to output material decomposition analysis of the imaging subject having two or more materials. The material decomposition analysis can be based at least in part on a database of x-ray measurement properties of different materials.

In some configurations, an x-ray imaging system configured to produce images of a subject including two or more materials can comprise: an x-ray source configured to emit one or more x-ray beams having a plurality of energy levels and directed to the subject: an x-ray detector or detector assembly downstream of the imaging subject, the detector comprising spectral sensitive detectors or spectral non-sensitive detectors, or silicon shift detectors, or spectral sensitive detection assembly comprising energy dispersive optics element, or spatially sensitive detector; and a beam selector configured to selectively allow or prohibit passage of preselected beams, wherein a processor of the system can be configured to output material decomposition information about the two or more different materials in the imaging subject.

In some configurations, the material decomposition information can be obtained based at least in part on a database of x-ray measurement properties of different materials. Materials the same as or similar to the two or more different materials of the subject or the actual materials of the subject can be used for calibration so as to build the database, or quantitative numeric relationship can be derived between measured data between unknown materials and its known equivalent material. The x-ray measurement properties can comprise material or contrast agent of distinct atomic z number, density flow dynamics, fluidics, flow direction, movement characteristics, spatial characteristics, dimensions, shapes, volume, chemical, energy, or mechanically induced changes and/or state transformation. The x-ray source can be configured to emit a plurality of x-ray thin beams spaced from each other by a distance. The distance can be at least an integer multiple of a pixel pitch of the detector.

In some configurations, a contrast agent complex configured to label an imaging target comprising an epitope can comprise: a first molecule including a domain configured to bind the epitope, the molecule conjugated with a first contrast agent, wherein binding of the domain and the epitope can cause the first molecule to change from a first conformation of the first molecule to a second conformation of the first molecule, the second conformation of the first molecule comprising a second epitope, wherein the second epitope can be configured to bind with a second domain of a second molecule conjugated with a second contrast agent.

In some configurations, the first molecule can be an antibody or nanobody, or small molecule or peptide, or protein. The first contrast agent can be selected from an organic-based, ionic-based, nonionic-based, nonmetal-based, intrinsic-based, endogenous-based, or metal-based contrast agent. The contrast agent can be selected from the group consisting of calcium, zinc, air, argon, nitrogen, carbon dioxide, nitrogen dioxide, methane, helium, oxygen, gadolinium, iron, magnesium, manganese, cooper, chromium, gold, silver, thulenium, and barium. The endogenous-based contrast agent can be selected from sodium, magnesium, potassium, calcium, phosphorous, sulfur, chlorine, manganese, iron, cobalt, nickel, copper, zinc, molybdenum, selenium, iodine, and chromium. The first molecule can further comprise an antigen specific molecular label. The first contrast agent can be a liposome-based molecule. The first contrast agent can be an iodine-based compound. The metal-based contrast agent can be selected from a barium, tantalum, tungsten, gold, silver bismuth, gadolinium, or ytterbium-based contrast agent. The contrast agent complex can have an effective particle size of less than 300 nm or greater when assembled internally. The effective amount of the first contrast agent can be from 10-12 molar to 10-3 molar. The second contrast agent can be selected from an organic based, ionic-based, nonionic-based, nonmetal-based, intrinsic-based, endogenous-based, or metal-based contrast agent. The contrast agent can be selected from the group consisting of calcium, zinc, air, argon, nitrogen, carbon dioxide, nitrogen dioxide, methane, helium, oxygen, gadolinium, iron, magnesium, manganese, cooper, chromium, and barium. The endogenous-based contrast agent can be selected from sodium, magnesium, potassium, calcium, phosphorous, sulfur, chlorine, manganese, iron, cobalt, nickel, copper, zinc, molybdenum, selenium, iodine, and chromium. The first contrast agent can be a negative contrast agent. The second contrast agent can be a negative contrast agent. The negative contrast agent can occur naturally in the imaging target. The negative contrast agent can comprise calcium ions or calcium ion complexes. Binding of the second domain to the second epitope can cause the second molecule to change from a first conformation of the second molecule to a second conformation of the second molecule, the second conformation of the second molecule comprising a third epitope configured to bind a third molecule. The complex can be self-assembled. The first molecule and the second molecule can be repeating units. The self-assembled complex can comprise a cage structure, one or more contrast agents enclosed by the cage structure, or contrast agents enclosed in one or more microbubbles or linked to one or more microbubbles. The complex can comprise a mesh with one or more contrast agents interlaced in the mesh. The first molecule can comprise more than one domain configured to bind more than one contrast agent. The first and second contrast agents can be the same. The first and second contrast agents can be different so as to suit different imaging modalities. The bond between the domain and the first epitope can be configured to dissociate based on a time required for imaging. The dissociation of the bond between the domain and the first epitope can disintegrate the complex. The contrast agent complex can be formed in an intracellular or extracellular environment.

The system and/or method disclosed above can comprise a contrast complex having any of the features of the contrast complex described above.

In some configurations, a method of monitoring a cellular or enzymatic event inside a target labeled with a plurality of contrast agent complexes using x-ray imaging can comprise: emitting an x-ray beam or a plurality of x-ray thin beams from an x-ray source, the beam or thin beams penetrating the target located between the x-ray source and an x-ray detector: receiving x-ray signals at the x-ray detector, wherein portions of the signals from the target are amplified relative to background signals by the plurality of contrast agent complexes, each contrast agent complex comprising more than one contrast agent molecule; and detecting the cellular or enzymatic event based at least in part on the received x-ray signals.

In some configurations, the contrast agent complex can label a marker molecule of the target without interfering with the cellular or enzymatic event being monitored. The contrast complex contrast complexes can be in a form selected from micelles, nanomicelles, polymeric micelles, nanosuspensions, nanocapsules, or nanoemulsions. The method can further comprise administering a first contrast agent at a first time point and a second contrast agent at a second time point. The method can further comprise detecting the progression of the first contrast agent at the first time point and the second contrast agent at the second time point. The method can further comprise administering a plurality of contrast agent complexes to a subject. The contrast agent complex can be administered orally or intravenously. The contrast agent complex can further comprise a pharmaceutically acceptable carrier. The contrast agent complex can further comprise a stabilizer. The more than one contrast agent molecules can occur naturally in a biological body in which the target is located. The more than one contrast agent molecules can comprise calcium ions or calcium ion complexes. The contrast agent complex can be selected from an organic based, ionic-based, nonionic-based, nonmetal-based, intrinsic-based, endogenous-based, or metal-based contrast agent. The contrast agent complex can be selected from the group consisting of calcium, zinc, air, argon, nitrogen, carbon dioxide, nitrogen dioxide, methane, helium, oxygen, gadolinium, iron, magnesium, manganese, cooper, chromium, and barium. The endogenous-based contrast agent can be selected from sodium, magnesium, potassium, calcium, phosphorous, sulfur, chlorine, manganese, iron, cobalt, nickel, copper, zinc, molybdenum, selenium, iodine, and chromium. The contrast agent complex can be a liposome-based molecule. The contrast agent complex can be an iodine-based compound. The metal-based contrast agent can be selected from a barium, tantalum, tungsten, gold, bismuth, gadolinium, or ytterbium-based contrast agent. The contrast agent complex can have an effective particle size of less than 300 nm. The effective amount of the first contrast agent can be from $10^{-9}$ molar to $10^{-3}$ molar. The first contrast agent can be a negative contrast agent. The contrast agent complex can comprise: a first molecule including a domain configured to bind the epitope, the molecule conjugated with a first contrast agent molecule, wherein binding of the domain and the epitope can cause the first molecule to change from a first conformation of the first molecule to a second conformation of the first molecule, the second conformation of the first molecule comprising a second epitope, wherein the second epitope can be configured to bind with a second domain of a second molecule conjugated with a second contrast agent molecule. The contrast agent complex can be self-assembled. The bond between the domain and the first epitope can be configured to dissociate based on a time required for imaging. The dissociation of the bond between the domain and the first epitope can disintegrate the contrast agent complex. The contrast agent complex can be formed in an intracellular or extracellular environment. The x-ray source can comprise a single, dual, or spectral source. The x-ray imaging can comprise full view x-ray, x-ray microscopy, absorptiometry, x-ray spectral measurements, and/or measurements of detectors with difference in at least one of the following domains: sensitivity, frame rate, spatial resolution or spectral resolution compared to that of full field x-ray imaging system The x-ray measuring systems of the methods and/or the systems described above can include the one or more of the following features: the x-ray sources or x-ray emitting positions moving in at least two axes in a three axes three dimensional space to construct multiple dimension or 3D or 4D images of the region of interest, distance between adjacent x-ray emitting position being the dimension of the resolution needed in the third axis, and/or the minimum distance needed so that the two positions generates a set of illumination path which involves different combinations or different number of voxels in the region of interest: the distance between adjacent x-ray emitting positions being 1 pixel pitch, integer multiples of pixel pitch, or less than 1 pixel pitch: a total number of emitting positions, or a total number of 2D images taken to construct the 3D image being a depth of the third axis divided by the resolution of the third axis: when moving x-ray emitting position or x-ray source in a x y plane, a total movement angle from emitting positions that are furthest apart being less than 0.1 degree, or 0.1 degree, or between 0.1 to 1 degree: when moving x-ray emitting position or x-ray source in x, y, and/or z axes, a total movement angle from emitting positions furthest apart long each of the axis, being less than 0.0008 degrees, or 0.0008 degree, or between 0.0008 to 0.5 degree, or between 0.5 degrees to 1 degree: x-ray emitting position or x-ray sources not being moved, and multiple x-ray emitting positions or multiple x-ray sources being used: two or more sets of x-ray emitting positions or x-ray sources being placed at a spatial location away from the each other, opposite to the corresponding detector or detectors, each set comprising an x-ray source generating x-ray of one or more energy levels that are different from the rest of the set(s); and/or a material decomposition method being configured to separate components or materials, enabling 3d imaging relative to that of other components or region of interest, and/or deriving 6D or 7D image in space and time compared to that of the background or an external spatial marker or sensor.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure. Corresponding numerals indicate corresponding parts.

FIG. 4 illustrates a flow diagram of an example imaging method based on the x-ray source illustrated in FIG. 3.

FIGS. 12B and 12C illustrate schematic diagrams of hybrid systems of x-ray microscopy and full field x-ray imaging.

FIG. 15G illustrates is a summary of methods and apparatus in 2D primary and scatter image separation.

FIG. 15H is a summary of 2D functional imaging.

FIG. 25 illustrates an example flow diagram of colocation of quantitative x-ray images with non-x-ray imaging modalities.

FIGS. 26 and 27A-27C illustrate examples of various configurations of multiple components and targets in a region of interest.

FIG. 28 illustrates an example flow diagram for positioning and tracking component and target of interest in region of interest based on first measurements of data point, 1D, 2D images of components and targets in the region of interest and matching with single energy live measurements of the same for components and targets in the region of interest.

FIG. 30 illustrates an example process of introducing a cascade reaction for amplifications of signals of interest.

DETAILED DESCRIPTION

Aspects of the disclosure are provided with respect to the figures and various embodiments. One of skill in the art will appreciate, however, that other embodiments and configurations of the apparatus and methods disclosed herein will still fall within the scope of this disclosure even if not described in the same detail as some other embodiments. Aspects of various embodiments discussed do not limit scope of the disclosure herein, which is instead defined by the claims following this description.

Overview

The apparatuses, and methods and materials disclosed herein can be used for x-ray measurements of components, especially in some cases when various components of the subject being x-rayed are not easily differentiated using x-ray measurements of conventional 2D radiography due to scatter noise and/or when conventional CT scanner may not be used routinely due to high radiation, and/or the CT scanner being too time consuming, not real time, and/or infeasible.

Figure 1A:
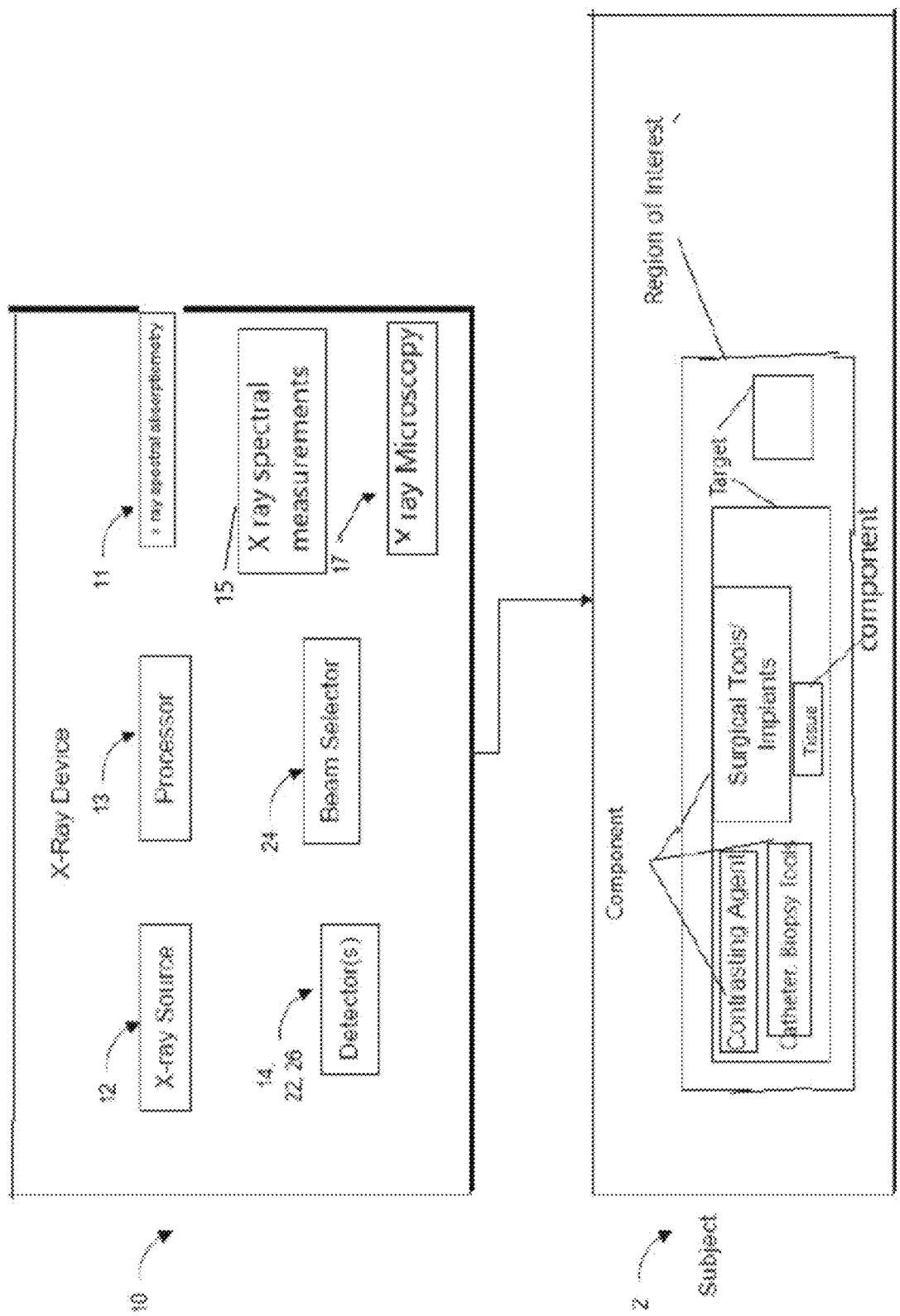
FIG. 1A illustrates schematically an example x-ray imaging apparatus of the present disclosure.

As illustrated in FIG. 1A, an example 2D x-ray imaging apparatus 10 can include an x-ray source 12, a beam selector or a collimator or beam blocker 24 and an x-ray detector or detector assembly 14. The detector or detector assembly 14 can include a single flat panel detector, or an assembly of a front two-dimensional x-ray detector 22 and a rear two-dimensional x-ray detector 26 (see FIG. 1B). The x-ray radiation and/or the x-ray source and/or the relative position of the x-ray source can be configured to be moved in a one to six dimensions spatially. Alternatively, an x-ray source may have two or more x-ray emitting positions, or there may be multiple x-ray sources placed in 3D or 2D space.

A subject 2 is located between the x-ray source 12 and the detector 14. The x-ray source 12 can emit x-ray beams 30 toward the subject 2. The x-ray beams 30 may be of a broad band spectrum, in some instances with a single energy peak, dual-energy peaks, or multiple energy peaks. The subject 2 or a region of interest 4 in subject 2 may include more than two materials or two components as illustrated in FIG. 1A internal to a target that have different x-ray measurement properties. The x-ray beam 30 may also be monochromatic. Each beam may be pulsed. The x-rays beams 30 include primary x-ray beams 32 having their direction of travel unaltered by interaction with the subject 2 and scatter x-ray beams 34 having their direction of travel altered by interaction with the subject 2. The detector 14 can receive both the primary and scatter x-ray beams 32, 34.

Figure 7:
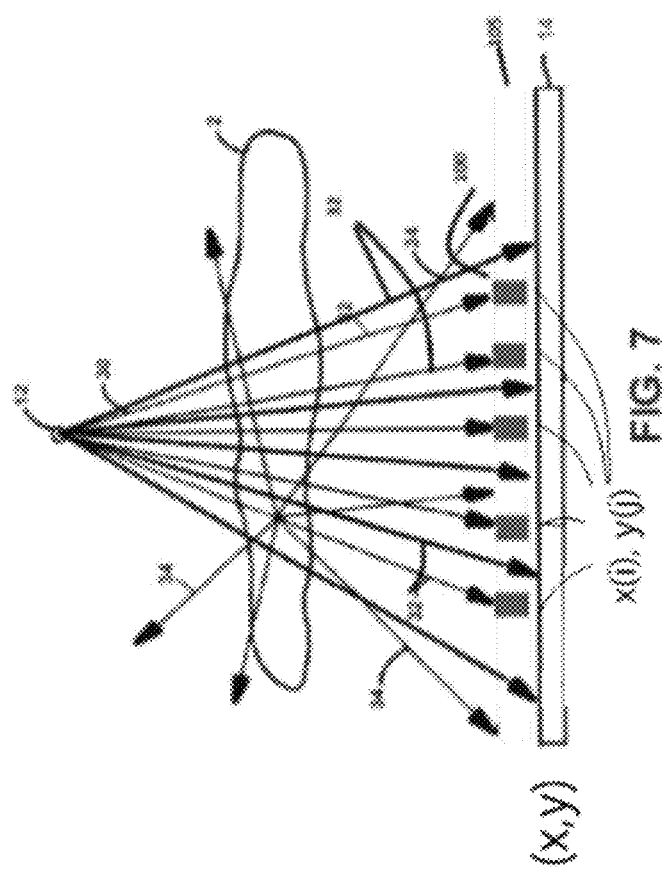
FIG. 7 illustrates schematically a side view of an example beam selector to remove scatter.

The beam selector 24 (also referred to as a collimator) can be located between the detector 14 and a subject 2 or between detector 14 and an absorptiometry assembly 11, or spectral measurement assembly 15, a fast detector or a detector different than detector 14 and relevant assemblies and/or a microscopy assembly 15, or between a front detector and a rear detector. The beam selector 24 may be placed between x-ray source 12 and the subject 2. The beam selector 24 can permit passage of a portion of the primary beams 32 and prevent or block the rest of the x-ray beams 30. Alternatively, the beam selector 24 (similar to the beam absorber plate 105 as shown in FIG. 7) can pass scatter beams 34 only to certain locations of a second detector (which may be an absorptiometry detector, a spectral sensitive detector, a microscopy detector, or a rear detector), blocking primary x-ray beams 32 to those locations, and pass both primary beams 32 and scatter beams 34 to the remaining locations of the second detector. The x-ray related measurements of spectral measurement, x-ray microscopy and other type of detectors can be done on a selected region after full field x-ray imaging is taken. The user selects or the digital program selects the region by one or more criteria. Generally such selected region are much smaller than the full field view, and can be in um, or mm in dimensions. High spatial resolutions and high spectral resolution can be achieved on the selected region using the modality chosen. Such imaging systems can move in and out of position to measure the selected region in real time. The modalities can be placed downstream of the x-ray full field detector or upstream. The modalities can have its own source and detector assembly, which can be placed at an angle to the x-ray source and flat panel detector pair, but still be able to access the selected region. The non x-ray based modalities can collocate or measure synchronously with the x-ray measurements and imaging or at a different time frame.

The x-ray detectors are configured to detect x-ray radiation after attenuation by the subject 2 and provide an indication of the detected x-rays. The apparatus 10 can also include a processor 13 configured to receive signals of the detected x-rays and resolve the detected x-ray radiation into images.

The beam selector 24 allows for structural illumination on the second detector, which can be used for removing scatter to receive a high resolution primary signal of a subject 2 as will be described in greater details below, for example, by obtaining a high resolution scatter signal based on the signal received by the second detector so that the high resolution scatter signal can be subtracted from the high resolution image at the first detector to obtain a high resolution primary signal.

The beam selector 24 can allow for structural illumination of the second detector through the area of interest 4 of the subject 2. By focusing on a smaller area than the entire subject using the structural illumination technique, the amount of total radiation exposure to the subject can be reduced. The images obtained from the x-ray apparatuses disclosed herein can have improved resolution and/or sensitivity spatially, spectrally and/or temporally, including additional information such as material decomposition and/or tracking of surgical instruments, with improved apparatus mobility and/or availability, and/or with reduction in time, radiation level, toxicity, and/or expenses.

The improved x-ray apparatus can also provide locating and tracking of an internal target or a component of a region of interest in static positions and dynamic movement positions. A region of interest in the subject and/or its components in time and space, thereby by forming 4D images. The spatial resolution of the components or targets in the region of interest can have six degrees of freedom, that is, translation in the x, y, z axes, pitch, yaw, and roll. The tracking can be performed via obtaining a first set of measurements about the target, components, and/or areas of interest of a subject and a set of live measurements about the target, components and/or areas of interest of the subject, and matching the first set of measurements and the live measurements or second measurements.

The present disclosure provides example materials, apparatuses, and/or methods of static and/or real time x-ray imaging in performing dual and/or multiple energy, microscopic or spectroscopic x-ray measurements, and/or K-edge or A-space x-ray imaging using lower or non-toxic contrast agents with 2D detectors, for imaging and measurements of individual component of a subject having at least two different materials, which may overlap one another.

The present disclosure can include contrast agents used with the improved x-ray imaging systems and methods. The molecular contrast agents disclosed herein can be combined with the combination of the 2D flat panel detector and the spectral material decomposition improved 2D and 3D imaging systems and methods. The improved x-ray imaging systems, such as with the addition of spectral absorptiometry on small area of region of interest and x-ray microscopy, as well as photon counting detectors or PMTs disclosed herein, can reduce the required concentration of contrast agents thereby reducing the toxicity, for the contrast agents to be visible in the CT or 2D radiographs. Optionally, endogenous elements, especially $Ca^{2+}$ and other naturally high quantity elements in the body are not toxic in a large range of concentrations and can be used. Optionally, the endogenous elements can self-assemble into structures suitable for increasing the concentration of contrast agents in imaging, such as with 2D radiograph and any other imaging systems disclosed herein.

The 2D x-ray imaging apparatus can be configured to produce 3D imaging and/or tracking of various components of the subject in six degrees of freedom and/or temporally. The 6D imaging can be produced using point measurements, 1D measurements, 2D measurements, 3D measurements, and/or 4D measurements (including time-based characterization of dynamic movements, a flow direction and/or speed, and/or the like). The imaging can be in both in full view and in focused selected region of interest, using x-ray spectral measurements, x-ray microscopy, spectroscopy, and/or spectral absorptiometry, detector of various frame rate and/or spectral resolution and/or spatial resolution. The imaging can be performed with single, dual, and/or other multi energy system, and/or including a K-edge measurements, via for example, the use of filter.

Advantages of the materials, apparatuses, and/or methods disclosed herein can include one or more of the following. 1) Improved resolution, such as to the nanometer range, including, such as, tracking of small component in a large sample. 2) Improved detector speed and/or tracking speed, which can be as fast as in the 10-15 seconds, or terahertz, or yotahertz ($1\times10^{24}$ Hz) range, or as high as highest speed detector such as a single photodiode or photo counting detector or a PMT allow: 3) Improved spectral solution in energy spectrum measurements, such as for use in characterizing materials and/or components of a subject. 4) Improved sensitivity due to improvement on spatial resolution, spectral resolution, and/or time resolution, such as being much more sensitive compared to conventional 2D x-ray measurements and approaching or comparable to that of PET and MRI or photoacoustic imaging, optical imaging and ultrasound. Due to increase in the speed of tracking, a single or small number of photodiodes may be sufficient to track or measure a small region of interest, with a detector speed of as fast as one yotahertz. Physical phenomena, for example, atomic physics or quantum mechanics phenomena, and/or ultrafast laser induced changes in molecule, atom, electron, and/or cellular, may be measured or characterized based on the x-ray measurements. (5) Enhanced amplification of signals by molecular mechanisms (such as formation of complexes and structures). (6) Better detection of presence and absence of signals, especially those of endogenous matters, such as calcium, zinc, and magnesium. (7) Improved detection of activation and/or deactivation of a state of a substance or component or transformation of a component by energy, chemistry, electro, electromagnetic, and acoustic methods. For example, during RF ablation, the cardiac tissue goes through necrosis, transforming the molecular and cellular makeup of the tissue from live tissue to dead cells and dead tissues. Accumulation or disintegration of molecule complexes and cellular structures during this transformation can be measured. As another example, additional energy such as ultrasound disturbance of the region of interest may give rise to different x-ray measurements that can result in improved differentiation and monitoring or tracking of the region of interest or components in a subject. (8) Lowered and/or eliminated toxicity by labeling a marker, which may be different molecular ligand, protein, small molecule oligo, organic and/or inorganic molecules, with endogenous molecules such as calcium, zinc and magnesium as contrast agents to target the marker for the region of interest or component of the interest. (9) Improved imaging of bone tissue in a plaster cast. Instead of a molecular label, contrast agents can be mixed with a material of interest or component of interest to quantify or separate such a component, such as mixing of iodine with plaster cement or mixture, or mixing of surgical, biopsy, and/or treatment apparatus and/or a guidance tool with a contrast agent or an x-ray measurement sensitive material.

The methods and/or apparatuses disclosed herein can be implemented in a modular manner, by implementing independently and/or simultaneously any combinations of a low or non-toxic contrast agent, scatter removal of a multiple energy system for a subject including two or more materials, combining full view x-ray with spectral measurements, x-ray microscopy, spectral absorptiometry, and/or spectrometer, using x-ray measurements in various dimensions for surgical guidance. For example, the low or non-toxic contrast agent disclosed herein may be implemented in a conventional 2D x-ray or other conventional imaging modalities. In the present disclosure, spectroscopy refers to x-ray spectral measurements: microscopy refers to x-ray microscopy; and absorptiometry refers to x-ray absorptiometry.

The x-ray apparatuses disclosed herein can be in a portable format, such as in handheld or carry-on versions as combined with a battery-operated x-ray source. The x-ray source can include, for example, a compact pulsed x-ray source giving a single-shot x-ray pulse having an x-ray output corresponding to a stored electric energy between 100 Joules and 1,000 Joules per pulse, and a typical pulse duration between 0.1 ms and 10 ms. Time of flight x-ray source may also be used, with pulse duration in the ps range. Cold cathode field emitter based x-ray source may also be used. Such an x-ray source can be lightweight, compact, and require very low power supply. The apparatuses can be suitable for human body imaging, other types of imaging of biological tissues, and/or industrial applications (such as semiconductors, construction, environmental application, or otherwise). The portable version can include a foldable system that is battery operated. The foldable system can be used in field inspection, diagnostics, image guidance, and/or material characterization.

Multi Energy Scatter Reduction Examples

Clinical x-ray imaging can use the Bucky grid for relieving adverse scatter effects. However, the Bucky grid can be an inefficient and crude apparatus, at best reducing the scatter to 30% or 20% of its total intensity, with an increase in the patient's x-ray exposure by two to four times. Various other methods have also been developed to reduce scatter radiation, such as by using spatial frequency modulators or time of flight sources. However, each method has its major drawbacks. For example, the beam hardening technique introduces measurement errors or requirements of ultrafast measurements on a 2D detector, which is not practical in most clinical applications.

A beam selector can also be used with single-energy, dual-energy, and/or multiple energy methods, with the beam selector sandwiched between a dual-detector arrangements. The front detector measures both scatter and primary images, and the back detector measures only primary x-ray as a result of the selectively transmissive channels designed for primary x-ray transmission embedded in an x-ray absorbing plate (that is, the beam selector). Scatter can be essentially eliminated from x-ray images with a high accuracy. Such a beam selector and dual-detector arrangement are described in U.S. Pat. Nos. 5,648,997, 5,771,269, 6052433A, 6134297A, and 6173034B1, and International Patent Application No. PCT/US2019/022820.

The present disclosure provides improvements over the beam selector and dual-detector arrangement, such as in improving manufacturability, reducing cost, and/or maintaining the accuracy of scatter removal, including by providing, for example, a more refined separation of primary and scatter x-rays. An example 2D x-ray imaging apparatus disclosed herein can distinguish images or derive facts and structured results from one or more x-ray measurements of various components in a subject in a region of interest in a subject, generally overlapping along the x-ray projected beam path. The apparatus may improve identification and characterization of various tissues or tissue regions by anatomical markers and/or temporal indicators in in vivo and ex vivo imaging, and/or improve measurements, image quality, identification, and analysis of material composition in a subject including two or more materials. The 2D x-ray images obtained with the apparatus can have the scatter interference substantially or almost completely removed.

The 2D x-ray imaging apparatuses disclosed herein can also allow visualization and/or quantitative data analysis performed previously on Computed Tomography (CT) scanner, Magnetic Resonance Imaging (MRI), Positive Emission Tomography (PET) and Single Photon Emission Computed Tomography SPECT and other existing quantitative tomography and imaging methods, which are much expensive and/or time-consuming than 2D radiography. The visualization and/or quantitative data analysis performed on the 2D x-ray imaging apparatuses disclosed herein can be done by running algorithms developed for diagnosis and identification and characterization using artificial intelligence, deep machine learning, artificial neural network, convolution neural network, and/or deep neural network.

The present disclosure provides examples of 2D x-ray imaging apparatuses and methods configured to reduce and/or remove scatter x-ray.

The 2D x-ray imaging apparatuses and methods disclosed herein can be single energy, dual energy, or multi-energy. The example 2D x-ray imaging apparatuses can allow for multiple energy scatter removal. An x-ray source of the apparatuses disclosed herein can emit x-rays of a single energy spectrum, two different energy spectrums, and/or multiple energy spectrums. Scatter may be removed respectively, using the single energy method, the dual energy method, and/or an extended multiple energy method for a multiple energy system at each energy level (also known as spectral imaging, if the application requires the use of multiple energy x-ray imaging and analysis for material decomposition).

Figure 1B:
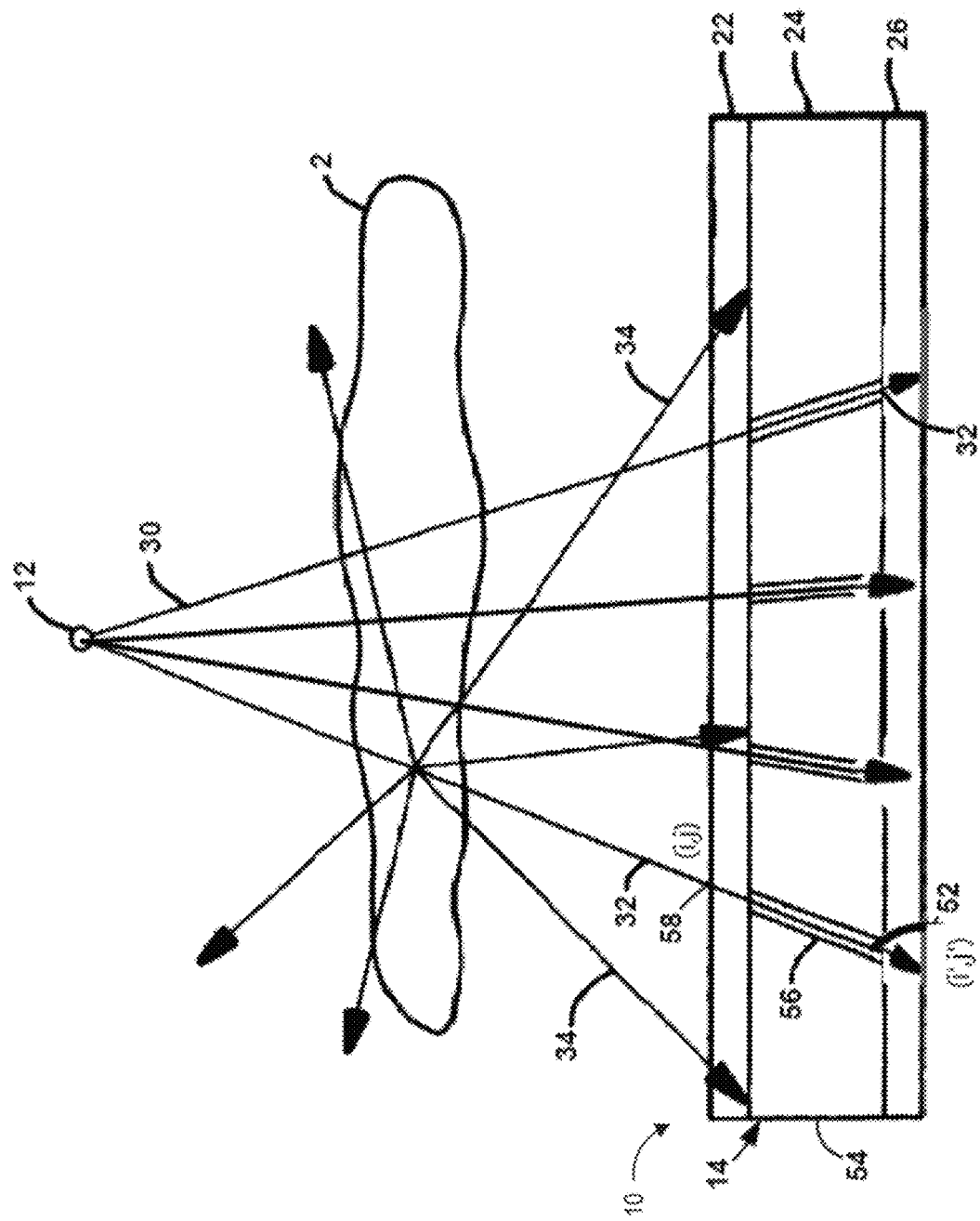
FIG. 1B illustrates schematically an example 2D x-ray imaging apparatus with two flat panel detectors.

In the apparatus 10 in FIG. 1B, which incorporates any of the features of FIG. 1A, a subject 2 is located between the x-ray source 12 and the front detector 22. The x-ray source 12 can emit x-ray beams 30 toward the subject 2. The x-ray beams 40 may be of a single-energy spectrum, a dual-energy spectrum, or a multiple energy spectrum. The x-rays beams 30 include primary x-ray beams 32 having their direction of travel unaltered by interaction with the subject 2 and scatter x-ray beams 34 having their direction of travel altered by interaction with the subject 2. The front detector 22 can receive both the primary and scatter x-ray beams 32, 34. The beam selector 24 can permit passage of a portion of the primary beams 32 to arrive at the rear detector 26 and prevent or block a portion of the x-ray beams 30 from reaching the rear detector 26. The rear detector 26 can receive substantially only the passed primary x-ray beams 32. Alternatively, the beam selector 24 (similar to the beam absorber plate 105 as shown in FIG. 7) can pass scatter beams 34 only to certain locations of the rear detector 24, blocking primary x-ray beams 32 to those locations, and pass both primary beams 32 and scatter beams 34 to the remaining locations of the rear detector 24. The rear detector 26 can include a multi-detector or diode assembly instead of a single 2D detector.

Figure 2:
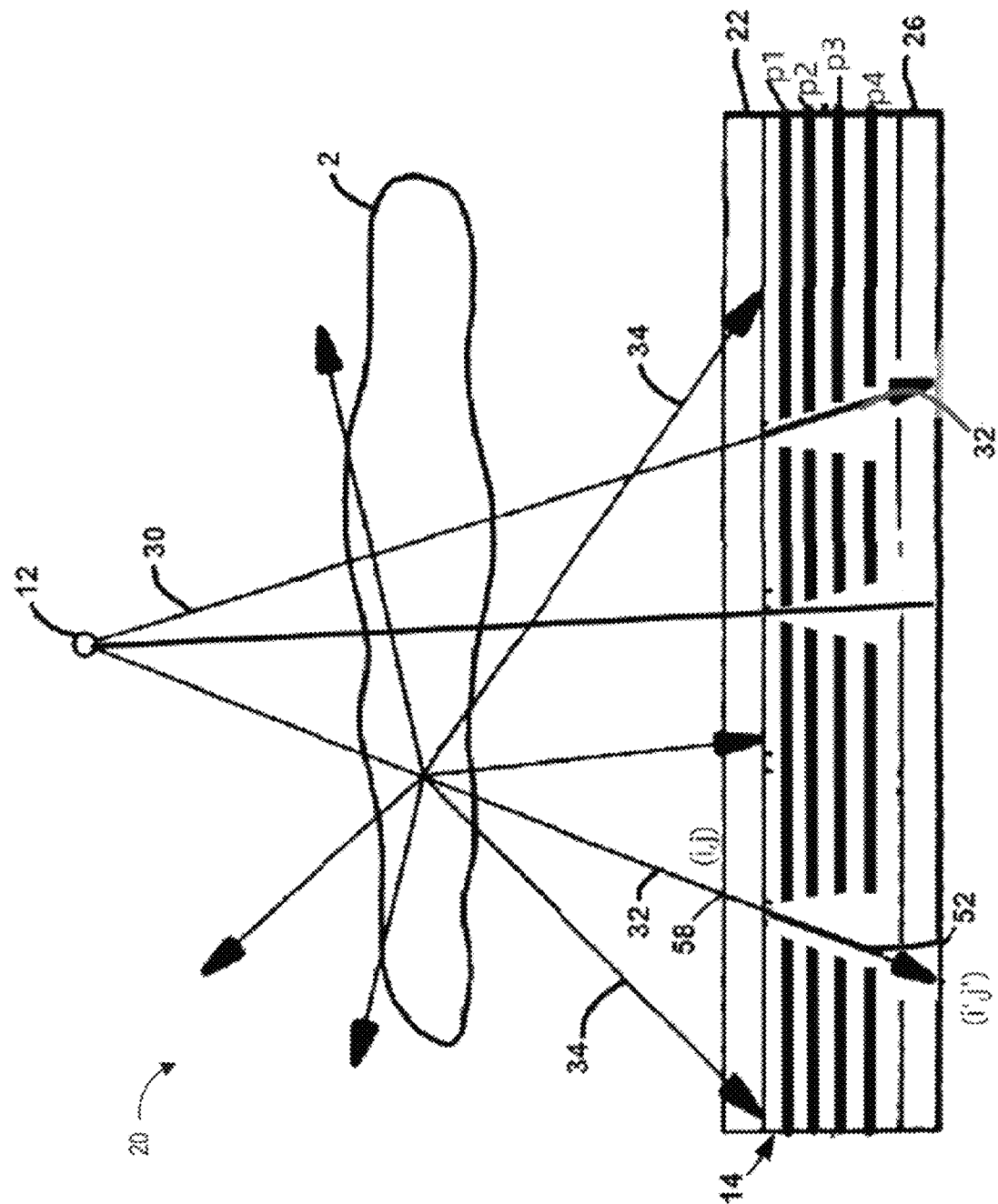
FIG. 2 illustrates schematically an example x-ray apparatus with a collimator for selective transmission of primary x-rays including multiple plates.

In addition, FIG. 2 shows an apparatus 20, which incorporates any of the features of the apparatus 10 in FIGS. 1A-IB except as described below. To align the transmission channels of a beam selector 24 with the x-ray emitting position of the x-ray source so that primary x-ray 32 may reach selected areas 52 on the rear detector 26, the beam selector 24 can include a plurality of x-ray absorber plates, p1, p2, p3, p4, with the transmission regions or holes lined up to allow primary x-rays 32 pass through selected illumination paths. Each plate can have a certain thickness. Spacer may be placed in between the plates to reduce the amount of scattered x-rays to reach the rear detector 26. The spacer may be a mechanical spacer, for example, including two or more spacers. Alternatively, the front detector 22 and the beam selector 24 can be attached to one or more first subjects, the back detector 26 can be attached to one or more second subjects, with the first subjects, and second subjects have a fixed distance between them. The total thickness of x-ray absorbing regions of the plates may be designed to absorb x-ray beams completely, while each plate may be thin enough for manufacturability of the plate, for example, to optimize the aspect ratio required for manufacturability. Having a plurality of plates can also allow the holes for x-ray transmission on each plate to be designed such that each hole on the plate in closer proximity to the rear detector 26 are slight larger than the corresponding holes in the plates further away from the rear detector 26.

Quantitative imaging and 3D imaging methods in the present disclosure generally require minimal or no scatter interference. Scatter removal methods involving measurements of primary x-ray and scattered x-ray passing through the subject are generally most accurate and practical for large field of view high resolution measurements in space and in spectral domains. Generally when scatter interference is less than 1% of the primary x-ray, the imaging method is considered quantitative, meaning, measurable attributes such as atomic z, density, composition and other properties can be determined accurately. The following are examples of scatter removal methods which are subject specific.

Scatter Removal with Calibration

Quantitative imaging and 3D imaging methods in the present disclosure and aforementioned PCT generally require minimal or no scatter interference.

A front high-resolution primary x-ray image can be determined using the following process in some configurations. A computer or processor can first determine a rear low-resolution primary x-ray image at the rear detector from an image of the passed x-ray beams 32, and then calculate a front low-resolution primary x-ray image from the determined rear low-resolution primary x-ray image. The computer or processor can also calculate a front low-resolution scatter x-ray image from the calculated front low-resolution primary x-ray image. The computer or processor can then calculate a front high-resolution scatter x-ray image from interpolation of the calculated front low-resolution scatter x-ray image, and thus derive a front high-resolution primary x-ray image from subtraction of the front high-resolution scatter x-ray image from the front composite image. Generally, the term "resolution" can be used to describe the image spatial resolution and/or the signal amplitude resolution for single pixels. In the present disclosure, "resolution" refers only for image spatial resolution except in the case of "spectral resolution" or "time resolution"

Examples of scatter removal process is disclosed herein. For instance, in one example, the process can include the steps of (a) illuminating the subject 2 with x-ray beams 30 from the x-ray source 12; (b) producing a low-resolution primary x-ray image, DrPl,(i'j'), based on the primary x-ray beam 32 that passes a location 58 on the front detector 22, through a transmission channel 56 of the beam selector 24, and landing at a region 52 of the rear detector 26; (c) calculating a low-resolution primary image DfPl (i, j) at the corresponding region 58 on the front detector 22 along the selected projection lines; (d) measuring a high-resolution image Dfh from the front detector; (e) producing a low-resolution composite image at the front detector Dfl(i, j)

from Dfh; (f) subtracting the low resolution primary image on the front detector DfPl(i, j) from Dfl (i, j) to determine the low-resolution scatter component DfSl(i, j); (g) smoothing the low-resolution scatter component DfSl by removing the high-spatial-frequency components: (h) calculating a front detector high-resolution scatter image DfSh by interpolation of the smoothed low-resolution scatter component DfSl at the front detector; and (i) subtracting the high-resolution scatter image DfSh on the front detector from the front detector high-resolution composite image Dfh to yield the front detector high-resolution primary x-ray image DfPh. The difference between the different types of blocking by the beam selector 24 described above is how the low-resolution primary image at the rear detector DrPl is produced.

The process for scatter removal described above may include a calibration step using calibration beams. The calibration beams can be used to derive the front low resolution primary x-ray images on the detector at a projected thin beam path by establishing a numerical relationship between primary x-ray measurements on the front detector and the primary x-ray measurements on the rear detector long the project thin beam path. The front low resolution scatter x-ray image can be extracted from the measured front image on the detector along the projected calibration thin beam path, which includes the front low resolution primary x-ray and the front low resolution scatter image. The front high resolution scatter x-ray image can be interpolated from the front low resolution scatter image and subtracted from the actual x-ray image including both primary and scatter x-ray to give rise to a front high resolution primary x-ray image.

The beam selector can be adjustable. The beam selector can be shifted and moved in one or multiple dimensions, and/or focal points. The adjustment can be done manually and/or automatically (for example, with actuators and electronics control or otherwise). The adjustability can allow flexibility in the x-ray source or x-ray emitting positions. The flexibility can be useful in calibration of the positioning of x-ray source relative to the detector(s). The calibration can allow for a more rapid adjustment of the relative positions of the x-ray source and the detectors when the source and/or the detectors move during measurements. The adjustment can be used to ensure measurements of the primary x-ray at selected locations on the rear detector when the subject moves.

The method involving the calibration step can include a structured illumination scatter removal method using two or more images. The 2D x-ray imaging apparatuses disclosed herein may include a single detector (see FIG. 3) rather than a dual-detector arrangement. An x-ray source in the apparatuses disclosed herein can emit a plurality of thin beams with a distance between the adjacent thin beams. The distance may be at least one pixel or otherwise when collected on a detector. Such collected measurements can include the primary signals and scatter signals. When the primary signals regions are small, for example, one or a few pixels, the scatter x-ray on these regions can be interpolated from the immediately adjacent regions, for example, one or more pixels in the surrounding area, which has scatter only signals.

Figure 3:
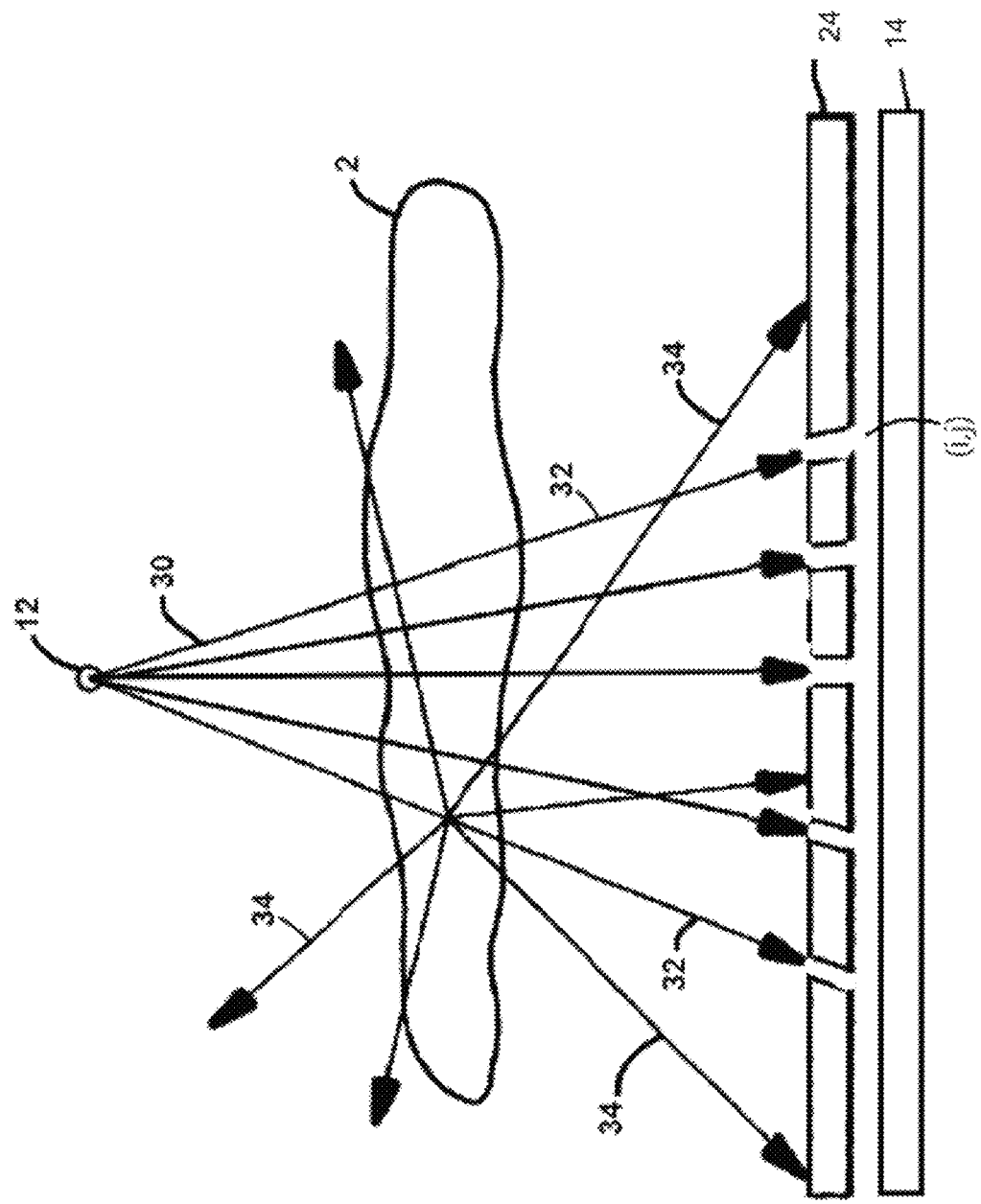
FIG. 3 illustrates schematically an example 2D x-ray imaging apparatus in which scatter is removed by using multiple x-ray thin beams in a two-image steps process.

FIG. 4 illustrates an example method of using structural illumination using x-ray thin beam for scatter removal at each energy level. As shown in FIG. 4, at block (a), the x-ray source can illuminate the subject a region of interest 4 in the subject 2 with a structural illumination apparatus with beam selector 24 such as shown in FIG. 3. The x-rays can have an energy level of H. At bock (b), the apparatus can acquire an image Dh(x, y) from the detector. Dhl(x(i), y(j)) can be the image file from the primary x-rays along the project line of path. At block (c), the x-ray source can illuminate the subject with x-ray thin beams of energy H, with spacing between adjacent beams. At block (d), the apparatus can acquire an image Dlc(x(i), y(j)) from the detector. The sequence of blocks (a)-(b) and blocks (c)-(d) can be switched. At block (e), the apparatus can obtain images Dsl(x(i), y(j)) using the equation Dsl(x(i), y(j))=Dhl(x(i), y(j))-Dlc(x(i), y(j)). The apparatus can interpolate the low resolution image Dsl(x(i), y(j)) to the remainder of the detector to derive an image Dsh(x, y), before obtaining a high resolution primary image Dhp(x, y) at block (f) using the equation Dhp(x, y)=Dh(x, y)-Dsh(x, y).

The structural beams can include a low dosage thin beam 32 with spacing as illustrated in FIG. 3. The beams 32 can be used as the calibration beam to obtain a primary beam signal at selected regions (i, j) on a detector 14 via the beam selector 24. The region can have one or multiple pixels. Some level of scatter x-rays 34 may still reach the selected regions on the detector 14. The scatter x-rays 34 are the beam scattered from other calibration beams. In such instances, as described below in equations (1)-(3) in Step 1 of the scatter removal process shown in FIG. 4, the scatter signal at (i, j) can be derived by interpolating scatter signals of pixels immediately adjacent to the selected region (i, j).

If spacing between the calibration beams 32 is increased, the amount of scatter reaching the detector 14 in the same location as the primary beam from the calibration beam is reduced. In some examples, widely spaced calibration beams can be emitted simultaneously at different positions to ensure there is enough spacing between the calibration beams when the calibration beams reach a density needed for the derivation of a low resolution primary x-ray signal and a low resolution scatter signal on the detector 14. To reduce the amount of scatter on the detector area where the primary x-ray images are formed by the x-ray thin beams, thin beams can also be emitted two or multiple times. Each time, the position of the thin beams can be far from each other. The combined calibration beam images can reach the density of primary x-ray images needed to calculate a scatter x-ray image, which can be extracted to obtain the final high resolution primary x-ray image. The mathematical method are described below in equation (4) of FIG. 4, where the primary signal is the measured signal at (i', j').

The calculations in the method of FIG. 4 can include several steps. At Step 1, the number of x-ray thin calibration beams can be determined by the minimally required number of thin x-ray beams to allow actual x-ray scatter measurements on the illuminated path to be interpolated to the entire image. The determined number of beams can thereby give rise to an extracted high resolution primary image p (i, j). The number of beams can be selected to reduce scattered x-ray that reaches the detector in the illuminated path. The number of thin beams can be selected so that as small as less than 1% scattered x-ray compared to that of the primary x-ray can reach the detector in the illuminated path. Alternatively or additionally, wider spacing beam sets can be emitted at different times to reach a density required for calculating the scattered x-ray and the interpolation needed to obtain a higher resolution primary x-ray image as would have been obtained without using the structured illumination scatter removal method. The scatter removal process can also be done at each energy level using the scatter removal methods disclosed herein.

The primary x-ray signal on the illuminated path can be extracted by direct measurements of the x-ray beam illuminating a region of interest on the detector minus the scattered x-ray in the same region. The scattered x-ray in the illumination path can be derived by interpolating the signal of x-ray in the adjacent pixels, which may be one or several in each direction adjacent regions, surrounding the pixels in the illumination path. The calculations are summarized in equations (1)-(3) below:

$$D\ sl(x(i),y(j)) = \text{interpolate}(D\ sl(x(i+1),y(j)), D\ sl(x(i+1),y(j+1)), D\ sl(x(i-1),y(j-1)), D\ sl(x(i),y(j+1)), D\ sl(x(i-1),y(j), D\ sl(x(i),y(j-1))). \quad (1)$$

$$D\ lc(x(i),y(j)) = D\ hl(x(i),y(j)) + D\ sl(x(i),y(j)) \quad (2)$$

$$D\ hl(x(i),y(j)) = D\ lc(x(i),y(j)) - D\ sl(x(i),y(j)) \quad (3)$$

In some cases, interpolation of scattered signals from adjacent pixels may be omitted and the measured signals from the x-ray thin beam can be the primary x-ray signal with minimal or no scatter interference, for example, in the case when x-ray thin beam has a small diameter, in the um or nm range as in microbeam or nanobeam and sometimes, in millibeams leading to equation (4) below.

$$Dhl(x(i),y(j)) = D\ lc(x(i),y(j)) \quad (4)$$

At Step 2. X-ray cone beams can illuminate a region of interest and equations (5)-(7) can apply.

$$D\ sl(x(i),y(j)) = D\ h(x(i),y(i)) - D\ hl(x(i),y(j)) \quad (5)$$

$$Dsh(x,y) = \text{interpolation of } D\ sl(x(i),y(j)) \quad (6)$$

$$D\ hp(x,y) = Dh(x,y) - Dsh(x,y) \quad (7)$$

Where, D sl (x(i), y(j)) is the scatter signal on the detector on the thin beam illuminated path at selected regions (i, j) on the x-y 2D plane of the detector: D sl (x(i+1), y(j)), D sl (x(i+1), y(j+1)), D sl (x(i-1), y(j-1)), D sl (x(i), y (j+1), D sl (x(i-1), y(j), D sl (x(i), y(j-1))) are representations of examples of pixels in some of the immediately adjacent regions to (i, j).

D lc (x(i), y(j)) is the measured x-ray signal along the illuminated path of the x-ray thin beams at selected regions (i, j) on the detector. D hl (x(i), y(j)) is the primary x-ray signal of the x-ray thin beam along the illuminated path of the x-ray thin beam at selected region (i, j) on the detector.

D sl (x(i), y(j)) is the scatter x-ray at the selected region (i, j)-due to x-ray cone beam illumination on the detector from Step 2.

Dsh(x, y) is the scattered x-ray component of the measured x-ray signal from the x-ray cone beam illumination on the detector from Step 2.

Dh ((x, y)) is the measured x-ray signal from the x-ray cone beam illumination of the subject on the detector from Step 2.

D hp (x, y) is the primary x-ray signal from the x-ray cone beam illumination of the subject on the detector from Step 2.

Generation of multiple x-ray thin beam or structured illumination pattern may be achieved by using a collimator 24 or a beam selector with regions which allow x-ray transmission, ranging from 100% transmission to a small percentage of transmission, and regions which block or absorb x-rays completely. The beam selector 24 may be placed downstream of the x-ray source, but upstream of the subject 2. Multiple plate version p1-p4 as in FIG. 2 of the beam selector 24 may be used in some instances. In one example, such a configuration enables spectral measurements and/or densitometry of components or targets in region of interest at low radiation level when x-ray source capable of multiple energies or broad spectrum emission. An energy filter, such as K-edge filter or K-edge coded aperture may be placed down stream of the transmissive region of the collimator 24.

For low scatter and high spatial resolution imaging, beam selector 24 may be moved by a mover driven mechanically or by energy modulated method or electrically.

The x-ray thin beam with a sparsely distributed pattern may be generated by a patterned target on the anode for electron beams from the cathode to only generate x-ray beams at selected regions of the target. The patterned target can rotate or move in and out of the electron target region for the x-ray source to generate x-ray fan beam using a conventional target or x-ray structured illumination or patterned illumination or spatially distributed x-ray thin beams.

Optionally, the anode target of the x-ray source may be modified so that the x-ray cone beam generated may have selected regions which have no primary x-ray emitted. Using the modified x-ray source can result in the illuminating x-ray passing the subject with distributed x-ray beams which illuminated paths sparsely distributed. When for example, collected by a flat panel detector, the x-ray measurements may have multiple regions void of primary x-ray signals. Each region can have one or more pixels.

Optionally, where light source, such as a laser or LED source, is the source generating the electron beam, either a beam steering apparatus, such as a Microelectromechanical (MEM) apparatus, or an optical absorber or modulator, may be used to block or modulate optical signals at certain regions, thereby creating electron beams with a structured profile where there are certain regions on the anode target are not reached by the electrons beam. The beam steering apparatus or the optical absorber or modulator can be placed in a fixed position or movable. The generated x-ray beams can pass through the subject with a programmed path so that when the beams reach the detector, there are regions that are devoid of primary x-rays.

The structural beam method described in this present disclosure can be particularly useful for stacked detector methods where a beam selector is not able to be implemented and stacked detectors are used for functions different than scatter removal, such as dual energy imaging for material decomposition using one x-ray pulse, or x-ray microscopy, where x-ray images of the primary x-ray are used downstream for further processing by microscopy hardware setup and analysis.

One benefit of this calibration beam method can include that this method would work for any material type without prior material calibration or simulation steps described above needed. This is useful for quantitative analysis of most material type or thickness or composition including two or more overlapping materials. Another benefit is that this method reduces the cost by reducing the number of detectors or detector planes, and/or size of detector plane needed for separation of scatter and primary images.

Collimator 24 or beam selector 24 in FIG. 3 may also be placed between x-ray source and the subject. Similarly, stacked plates p1 to p4 configuration in FIG. 2 may be placed between x-ray source and the subject or between the subject and the detector.

Optionally, when requirement of the resolution is low for primary x-ray measurement, the use of collimator 24 and stacked plates P1-P2 may be used for scatter removed primary x-ray imaging in a single step. In one example, wavelength or energy filters are used downstream from the collimator and upstream of the subject, or between the collimator and the x-ray source, spectral measurements and low resolution densitometer may be obtained.

Multiple Energy Scatter Removal

Figure 5:
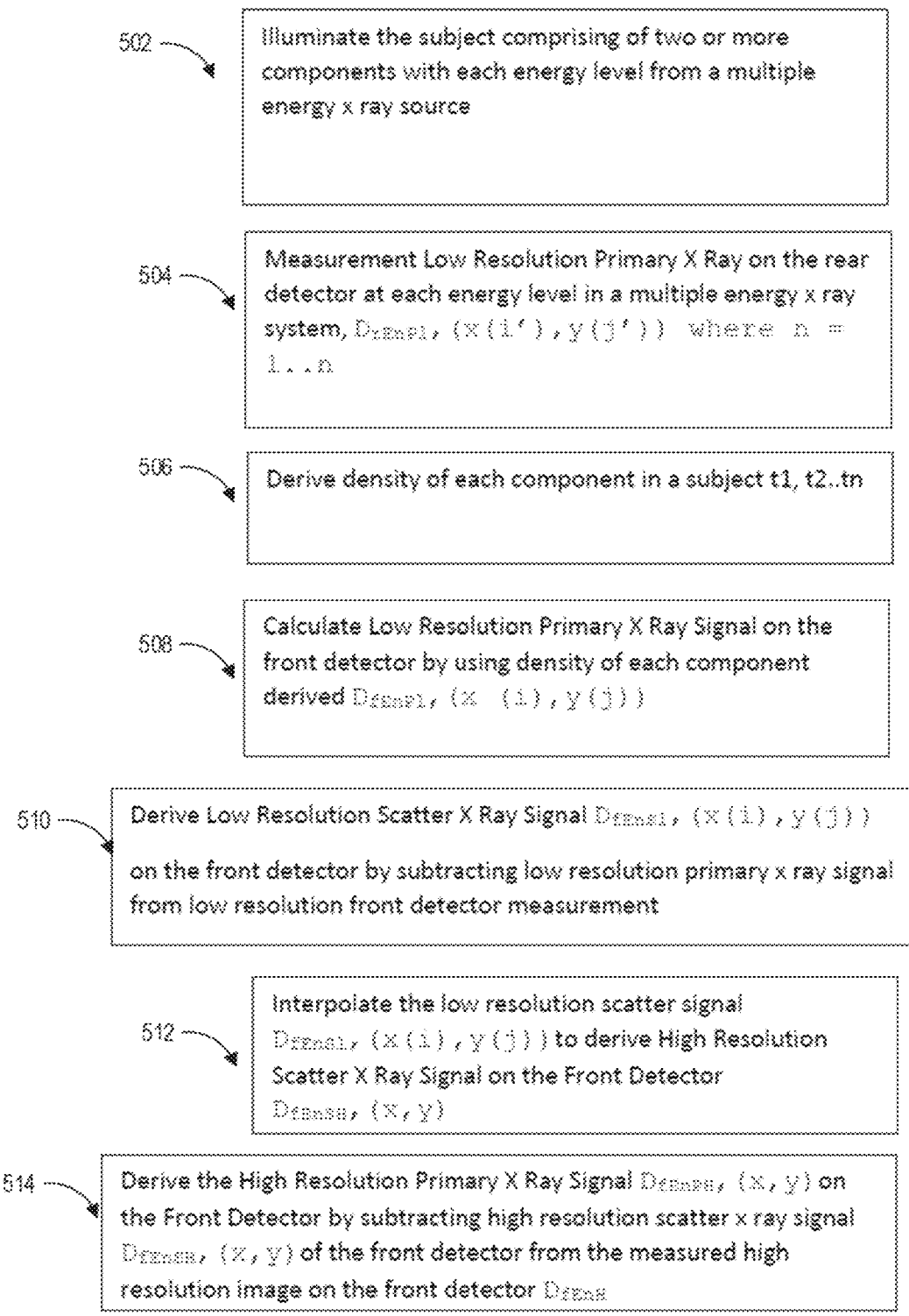
FIG. 5 illustrates a flow diagram of an example method for removing scatter for a multiple energy system using a dual-layer detector system as described herein.

The correlations disclosed herein can be done at each x-ray energy level. For more thorough scatter removal for quantitative imaging and 3D tomography or application requirements, such calibration beam method can be extended to be used in dual or triple or more energy x-ray scatter removal processing using similar mathematical processes described above. The multiple energy scatter removal methods may be used for dual energy x-ray systems when the subject includes three different components or substances, each may have a different x-ray measurement property or properties, for example, different atomic z number, different composite material, different temporal and/or spatial markers. If four or more energy level measurements are performed, calibration of similar or actual material and subject at each of the four energy levels may be used, and in some instances, calibrated with at least four different components, each with a different x-ray measurement properties, such as different atomic z number, and their composite materials comprising two or more components.

Where multiple x-ray thin beam illumination is used, removal of scatter image at each energy level may be achieved by performing the example method illustrated in FIG. 5 for each energy level at which the x-ray image is taken. At block 502, a multiple energy x-ray source can illuminate a subject including two or more components with each energy level. At block 504, the apparatus can receive measurements about a low resolution primary x-ray image on the rear detector at each energy level, DrEnPI, (x(i'), (y(j')), where n is an integer. At block 506, the apparatus can derive the density of each component in the subject, t1, t2, . . . , tn. At block 508, the apparatus can calculate a low resolution primary x-ray signal on the front detector by using the derived density of each component, DrEnPI, (x(i), (y(j)). At block 510, the apparatus can derive a low resolution scatter x-ray signal DrEnSl, (x(i), (y(j)) on the front detector by subtracting the low resolution primary x-ray signal from the low resolution front detector measurement. At block 512, the apparatus can interpolate the low resolution scatter x-ray signal DrEnSl, (x(i), (y(j)) to derive a high resolution scatter x-ray signal DrEnSH, (x(i), (y(j)) on the front detector. At block 514, the apparatus can derive a high resolution primary x-ray signal DrEnPH, (x(i), (y(j)) on the front detector by subtracting the high resolution scatter x-ray signal DrEnSH, (x(i), (y(j)) on the front detector from the measured high resolution image on the front detector DfEnH.

Instead of using a rear detector image file, the image file can be contained in the single detector so that no scaling or derivation of calibrated relationship is needed to correlate calculated images on the front detector with measured image data on the back detector. Where only a single image is taken to remove scatter as well as to derive a high resolution image, the beam particle absorbers can be utilized. The scatter removal method is performed at each energy level to provide the high resolution primary x-ray at each energy level.

Figure 6:
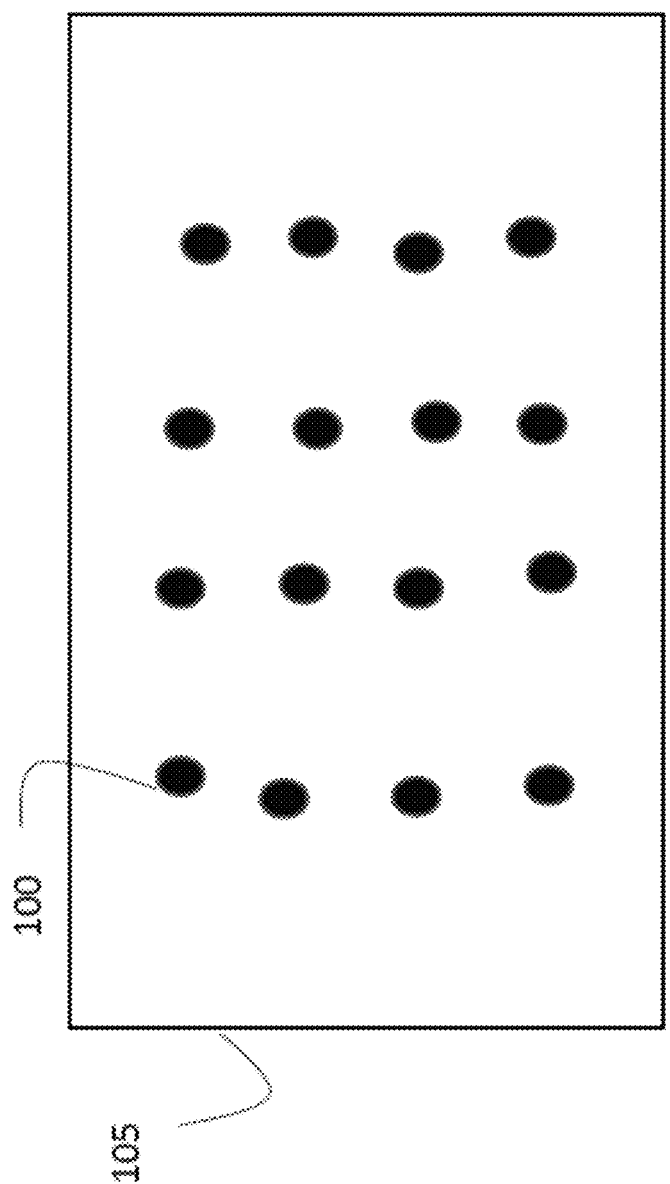
FIG. 6 illustrates schematically a top down view of an example beam blocker to remove scatter including beam absorbing particles.

As discussed above, the scatter x-ray data can be derived by interpolation for the region with primary x-ray signals, and subtracted from the measured data. The extracted primary x-ray data can then be used for 2D and/or multiple dimensional image construction and quantitative analysis for the component or the region of interest or the sample, for example, using equations (8) and (9) below:

$$D\ sh(x,y) = \text{interpolation of } D\ sl(x(i),y(j)) \quad (8)$$

$$D\ hp(x,y) = D\ h(x,y) - Dsh(x,y) \quad (9)$$

Where D sl(x(i), y(j)) is the selected detector region (i, j) where there are only scatter x-ray signals due to the fact that the primary x-ray along the x-ray illumination path is blocked by a beam absorber or beam absorber particles (such as one shown in FIG. 6). D sh (x, y) is the high resolution scatter x-ray component of the measured x-ray on the detector. D hp(x, y) is the high resolution primary x-ray component of the measured x-ray on the detector. D h(x, y) is the measured x-ray signal on the detector, which can include both primary and scattered x-ray signals.

For regions (i, j) where there are no primary x-ray signals detected due to the fact there has been no x-ray primary beam on the illumination path to give rise to signals at region (i, j), the primary x-ray signals at regions (i, j) of Dhp(x, y) may be derived by equation (10) below.

$$Dpl(x(i),y(j)) = \text{Interpolation of } Dpl \text{ of regions immediately adjacent to}(i,j) \quad (10)$$

This method may be sufficient for most applications. In a tracking or surgical guidance application such as disclosed herein, when two or more images are taken, where the beam absorber may be moved, or the x-ray emitting position may be adjusted, each time the beam absorbers blocks a different illumination path, and imaging gap is varied from one image to the next, may provide sufficient information to retroactively fill in the image gap by extracting measurements in the region (i, j) from one or more different measurements in the sequence.

Alternatively or additionally, in situations where ultra high resolution images are required and/or there is a need to make sure all areas of the regions of interested are illuminated, therefore no or much less missing data of the subject on the detector, two or more images may be required to be taken of the same subject along the same illumination path with the beam absorber blocking the primary x-ray be moved, so that the region (i, j) from the last image may receive primary x-ray. Alternatively, such images on the region (i, j) may be derived from a structured beam illuminating only the regions (i, j) where the beam absorber is adjusted away from its original position.

For a dual energy system or a three or more energy system having a plurality of beam absorbing plates to measure a subject having multiple components, low resolution primary and scatter images on the front detectors, Df E1Pl, Df E2Pl, Df E3Pl, . . . , Df EnPl can be calculated by equations (11)-(18):

(a) solving the low-resolution primary x-ray imaging set for the area densities t1, t2, t3, . . . , tn, wherein $$DrE\ 1l(i,j) = \int [\Phi 0E1(E) \times \exp(-(\mu 1(E) \times t1(i,j) + \mu 2(E) \times t2(i,j) + \mu 3(E) \times t3(i,j) + \ldots + \mu n(E) \times tn(i,j))] \times Sr(E) dE \quad (11)$$

$$Dr\ E2l(i,j) = \int [\Phi 0E2(E) \times \exp(-(\mu 1(E) \times t1(i,j) + \mu 2(E) \times t2(i,j) + \mu 3(E) \times t3(i,j) + \ldots + \mu n(E) \times tn(i,j))] \times Sr(E) dE; \quad 15\ (12)$$

$$Dr\ E3l(i,j) = \int [\Phi 0E3(E) \times \exp(-(\mu A(E) \times t1(i,j) + \mu B(E) \times t2(i,j) + \mu C(E) \times t3(i,j) + \ldots + \mu n(E) \times tn(i,j))] \times Sr(E) dE \quad (13)$$

and $Dr\ En1(i,j) = \int [\Phi 0En(E) \times \exp(-(\mu 1(E) \times t1(i,j) + \mu 2(E) \times t2(i,j) + \mu C(E) \times t3(i,j) + \ldots + \mu n(E) \times tn(i,j))] \times Sr(E) dE \quad (14)$ (b) inserting the t1, t2, t3, ... tn solutions into equations (15)-(19) for the image set:

$$DfE1Pl(x(i),y(j)) = \int [\Phi 0E1(E) \times Sf(E)] \times \exp(-(\mu 1(E) \times t1(i,j) + \mu 2(E) \times t2(i,j) + \mu 3(E) \times t3(i,j) + \ldots + \mu n(E) \times tn(i,j)))dE \quad (15)$$

$$Df E2Pl(x(i),y(j)) = \int [\Phi 0E2(E) \times Sf(E)] \times \exp(-(\mu 1(E) \times t1(i,j) + \mu 2(E) \times t2(i,j) + \mu 3(E) \times t3(i,j) + \ldots + \mu n(E) \times tn(i,j)))dE \quad (16)$$

$$Df E3Pl(x(i),y(j)) = \int [\Phi 0E3(E) \times Sf(E)] \times \exp(-(\mu 1(E) \times t1(i,j) + \mu 215(E) \times t2(i,j) + \mu 3(E) \times t3(i,j)) + \ldots + \mu n(E) \times tn(i,j)))dE \quad (17)$$

$$DfEnPl(x(i),y(j)) = \int [\Phi 0En(E) \times Sf(E)] \times \exp(-(\mu 1(E) \times t1(i,j) + \mu 2(E) \times t2(i,j) + \mu 3(E) \times t3(i,j)) + \ldots + \mu n(E) \times tn(i,j)))dE \quad (18)$$

where $(x(i),y(j))$ is the coordinate of the front detector cell intersected by the projection line that also intersects the rear detector cell $(i, j)$, $\Phi 0\ E1\ (E)$ is the energy spectrum of the x-rays of energy E1, $\Phi 0\ E2\ (E)$ is the energy spectrum of the x-rays of energy E2, $\mu 1\ (E)$ is the mass absorption coefficient of the material having area density t1, $\mu 2\ (E)$ is the mass absorption coefficient of the material having area density t2, and $Sf\ (E)$ is the spectral sensitivity of the front detector, $\Phi 0\ E3\ (E)$ is the energy spectrum of the x-rays of energy E3, $\mu 3\ (E)$ is the mass absorption coefficient the said material having area density t3, $\Phi 0\ En\ (E)$ is the energy spectrum of said x-rays of energy En, and $\mu n\ (E)$ is the mass absorption coefficient of the material having area density tn.

In one implementation, the primary x-ray signal on the front detector at each energy level of the subject having three or more different components can be derived. When the density of four or more components of the subjects are to be resolved by primary x-ray measurements in the rear detector at four or more energy levels; inserting solutions of density for each component from multiple energy measurements can give rise to the derivation of the front primary x-ray low resolution signal at each of the energy levels, based on calibrated or known corresponding relationship of regions on the front detector and those on the back detector. In turn, the low resolution scatter image at the front detector can be derived by subtracting the derived low resolution primary x-ray image of the front detector from the high resolution measured composite image on the front detector. The calculations can be carried out in equations (19)-(24).

$$DfElS1(x(i),y(j)) = DfE1l(x(i),y(j)) - DfElP1(x(i),y(j)) \quad (19)$$

$$DfElSH((x,y)) = \text{Interpolation}(DfElS1(x(i),y(j))) \quad (20)$$

$$DfElPH((x,y)) = DfElH((x,y)) - DfElSH(x,y)) \quad (21)$$

$$DfEnS1(x(i),y(j)) = DfEn1(x(i),y(j)) - DfEnP1(x(i),y(j)) \quad (22)$$

$$DfEnSH((x,y)) = \text{Interpolation}(DfEnS1(x(i),y(j))) \quad (23)$$

$$DfEnPH((x,y)) = DfEnH((x,y)) - DfEnSH((x,y)) \quad (24)$$

Where $DfElS1\ (x(i),y(j))$ is the low resolution scatter image on the front detector, at the region $(i, j)$, taken at the energy level E1, $DfEn1\ (x(i),y(j))$ is the low resolution image measured by the front detector at the region $(i, j)$, $DfEnS1\ (x(i),y(j))$ is the low resolution scatter image on the front detector, at the region $(i, j)$, at the energy level En, derived from substracting low resolution primary image at the region $(i,j)$ from the composite image on the front detector DfEn1.

The low resolution scatter image can then be further interpolated into a high resolution scatter image, which is subtracted from the measured high resolution image to give rise to the high resolution primary image at each energy level.

Accordingly a single energy method, that is, using the scatter removal for a single energy system as described above for each energy measurement, can be used to remove scatter at each selected energy level.

In all scatter removal methods disclosed herein, the interpolated or measured scatter image may be presented for visual analysis.

Other implementations of scatter removal at various energies, based on the disclosure herein, are possible.

In the case when the front detector and the rear detector are the same or very similar, a simple scaler factor may be used in correlating measurement data. The primary x-ray signal on the front detector can be correlated to that on the rear detector using the simple scaler factor. Such relationships in one implementation can be simulated based on relevant data and/or measurements.

Preferably, the front detector is designed so that some of the x-rays coming out of the subject can be measured by the front detector and some can pass though, for further analysis such as the rear detector and beam selector assembly for scatter removal and/or other detection and measurement methods, with hardware such as a fast detector, a dynamic detector or high resolution spectral or multiple energy detector, details of which are as disclosed below. The front detector therefore can be transmissive or partially transmissive. Preferably, ere is no or minimal beam hardening and without or with minimal any x-ray modification features. Preferably, the electronics of the—detector can be placed on the side instead of downstream of the detector. Optionally, the detector may be completely transparent to x-ray, or in some cases, to visible light. Effect of the front detector on the x-ray may be calibrated and removed for analysis of the measurements downstream of the subject and the detector.

In x-ray imaging of live subjects or biological tissues (in vivo and/or ex vivo), there may be tissues or materials in addition to bone and soft tissue, such as foreign subjects including but not limited to surgery tools, implants, contrast labels or agents, and/or a third component in an imaged subject, such as blood vessels. In industrial x-ray imaging, there may be a need to characterize various components in a complex mixture or multiple component subject. Various materials can be used to calibrate or establish a database for different materials and composite materials or regions with unique x-ray measurable properties. The material types in the database can include more than bone and soft tissues.

Materials of various spatial complexity and/or composition complexity may be used for calibration or establishment of the database (which will be described in greater detail below). For example, materials similar to those of the components in the region of interest internal to the subject can be used in x-ray measurements in the calibration step, so that the primary x-ray signals on the front detector and their corresponding signals on the rear detector are correlated for those material types. In one example, the microstructures of various spatial complexity and dimensions and composition complexity that are capable of perturbing the x-ray energy spectrum differently, for example, which are similar to those expected in the imaged subject, are introduced in the calibration step for each energy level image received on the detector. For example, in chest imaging, microstructures similar to bone, cardio tissue, endovascular tissue and blood, and other components such as the catheter and surgical tools, can be used for calibration.

For calibration purposes, the apparatus can adjust or maintain the relative positions and/or alignment between the beam selector and the front detector, between the beam selector and the rear detector, and/or between the front detector and the back detector. The adjustment can be done by a mechanical structure, such as one or more side frames. For example, the apparatus may include a plurality of screws to attach all the components and to serve as spacer: chemicals such as glue can also be used. Magnetic spacers may also be used.

The apparatus can determine positions of pixels on front detector and back detector corresponding to the same primary x-ray projection path, for example, mechanically and/or using software, with the design of detector and beam selector geometry as an input. Prior to the imaging process, the position of the relevant pixels can be selected as part of the mechanical design and can be stored and registered in the software.

The software can also optionally algorithmically determine the relevant pixel positions based on imaged signals of a component, such as a target, or part of subject that can serve as a reference and design parameters of position of detectors and/or beam selectors.

The software may facilitate the measurement of spatial position of the x-ray source position relative to the subject, relative to the detector, or markers on the detector and the beam selector, and calibrate geometry and spatial positions of each hardware, the subject, fiducial marker on the subject, and/or relevant component inside the subject.

The database can include relationship data including derived relationship algorithms of primary x-ray signals based on a few different options. Simulated material x-ray signals, or synthesized x-ray signals based on previous measurements of the material or similar materials by the detectors or the same type of detectors, or any known established x-ray measurement properties of certain materials may be used for the correlation. Correlating front and back detector measurements can be done using simulated data.

The relationship can also be derived from previously measured data of materials of different types, physical compositions, and/or dimensions at one or more energies on the front detector and corresponding back detector. The relationship can also be derived from the properties of specific front and back detectors and predicted signal level based on such properties. For example, if the front detector and back detector are the same, a linear relationship may exist for certain materials. In some examples, such relating algorithms are correlated based on both factors described herein. The algorithms can also be correlated based on each individual factor, and of the combined factors, from a library containing accumulated detector measurements of various material type and thickness at one or more energy levels historically by the same type or similar detectors.

The x-ray apparatus disclosed herein can include an algorithm software operation in which a calibrated database stored in the computer may correlate imaging properties of different detectors. Signals from one pixel or more pixels on the front detector may be correlated to the corresponding region on the back detector for certain material or subject along the projected x-ray beam path. Materials and energy levels can be used to calibrate primary x-ray signals from a region on the front detector and the corresponding region along the projected path on the back detector. The establishment of a calibration database may be optional depending on the application need. When the materials of the subject to be imaged or measured are known and defined, x-ray measurement properties can be predicted.

Simplified versions and/or material equivalent of structures in terms of complexity, composition, and thickness can be used for calibration as well as actual materials. The complexity in calibration material selection can be due to a number of factors, such as compositions of the material, which can be multiple or mixed of molecules of organic and/or in organic molecules, spatial composition, density, and/or whether the material is in a powder form, the atomic number of the material, whether it is single material or composite material, the thickness of the material. Some materials may be overlapping in space. For example, microcalcification may be present in the matrix of soft and lean tissues. Implants, such as heart valves or stents, may be mixed with blood, which includes blood cells and plasma, blood vessels, bone, muscle, and other soft tissue in the imaging path outside of the blood vessel. Microchip layers may be of two or more different metal, polymer, or mixture or composites. The subject may also include metal or polymer components such as machine parts used in planes or automotive.

A database can be established for measured properties of materials and material equivalent at a single energy x-ray, especially such x-ray spectrum characterized as having one single energy peak in the energy spectrum. Preferably, material decomposition using single energy x-ray combined with a reference database may be utilized to determine component density and identify component in the illumination path of the x-ray.

Second order approximation can be included for calibration in dual energy and extension from dual and single energy to multiple energies. As described, measurements of known materials, for example, three known materials (for example, u, v, w), can be related to measurements of actual materials which are similar to each of the known materials, such as p, q and o. Actual materials may be difficult to be directly measured and therefore unknown, but detector measurement of u, v, w can be correlated with that of p, q and o. Therefore, a mathematical relationship can be derived for each of p, q, o, in terms of density and other x-ray sensitive or measurable parameters from measurements of corresponding u, v, w at multiple energies, in this case, triple energies. This method can be extended to more than three energies.

The x-ray apparatus disclosed herein can also include one or more beam stoppers on the outer periphery defined by the side of beam selector for the space in between the beam selector and the rear detector to block the x-ray beam not of interest from reaching the rear detector.

In order to better correlate primary beam signals on the front detector and corresponding primary beam signals on the back detector, to determine thickness of each material or composite material or components and/or to provide data for the calibration or reference database, x-ray measurements on the front detector and back detector can be made with a varying thickness of materials, which can be the same of or similar to selected calibration materials having varying atomic z numbers and/or material compositions and/or contrast labels in the region of interest. In an example industrial application, when one type of powdered chemicals is to be identified or detected in a subject of multiple components, the measurements of the powdered chemical of various amount, and/or various thickness may be used to correlate the front and the back detector.

In cases where the thickness of region of interest or thickness of various components in the region of interest is known, for example, if a three dimensional (3D) quantitative measurement has already been obtained for the specified subject, in which case, each known voxel is solved in the subject or region of interest or previous measurements were already done to determine the thickness of relevant component, or the thickness of the subject or components is provided (such as that of a surgical tool with defined material type and dimensions), the calibration step may be simplified by including into the reference database or library the preexisting data as described.

In addition to the dual detector assembly scatter removal system, FIG. 6 illustrates an example of scatter removal and/or a densitometer that can measure density of each component using only one detector, it can include a beam absorber plate 105. A plurality of beam absorber particles 100 can be spatially distributed on the plate 105. The density of the particles 100 can be adjusted. Each particle can have at least two state positions, "on and off", or "opaque or transmissive to primary x-ray". The plate 105 at where the particles 100 are located may be tilted by one or more actuators to adjust transmission of primary x-ray. The plate 100 may also be moved in a 2D space by one or more actuators in the plane parallel to the detector. Multiple of such plates may be used as one beam selector.

Where multiple x-ray beams are generated such as shown in FIG. 7, the plate 105 of FIG. 6 with varied x-ray absorbing properties or being completely transparent to x-rays, for instance, a polymer plate, may be used to hold the beam absorbing particles 100 in position. The plate 105 can be placed between the subject 2 and the x-ray 10 source, or may be placed between the subject 2 and the front detector 22.

Two or more plates with varying densities of beam absorbing particles distributed in a predetermined pattern may be used in the apparatus of FIG. 7. The movement of such plates in the x, y, and z directions by a mover or one or more axis positioner or the like may adjust the x-ray absorbing properties of the plates from 0% to 100% in one or more movements. The density of beam absorbing particles 100 can affect the radiation exposure to the region of interest and the resolution of the image. A higher density of particles 100 can result in the less radiation exposure to the region of interest. A lower density of particles can result in more radiation exposure but the higher resolution the measurements can be. A balance can be achieved with a high enough resolution and at the same time the lowest position radiation exposure.

The size of the particles 100 may be about 0.1 um to up to about 10 mm in the x and y plane parallel to the detector 14. The position of beam absorbing particles 100 in the x and y 2D plane parallel to the detector 14 may be moved to adjust the position where the primary x-ray beam is blocked, therefore allowing for illumination paths through the region of interest which are previously blocked and eliminating any holes or missing measurements within region of interest, which would otherwise exist.

The scatter removal processes described herein can reduce time and radiation exposure, in constructing quantitative 2D and 3D images and measurements of the subject. As few as one image measurement can be taken of the sample in order to derive the high resolution primary x-ray measurement data. X-ray radiation can be reduced for specific location of regions of interest in the subject in multiple measurements, each at a different time. For example, the measurements of the sample can be repeated using x-ray beam illuminated in a different location of the same component, for example, immediately adjacent to it. Although the total radiation level received by the sample may be the same, any specific area of the sample in the region of interest only gets a fraction of the total radiation. Depending on the resolution required or desired, the size of the regions illuminated with primary x-ray signals may be adjusted and in some cases, minimized so that the direct x-ray radiation on the sample can be reduced for any particular location of the sample. X-ray radiation exposure can also be reduced for a region of interest in one measurement. For example, the x-ray beam can be adjusted to illuminate only a selected region of interest, x-ray thin beams. Alternatively or additionally, a distribution of x-ray illuminated regions on the region of interest may be adjusted to generate measurements of desired resolution. Alternatively or additionally, the x-ray beam can be steered by steering mechanisms such as magnetic or activated for the select regions for electron beam generation, as in a cold cathode x-ray source. This can be accomplished by, for example, the beam absorbing particle plate 105 as in FIG. 6 and FIG. 7, or collimators with transmissive holes as in FIG. 3 or the beam selector 24 as in FIG. 1B, placed between the x-ray source 12 and the subject 16 or between the subject 16 and detector 14, or the x-ray source with selected region of anodes capable of generating x-ray beam to illuminate region of interest with sparsely spatially distributed path as in FIG. 26. 2D or multiple dimension images and 3D images may be constructed based on methods as described in the present disclosure. Different regions of interest in the sample may require different resolutions, how sparse the primary x-ray illumination path can vary for different regions or in some instances, and/or for different components of various composition, composite materials, inhomogeneous materials, homogeneous materials and interface region of two or more materials, or atomic z numbers in the region of interest.

The apparatus with beam absorption plate(s), for example as in FIG. 6 may also be used to measure adjustable resolutions and/or fast tunable resolution measurements depending on application needs. For example, the beam absorption particles can be distributed with a high density in order to provide measurements for a lower resolution image. The beam absorption particles can be more sparsely distributed to achieve a higher resolution image. The apparatus with beam absorption plate(s) can include a beam absorbing region or beam transparent region, which can include materials like beryllium. One or multiple plates may be stacked on top of each other to allow the complete attenuation of x-ray, especially spectral x-ray. The plates may be used to measure adjustable resolutions and/or fast tunable resolution measurements depending on application needs. For example, the beam absorption particles can be distributed with a high density in order to provide measurements for a lower resolution image.

In one preferred implementation, the configuration as described in FIG. 6 the density of the beam absorption particles may be adjusted to have the resolution equivalent to that of a densitometer, such a dual energy densitometer and at the same time have radiation level similar or less than that of a densitometer based on linear detector scanning dual energy system. In this case, the beam absorbing particle may include cylindrical rods, each longitudinal axis of the rod is along the primary x-ray irradiation direction.

Traditional, a scanning linear detector based dual energy densitometer is time consuming, low resolution, for example, at a 500 um resolution and 1/10 of radiation of a 2D image by flat panel detector. Using the configuration in FIG. 6, the plate can be placed between an x-ray source and the subject, if the beam absorption particle is set at, for example, 50-500 um in the xy dimensions parallel to the detector, with thickness high enough to attenuate the x-ray from the generator completely. If such particles are designed with density high enough to reduce radiation and sufficient to achieve 500 um resolution for x-ray measurement, a real time, low radiation densitometer may be achieved. In addition, energy filter may be used in the x-ray transmissive region to speed up dual or multiple energy measurements. Bone density and/or density of other tissue types and component types may be measured.

Alternatively, collimators or beam selector plates as in FIG. 3, FIG. 2 and FIG. 1B may be placed between x-ray source and the subject. In addition, primary x-ray transmitted through the holes of the beam selector plate may be filtered by energy filters, for example k-edge coded filters.

Beam absorption particle plate or collimators with holes or beam selector can each be used in tracking and monitoring of components, provided the component can be characterized with the resolution achievable by each of these hardware elements.

For the purpose of high resolution imaging, there can be a minimum density of beam absorption particles in order to achieve scatter removal required for the high resolution primary x-ray imaging. Beyond that, the regions of primary x-ray imaging measurement may be adjusted. How many pixels in the primary x-ray region can be selected in order to obtain an image with sufficient information for one particular image measurement can determine the amount of the radiation the sample will receive and the resolution of the image. Primary x-ray signals on one pixel out of every two or three or more adjacent pixels or a clustered pixel region can be received using a denser or larger number or larger opaque region of beam absorbing particles to block the primary x-ray. The resultant measurement can be interpolated to the adjacent pixels in the same cluster region where the primary x-ray does not reach. A complete image including multiple of such clustered pixel regions can give rise to a low resolution as well as a relatively high resolution primary x-ray image while the highest resolution primary x-ray image achievable by the hardware, for example, as limited by the resolution of the detector, may not be required. Both material decomposed imaging and densitometer of various components, such as tissues, for example bone, lean tissues or contrast agent labeled tissues may be achieved at the same time using single, dual or multiple energy methods. The beam selector or collimator or the beam absorption particle plate may be placed preferably between subject and the detector, especially if high resolution imaging is desired.

Alternatively, a larger segment of regions may be blocked by beam absorption particles in order to limit radiation in the region of interest for measurements where only an image of a small region of a target or a component contained in a region of interest may be needed for the particular application. Such configuration may be used in 3D imaging or tomography applications, where the beam absorption particle is spherical, and/or where the diameter of the sphere ensures complete attenuation of x-ray. As the x-ray emitting position/x-ray source moves, the sphere attenuates the incoming x-ray from any orientation or angle.

In conventional usage of collimators, output of a fan beam x-ray may be adjusted by a collimator, which limits the area or the angle of emission. In this case, the beam absorption particles may be used to achieve the same result. Optionally, both collimators and/or the beam absorption particles may be adopted to achieve the desired x-ray emission in the region of interest.

The imaging methods disclosed herein can be used to locate and analyze a component in a sample, for example, to locate a diseased tissue area. A low resolution image therefore with low radiation level may be first obtained by using denser beam absorption particles for locating a region of interest where the target component is known to be present and/or to detect a target component. A high resolution image of the component can then be measured while limiting the radiation to the sample only to the location of the component to further derive detailed data for the component for analysis purposes.

The imaging methods disclosed herein can be used to track a component in a region of interest, for example, to scan for a presence of a contrast labeled component. A high resolution measurement of the region of interest can be obtained to detect and locate the component, especially when the component is small and/or is of low concentration. The component can be tracked by measuring with high resolution and/or with low resolution at the selected areas of the component, while measuring with low resolution at one or multiple areas or regions external to the component to locate, track, analyze, and/or monitor the component in the region of interest.

Additional examples of scatter removal are described further below with reference to FIG. 14.

Accessory Hardware

The x-ray systems disclosed herein can include a subject holder, either it is a table, or a microfluidic chip on a microfluidic chip holder, or a sample holder. Microfluidic chip and/or its holder may be transparent to the x-ray.

In some cases, A detector holder, such as in a C arm assembly, can be included with the x-ray source on one end and the detector on the opposite side of the subject, connected by an arced C arm. The detector may optionally be placed on a holder, supported and capable of moving independently from that of the holder for the subject, if any, and the positioner or holder of the x-ray source, if any.

Measurement and Image Database

Figure 8:
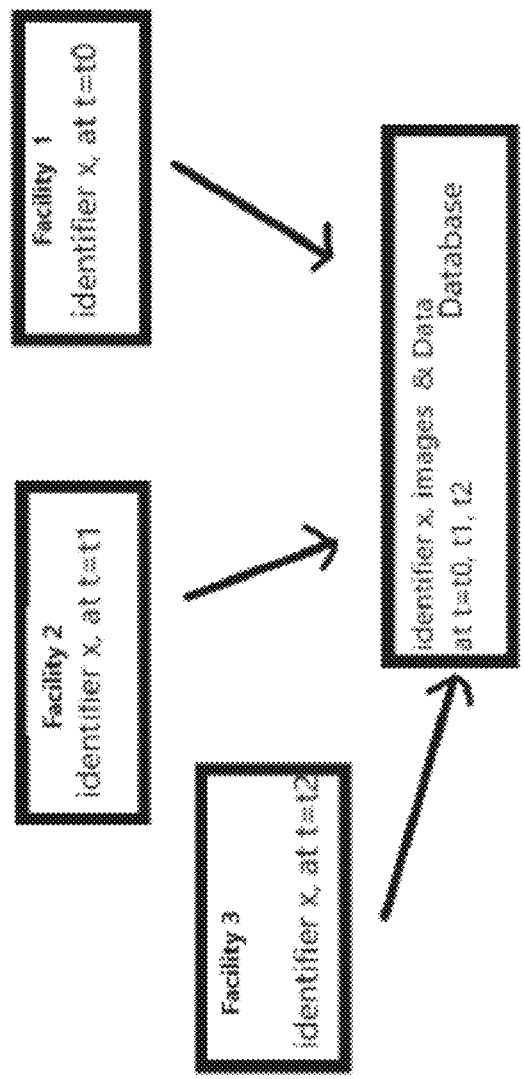
FIG. 8 illustrates schematically an example database include data for a same subject derived at various times from one or multiple x-ray imaging facilities.

The apparatuses disclosed herein can include a storage and/or a database as illustrated in FIG. 8, which stores images produced by the apparatuses disclosed herein and/or using the imaging methods disclosed herein. Each image or a dataset including images and/or data can be associated with a time label at time t=t0, t1, t2, the units of the time may be in seconds, or minutes, or hours, months or years, or any range from sub-seconds to years. Such time label can be associated with the time at which the image or data is acquired. Each image or dataset may or may not be acquired at the same facility. The time sensitive database may store images of the subject from one or more locations or facilities or different imaging sites, such as location 1 or 2 or 3 in FIG. 8, which may be linked with unstructured and structured data other than x-ray images relating to or of the subject with the same identifier or related identifier. Such data may be labeled with a time label at time t=t0, t1, t2 . . . . Such database may contain unstructured and structured data relating to a fact extracted from the data and/or the images and/or associated with a specific time. Such a system allows for tracking and monitoring of the images of the same region of interest of the subject overtime.

The apparatuses disclosed herein can generate time sensitive scatter removed x-ray images and their post-processed images, for example, after material decomposition. Such images can be labeled with a time specifier, generally the time of when the images are taken. Such images and related image set taken of a subject spatial and/or temporally may be labeled with a time stamp and/or a unique identifier to associate with a specific time for each image or image set, and an identifier associated with the subject. One or more facts may be extracted from such database, including time sensitive data.

The label and database system described above may incorporate any features of DICOM labels, including but not limited to a custom DICOM (Digital Imaging and Communications in Medicine) label. In some instances, such a label with specific time and an unique identifier may be made with a second ID, for example, a social security number of the subject (that is, a human patient), which is relatively permanent, or an identifier chosen by the subject. Such identifiers can be integrated with a random number to generate an encryption. The identifier may be one fact relating to the subject or one set of two or more facts relating to the subject. The identifier may be a second fact or a second key about the subject or a set of two or more facts or numbers assigned to or chosen by the subject, so that the first identifier or first set of identifiers may not be made public, or may be hidden when accessing the image or the image set of subject. The second key or second identifiers can include additional security measures of using a second identifier, which may enable retrieving of images and/or linking continuity of images of a particular subject without having to access private information. The second identifier may be a number or a method of access such as a physical key or an apparatus such as cell phone.

The database may not contain private information of the subject, but rather a key assigned to the subject or chosen by the subject or associated with the subject, such as, unique identifier for the subject, which may be social security number in the US. The subject and/or designated entities can have access to confirm or further validate the permission to access. Different combinations of second identifiers may be used together to increase the security of access. The database may include some or the complete private information relevant to the subject. In the case where there is no private information or partial private information, an encryption or access or tracking methods is used to ensure continuity of the image data and other data relating to the subject over time. One or more of the following methods may be used, such as random number mixing with a secondary key: a second access apparatus, remote and/or on-site; and/or a second access component from the same apparatus. The secondary key may be of long term and non-changing nature, such as a social security number. The second access apparatus may be a physical key or wireless or wired apparatus may be used on site. Alternatively or additionally, an apparatus can be used remotely if there is Internet or Intranet communication to the database.

The database system can therefore enable linking, retrieving, and/or storing image data continuously and/or intermittently over time for a subject. For example, to diagnose, treat, and/or post-therapeutic monitor a disease or health state of a patient, such a system allows for accessing and evaluating images of the patient over time.

The apparatuses disclosed herein can include one or more of the following software and/or algorithms for: correlating imaging signal on the front detector and rear detector on the same x-ray beam projected path: scatter removal image processing at single energy; and/or scatter removal with two or more energy levels.

Retrofit Kits

Retrofit kits can be used to modify an existing x-ray imaging system and/or to augment the systems disclosed herein. The kit can include any one or more hardware and/or software such as:

A software to integrate the control of hardware of different vendors of x-ray sources, detector or motion controllers for collimators and beam selectors.

An instruction manual for methods used in integrating existing hardware set and existing software set. Or an instruction manual for using existing methods including one or more hardware or software items, in addition or one of more hardware or software items provided in the retrofit offered.

Software as described above for image processing

At least one hardware beam absorber particle plate as described in FIG. 6 and FIG. 7 for retrofiting an existing radiography system with an x-ray source and a detector.

A beam absorbing collimator or a detector and a beam absorbing collimator as described in FIGS. 1-3, or beam absorbing particle plate such as 105 in FIG. 6 to retrofit an existing radiograph systems having an x-ray source and a detector. Such retrofit systems may also include software for image processing measured data for scatter removal. Integrating hardware can be included for integrating hardware offered in the retrofit kits such as x-ray source and the detector or detector assembly to existing hardware, such as a C-arm or radiology suite for positioning.

The hardware and software described herein may be used or adapted for measurements in one or more of the following modalities and methods: K-edge imaging and dual and multiple energy (alternatively called spectral imaging), flow dynamic, fluid related, flow direction, dynamic movement, characteristics of temporal markers, anatomical markers, ghost imaging, interferometry, phase contrast, dark field, x-ray diffraction, integration with x-ray fluorescence, multiple photon x-ray, x-ray scatter, x-ray spectroscopy methods, and/or all x-ray detectable contrast agents and energy apparatus induced measurement and quantification.

At least one of the hardware and software items and method used in a system as described herein, for example, a detector, a beam particle absorber, beam selector, a collimator, software for imaging processing.

A viewing or display software which includes the capability to display for the application needed for the user, such as for orthopedic imaging, breast, lung, any in vivo imaging display or in vitro or ex vivo, which displays the density information as well as thickness or material decomposition and other quantifiable parameters measured. The viewer can record and/or display temporal information, which may include tracking of components, identification of a subject, or dynamic characteristics, of components in the region of interest, fluidic dynamic and flow direction information in the region of interest based on x-ray imaging or x-ray imaging combined with other imaging modalities, such as MRI, PET, SPECT or optical measurements, and/or other energy or electro or chemistry based measurements.

A data analysis software for a user, which can display density measurement and quantitative analysis information.

Software for data output used for quantitative point, small 2D region, 1D, 3D-6D multiple dimension imaging analysis, single energy, dual energy and multiple energy material decomposition analysis, K-edge measurement analysis, phase contrast imaging analysis, coherent and in coherent and partially coherent or incoherent x-ray imaging, and/or other quantitative analysis task including determining atomic number, characteristics of component, or subjects, identification of a subject, or component in the region of interest, for data output used for deep machine learning, data output needed for multiple dimensional tomography, data output needed for integration with other structured and unstructured data types from other sources via internet and intranet and in the same computer including measurement data of other imaging modalities and analysis methods. Integration can also include simulated and measured properties, facts derived from unstructured data and/or structured data based on one or more data matrix for one or more components, and/or subjects and similar type of components and subjects.

Software for integration with other structured and/or unstructured document or facts derived from such documents for the same component, or same subject or same region of interest or same type of samples for quantitative analysis and relevant display.

Transferring the image, unstructured and/or structured documents based on the measurements and quantified data and analysis results between apparatuses and over the internet for the analysis and measured data of the same sample, tracking, extracted measurements at certain frequency and other time relevant parameters (seismocardiographic (SCG) signal features), gated movement monitoring such as measurements based on ECG gated cardiac movement, and/or fact derivation (diagnosis and behavior characterization) from one or more samples. For example, the same patient with measurements of various modalities, and/or data from various patients to derive one or more facts or to remotely visualize and monitor subjects can be analyzed.

Chemistry to use for quantification and visualization of contrast agents, regions identifiable by x-ray imaging such as using algorithms developed for CT, including single energy, dual energy, spectral CT, PET, SPET, MRI, and/or magnetic particle based imaging and photoacoustic and optical imaging and spectroscopy.

Algorithms, hardware and chemistry to carry out tasks including quantify, identify, differentiate and characterize energy or chemically, temperature modulated component in the region of interest. Chemically modulation can refer to pH, or enzymatic functions, such as protease or catalytic function of enzymes to break down and form certain protein molecules which in turn having high affinity epitopes which can bind to certain contrast agents conjugated ligands. The tasks can be time sensitive and/or recurrent, include those applicable to CT and potentially CT, SPECT, PET, MRI, optical and acoustical methods if limitation of each modalities in time and radiation level considerations is overcome. For example, tracking of endogenous molecules or ions based contrast agents, or tracking dynamic flow and movement of one or more component and kinetics of molecular interaction at short time difference down to ultrafast x-ray or ultrafast laser can allow, for example, measurements in pico or femtosecond, so long as permitted by the design or the speed of the detector used, such as photocounting detector, PMT and photodiodes and 1D or 2D detectors sensitive to x-ray or x-ray scintillated visible light. Quantification and analysis can include using deep machine learning artificial intelligence, especially those applicable for CT, or PET or MRI or Optical Methods.

Adapt the current methods for x-ray microscopy with visible light optics for quantitative measurements at very high resolution, down to the nanometer range, such as by adding a scintillator screen to convert x-ray to visible light. Conventional x-ray optics and visible light optics known to x-ray microscopy can also optionally be added to further increase performance and resolution of sample measurement.

Software with cybersecurity features for store, use, transfer of the measured data.

Portable hardware assembly, include a portable x-ray source, shields, cases and accessories to carry or hardware to move or cases to store.

X-ray Source of one or more energy levels.

Synchrotron, synchrotron like, or linear accelerator like x-ray source.

Cold cathode x-ray source of one or more energy levels.

Figure 15A:
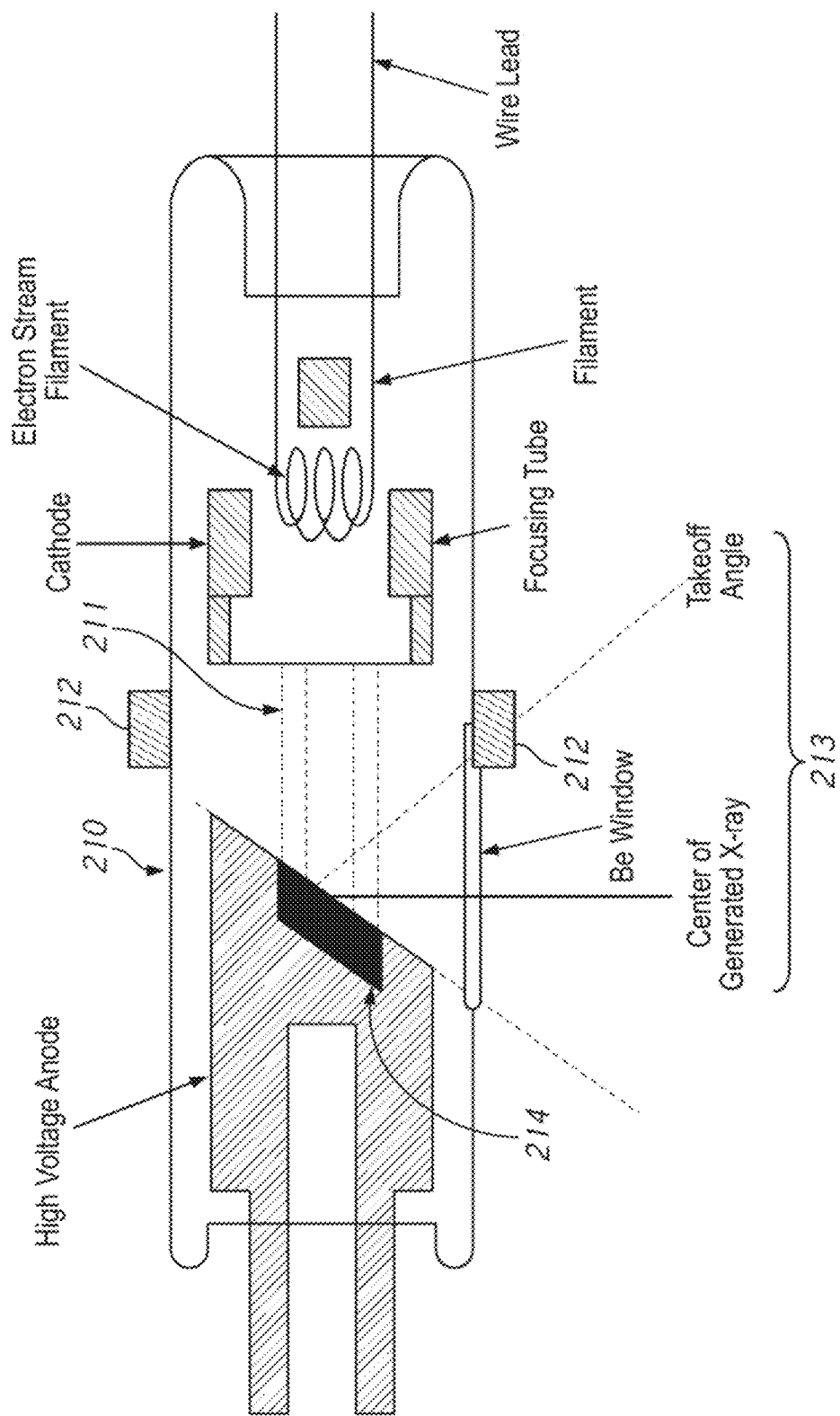
FIG. 15A illustrates an example x-ray beam deflection using magnetic plates.

X-ray source including type of cold cathode, nanotube or nanowire based which may have built-in electron beam deflector using, for example, magnetic mechanisms such as magnetic plate or solenoid coil based deflection apparatus as illustrated in FIG. 15A. Such a magnetic mechanism is not limited in steering nanotube based x-ray source, but rather may be useful for steering of all electron beams in various type of x-ray source to generate x-ray radiation, or nanotube sources, where various region of the nanotube may be activated or deactivated for generating electron beams or steering electron beams for generating x-ray beams at different spatial locations. For example, such type of nanotube source emitting location may be steered or moved by deactivate or activate regions of field emitter regions or each field emitters for generation of electron beams. The movement of x-ray emitting position or x-ray source having multiple x-ray emitting positions such as pixelated x-ray source, may be used in multiple dimension x-ray imaging and 3D imaging described in the present disclosure.

Light-based X-ray sources including types of PMT based cathode, cold cathode, some of which has built-in light beam position steering mechanisms, for example, light beam steering or photoelectron multiplier tube position moving mechanisms.

Time of flight x-ray source including the type with cold cathode, and carbon nanotubes, which have built-in electron beam position steering mechanisms, for example, light beam steering or photoelectron multiplier tube position moving mechanisms.

Linear accelerated x-ray source, different radiation path each time, with reduced radiation on the target for each individual region.

Metal liquid anode x-ray source, including the type with cold cathodes.

Interpolation of scatter x-ray from the measured data.

Interpolation of scatter x-ray for x-ray thin beam illumination method.

Interpolation of scatter x-ray from the measured data including linear, cubic, cosine, and/or radial grid.

Structured illumination with varied spatial density distribution of x-ray thin beams of various dimensions in sub nm, or nm or um or mm or cm range.

Structured illumination with each beam size at measurements done each time may be varied from one or more beams distributed differently spatially.

Hardware items used for structured illumination method disclosed herein.

Software, algorithms for deducing primary x-ray, varied interpolation methods in the structured illumination method.

Hardware and methods in obtaining scatter removed image and/or material decomposition in a single shot with one detector, including using one beam absorber collimator with distributed transmissive holes, or a stack of such beam absorber collimators or beam absorbing particle plates 105 as in FIG. 6 which may be placed between the x-ray source and the subject or between the detector and the subject, including one or more following apparatus: multiples of beam absorber particles, as illustrated in FIG. 6, dispersed in distance from each other, each absorber may be in varied shapes and volumes or similar to each other, and may have one or more holes or varying thickness or absorbing properties to allow x-ray to pass through at certain regions. Such beam absorber, when oriented certain way, may block x-ray completely; when oriented another way, (for example, when moved angularly,) may allow transmission, levels of transmission varying from 0-100%. The location of such a apparatus in at least one axis in space may be moved so that the locations of where primary x-rays are blocked are different when multiple illumination or imaging take place.

Hardware and methods in obtaining scatter removed image and/or material decomposition in a two images with one detector, including using one beam absorber collimator with distributed transmissive holes, or a stack of such beam absorber collimators or beam absorbing particle plates 105 as in FIG. 6, which may be placed between the x-ray source and the subject or between the detector and the subject, including one or more following apparatus: multiples of beam absorber particles, as illustrated in FIG. 6, dispersed in distance from each other, each absorber may be in varied shapes and volumes or similar to each other, and may have one or more holes or varying thickness or absorbing properties to allow x-ray to pass through at certain regions. Such beam absorbers, when oriented certain way, may block x-ray completely; and when oriented another way, (for example, when moved angularly,) may allow transmission, levels of transmission varying from 0-100%. The location of such an apparatus in at least one axis in space may be moved so that the locations of where primary x-rays are blocked are different when multiple illumination or imaging take place. Each of the hardware can be used to derive high resolution scatter signals from the first image and a second high resolution image may be taken to give rise to a high resolution primary image after subtracting high resolution scatter image from the first image.

The move or rotation may be mechanical or energy based to move the entire particle apparatus, when the relative position between micro particles can be fixed.

The relative position of each unit of micro particles may be moved in at least one dimensions by mechanical methods such as an actuator, for example, in a MEM-like apparatus or energy based such as ultrasound or laser or electrical methods such as voltage or magnetic force.

The medium between the beam absorption particles can be liquid or air or translucent material, such as polymer, berullium, structured for instance, like a plate.

Liquid crystal apparatus, each liquid crystal cell with an x-ray absorber, which can be modulated in terms of location.

Units of Crystal, which can be modulated to allow x-ray to transmit through or be opaque to x-ray.

Each particle may block x-ray beam or prevent primary x-ray from reaching the detector, so that at least one pixel, or more pixel to be composed of entirely of scatter x-ray signals or light or electrical signals can result from scattered x-ray signals. Such a pixel may have a size as small as in the nm range or between 0.01 nm-10 mm range. X-ray signals can be scintillated and converted to visible light for imaging.

Scatter measurement, interpolated image, and primary images may be used for derivation of high resolution scatter image and therefore high resolution primary image of the same sample if a second image is taken without the beam absorbing particle in place. In another words, such a beam selector is moved out of the way completely.

In applications where the same images needed to be taken of a sample of the same region, the beam absorption particle can be slighted shifted to a different position and the blocked primary image in the first image may be derived from extracted data of one or more images taken after of the same region of interest in a sample.

The 2D x-ray imaging system or components thereof (hardware and/or software) or a method of using the same, or a retrofit kit described above, may be provided using a pay per use method. For example, a use may be defined as one or more of the following activities: taking one image or more images of one patient, or one subject, or output of one or more images derived from measured x-ray images, or extracting one or more facts from image analysis results or providing data for one or more diagnostic or therapeutic procedures.

Alternatively, charges may be calculated as a fraction of the retail price of an equivalent system. The 2D x-ray imaging system or components thereof (hardware and/or software) or a method of using the same, or a retrofit kit described above may be provided free of charge.

Examples of Combining 2D X-Ray Radiography with X-Ray Microscopy and/or Spectral x-Ray Measurements and/or Spectral x-Ray Absorptiometry and/or Time Sensitive and/or High Spatial Resolution and/or High Spectral Resolution Detectors—Hybrid Quantitative X-ray Systems In the present disclosure, the scatter removal methods can aid in combining microscopy and/or absorptiometry with x-ray radiography technology for producing 3D images and/or quantitative analysis.

Conventionally, multiple images typically need to be taken of the entire subject in 180° to reconstruct a 3D image of the subject using 3D x-ray microscopy. Because of the need to rotate and the hardware required to achieve a high resolution and quantitative measurement, the 3D CT and 3D Microscopy apparatuses are not only time consuming but also bulky. 3D microscopy systems are generally not suitable for portability, especially outside of hospital, research labs, surgical center or mobile diagnostics and surgical stations. The subject would receive a relatively high dosage of radiation in a rotational CT based system.

Multiple beam 2D imaging can expand the imaging field of view and speed to cover a larger area, but rotational motions center around the subject or rotation of the subject are still needed to achieve 3D imaging in x-ray microscopy. Inverse geometry CT tomography-based techniques require the use of a two-dimensional (2D) collimator with holes combined with a scanning x-ray source that emits through these holes before passing through the subject. The resultant 3D images in the third axis may not have a high enough resolution and cannot offer quantitative information including precise location information, as well as other quantitative information generally provided by a 3D CT scanner.

Enhanced signal-to-noise ratios (SNR) may be achieved when probing a subject if the signals of multiple x-ray beams are measured recorded individually. When the subject position is then systematically scanned (for example, in x- and y-coordinates) while being exposed to multiple parallel x-ray beams, a systematic "map" of the properties at the various coordinates where the x-ray beams interact with the subject can be created much faster than when using a single x-ray probe to scan the same area. Faster tomographic and spectral measurement analysis by moving in 6 Dimensions the relative position of x-ray emitting position to the subject and/or scanning the subject according to various protocols can be achieved using radiated primary x-ray beams in cone beam shape, but each beam of the primary x-ray beam can have a spatial gap from its adjacent primary beams. The gap can be one pixel or more as sensed on the detector. Alternatively, parallelized x-ray beams can be generated to illuminate the subject However, in the aforementioned multiple beam systems, there are some limitation. A pre-existing beam mask needs to be placed in the beam paths from the x-ray source before the x-ray reaches the subject and the detector. As rotational or three axis methods are still used for 3D imaging, usage and sample repertoire utilizing this multiple beam method are limited in 3D imaging. The subject needs to be thin to meet the required x-ray microscopy sample dimensions in order for this multiple beam method to work. Furthermore, such multiple beam methods are not combined with a full field x-ray imaging based on 2D detectors upstream of x-ray microscopy detectors to locate a region of interest for more detailed, higher resolution microscopy imaging.

Optionally, detectors which have faster frame rate and higher resolution than the full field x-ray detectors can be placed downstream from the full field x-ray detectors, such as photon counting detectors and PMTs are used to image the selected of the region of interest, without using x-ray optics used a x-ray microscope.

X-ray spectral absorptiometry or x-ray spectral measurements may also be combined with x-ray radiography apparatuses for both 2D and 3D imaging and high spectral resolution in selected regions of interest. In general, x-ray absorptiometry is limited to the densitometry of bone using a dual energy system. Conventionally, x-ray absorptiometry is done with a linear scanner to scan across the spine in order to achieve quantification of bone density based on absorption of x-ray by bone tissues being different from that of the soft tissue. Such system has a limited application and is time consuming and limited in achievable resolution. In vivo studies using dual energy absorptiometry for analysis of different components in a subject are still not widely adopted due to inherent hardware complexity, time required, and limited resolution.

In addition, conventional x-ray radiography may not be readily combined with x-ray microscopy or absorptiometry due to limitations on the x-ray source, as the requirements for each application are different. Additionally, interference of scatter can affect forming quantifiable primary x-ray image for quantitative analysis in the full field x-ray imaging. Further, rotational requirements for multiple dimensional measurement on both x-ray full field imaging as well as x-ray microscopy systems can limit practicality of combining both to achieve the large dimension quantitative measurements as well as high resolution measurement achieved in x-ray microcopy. For example, in in vivo measurements, x-ray microscopy or high resolution spectral measurement or high resolution photodiode, point, 1D and small 2D array detectors may reveal single cell or molecules, rare cell or small cluster of cells and molecule related events and morphology and presence, while a full field x-ray may cover larger dimension quantitative measurements and imaging for colocation and sample analysis.

Using material decomposition and imaging method disclosed herein, a region of interest of a subject the x-ray radiography may be selected as in 4s in FIG. 1A for more detailed spectral measurements, absorptiometry and/or microscopy imaging and analysis and/or faster frame rate imaging. The present disclosure provides an x-ray imaging, measurement, and quantitative analysis system having one or more x-ray beams to interrogate a selected region of interest 4s. The functionality of the system can include a 2D dual, or spectral imaging, 3D full field x-ray imaging, 3D full field and/or single, dual energy or multiple energy imaging, non-rotational 2D and 3D x-ray microscopy, and/or point, 1D, 2D or 3D spectral absorptiometry or spectral measurements of selected region of interest 4s, for instance, a user select or a digital program 13 in the processor selects 4s based on one or more criteria as the result of full field imaging and/or spectral imaging in 2D or multiple dimension or 3D dimensions. The system may optionally provide scatter removal in full field view of region of interest 4 or on selected region of interest 4s using one detector and/or multiple x-ray beam configuration with either 2D x-ray microscopy or 3D x-ray microscopy or spectral absorptiometry or spectral x-ray measurements. Alternatively, scatter removal may use dual detector with beam selector collimator in between in the microscopy and 3D microscopy assembly. The system can be considered a hybrid system of full field imaging combined with high spectral resolution spectral measurements and/or with detailed high spatial resolution measurements or imaging by x-ray microscopy, and/or high spatial resolution detectors and/or high speed spectral measurements and multiple dimensional and 3D measurements and imaging in point, 1D-3D and 4D dimensions of selected region of interest 4s, target and component.

Scatter removal can be achieved by aforementioned hardware and methods as described in the present disclosure in the hybrid systems disclosed herein.

The region of interest 4 may have one or more components. Each component may be of various compositions, or composite materials, or inhomogeneous materials, or homogeneous materials and/or interface region of two or more materials or materials of varying atomic z numbers or x-ray measurable properties.

Material decomposition method disclosed herein may be used for determining density, thickness, composition, x-ray measurable properties of each component in the region of interest. Alternatively, basis function spectral x-ray imaging method, and other methods and algorithms used in spectral CT and dual or multiple, or spectral x-ray imaging, or those of prior art may also be used.

Placement of Hardware in Hybrid Systems

The hardware may be static in position, placed in an angle such that all x-ray measurement modules can access the subject, while still maintaining the ability to locate the region of interest and interrogate a component or components from one or more sources. One or more detectors or associated hardware for measurements of selected region of interest in the hybrid systems may be placed downstream from the full field flat panel detector, opposite to the subject.

The full field detector may be placed closest to the subject. Other hardware and other detection module for in the hybrid system may also be placed at an angle relative to the flat panel detector for full field imaging, using the same x-ray source or a different x-ray source on the opposite side of the subject.

Alternatively, flat panel detector may be furthest to the other detection modules.

The spectral absorptiometry may be placed downstream from the flat panel x-ray detector, or upstream between the flat panel x-ray detector and its relevant hardware and the subject. Alternatively, except the flat panel detector, all hardware can be moved in and out of the place between x-ray source and subject, or subject and the flat panel detector, or in place of the flat panel detector after the flat panel has shifted to a different location or downstream from the flat panel detector.

Figure 36A:
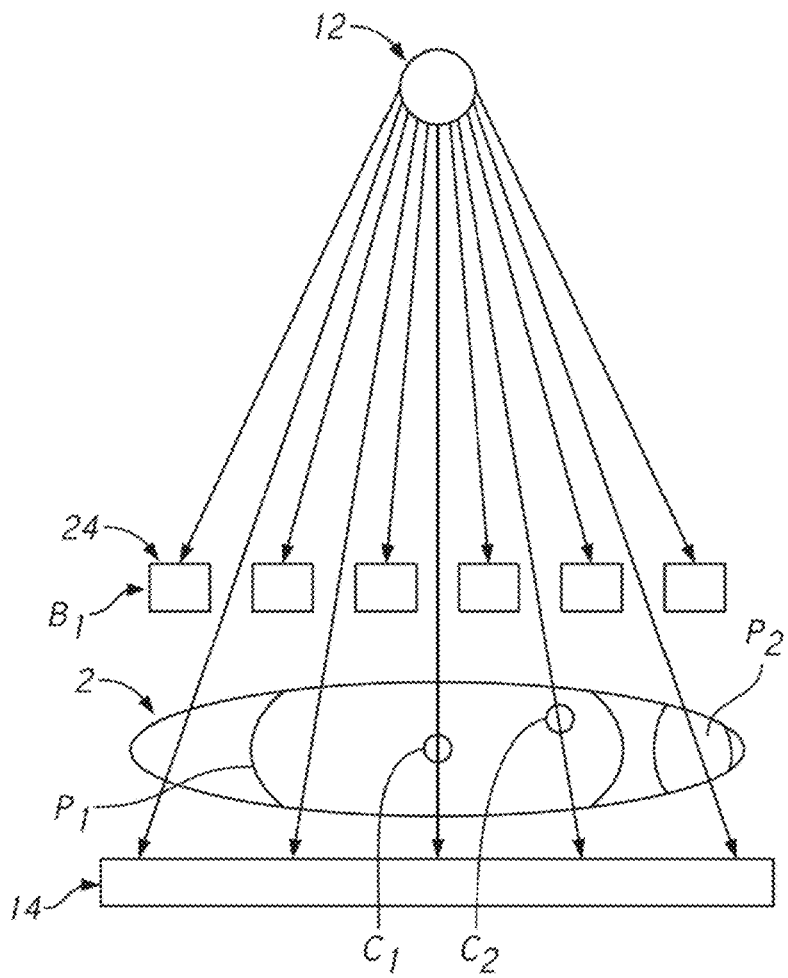
FIGS. 36A and 36B illustrate a beam absorbing plate as in FIG. 7 being placed upstream and downstream of an x-ray subject respectively. Such a configuration may be used as to generate fast low resolution primary x-ray measurements and imaging, when combined with single energy and spectral measurements and imaging, may be used in a real time densitometer or tracking system. Such a plate may be move in the x y plane slightly or static in tomographic measurement when it is used as a scatter removed primary x-ray measurement and imaging device. The missing data due to the blockage of primary x-rays may be sufficiently small to be relevant in a tomographic application. In case of high spatial resolution complete 3D imaging is required, either x-ray source may be moved relative to the subject or the plate 24, far enough from its original position that the data missing can be captured by subsequent measurements. Optionally, the plate may be moved in 3D space so that the missing data may be captured in subsequent measurements.
Figure 36B:
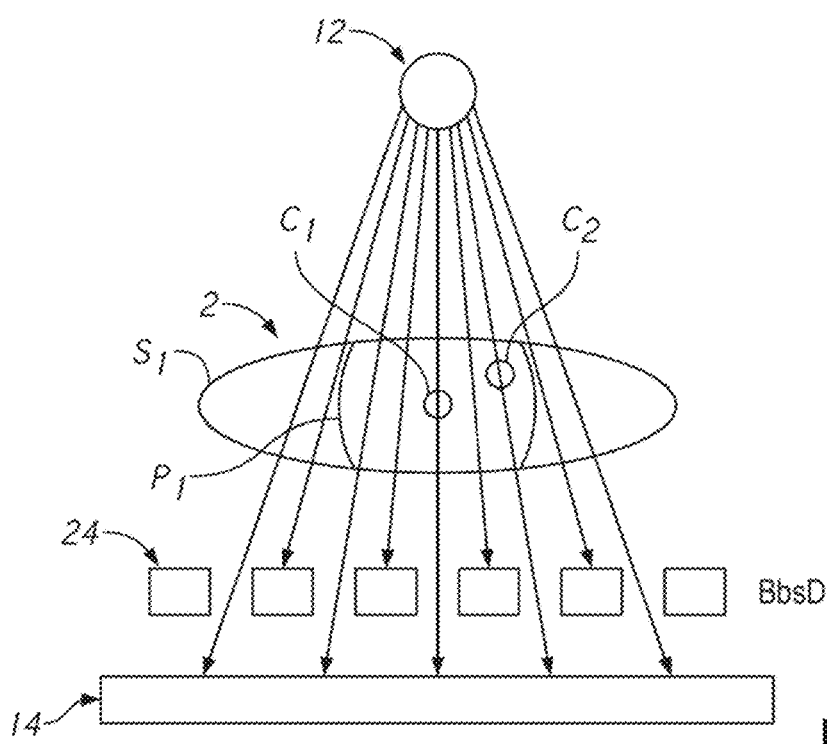

The hardware required for single or spectral x-ray microscopy can include the condenser. If the same or additional x-ray source beam apertures are used, they may be placed in between the x-ray source and the subject. The subject and detector or detector modules including the photon counter and silicon shift detector and energy sensitive detector may be placed either upstream or downstream of the flat panel detector, such as shown in FIGS. 36a-B. In some cases, the hybrid systems may be diagonal from each other, with the subject in the middle.

As illustrated in FIGS. 12B and 12C, 2D or 3D full field x-ray imaging can be combined with faster frame rate and/or higher spectral resolution and/or higher number of energy sensitive detectors or detector cells, 320, which may be placed downstream of the full field x-ray imaging detector 14, away from the subject or between the subject and the full field x-ray imaging detector 14. For example, a fast frame rate2D detector, which is smaller than the full field x-ray imaging detector 14, or point detector or 1D linear array may be used to capture additional information with higher spatial resolution, and/or higher spectral resolution and/or higher frame rate for selected regions or selected components or selected targets to be further quantitatively analyzed.

Such hybrid system detectors 3 may be moved in 6D space mechanically, or preferably, for example, moved by a mover in the x and y plane parallel to the detector 14 in order to dynamically position itself spatially to measure x-ray projected through selected region(s) 4s on the region of interest.

Similarly, hardware relating to the detection module of the spectral measurements or spectral absorptiometry, or objective and detectors in x microscopy may be placed either downstream from the full field detector opposite the subject and x-ray source or in between the subject and the full field x-ray detector, the condenser and beam aperture, or illumination module of the x-ray microscopy system may be placed between subject and the x-ray source.

Figure 35A:
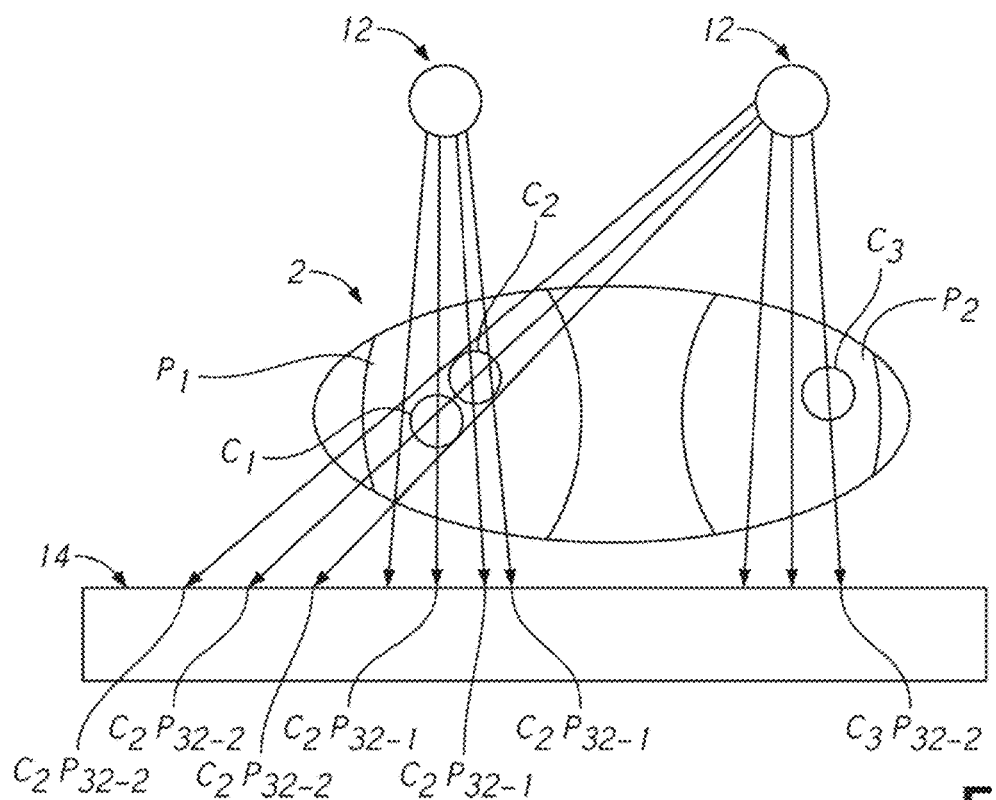
FIGS. 35A and 35B illustrate an example of regions of interest or components in an x-ray subject being illuminated by different x-ray sources of various x-ray energies, where regions of interest or components in an x-ray subject can be illuminated at the same time or at different time frame by at least two x-ray sources, each capable of emitting x-rays of different energies. X-ray signals coming out of the region of interest may be projected to one or more detectors.

Or such hardware, for example, of 11, 15 may be moved by mover in place of the full field x-ray detector as the full field x-ray detector 14 may be moved out of the line of sight of x-ray beam by a mover. Optionally hybrid imaging hardware submodules, for example, 11 or 15 for detailed analysis of selected region of interest 4s may be placed at angle from the full field detector 14, with the same source 12, for example, if the x-ray beam from 12 is steered by an x-ray optics or related assembly to illuminate 4s from a different angle than the original path or using a different x-ray source Multiple Energy X-ray Source Placement The x-ray system of the present disclosure can have more than one x-ray source, for example, to illuminate same region of interest RI from different spatial locations on the opposite side of the detector 14 relative to the subject 2. For example as illustrated in FIG. 35A and regions of the detector can be read corresponding to each of the x-ray sources. Each source may generate one or more x-ray energies or wavelength different from the other sources. Both 2D and 3D images may be generated based measurements generated by each x-ray source. This can increase the speed of measurements for multiple energy applications.

Figure 35B:
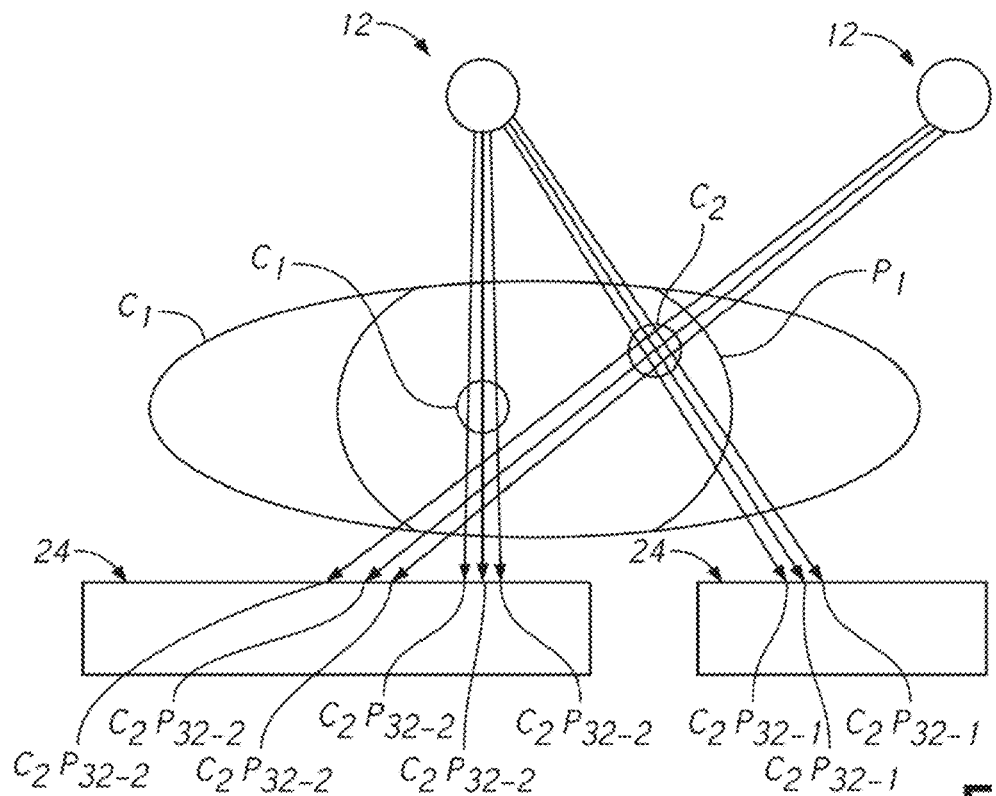

In addition, more detector may be used as illustrated in FIG. 35B, so that two or more detectors 24 collects x-ray output from the region of the interest RI from corresponding x-ray source.

X-ray Source

Any suitable x-ray tube may be used for x-ray full field imaging using flat panel x-ray detector, 2D detector, 1D detector, and photodiode and photon counters, or x-ray microscope or x-ray spectral measurements and spectral absorptiometry. X-ray tubes of polychromatic nature may be used. When x-ray absorptiometry is performed with a polychromatic source and the selected region for detailed analysis in the hybrid system in region of interest is determined from results of the full field x-ray imaging, or user or computer input based on one or a set of criteria. The SNR may be compared to full field x-ray image for various wavelength. The polychromatic x-ray source can be converted to a monochromatic source, such as using an x-ray monochromator or an x-ray wavelength or energy filter or x-ray optic, such as mirrors made of polygraphite. A microsource, a synchrotron source or synchrotron-like or linear accelerator based or similar type of sources, or a laser Compton scatter source may be used. An x-ray tube used with a mirror, for example, a pyrolytic graphite mirror, can include an exit slit defining the Bragg angle for the desired energy and serving as a fan beam source. Nanotube or nanowire based x-ray sources may also be used.

A source producing an array of x-ray micro-sources can be imaged onto the subject for structured illumination such as disclosed herein. A crystal or MEM apparatus, a refractive grating, or an x-ray optics capable of dividing up the original x-ray beam spatially, may generate spatially separated, sparsely distributed multiple thin beams. Alternatively, a spinning disk with holes to selectively transmit the x-ray beam at selected area may serve as the microbeams generator. Final image of the subject in the entire region of interest may be stitched together in mosaic fashion from the images generated by the thin beams if they are spatially arranged in a way that allows for stitching.

The x-ray system disclosed herein can perform spatially resolved x-ray transmission analysis. When an incident x-ray beam is directed upon a subject, the x-ray can be transmitted along the projected path. The incident x-ray beam can be a cone beam or fan beam or point beam or can include an array of x-ray thin beams. The transmitted x-ray can be measured with a spatially resolving x-ray detector.

The x-ray system disclosed herein can also perform a phase contrast analysis. When an incident x-ray beam is split into two and directed upon a subject, the x-ray can be transmitted along the project path and combined downstream to form interference patterns on the detector.

The x-ray system disclosed herein can include hardware and software to perform phase contrast information, or spatially resolved x-ray diffraction analysis. An incident x-ray beam can be directed upon a subject to generate diffracted x-rays. The incident x-ray beam can be a thin beam or can include an array of x-ray thin beams. Diffracted x-rays and/or interferogram can be measured with a spatially resolving x-ray detector.

The x-ray system disclosed herein can perform spatially resolved x-ray fluorescence analysis. An x-ray excitation beam can be directed upon a subject to generate fluorescent x-rays, wherein the x-ray excitation beam includes a planar array of x-ray micro-beams. The individual x-ray microbeams can each have a diameter smaller than low double-digit microns. The fluorescent x-rays can be imaged with an x-ray imaging system that includes an x-ray imaging optical system and an energy resolving and spatially resolving x-ray detector. The x-ray imaging optical system can collect fluorescent x-rays generated when a subject is illuminated by the x-ray excitation beam positioned such that its subject plane is coplanar with the plane of the planar array of microbeams within the depth of field of the x-ray imaging optical system. The energy dispersive and spatially resolving x-ray detector can be positioned at the image plane of the x-ray optical imaging system.

An x-ray source in the disclosed system may illuminate a "beam splitting" grating that produces a set of self-replicating beams in space, called a "Talbot Interference pattern," that may be used to illuminate the subject. Each of the one or more beams may have a high resolution, for example, having a diameter of about low double-digit microns or less, at the surface of the subject. The one or more thin-beams projecting generating an image of the subject can have high resolution in one dimension and/or two dimensions.

An x-ray optical assembly may be employed on the x-ray source side and/or on the x-ray microscope detector side. When an x-ray full field imaging detector is used with the microscopy method, the x-ray optics may preferably be implemented on the x-ray microscope detector side.

The optical assembly can include one or more optics in which at least a portion of the reflecting surface is paraboloidal or ellipsoidal. The optics may optionally be paraboloidal on its reflecting surface, followed by an ellipsoidal profile. The x-ray optical assembly may include a double paraboloid that includes a collimating lens or optic, and a focusing lens or optic.

The optical assembly can include one or more central beam stoppers to remove x-rays transmitted through the center of an axially symmetric optic. The optical assembly may include any suitable x-ray optical elements known in the art, for example, an interrogation system that utilizes a confocal optic. The optics can include an aperture element to remove x-rays from the beam path x-rays other than that of the primary x-ray (such as for a primary transmitted x-ray microscope configuration) transmitted through the sides of the optic: or x-rays unreflected but transmitted through the side of the optics in fluorescence, diffraction, and/or interferometer configurations. The x-ray optical assembly may include one or more zone plates.

The x-ray optics can have a wider field of view compared to a single beam version to accommodate a greater input view angle for accommodating the multiple x-ray input beams field of view.

Spectral Measurement or Absorptiometry and or Microscopy Configuration Examples

Figure 12A:
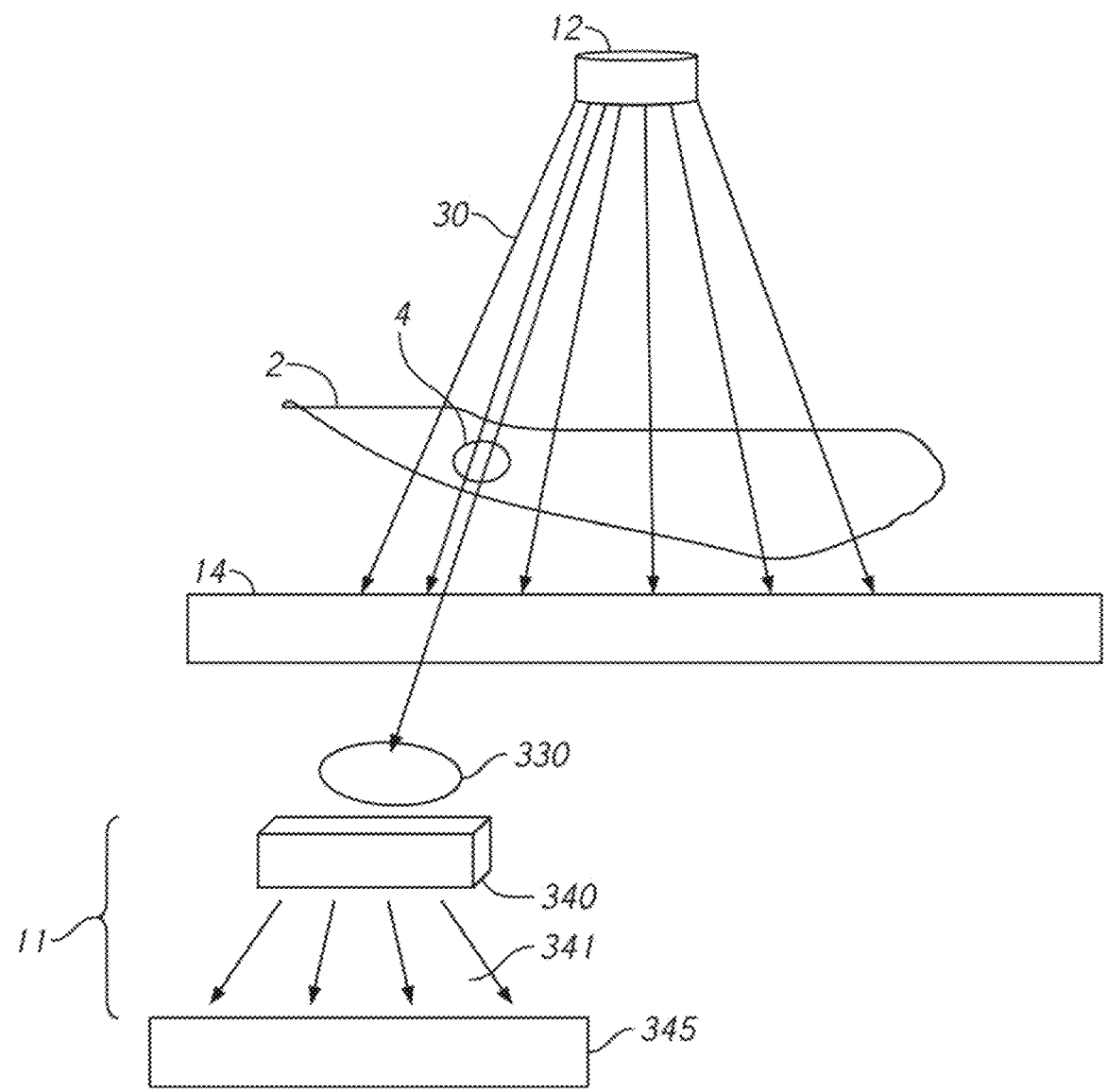
FIG. 12A illustrates a schematic diagram of a hybrid system of x-ray spectral measurements and spectral absorptiometry of selected region of interest and full field x-ray imaging.
Figure 12B:
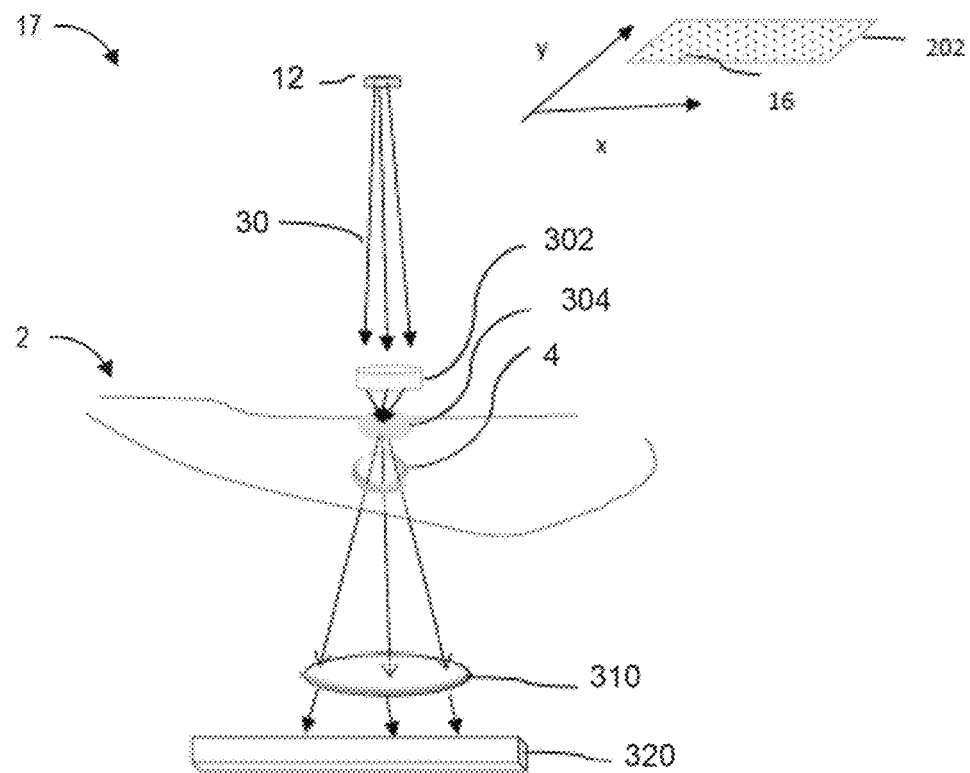
Figure 13A:
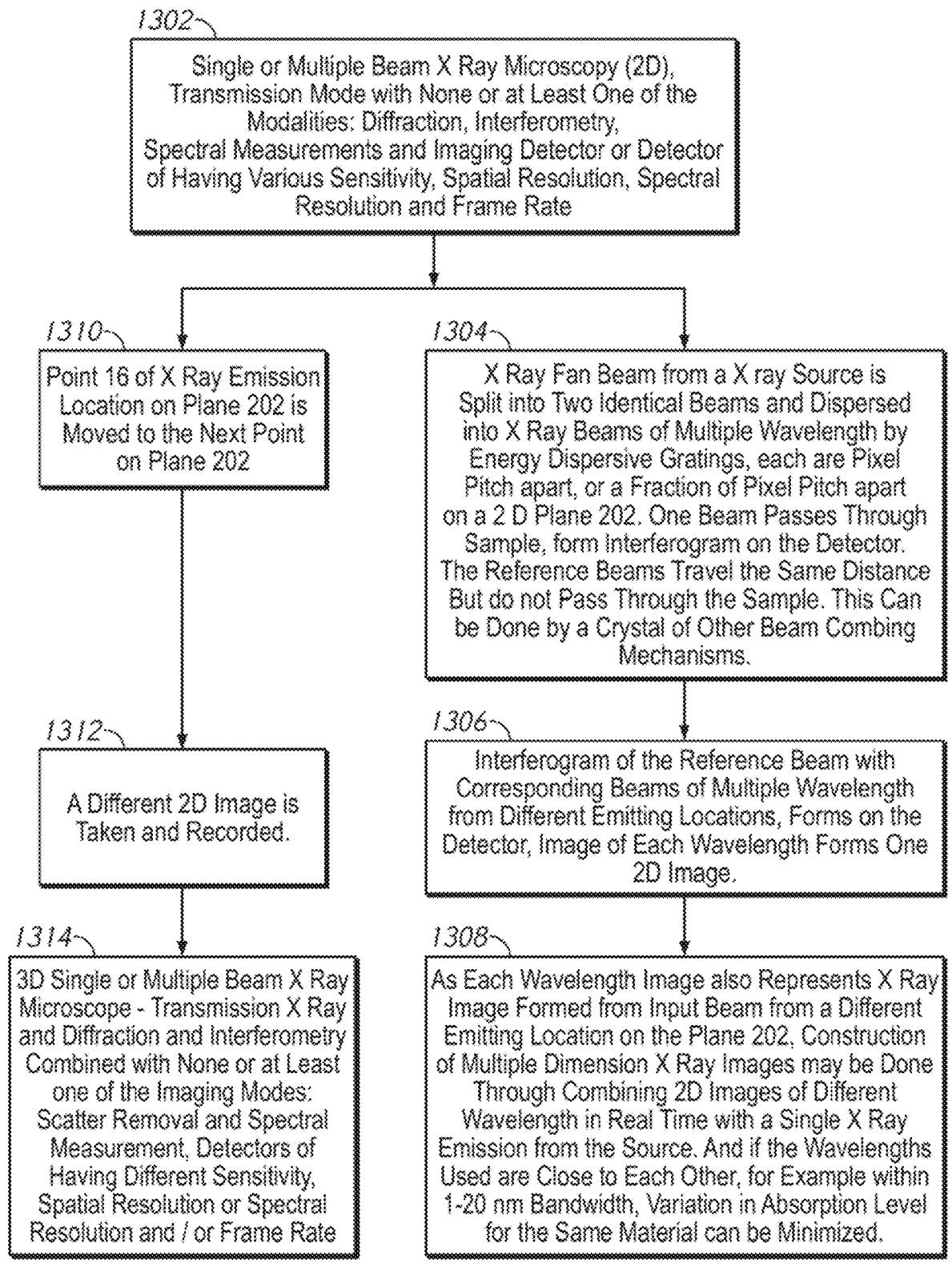
FIG. 13A illustrates an example flow diagram of 3D microscopy imaging.
Figure 13B:
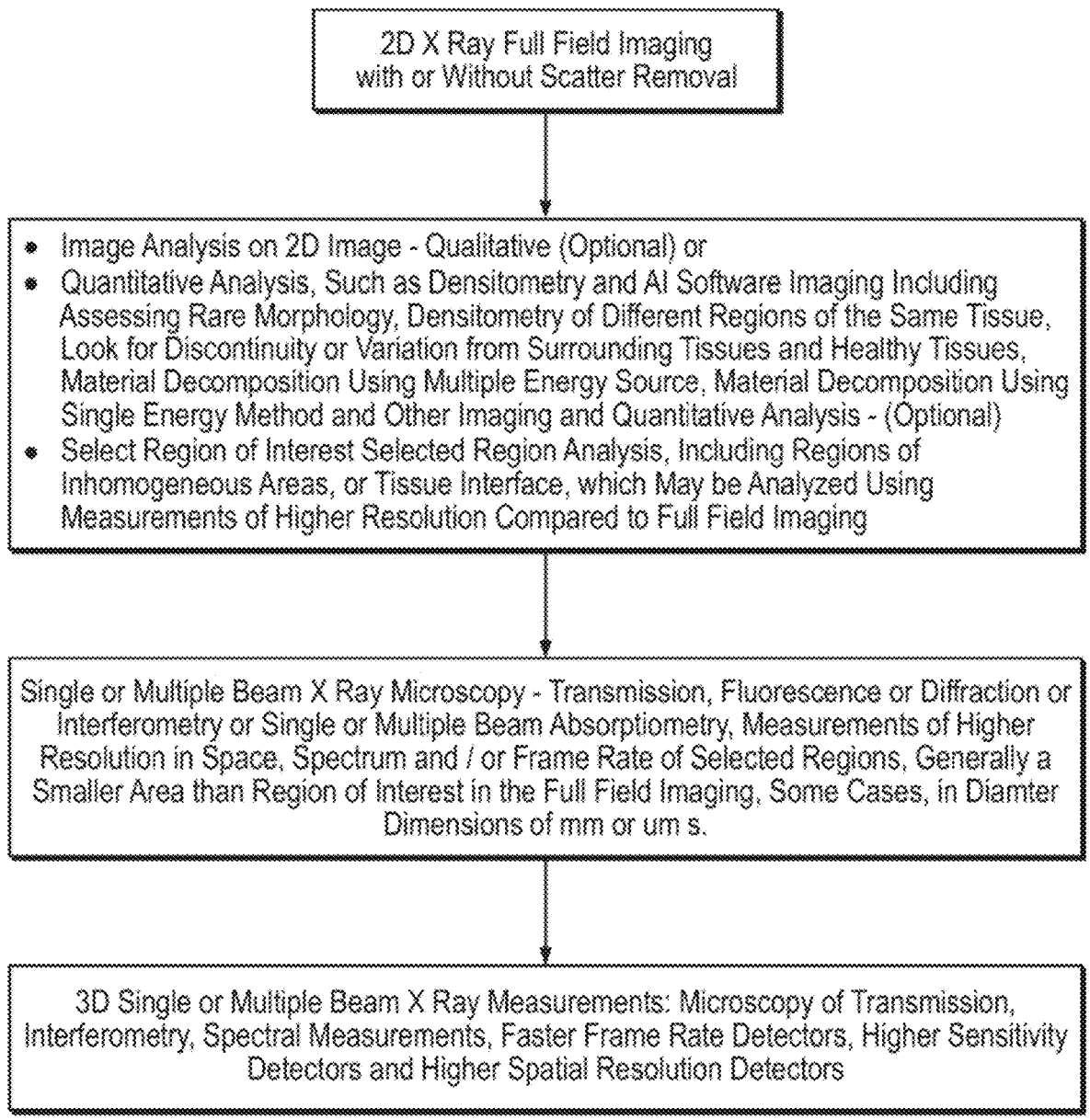
FIG. 13B illustrates an example flow diagram of 2D full field x-ray imaging combined with x-ray microscopy, absorptiometry, and/or spectral measurements.
Figure 13C:
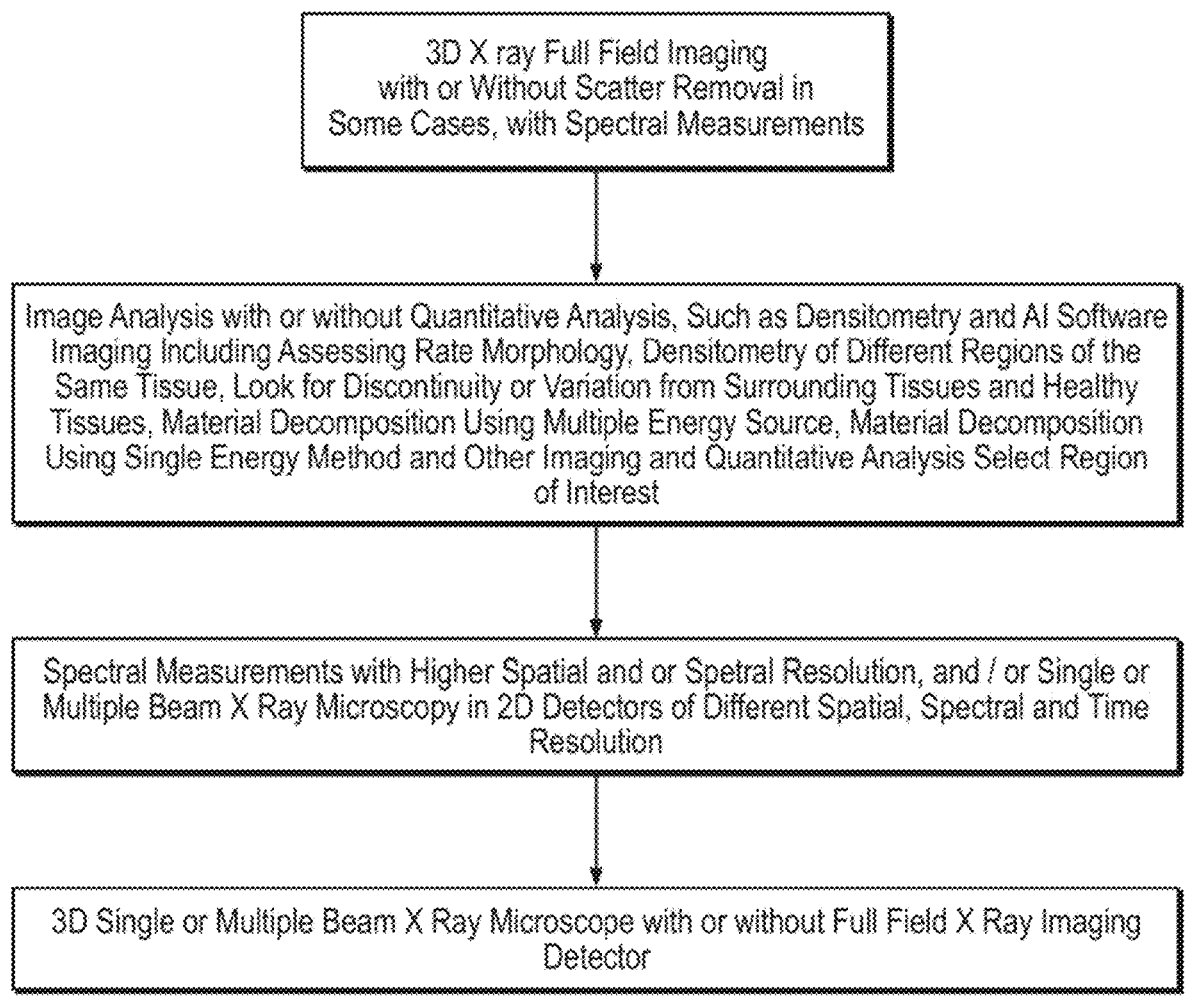
FIG. 13C illustrates an example flow diagram of 3D full field x-ray imaging combined with 2D and 3D x-ray microscopy, spectral measurements and/or absorptiometry.

FIGS. 12A-12C illustrate example combinations of full field x-ray imaging detector and spectral absorptiometry 11 (12A) or microscopy 17 (12B-12C). The full view x-ray imaging aspect of the x-ray systems in FIGS. 12A-12C can have any of the features of the x-ray apparatus 10 in FIGS. 1A and 1B. FIGS. 13A-C illustrate several examples of measurement and analysis methods based on hybrid configuration.

X-ray absorptiometry or x-ray spectral measurements uses dual multiple energy or wavelength, or broadband x-ray to perturb a subject including one or more components, analyze and identify materials and components based on x-ray absorption or attenuation or transmission characteristics and density characteristics. The technique measures perturbance of various x-ray energies or more specifically absorption of primary x-ray by the subject using, for example, energy sensitive detectors, photon counting detectors, PMT or an x-ray optics assembly combining energy dispersive grating and spatially sensitive detectors or silicon drift detectors. This technique can be combined with 3D imaging described herein to provide 3D quantitative analysis of materials and localization and positioning of such materials in the 3D and 6D space and in time relative to the subject or other materials and components in the subject. Rather than a larger area of imaging as in 2D spectral x-ray imaging or 3D spectral x-ray imaging, or spectral x-ray tomography where a number of spectrum are typically selected, such as the imaging energy for bone and imaging energy for soft tissue and some k-edge energy levels, in spectral absorptiometry, a plurality of different discrete energy levels can continuously sweep through or a broadband x-ray spectrum can be used to illuminate the subject. Photon counters or photon detectors or 1 D, or 2D detectors and sometimes can be combined with energy dispersive gratings. A multiple channel absorptiometry or a scanning x-ray absorptiometry can be used to achieve wider field of view and at the same time, maintain higher sensitivity. Spectral resolution achieved can be as high as 0.01 nm.

A multiple channel absorptiometry, or scanning spectral x-ray measurements or a scanning x-ray absorptiometry can be used to achieve wider field of view and at the same time, maintain high sensitivity.

Various apparatus and methods may be used to limit the x-ray beam size therefore radiation level of absorptiometry and sensitivity of the technique for the region of interest. 3D characteristics of the region of interest can be revealed and detected more easily when the detector selected to be used has much higher sensitivity. 3D imaging can be used in 3D correlation of the region of interest with the absorptiometry data. For example, the beam size adjustment elements can be an aperture, fixed, or adjustable, or a beam selector based on one or more x-ray absorption materials. Adjustable position or property of the selected target area for the electron beam used to generate the x-ray beams in the x-ray source may be used to generate x-ray of narrow beam size. In some cases, a tunable x-ray modulator, such as a MEM apparatus or a modulated crystal, downstream from the emitted x-ray source may be used to limit the field of view to illuminate only a selected region of interest on the subject.

As shown in FIG. 12A, the system can include an x-ray source 12, a subject 2, a full field x-ray detector 14, and an absorptiometry assembly 11. The x-ray source 12 can be any type of source that generates polychromatic or monochromatic x-rays penetrating the subject of interest. The detector 14 can optionally be of an energy sensitive type. The full field x-ray detector 14 may be placed between the subject 2 and spectral absorptiometry optics to provide a larger field of view imaging. A region of interest 4 can be selected for spectral absorptiometry analysis. The detector 14 may also be displaced or removed during spectra absorptiometry measurements. Unabsorbed x-ray passes through the full field x-ray detector if the full field x-ray detector is not removed. Optionally, the full field x-ray detectors and x-ray optics may or may not be displaced during x-ray absorptiometry measurements as calibration steps can be performed prior to the measurements to enable extractions of interference signals related to such hardware during image processing.

The x-ray beam 30 can pass through the region of interest 4 and optionally pass through the full x-ray field detector 14 before reaching a diffractive element 340, which may include elements such as a crystal or a diffractive grating or an energy dispersive grating. The diffractive element 340 can split and diffract the x-ray beam into multiple x-ray beams 341 of different energy and/or wavelengths. Certain x-ray optics 330 can be placed in the beam path, for example, between the subject 2 and the diffractive element 340, to manipulate, focus, or steer the x-ray beam 341 in the preferred direction, to be energy dispersed by a diffractive elements 340, each energy level or wavelength reaching a spatial location different than others and to be directed to the detector 345 for measurements. Detector 345 can be a spatially sensitive detector. The optics 330 can be a telescope lens, which can further reduce the x-ray fan beam on to a smaller beam size. Alternatively, optics 330 can collect primary x-rays exiting out of the subject and concentrate or focus the output x-ray dimension to a smaller area, which can be further processed by energy dispersive grating and detector downstream. Advantageously, there can be no moving parts. Selected regions can be measured in real time.

Beam stoppers, such as apertures, may be used to block interfering x-rays of various sources or x-rays that are not useful for the measurements of interest. Alternatively, the grating element 340 can be transmissive and disperse the x-ray chromatically onto the x-ray beams 341 of various energy level or of discrete wavelength.

The absorptiometry assembly may include a spectrally sensitive detector 345 such as a silicon drift detector, a silicon lithium detector, or any type of x-ray detector or detector assembly used in combination with an x-ray wavelength dispersive component, such as a diffractive crystal or synthetic multilayer, or a linear array of x-ray sensitive measurement element, such as a photodiode, photon counting detector, or may be of any type of x-ray sensitive camera or energy counting detector or photo multiplier tube with scintillator upstream to convert an x-ray signal to a visible photon signal. The spatially sensitive detector 345 can measure the x-ray beams 341, each pixel location, or each region of detector 345 collecting signals at a specific energy level or wavelength level. The spatially position sensitive x-ray detector 345 can thus be used to measure signals from the x-ray of each discrete energy level. An aperture may be used for additional refinement of the interested spatial area.

Alternatively, an absorptiometry assembly downstream from the region of interest can include a spherical mirror directing the x-ray to a grating system, which can disperse x-ray chromatically and onto a spatially sensitive detector.

Optionally, an x-ray spectrometer module with one or multiple channels can be utilized to allow high resolution x-ray measurements at various discrete wavelengths.

Optimally, a spectral absorptiometry module may be capable of multiple channel measurements, such as using fiber to transport x-ray from the input to a detector, such as a linear detector or a row in a 2D detector. The configuration can allow for a wider field of view for the absorptiometry on the subject.

Correlating absorptiometry with or without x-ray optics, for example, those used in x-ray microscopy, can measure chemical compositions at a molecular level at high resolutions spatially, temporally and spectrally, with 3D or multiple dimensional measurements in x-ray microscopy and/or 2D or 3D full field x-ray imaging for determining physical characteristics, including shape, thickness, and/or location. The combination may allow for localization and characterization of very small element, such as molecules, cells, and/or foreign bodies, with or without labels such as contrast agents.

As shown in FIGS. 12B and 12C, x-ray microscopy or x-ray microscopy combined with spectral absorptiometry can be used to zoom in the region of interest selected based on, for example, the results from imaging and quantitative analysis using x-ray full field method with or without spectral measurements in 2D, multiple dimension or 3D configuration for detailed imaging and analysis. In this case, x-ray is preferably, a monochromatic source, for example, a monochromator modifies a polychromatic x-ray source, condenser further focuses the x-ray beam into a focal point, down steam of the focal point, x-ray fan beam illuminates the region of interest, and magnified image enters the back aperture of an objective which in some cases, is a zonal plate, focuses the beam onto a 2D detector. 3D x-ray microscopy can be further implemented as described above in 3D imaging methods. Absorptiometry may be combined with x-ray microscopy, similar to the configuration described in FIG. 12A, instead of directly downstream from the full field x-ray imaging. The absorptiometry can be downstream of the x-ray microscope detector especially when x-ray optics are used, for example, in x-ray microscopy, if the x-ray source for x-ray microscopy is polychromatic.

As shown in FIG. 12B, the x-ray microscopy apparatus 17 can include x-ray optics required for high resolution microscopy. In FIG. 12B, the apparatus can include an x-ray source 12, x-ray optics 302 that can include focusing optics, such as a condenser, and an aperture 304 to illuminate the subject 2. The optics 304 can be a crystal or a monochromator or MEM apparatus or energy selective x-ray filter or transmitter. The apparatus can include x-ray optics 310, which can include a subjective lens and relay lens. The apparatus can also include a 2D sensor 320. The image subject 2 can be positioned between the x-ray optics 304 and x-ray optics 310.

Figure 15B:
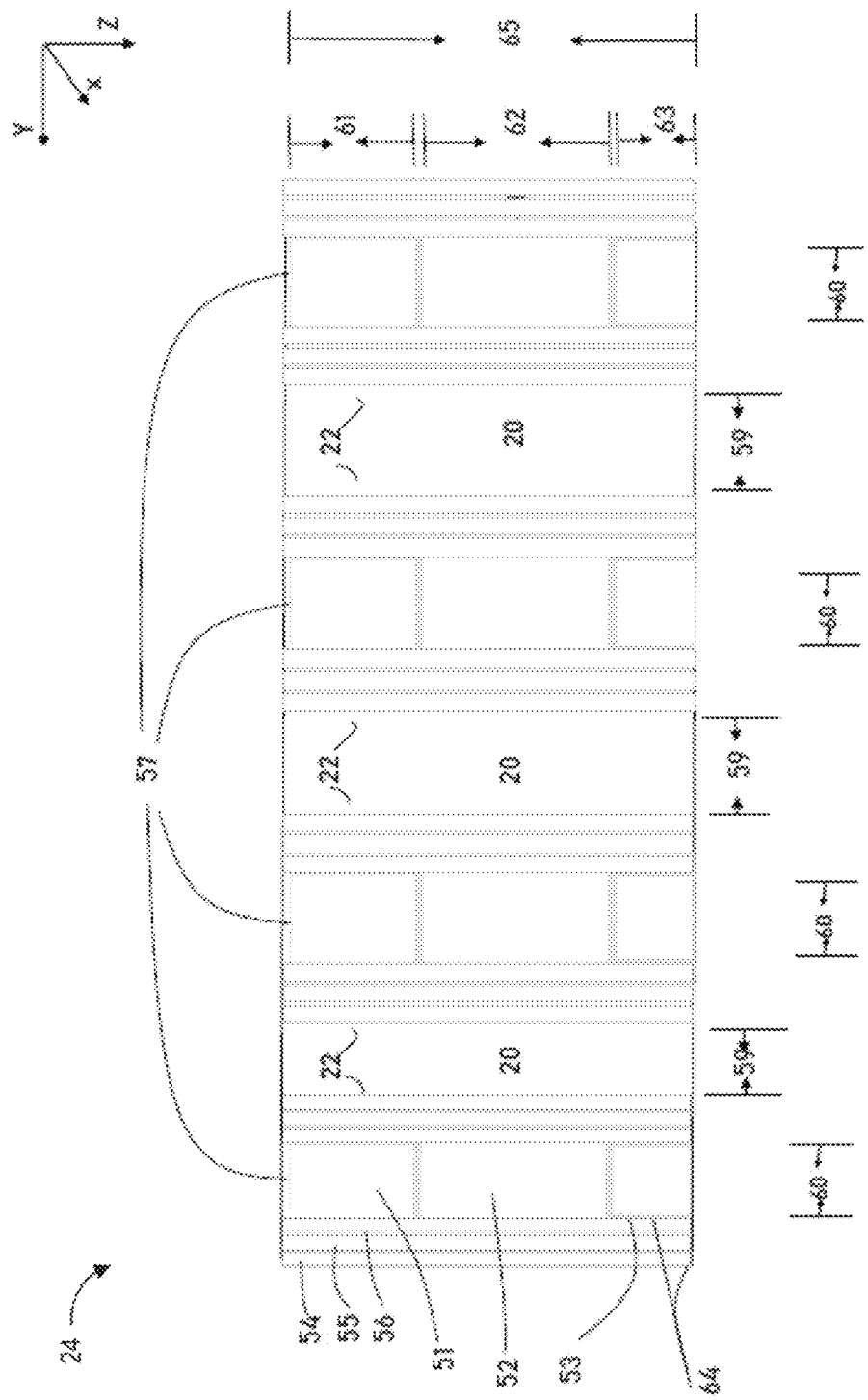
FIG. 15B illustrates an example construction of a collimator.
Figure 15C:
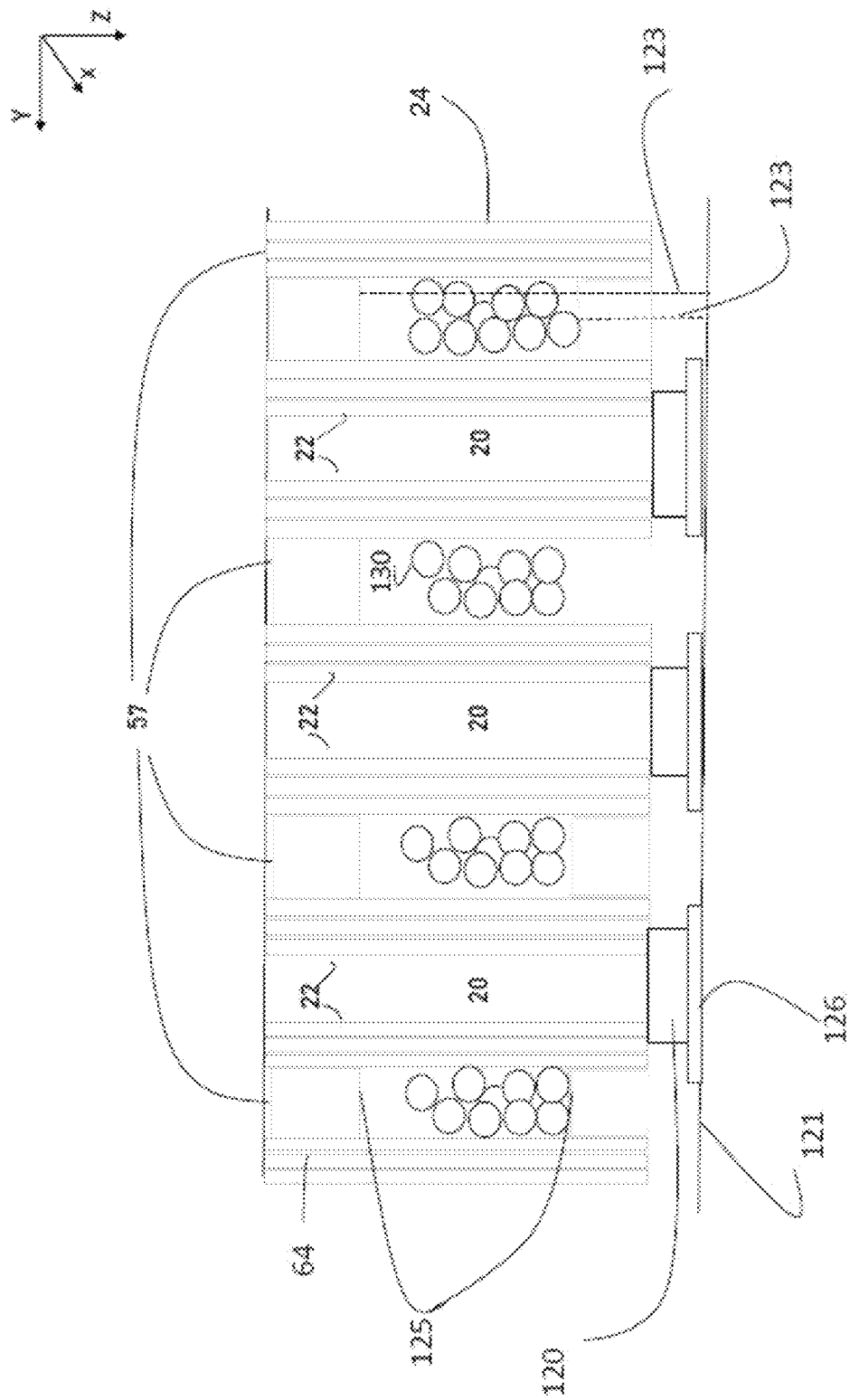
FIG. 15C illustrates an example assembly of a collimator and a 2D x-ray detector.

In FIG. 12C, an x-ray apparatus 1200 can combine 2D or 3D x-ray microscopy with full field x-ray imaging by having a full field x-ray detector 14 placed between the subject 2 and the x-ray optics 310. In FIG. 12C, the apparatus 1200 includes a beam selector or collimator 24. The beam selector 24 can remain fixed relative to the emitting location 16. This is because the beam selector 24 can have fixed focal points. The beam selector 24 also may not remain fixed relative to the emitting location 16 because the beam selector 24 can have adjustable focal points. An example construction of collimator 24 is illustrated in FIG. 15B. An example assembly of collimator 24 and a flat panel x-ray front detector 22 is illustrated in FIG. 15C.

Alternatively, x-ray microscopy may be modified with a scatter removal apparatus using for example, a beam absorbing particle plate as illustrated in FIG. 6, or a collimator or beam selector embedded with holes of defined size for x-ray transmission or a stack of such beam selectors.

The x-ray optics 302 can focus the x-ray beams 30 and/or convert a polychromatic x-ray to a monochromatic thin beam via filtering or a monochromator such as a crystal and/or the like. The conversion function may not be required, for example, in cases where the source is of monochromatic in nature.

For x-ray absorptiometry done on multiple channels, multiple fibers or total internal reflection based x-ray optics can direct the x-ray coming from the region of interest to a detector. If a linear detector serves as the absorptiometry detector, multiple linear detectors may be used for a multi-channel system, with each linear detector correspond to each channel.

Optionally, x-ray absorptiometry and/or microscopy may be done on multiple channels for multiple areas of interest. For instance, the x-ray microscopy apparatus as illustrated in FIG. 12C can include an x-ray detector that can form a 2D image as well as be energy sensitive. Alternatively, an absorptiometry assembly similar as described above can be downstream of the detector used in x-ray microscopy. Both x-ray microscopy and absorptiometry can be combined with full view x-ray imaging. The x-ray source may be polychromatic. The apparatus can include a spectra sensitive detector for x-ray microscopy and/or analyze x-rays passing through the x-ray microscopy detector, which can be optional, and/or dispersed by diffraction grating, and to generate a signal on a spatially sensitive detector.

Figure 15D:
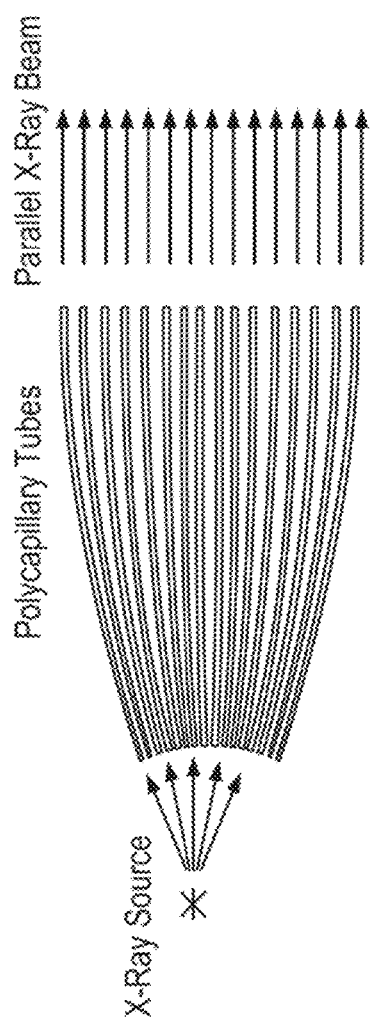
FIG. 15D illustrates x-ray beam projections through an example total internal reflection tube as a collimator.
Figure 15E:
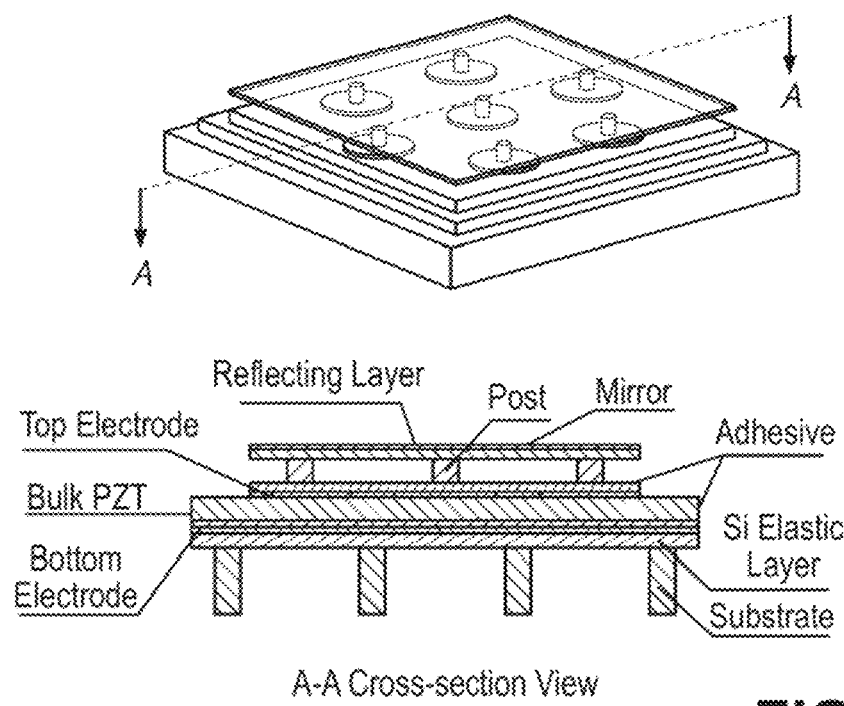
FIGS. 15E and 15F illustrate examples of diffraction or steering of the x-ray beams by modulating control systems, such as microelectronic device, that is, a tunable mem x-ray optics, x-ray mirror as in FIG. 15E or grating or acoustic modulator, as in FIG. 15F such as a ultrasound system. Such apparatus and related methods may be used in generating x-ray emitting locations in multiple dimension imaging or in interferogram generation or in scatter and primary x-ray separation or structural illumination beam measurements.
Figure 15F:
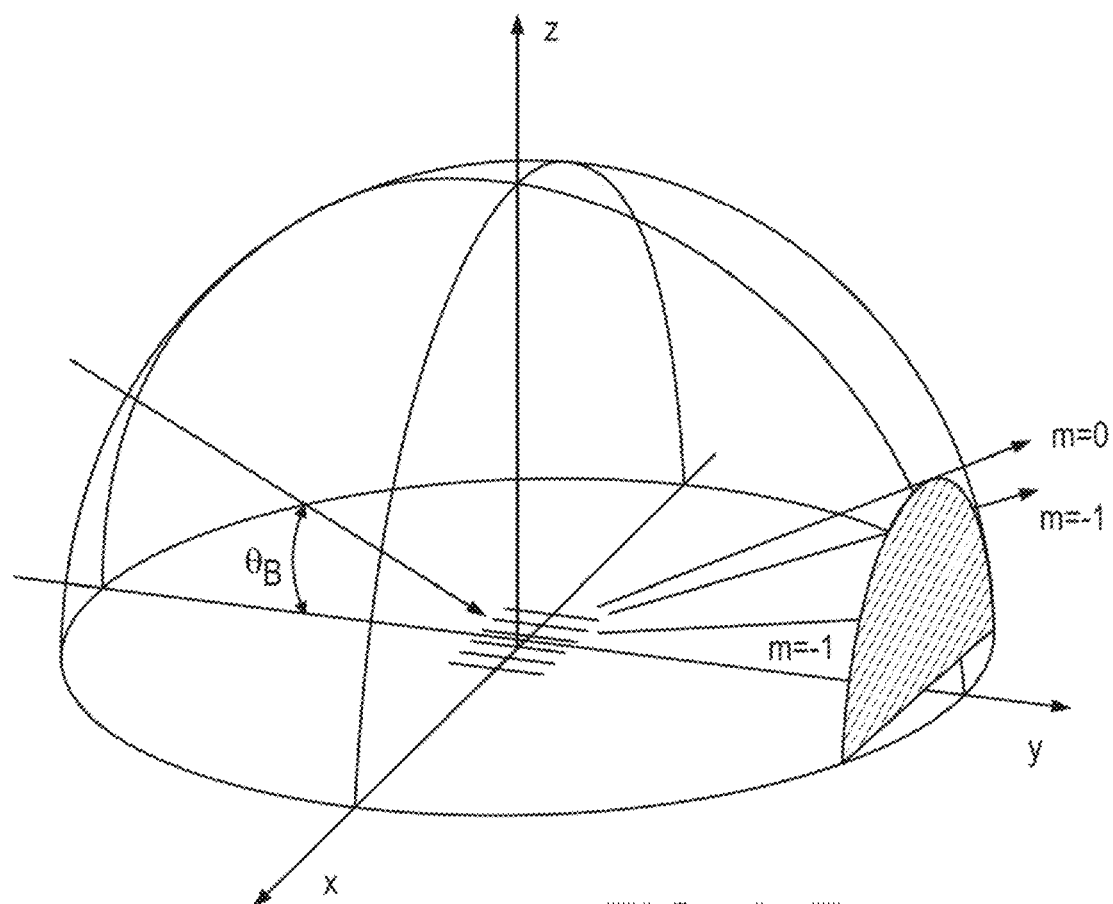

An example diffraction grating with tunable arrays of MEMs is illustrated in FIG. 15E. As shown, an incident angle is restricted to that of the primary x-ray angle meeting the center location of the MEM mirror. The x-ray diffracted by the MEMs can be collected on a second detector corresponding to the MEM location. As will be discussed below, a grating can also be used for interference pattern generation in phase contrast and absorption imaging of the x-ray. FIG. 15F illustrates an example beam selector using the incident angle for crystal diffraction or a critical angle for crystal surface diffraction. In static 2D imaging, when the incident angle is outside of a defined angle, there is no diffraction of a high energy x-ray by the crystal. In dynamic 2D imaging, modulation can be achieved without moving parts for the beam selector alignment, for example, using an acoustic wave modulation in the crystal structure. The x-ray can interact with sound waves in the crystal.

The input x-ray beam for x-ray spectral measurements, absorptiometry or microscopy may be scanned over an area of interest to expand the field of view as well as for acquisition of images or measurements needed for construction of multiple dimension and 3D images. The x-ray beams can be moved by different mechanisms, including magnetic, electromagnetic, electric and mechanical methods as described used in 3D imaging as disclosed herein. The scanned x-ray spectral measurements, or absorptiometry or transmission microscopy input may be combined with the multiple beam methods to increase further the total field of view and increase the imaging speed for a defined region of interest.

Multiple Beam Configuration

The pitch of the detector can be matched to the pitch of the multiple x-ray sources, so that each pixel is positioned to only detect x-rays emerging from the interaction of the subject with a single micro-beam, and the cross-talk between pixels due to neighboring micro-beams can be reduced. The data collection and final reconstruction of the properties of the subject may proceed knowing that the distinct signals from each pixel need not be further deconvolved. If there is cross-talk between micro-beams and pixels, additional image analysis may be used to remove some of the cross-talk with proper calibration.

This matching can be achieved in different ways, for example, by the detector pitch having a 1:1 match to a single micro-beam, that is, the image of each beam being formed onto one pixel in the detector. Smaller detector pitches that are integer fractions of the pitch of the micro-beams (for example, a 2× reduction in pitch, which would indicate for a 2-D array that 4 pixels are positioned to collect the x-rays corresponding to a single micro-beam, or a 3× reduction in pitch, which would indicate that 9 pixels are positioned to detect the x-rays corresponding to each micro-beam) may also be used. This may offer some advantages if the x-rays being detected have some spatial structure.

Likewise, larger detector pitches may also be used if the x-rays emerging from the subject under examination are imaged onto the detector using an x-ray optical assembly that creates a magnified x-ray system. This imaging system may be any of the x-ray optical trains disclosed herein. The optic may be implemented as an achromatic imaging optic that has a field of view equal or greater than the micro-beam diameter. For example, an axially symmetric condenser optic that utilizes glancing incidence reflection to reflect x-rays with inner reflecting surfaces to collect a diverging x-ray beam and focus the beam can be designed to create a 1:1 image. The optic may also be used to produce a magnified image.

The detector may be any one of a number of spatially resolving detectors having a scintillator screen and visible light optic and used to form x-ray images. The detector may be an array x-ray detector that converts spatially dependent x-ray intensity to an electronic signal, including linear detectors, flat panel detectors, energy-resolving array detectors, photon counting detectors, PMTs, photodiodes, silicon drift detectors, dual or multiple layer detectors, a dual detector layer with a beam selector sandwiched in between, or the like.

For single beam and/or multiple beam configuration in x-ray microscopy, an example of an x-ray detector includes a fluorescent screen or scintillator, which emits photons in the visible wavelength when exposed to x-rays. The fluorescent screen or scintillator can include a layer of cesium iodide (CsI), thallium doped CsI, yttrium aluminum garnet (YAG), or gadolinium sulfoxylate (GOS). The photons generated can be detected by a sensor that converts visible intensity into electronic signals, optionally adding a relay optics assembly which enlarges and magnifies the intensity pattern of the photons. The scintillator and electronic components may be thin enough so that each detector pixel is collecting only x-rays corresponding to a single micro-beam.

When using relay optics and a magnified image, detection may be limited to the field of view of the x-ray optics. To image larger areas, multiple images can be combined in a mosaic fashion as described above.

Detectors with additional structure within each pixel may also be employed, for example, to selectively collect fluorescent signals or scattered signals or diffracted signals, or primary x-ray in the original illumination path.

Detector for x-ray spectral absorptiometry may be of spectrally sensitive detectors such as silicon drift detector, a silicon lithium detector, or any type of x-ray detector or detector assembly used in combination with an x-ray wavelength dispersive component, such as a diffractive crystal or synthetic multilayer. The detector system can include a diffractive component, such as a crystal that splits and diffracts the x-ray beam into multiple x-ray beams of different energy and wavelengths downstream of the position the sensitive x-ray detector uses to measure signals from the x-ray of each discrete energy level. In such case, an aperture may be used for additional refinement of an interested spatial area.

For a full field x-ray imagining combined with absorptiometry, or x-ray microscopy, or both, an x-ray 2D flat panel detector may be placed in between the subject and the downstream x-ray optics and x-ray detector for transmission. The final x-ray microscopy images may be derived by utilizing image processing to remove artifacts resultant from the full field detector being between the subject and the x-ray microscope optics.

Alternatively, such a flat panel of a full field x-ray imaging detector may be placed in and out of the imaging pathway of the x-ray microscope as the application requires.

Single Beam Configuration

Transmission full field x-ray microscope can be with a single beam. Additionally, transmission, fluorescence, interferometer, and diffraction x-ray microscope may be combined with spectral absorptiometry, spectral measurements or spectroscopy with a single beam. The same type of detector as used in an x-ray microscope can be used. For transmission full field x-ray microscope, the detector assembly used for scatter removal or a multiple energy dual or multiple detector assembly may also be used.

The detector may be any one of a number of linear or 2D detectors used to form x-ray images, such as a detector system including a scintillator screen and visible light optic. In some instances, the detector may be an array x-ray detector that converts spatially dependent x-ray intensity to an electronic signal, including linear detectors, flat panel detectors, energy-resolving array detectors, photon counting detectors, dual or multiple layer detectors, and/or scatter removal detector assembly.

As shown in FIG. 12C, a full field x-ray detector 14 may be placed between subject 2 and optics 310 without interfering microscopy imaging as the image of detector 14 can be extracted from the image formed on the detector 320 (similarly, the image of detector 14 can be extracted from the image formed on the detector 345 in FIG. 12A). The full field x-ray image can be formed first with the same x-ray source or a conventional x-ray source. A region of interest can be selected to be imaged by absorptiometry or microscopy optics and absorptiometry or microscopy detectors to resolve the region of interest image with higher resolution.

The x-ray source 12 can emit x-rays with controllable energies. The source 12 can emit x-ray of single energy for each imaging operation. The source 12 can emit two consecutive x-ray pulses with controllable energies for each imaging operation: a high-energy pulse at an average energy level H followed by a low-energy pulse at an average energy level L. Each pulse can have a single, reproducible energy spectrum, which can be composed of bremsstrahlung radiation and discrete line emissions. The source 12 can also three or more consecutive pulses of various energy levels for each imaging operation, for example, a high-energy pulse at an average energy level H, followed by a medium-energy pulse at an average energy level M, followed by a low-energy pulse at an average energy level L. Each pulse can have a single, essentially unchanged energy spectrum.

Alternatively, the x-ray source may be of monochromatic nature, such as a synchrotron, or laser Compton scatter source, or a polychromatic source described as above, modified or filtered, for example by an optics assembly 304 to be a monochromatic source.

As shown in FIGS. 12B and 12C, an x-ray emitting location 16 can move relative to the subject 2 so that the wave front of x-ray beam is in a plane 202 parallel to the detector assembly 14. A mechanism 200 can move the emitting location 16 either angularly, linearly, or a combination of both. The movement is preferably done to solve the unknown pixels in the third dimension in the region of interest 4 within the subject 2, while minimizing the introduction of new unknown pixels in each movement and minimizing introduction of a total number of new unknown pixels for the complete derivation of unknown pixels in the third dimension for the region of interest 4. The subject 2 can also be physically moved relative to the emitting location 16, particularly in applications, such as industrial applications, where the subject 2 is already in motion while being imaged. To minimize total imaging time and radiation exposure, each movement, either angular or linear, can resolve the unknown pixels in the third dimension, preferably in integer multiples of pixel pitch.

To minimize total imaging time and radiation exposure, the mechanism 200 may optionally move the emitting location 16 rapidly (at or faster than the frame rate of the detector assembly 14). The mechanism 200 can provide this motion in increments of integer multiples of pixel pitch (the distance between adjacent detector cells). The motion can be designed so that in the direction of motion, only integer multiples, or the maximum of one pixel pitch, of an unknown nature is introduced in the axis of the motion movement for the region of interest with each new measurement on detector.

The motion can be in increments of a fraction of pixel pitch. For example, in order to resolve unknown pixels along the third axis to reconstruct the multiple dimension image, the motion can result in measurements on the detector 14 with no new unknown pixels introduced along the projected image, but with new measurements on the detectors with a different projected path for the selected image of the region of interest.

The mechanisms 200 can provide for a moving emitting location 16 and, optionally, a moving detector assembly 14. For example, two or more x-ray sources 14 can be positioned at different locations in the plane 202 and emit pulses sequentially from those locations. The detector assembly 14 may be fixed. For this mechanism 200, the beam selector 24 has either multiple fixed focal points or an adjustable focal point.

Alternatively, a single x-ray source 12 can emits x-ray pulses sequentially from different locations on the plane 202. The x-ray source 12 can include microns-scale metal x-ray emitters which can be modulated and switch on and off to control the emitting location 16.

An 2D array of collimators (or a beam selector 24), with each hole being integer multiples of pixel pitch apart, can raster scan an x-ray beam using different mechanisms. A two-dimensional actuator can physically moves the x-ray source 12 and the x-ray detector assembly 14. Preferably, the actuator can move the x-ray source 12 and the x-ray detector assembly 14 with each increment being a low integer multiple of pixel pitch in the plane 202 at or faster than the frame rate of the detector assembly 14. For this configuration, the beam selector 24 (collimator) can have a fixed focal point. A two-dimensional actuator can physically move only the x-ray source 12. Preferably, the actuator can move the x-ray source 12 with each increment being a low integer multiple of pixel pitch in the plane 202 at or faster than the frame rate of the detector assembly 320. For this configuration, the beam selector 24 aligns with the emitting location 16. The beam selector 24 may have an adjustable focal point. A two-dimensional actuator can physically rotate only the x-ray source 12 so that the emitting location 16 moves in an arc. Preferably, the actuator can rotate the x-ray source 12 with each increment being an angle along the arc to simulate a planar motion of one pixel pitch at or faster than the frame rate of the detector assembly 14. For this configuration, the beam selector 24 must align with the emitting location 16. The beam selector 24 in this configuration may need to adjust its focal point. In some cases, the movement to each x-ray emitting positions may not accompanied by the adjustment of the focal point each time. Optionally, not all movements to x-ray emitting positions require adjusting of the focal point.

For scatter removal using multiple plates, for example, P1 to P4 such as illustrated in FIG. 2, such adjustment of focal point or movement spatially may not be required, In addition such configuration may be used when two or more x-ray sources are used for spectral measurements and/or in hybrid systems.

Figure 9:
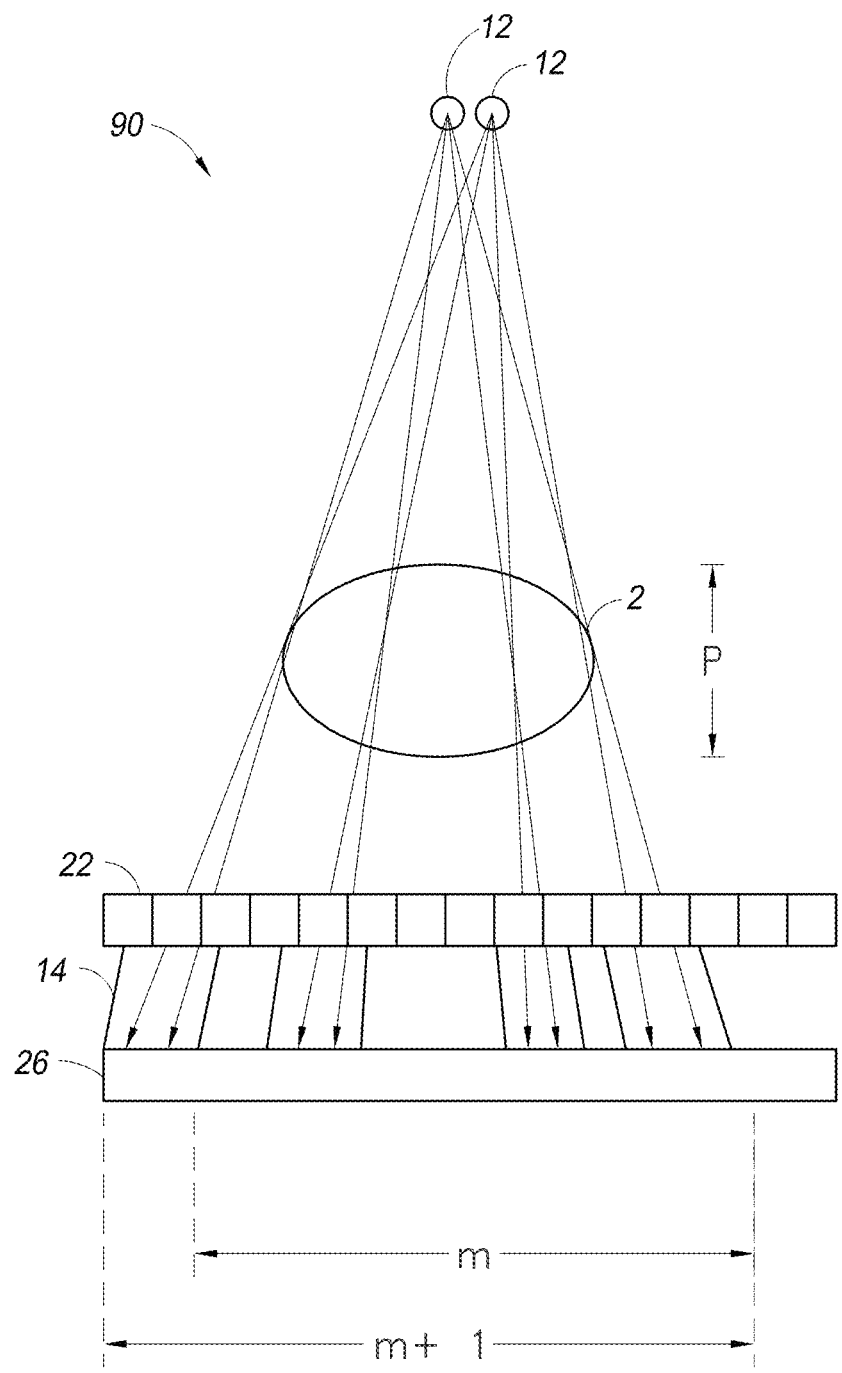
FIG. 9 illustrates newly introduced unknown regions during imaging acquisition for multiple dimensional and 3D imaging acquisition.

For scatter removal method using one piece of hardware, such as a beam selector, a collimator 24 as in FIG. 1B or FIG. 3 or FIG. 9, or beam absorbing particle plates 105 as in FIG. 6 and FIG. 7, or multiple plates configured collimator or beam selector, as in FIG. 2 such hardware may be moved or not moved depending on the requirement of the imaging method.

Movement of x-Ray Emitting Source or x-Ray Sources

A mechanical mover may move emitting x-ray position of an x-ray source or the x-ray source in for example, 3D imaging. An x-ray source may have two or more x-ray emitting positions such as in a pixelated x-ray source or in a field emitted based source. Multiple x-ray sources may be placed at various spatial locations. Alternatively, field emitter based cold cathode x-ray source may activate or deactivate regions of multiple emitters or each emitter to generate varied x-ray emitting position spatially.

The mechanism 200 can also optionally deflect the electron beam within the x-ray source 12 to hit a different location on the anode, thereby causing the x-ray beam to be emitted from a different emitting location 16. As shown in FIG. 15, a changing magnetic field can be generated by a solenoid coil 212 (also referred to as magnetic plates or steering plates) attached to the housing of the x-ray tube 210. The magnetic field can deflect an x-ray beam 211. When energized, the coil 212 produces a magnetic field and an associated Lorentz force on the electron beam in the x-ray tube 210, shifting the impact spot on an anode target 214 from which x-rays are emitted. The emitting location 16 in FIGS. 12B and 12C can move due to the displacement of the focal spot of the cone beam 213 on the anode target 214. The result is that the emitting location 16 can move from one location to another. Careful control of the coil 212 can produce movement in as small as a pixel pitch in one or two dimensions.

Optionally, the electron beam can also be deflected as the beam passes through charged metal plates or electrooptical lens. The direction of deflection depends on the polarity and amount of charge of the plates or design of the electrooptical lens.

Optionally, light source, such as a light-emitting diode (LED) or laser, can be used as the source to generate the electron beam, which can be amplified by a multiplier tube. A light deflector such as optics or mirrors and/or acoustic/optical deflectors can be used to deflect the light. An ultrafast laser may be used to generate an ultraviolet emitter that emits ultraviolet light. A photocathode can be operably coupled to the ultraviolet LED and emit electrons. An electron multiplier can be operably coupled to the photocathode to multiply the incident electrons. An anode can be operably coupled to the electron multiplier and configured to produce X-rays. The ultraviolet emitter may be steered in different angles to control the output of the electron beam, which in turn can control the direction or the location of the x-ray beam emitted from the anode.

Optionally, irradiating arrays of metal components, such as nanowires, with intense femtosecond laser pulses can produce high-brightness picosecond X-ray pulses. The emitting location 16 can be moved by using optical steering apparatuses to change the impact location of the laser beam on the metal components.

Ultrasound can modulate an x-ray beam in space and time. For example, a space-time modulation of an x-ray beam can be done by a total external reflection on a YZ-cut of a LiNbO/sub 3/crystal modulated by surface acoustic waves. The x-ray diffraction can be determined by the amplitude and wavelength of the surface acoustic waves. The emitting location 16 of x-ray can also be moved due to modulated diffraction from a crystal by ultrasound or surface acoustic waves. The x-ray beam emitted by a single beam source can also be moved to different emitting locations 16 using total internal reflection of, for example, polycapillary tubes as shown in FIG. 15D.

In other words, optical, electric, magnetic, x-ray optics such as crystal, acoustic such as ultrasound and/or other steering mechanisms can be used to steer the x-ray beam output position quickly (such as in picoseconds, nanoseconds, or as fast as $10^{-15}$ s, in some cases, same or close to the duration of the ultra short x-ray pulses, or otherwise as disclosed herein).

Scatter Removal

The x-ray microscope, with or without any additional modalities, such as absorptiometry, spectroscopy, or otherwise as disclosed herein, can separate the scatter x-ray from the primary x-ray. A beam selector may be placed downstream of the x-ray source and upstream of the subject in full field x-ray imaging, or in between the condenser and the x-ray source in x-ray microscopy. When such an implementation is adopted, in order to further acquire images required for 3D imaging, the below-described process may be implemented.

Figure 14:
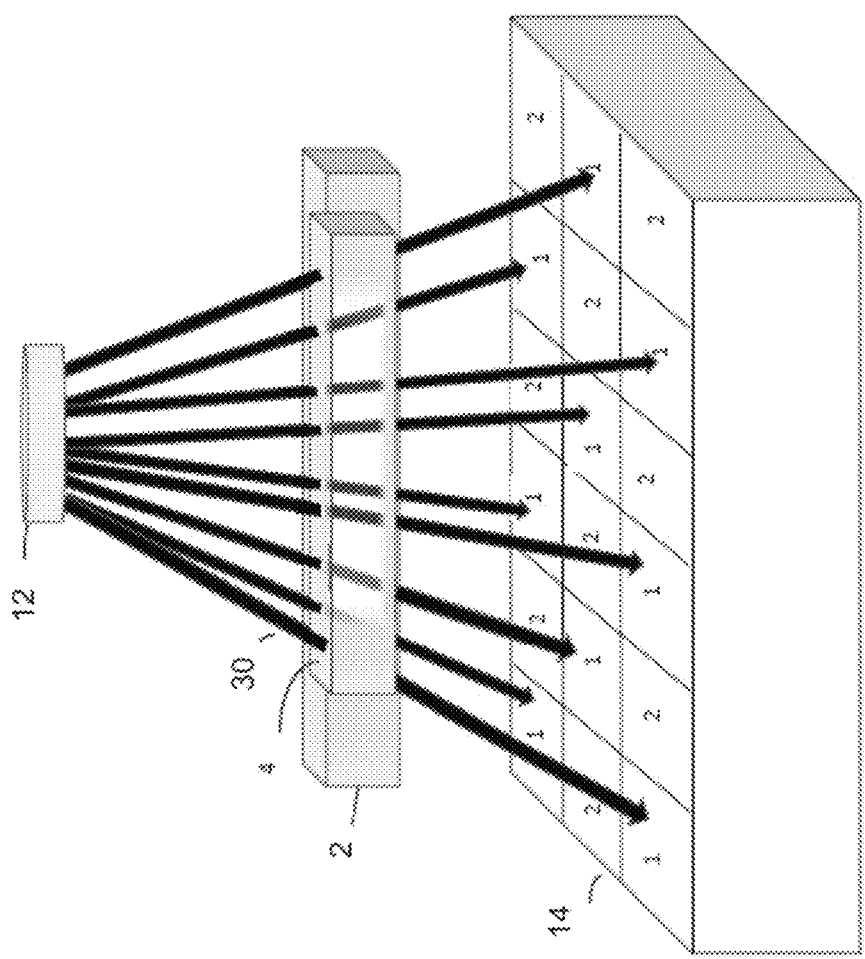
FIG. 14 illustrates scatter removal using multiple microbeams.

A first position of the beam selector can be used in generation of a portion of one 2D image as illustrated in FIG. 14, which are described in greater detail below: Only region 1 provides primary x-ray images of region of interest. The beam selector can of the checkerboard design or otherwise in order to create region 1 images as illustrated in FIG. 14. As the beam selector is placed at its first position and the x-ray is emitted from the first position of the x-ray emitting location, a 2D image is taken on the detector 14, but only half of the areas are of primary x-ray projected area. The x-ray source 12 may raster scan to various locations on plane 202 as illustrated in FIG. 14. After all x-ray emitting positions are reached and images recorded by the detector 14, or the detector 320 at each of x-ray emitting positions on plane 202, the beam selector moves to the second position on the plane 202, where region 1 on the detector from the first scan can become the region adjacent to region 1 of the detector at the second position of the beam selector. The x-ray source or other component that changes the emitting location of x-rays can start the raster scanning motion from the first position and a second portion of the 2D images can be recorded. The first and second portions of the 2D image can be taken at the same x-ray emitting position but at different beam selector position. The first second portions can be stitched together to form part of a single 2D image used for reconstruction of multidimensional image. While it is preferred that only first and two portion of the 2D image are sufficient to form the first 2D image, in some cases, a 3rd portion or more may be needed where the x-ray source can perform the raster scan three or more times from the first position to the last position on the plane 202 in order to form the complete 2D images required to reconstruct 3D image for the region of interest.

As shown in FIG. 14, a different pattern can created on the detector 14 by moving the modulator. To form such patterns as illustrated on the detector 14, the x-ray source 12 can be modified to generate such structured illumination on the region of interest 4. There are a number of ways to do this.

The x-ray source 12 can be capable of emitting multiple thin beams of selected emitting positions, to illuminate spatially separate beam paths on the region of interest 4 in the subject 2, for example, to form a primary x-ray image area 1 with low scatter interference on the detector 14, as illustrated in FIG. 14. An electron beam target in the x-ray source 12 may be tunable spatially and/or in time so that certain regions of the target generate x-ray beams in a controllable fashion in time. These regions can selectively generate x-ray beams or be switched off so no x-rays are generated.

In one example of the hybrid system, the x-ray source 12 can also be capable of emitting a full cone beam illuminating the region of interest 4 as in a conventional x-ray cone beam for a complete microscopy image of the selected region 4s. A collimator (such as a beam selector 24 in FIG. 12C or a tunable collimator such as a crystal, which can be activated on at certain positions to allow transmission and deactivated at a delayed time) with fixed transmitting and absorbing regions can modulate the x-ray beam to generate multiple beams. A MEM mirror can allow on and off switches for generating x-ray beam sets at designated areas. X-ray beams can be split into two pulses that travel on the same path, first pulse experiencing one pattern modulator and second pulse delayed to pass through a second illumination modulator to generate second pattern of structural illumination. A first X-ray source may be switched on by a mirror to travel in the beam path of interest and switched off when a second x-ray source with a different pattern or complementary pattern are switch on. Such switches can be an x-ray mirror, such as a double-sided mirror.

As illustrated in FIG. 14, a primary image 1 can be formed on detector 14. The primary image 1 may be on one pixel or multiple pixels. Region 2 can be the area without primary x-rays, but may contain scatter signal. The scatter signal on the primary image 1 can be interpolated from the pixels 2 immediately adjacent to the image 1 or region 1 on detector 14. The shape of the image 1 or region 1 can be of any shape. This step may be optional if the scattering interference is low or not required to be removed for the certain subjects and/or applications.

The x-rays can generate a "checker board" pattern illustrated in FIG. 14 or other type of patterns on the detector 14. In an example "checker board" pattern, the entire collimator or modulator can move in the plane parallel to the detector 14. If the size of regions 1 and 2 each is a detector pixel pitch in dimension, the movement can be in the order of the detector pixel pitch range, which can be a single digit micro range, a 100 um range, or a single-digital mm range, depending on the detector pixel size of detector 14. If the size of regions 1 and 2 are more than one pixel pitch, the movement of the modulator can be larger.

Such movements can be designed so that region 1 of the first image do not exactly completely lay in the same position as region 1 of the second image and there is a certain degree of overlap between region 1 of the first image on the edge and region 2 of the second image. The overlap can improve the completeness, alignment, and/or accuracy of stitching images combined from region 1 of the first detector image and region 1 of the second image on the detector after the movement of collimator.

The interpolation of the scatter signal on the primary image 1 is described as the below. After the detector 14 reads a signal S2 on the region 2 adjacent pixels to region 1, which a processor of the apparatus can interpolate as the scattered signal on region 2 to that on region 1. The processor can derive the scatter signals S1 $(i, j)$ on region 1 from S1. The processor can derive P1 (i, j) the primary x-ray signal of region 1 by subtracting the result S1 $(i, j)$ from the raw LP1((i, j) signal read by region 1 of the detector 14. The processor can then derive HS1, a high resolution scattered image at point of interest (i, j) by HS1 $(i, j)$=H1$(i, j)$–P1 (i, j). H1$(i, j)$, a high resolution image, can be derived from reading the pixels on region 1 from the x-ray fan beam generated and the projected to illuminate the entire region of interest. P1 (i, j) is the result of a low resolution primary image. The processor can then interpolate HS1 $(i, j)$ to the rest of the projected image to derive a high resolution scattered image, HS. HP, a high resolution primary x-ray image, can be derived by the equation HP=H–HS. HS is the high resolution scattered image and H is the measured high resolution image of primary and scattered x-ray.

As described above, if the x-ray thin beams are generated far enough spatially, extremely low amount or no amount of scatter signals from adjacent beams reach region 1. One can reasonably assume P1=LP1.

Multiple energy, such as triple or more energy level can be used to separate scatter from primary x-ray. This method can be adopted to improve scatter separation from the primary x-ray when spectrum imaging is used. The multiple-energy x-ray primary and scatter separation method utilizes x-ray sources of three energy or more as there are three or more different materials respectively in the imaged subject. A multiple energy x-ray data decomposition method disclosed in the present disclosure can directly solve the a triple- or more energy x-ray imaging fundamental equation system in its original form without relying on any linear or second order approximations.

For example, a triple energy method can include: (1) constructing an explicit quantitative equation system DH=DH (b, s, f), DL=DL (b, s, f), and DM=DM (b, s, f) for each detector according to the nonlinear triple-energy x-ray imaging fundamental equation system in its original form. DH represents the high-energy primary x-ray signal, DM represents the medium-energy primary x-ray signal, and DL represents the low-energy primary x-rays signal. b, s and f may be tissue or i organic material or a mixture of both. f represents the density of a third material different from b and s. The multiple-energy x-ray imaging fundamental equation system in its original form does not contain any linearization approximations nor any series expansion processes. The method can include (2) reconstructing a three-dimensional surface equation system b=b (DH, DM, DL) and s=s (DH, DM, DL) and f=f (DH, DM, DL) by numerically inverting the equation system of step 1; and (3) determining the desired values for b and s and f at each discrete detector cell location by inserting the available data pair (DH, DM, DL) into the numerical equations of step 2, or determining the desired values for DH, DM, DL, or only one of them, at each discrete detector cell location. The available data set (b, s, f)

can also be extended into the numerical equations of step 1. The method can include (4) maintaining the accuracy at each step.

When such material set is not available all the time, b, s, f, similar known material to each of unknown material or substances, b, s, f, such as u, v, w correspondingly, can be used to establish a database. The database can be extended to material decomposition of more than two components or substances. Quantitative numerical relationship may be established among u, v, w and b, s f, via measured data.

Alternatively, simulated and synthesized data based on data derived other modalities such as CT, MRI, optical measurements, Photoacoustic, acoustic and PET and mechanical methods and preexisting data can be used to generate the database.

Facts, structured data, characteristics, results which are derived from Artificial Intelligence methods and algorithms based on data from measurements of all modalities may be part of the database.

In the scatter removal methods described herein, the beam selector may only need to move two or a few times, each time for a small distance, such as small as a pitch pixel distance, or half a millimeter or one millimeter. In contrast, if the beam selector in sandwiched between two detectors for scatter removal purposes, the beam selector may have to adjust in much more complex motions, for example, moving in multiple dimensions and with each beam selection region adjusting to the x-ray emission axis and relatively to each other. The x-ray emitting location movement can be much faster in this case, reducing bottlenecks created by other required motions and/or 3D image recording. This can reduce image distortion created by movements of the subject due to faster image acquisition.

Figure 33:
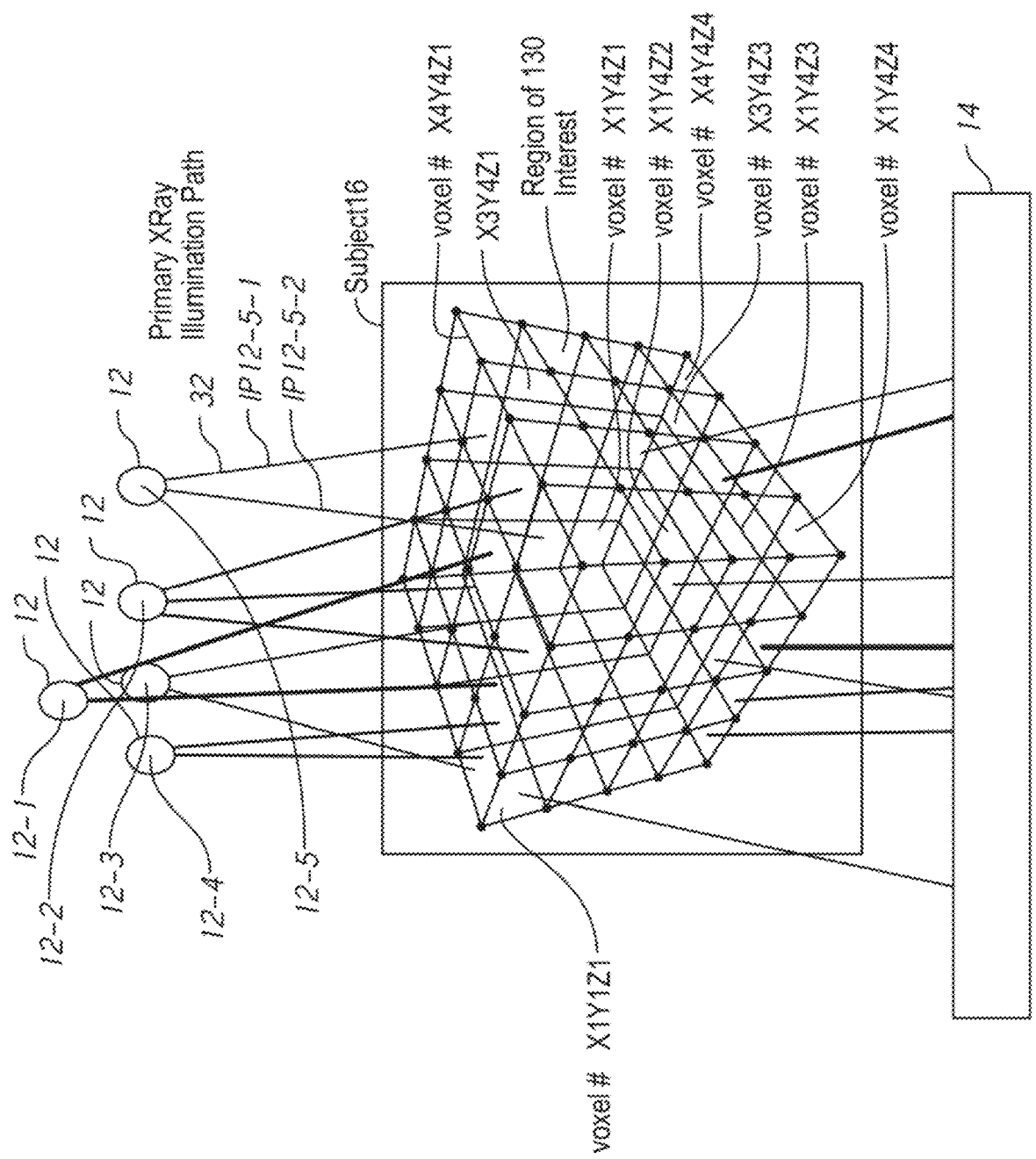
FIG. 33 illustrates an example 3D imaging method where the x-ray source emitting position may move in a combination of positions in at least two axes in the 3D space, described movement of x-ray emitting positions linearly along x, y z axis, and at the same time reduce or minimize the introduction of total new unknowns in the regions outside of the region of interest and reduce or minimize the number of images required to reconstruct a complete 3D image.

3D Imaging 3D x-ray imaging methods described herein can be applied to both x-ray microscopy, full field x-ray imaging, and spectral measurements of 2D regions. FIGS. 9, 13 and 33 illustrate examples of the 3D imaging method in stand alone and hybrid systems.

Figure 10:
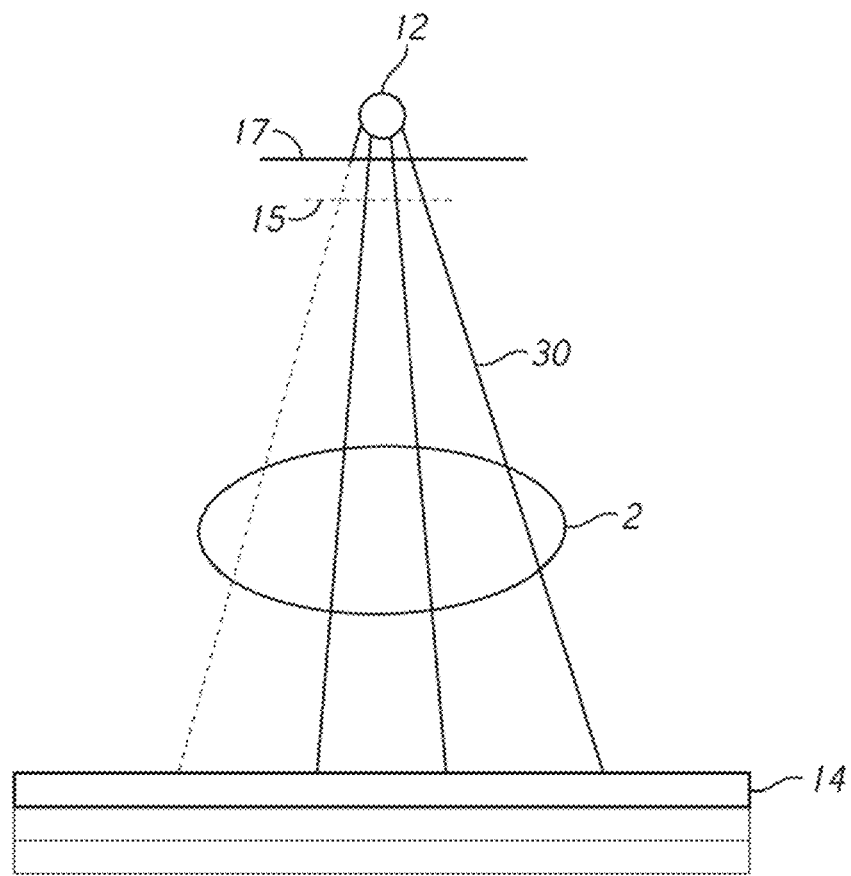
FIG. 10 illustrates use of pixelated K-edge coded aperture between an x-ray source and the subject.
Figure 34:
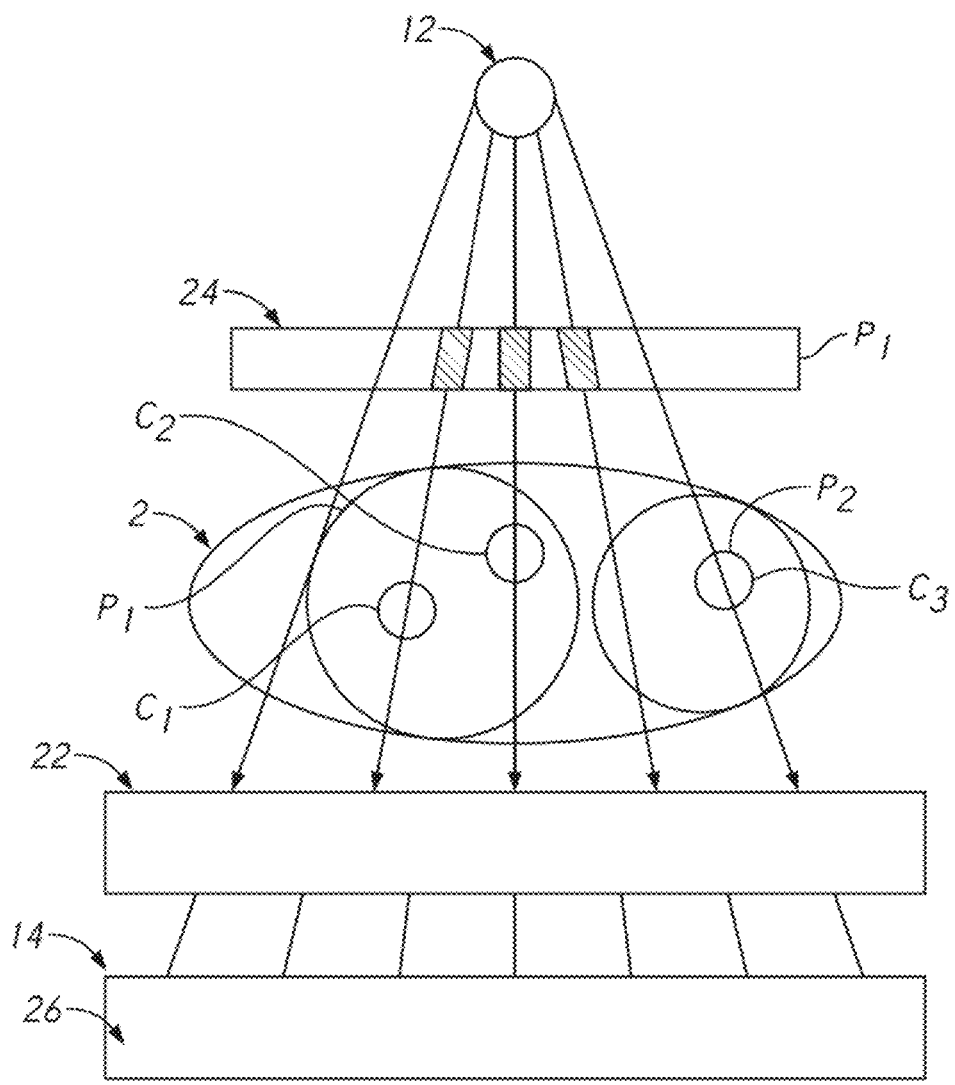
FIG. 34 illustrates an x-ray beam absorber plate $P_1$ placed downstream of the x-ray source 12 and upstream of an imaging subject 2.

For 3D tomography, x-ray measurements can be taken at an x-ray emitting positions as illustrated in FIGS. 9 and 33. In addition, low resolution x-ray images may be taken in order to be determined and selected for the region of interest for high resolution imaging, density measurement, and/or spectral measurements. For example, an image can be taken using a beam absorbing particle plate 15 placed in between the x-ray source and the subject as illustrated in FIG. 34 and FIG. 10 After the region of interest is selected, high resolution images can be taken using a collimator 17 on a smaller area of x-ray absorbing region as in FIG. 10.

The x-ray beam selector or collimator, or the x-ray plates with x-ray absorbing elements may be placed between the subject and the detector, such as in the case of high resolution tomography measurements. Each x-ray image can be taken with the plate or plates containing beam absorbing elements.

The unknown pixels on the projected paths that are blocked may be resolved in measurements of a different projected path. As each x-ray image is taken when the x-ray emitting positions are shifted, the beam absorbing plate or plates may be shifted relative to the x-ray emitting position or x-ray source in the z direction or x-y direction, or rotate while multiple x-ray images are taken so that the measurements involving the unknowns in the blocked projected path may be measured in the next set of measurements and its values can be resolved.

When the beam absorbing particle is small in the x-y dimensions, such as having one or two or small number of pixel pitch in size in the x-y dimension, the unknown pixels may be approximated from the adjacent regions.

When the resolution achieved may be at the highest (for example, 100× or more), and the speed of measurements is the highest, such as in ps range or higher, spectral sensitivity (12× or more) may be as high as possible for a selected pixel, and the overall sensitivity may be increased 106 or higher due to the improved resolution, speed, and spectral sensitivity. Such unknown pixels or voxels may be interpolated or derived from material decomposition even if one or one measurements out of a large number, for example, about 1000, measurements are missing.

The process can be applied to 2D single or multiple beam x-ray microscopy, with the transmission mode being stand-alone or combined at least one of the modalities such as diffraction, interferometry, fluorescence, and/or scatter, phase contrast and dark field x-ray microscopy. For these applications, the distance between each adjacent points where the x-ray is emitted to acquire images required for a multiple dimension image construction may be as small as being in the nm range.

A number of 2D images are first acquired. The processor can determine the number of 2D images needed for reconstruction of the desired 3D images. The processor can also determine whether it is feasible to produce fewer image layers than conventional 3D imaging. If the 2D detector array has m×n detector cells, and the processor can produce any number p of 2D images, where p<n and p<m. This results in P layers of 2D images with m×n pixels each. The 3D imaging method involves solving a linear equation system with m×n×p variables and m× n×p equations. The equations have three dimension, m points on the x axis, n points on the y axis, and p on the z axis. The method assume that each voxel in the region of interest of the subject is cubic, that is, the sides of each voxel are the same length, $Dx=Dy=Dz$ (or $Xa=Xb=Xc$, where Xa and Xb are the pixel pitch of the x-y plane and Xc is the resolution of the depth of sample). The method can also be extended to the case where the side in Dz is not equal to Dx and Dy. Additional details of 3D imaging from 2D images with references to FIGS. 9 and 10.

For each image, at process 1310, the location 16 (see FIGS. 12B and 12C) from which the x-rays 30 are emitted relative to the subject 2 is moved in a plane 202 parallel to the plane of the detector assembly 14 and/or sensor 320. The x-ray source 12 includes mechanisms for such motion as disclosed herein. The location from which the x-rays 30 are emitted is referred to as the emitting location 16 in the remainder of the present specification. After moving the point 16, at process 1312, a different 2D image can be taken and recorded.

Primary x-rays and scatter can be separated in the 2D images prior to using the images. Scatter can be removed. Scatter images can also be used separately, for example, for material differentiation and identification and inspection for better visualization of low atomic z number materials or materials with similar atomic z numbers. Different separation methods employ different configurations of apparatus involving the x-ray source and the x-ray detector. At process 1314, 3D single or multiple beam x-ray microscopy with or without the above-mentioned other modalities can be obtained.

In subjects with low scattering properties, the scatter separation step can be omitted. In addition, when an x-ray thin beam is used to illuminate the region of interest, scatter separation can also be omitted.

Through processes 1302, 1304, 1306, 1308, 2D interferogram of various wavelengths x-ray that is separated by gratings with pixel pitch or even smaller distance between adjacent gratings may be formed on the detector to provide 2D images. At process 1304, an x-ray fan beam from an x-ray source can be split into two identical beams and dispersed into x-ray beams of multiple wavelength by energy dispersive gratings, each are a pixel pitch apart, or a fraction of a pixel pitch apart on a 2D plane 202. A beam that passes through the subject 2 forms an interferogram on the detector 320. Reference beams travel the same distance but do not pass through the subject 2. This can be done by a crystal or other beam combining mechanisms.

At process 1306, an interferogram of the reference beam with corresponding beams of multiple wavelength from different emitting locations can form on the detector 320. Image of each wavelength can form one 2D image. At process 1308, as image at each wavelength also represents an x-ray image formed from the input beam from a different emitting location on the plane 202, construction of multiple dimension x-ray images may be done through combining 2D images of different wavelength in real time with a single x-ray emission from the source 12. If the wavelengths used are close to each other, for example within 1-20 nm bandwidth or even less, variation in absorption level for the same material can be minimized. This is because the absorption characteristics are similar for each material amongst x-rays of various wavelength. Therefore, each 2D image of different wavelengths can be correlated to different locations and used to resolve unknown pixels in the third axis to construct multiple dimension images. In either case, variation in absorption level due to variation in energy or wavelength can be taken into account in calculation and derivation of unknown units or unknown voxels along the projected beam path. In one implementation, the measurement of a material or composite material at one wavelength or energy level is correlated with that of another energy level, and a database may be established as reference.

The methods of using the x-ray apparatus in FIGS. 12A-12C for 3D imaging can include the following general steps: (1) Calibration: (2) 2D imaging: (3) image scatter removal: (4) 2D functional imaging: (5) multiple dimension and 3D image measurements, calculation, synthesis and construction: (6) 3D functional imaging; and (7) actual and synthesized 3D, 2D, multiple dimension, 1D, point region of one or a few pixels, and/or time stamped presentation of selected regions or components or targets. Steps 1, 2, 3, 5, and 7 can be used for high-resolution 3D imaging. Steps 3 and 6 may be optional steps, the employment of which depends on the application. Additional details are described in International Patent Application No. PCT/US2019/022820.

(1) Calibration.

Before performing any image acquisition of the subject, an image is taken for each x-ray source location. A detector cell (i, j) can receive a signal passing through various subpixels and each subpixel transmission can be calculated. For example, each subpixel can be half of a pixel. Assuming that within each pixel (a thin column), the x-ray attenuation is uniform and proportional to the volume. This geometric calculation can be done in advance. The data from the geometric calculation can be stored or a general formula can be derived to represent the data.

After the 2D images are taken, an equation system, m×n×p equations, with m×n×p variables can be solved. Each location of the x-ray source can produce an image of size m×n and there can be p layers. The linear equation system can be solvable by either an iterative method or a matrix method.

Three situations can be considered for the calibration. When the region of interest of the subject is located well within the x-ray imaging area, the completeness of the 3D image can be guaranteed by solving the linear equation system. However, when the region of interest extends beyond the imaging area in one dimension or in two dimensions, additional calculations may be required.

Assuming that region A is the region of the interest and region B is adjacent to region A, data in the region B would be needed for the second and third situations described above in order to acquire projection data of the region A. As the region A is surrounded by region B, by conducting a two-step scan, information in the region B can be accurately gained without further extending to a larger region.

Alternatively, the first step may be sufficient for most applications, especially in cases where newly introduced unknowns outside of the region of interest is sufficiently small compared to that of the number of unknowns in the region of interest.

Alternatively, to resolve the newly introduced unknowns in the region outside of the region of interest, as each new unknown or each set of unknown voxels are introduced, the region of detector where the measurements of the projected path of the unknowns need to be resolved to completely reconstruct the multiple dimension or 3D image of the region of interest are done can include those pixels which also read projected paths involving newly introduced unknown voxels. As the x-ray emitting position moves, more and more unknown voxels are introduced, more and more pixels on the detector outside of the initial m×n area region are read. To minimize number of pixels to be read on the detectors, therefore minimizing the number of images to be taken, and radiation level, the x-ray emitting positions which are adjacent to each other can have a minimum distance or optimized spatial position so that the overall total spatial dimension or distance from the positions furthest apart is minimized.

In an example of the two-step approach, in the first step, by using a two-directional move, the detector can acquire data along the x direction and y direction. The data can include NX data points and NY data points. N is the number of emission positions on any of the x, y, or z plane. Region A has pixel number NAX×NAY. Region B has pixel number NBX×NBY. Therefore, the total projections for NX and NY would be (NAX+NBX) (NAY+NBY). N^2 is the thickness or unknown pixel in the z axis. If movement is made along the Z direction, that movement can likewise be divided into NZ data points.

In the second step, the scan step can be refined so that the NZ projections are all contained in Regions A and B. For example, instead of integer multiples of the detector pixel pitch, the scan step can include a fraction of the pixel pitch size (such as ⅒ of the pixel pitch size) within the region of interest. With each new scan, no unknown pixels would be introduced but more existing unknowns can be solved. It is preferred in some cases, that the region to be illuminated in second step imaging is restricted only to the region of illumination path which involves the newly introduced unknowns in the region outside of the region of interest. Dimension or selected leafs of the collimator may be used to selectively limit the x-ray cone beam, so only beams illuminate regions involving the newly introduced unknown voxels are transmitted. The processor can then solve the equations and reconstruct the 3D image, that will give an accurate solution.

(2) 2D Imaging.

Multiple-dimension images can be generated from 2D images taken from at least two different positions of the x-ray source. The processor can determine the geometry and dimensions of the subject or the region of interest in the subject. If such information is predetermined or preset, this step can be skipped. The x-ray source can illuminate the subject with x-rays from the x-ray source at a first location and read the image at the detector assembly. The processor can then move the x-ray source to a second location in an XY plane parallel to the XY plane of the detector assembly. The displacement from the first location to the second location can an integer multiple of the pixel pitch as described above. When the displacement is for example, one pixel pitch, a projected image of the region of interest of the subject differs from the previous projected image by extending the outer edge of the image of the region of interest by one line of pixels on the detector assembly along the axis of the change of direction. In other words, moving the x-ray source location between two images generates two different projected images for a region of interest of defined dimensions, but the location of the projected images on the detector for the same region of interest is extended by one pixel cell in the direction of shift. The x-ray source can illuminate the subject with x-rays from the x-ray source at the second location and read the image at the detector assembly. This process can be repeated for as many different locations of the x-ray source as needed in order to produce a 3D image of the desired resolution in the Z axis.

(3) Scatter and Primary X-Ray Separation.

In this step, the scatter signal can be separated from the primary x-ray image in each of the 2D images acquired above. Any suitable scatter removal or scatter and primary separation methods, such as those described above, can be used.

The geometry or dimension of region of interest in the subject can be determined. In some cases, such information can be predetermined and stored for use by the processor. Based on the thickness in the third axis perpendicular to where the two dimensional plane x-ray source is at, the number of positions the x-ray emitting positions need to be in order to derive the complete 3D image can be determined. The number of positions P=Thickness of the subject or region of interest/pixel pitch or resolution along the thickness or depth of the subject or the region of interest=total number of x-ray source positions=$n^2$ if the x-ray emitting positions are designed to be a 2D plane. Such information may also be predetermined.

The x-ray source or x-ray emitting position as disclosed herein can be moved at least P times in a two dimensional space, referred to as "first positions", in each linear axis, at least n possible positions, or at least $\sqrt{n^2}$ positions in each axis. The unknowns units or unknown pixels referred here are used to describe a set of unknown pixels in a 2D sliced region described by m×n typically. In a case where the set of unknown pixels are referred to a 2D sliced region larger than m× n, the total number of unknowns or unknown sets are still $n^2$, which means only $n^2$ positions or n2 images are needed in order to complete the construction of 3D image.

The resultant 2D picture data can be combined to solve and determine unknown pixel in the third axis for the subject or region of interest, in a linear equation system m×n×p as disclosed herein. The new unknown voxels ware created from x-ray emitting positions at the first position.

To resolve the newly introduced unknown units or voxels outside of the region of interest with the total area of m×n×p, the following are optional examples.

If the number of newly introduced unknowns are sufficiently small compared to the region of interest, P images of m×n in 2 D dimensions are sufficient to describe the region of interest.

Optionally, additional images are taken at x-ray emitting positions on the x y plane differ than the first positions, referred to as "second positions", for example, in the same x y area of the first positions, however, the emitting location is centered at a location differ from the first positions. Or the distance between second positions may be less than the resolution of the depth or the distance of the adjacent first positions. Each movement step of second position is finer than that of the first position movement. Optionally, the x-ray beams are steered or collimated so that only beams that illuminate the regions of newly introduced unknowns are transmitted. 2D measurements of a limited dimension are acquired to further resolve the unknowns.

Optionally, as stated before, as x-ray emitting position moves in the area of first position, additional pixels on the 2D detector on the outer edge of the original 2D regions on the detector which are m×n pixels, are read to include the measurements of unknown regions outside the region of interest. Preferably, only when the illumination path involves newly introduced unknowns with the unknowns in the region of interest, pixel regions on the detector measure such projected path signals are read. As a result, more known pixels are read as the new unknowns are introduced. Still only P images needed to complete the solving of the linear equations involving the unknown units in the 3D volume of region of interest.

Additional details of separation of the primary and scatter images are summarized in FIG. 15G.

(4) 2D Functional Imaging.

Functional imaging can be performed as modifications to the 2D imaging obtained in the above steps. Functional imaging is defined as providing information in addition to the location or 2D visualization taken with a single-energy or dual energy or multiple energy x-ray source, with or without scatter and primary x-ray separation. Examples of functional imaging methods and systems are described below. Each example is independent of the others and may be combined to provide more information as needed for applications.

As one or more full field x-ray images are taken, through 2D and/or 3D image analysis, some with scatter removal, or some with material decomposition or further other types of quantitative and qualitative analysis on the images, some with combined scatter removal and material decomposition quantitative analysis. Examples can include analysis of various absolute physical properties, movements, location and density, and relative qualitative and quantitative measurements of components in the imaged subject, a certain area of interest (such as the region 4 as illustrated in FIGS. 12A-12C) can be identified for more detailed investigation.

The additional investigation can include material decomposition and different material imaging (such as described above). Decomposition includes the process by which single, dual- or multiple-energy x-rays decomposition methods are used to quantitatively analyze and separate components in the subject based on atomic z numbers and/or distinct x-ray measurable property or properties of the different components.

As described above, the x-ray source can emit two x-ray pulses from each x-ray source location: a high-energy pulse at an average energy level H, followed by a low-energy pulse at an average energy level L: or three x-ray pulses from each x-ray source location: a high-energy pulse at an average energy level H, followed by a medium-energy pulse at an average energy level M, followed by a low-energy pulse at an average energy level L. In each configuration, each pulse has a single, essentially unchanging energy spectrum. In another configuration, four or more energy pulses can be emitted from the x-ray source.

Rather than the 2D detectors described above that may not discriminate between different energy levels, the detector assembly can include energy-sensitive, photon-counting detectors and PMTs and Silicon Shift Detectors or Visible detectors combined with scintillation layer upstream. These detectors may be used with a conventional x-ray source, or with a time of flight x-ray source, such as a picosecond x-ray source, to collect the primary x-ray signal for densitometry and quantitative analysis and separation of images for different components or materials or substances with varied atomic z numbers and/or x-ray measurement differentiable properties. With a conventional x-ray source, the energy-sensitive photon-counting detector can replace the front detector, the rear detector, or both in the dual-detector plus beam selector assembly to ensure primary x-ray and scatter separation while allowing dual-, triple-, or multiple-energy and spectrum-energy imaging and absorptiometry of different materials or components in the subject.

Material decomposition may be accomplished by other material decomposition methods than those described above. For example, the method can include a dual energy method where imaging data is decomposed into at least one basis image representation, based on a model where a combination of at least two basic functions is used to express a representation of at least one linear attenuation coefficient. Any other suitable CT or x-ray based material decomposition methods in single energy, two or more energy methods may be adopted here. Such a method may not require scatter removal, for example, when the x-ray beam is small in diameter, in the mm or below range.

Functional imaging can be improved when primary x-rays and scatter are separated. Primary x-ray quantitative measurement can be used for quantitative analysis and densitometry of material and components in the subject without the need for mathematical decomposition. When there are multiple materials to be differentiated, measured, quantified, and/or imaged, a dual or multiple energy x-ray system may be used. An example of the beam absorber used in the x-ray multiple detector assembly is shown in FIG. 6. The beam absorber may be placed in between the x-ray source and the subject or between the detector and the subject.

In addition, preferably the exact same materials and composition of the material to be imaged can used for calibration with defined spatial as well as multiple energy dependent measurements in order to calibrate of each material to be imaged, as described above. For example, in characterization and inspection of biohazard or explosive materials, previous identified material or chemicals can be used to calibrate in the form it appears in the subject, such as powder, liquid, or solid. Such calibration can be done in presence of other materials, such as luggage material or clothing and other materials common in luggage. In addition, when there are more materials, for example, in breast imaging, the dual energy system can also be utilized to differentiate an additional material, such as for micro-calcification, stent, catheter, foreign subject, surgical tools, or unidentifiable material in the subject.

Additional application can include using triple energy and spectral energy system with greater than two energy level, in chest imaging for identifying catheter, stent, microsurgical tools, sometimes may be described as DRC, separation of bone from soft tissues, fat and lean tissue, and blood vessels and nerve (which may be labeled with contrast agents to be further differentiated from other soft tissue and bone). Foreign or unique components can be differentiated and identified based on calibrated value or looking up in a preexisting database (such as described above) or library, or a simulated value based on historic data (such as described above). Such components can be separated from the rest using software algorithm. Separation of DRC may use additional second order approximation as disclosed herein for separation of microcalcification, as an additional step to a dual energy decomposition based material decomposition method. Material decomposition of 1D, 2D or point region, described as a region comprising one or a few pixels, in which the measurement is low or without scatter, may also be included.

Spatial presence pattern of multiple subjects can be separated from those who have different but consistent spatial pattern. For example, a catheter is smaller and less continuous and only occur at certain location and more rare than soft tissue and bone. For example, in surgical guidance of orthopedic minimum invasive surgery, biopsy of tumor, the triple energy and spectral x-ray imaging system can differentiate bone, soft tissue and blood vessel and nerves. Surgical tools or sensors may be differentiated or decomposed from the background images composed mostly of organic materials using multiple energy imaging. The decomposition can be performed by recognizing the surgical tool or sensor's shape, size, discontinuous spatial pattern, and/or overlapping density, which can vary because of its presence compared to the overlapping tissue density measurements and composition. As the density value of the surgical tool or sensor compared to the background is identifiable and while overlapping with background tissues, the spatial dimension and density of the surgical tool along the projection line and its location within the composite background materials can be derived.

In radiation therapy, the area of tumor can be labeled with contrast agent or may have densitometry features or spatial features differ from that of normal tissue. Such regions can be identified with accuracies as good as in the submicron range in order to guide radiation therapy. The radiation dosage can also be adjusted by limiting the region of interest to the specific tissue or rare event or feature location, thereby limiting the x-ray exposure area to the region of interest, which may be the area where the tumors are at, acquiring high resolution real time 3D images of components, for example, rare cells, tumors, diseased tissues, materials, as well as the background images for localization and visualization, in the selected region of interest in real time, and/or proving more accurate surgical guidance with lower radiation level. In addition, such imaging methods allows for more accurate and precise surgical or radiation therapy pre-operation planning and operation guidance, especially useful when integrated with a robotics based surgical system. Additional details of tracking and contrast agents are described further below.

The additional investigation can also include interferometry, with or without scatter removal. With an interferometer (which can be any suitable existing or future interferometer), 2D images of absorption, dark field, and/or phase contrast images can be obtained. Such images can be used to construct a 3D interferogram.

The interferometer operates by emitting x-rays through a phase grating that introduces an interference fringe at specific distances downstream. When a subject is placed in the beam path, the subject modifies the observed interference pattern via absorption, refraction, and/or small-angle scattering. Once these signals are read by the detector, the properties of the subject and its components can be determined algorithmically.

In one example, Talbot-Lau interferometry can be used in order to have a larger field of view. In Talbot Lau interferometry, a beam-splitter grating (G1) can be placed in the beam path between an X-ray source(S) and detector (D). Due to the fractional Talbot effect, an intensity distribution (I) revealing the periodic structure of the beam splitter grating can occur in certain distances behind the grating. If a subject (O) is placed in front of the beam splitter grating, the intensity distribution changes due to the absorbing, scattering, and refractive characteristics of the subject. The fractional Talbot effect requires spatially coherent radiation. To meet this requirement, a microfocus X-ray tube with a sufficient small focal spot can be used. Alternatively, a slit mask (G0) can be placed in front of the focal spot of a conventional X-ray tube. This mask absorbs certain parts of the x-ray beam and thereby creates spatially coherent slit sources. Each of these slit sources can generate a self-image of the beam splitter grating.

By exploiting the Lau effect, these self-images can superimpose to a sharp intensity distribution. In general, these interference fringes are too small to be resolved by a conventional x-ray detector. To overcome this challenge, an absorbing analyzer grating (G2) with the same period as the interference fringes can be placed at the plane of these fringes. This analyzer grating can be used to sample the periodic intensity distribution by shifting the analyzer grating stepwise in its plain perpendicular to its grating bars. Variation of the aforementioned interferogram method, and its derivatives, phase contrast imaging, dark field imaging based on the imaging method described herein are also part of the present disclosure.

In order to generate coherent x-ray beams, the interferometer may use a pixilated x-ray source. The interferometer can also have a diffraction grating, which is MEM-based, crystal-based, or employs an acoustic modulated crystal grating. An example of a suitable diffraction grating with tunable arrays of MEMs is illustrated in FIG. 15E.

Additional details of 2D functional imaging are summarized in FIG. 15H.

(5) 3D Image Synthesis, Construction and Calculation

The processor can use a conventional computing tomography imaging algorithm to derive three dimensional image based on the above-described 3D combined data and the solution of the linear equation.

In addition, x-ray emitting positions can be in 6D space. When the x-ray emitting position moves in the x, y z linear axis described 3D space, or a x-ray source have multiple different x-ray emitting positions in 3D space relative to the subject, different set of illumination paths are generated at each emitting location, as illustrated in FIG. 33. In each x-ray emitting position, such as illustrated in 12-1, 12-2, 12-3, 12-4 and 12-5, a different set of projected paths IP 12-5-1 and IP12-5-2 on the region of interest 16 can be illuminated. Each illumination path can involve at least one column of voxels, either in different combination of various voxels out of the unknown voxels to be solved or different number of voxels. For example, at emitting location 12-5, beam IP 12-5-1 illuminates 4 voxels, Voxel #X3Y4Z1, #X3Y4Z2, #X3Y4Z3, #X3Y4Z4: IP 12-5-1 illuminates 4 voxels as well, #X1Y4Z1, #X1Y4Z2, #X1Y4Z3, #X1Y4Z4. As the emitting position moves to 12-4, the illumination path generated can project along new sets of voxels in the volume defined by coordinate numbers in the x y and z axis. For example, in addition to the 2D plane example as described herein for x-ray emitting positions, the region of emitting positions can be within a 3D volume as well. For instance, if the total number of images to be taken is 1000, the total minimum volume of x-ray emitting position movement to minimize number of new unknowns introduced outside of the region of interest, may be 10×10×10. The unit of such volume can be the resolution desired for the third axis. The x-ray emitting position may move linearly in the X, y, z axis.

Each unknowns here can refer to a set of unknown voxels at each layer along the depth separated by a distance in integer units of resolution desired for the third axis.

In summary, to derive a complete set of 2 d images for construction of a complete 3d image, and/or locating a 6D spatial position of the 3D volume of an component in a region of interest by adding spectral measurements, the following steps are included:

A two-dimensional (2D) x-ray detector downstream of the imaging subject, wherein the system is configured to obtain multiple dimension and/or three-dimensional (3D) images of the subject by moving or steering x-ray emitting positions or the x-ray source in at least two axes of 3D space, the 3D space including positions in x-y-z axis and obtaining 2D x-ray measurements.

Distance between adjacent x-ray emitting position is the dimension of the resolution needed in the third axis, and/or the minimum distance needed so that the two positions generates a set of x-ray beams, each set illuminates different voxel paths in the region of interest.

Distance between adjacent x-ray emitting positions is 1 pixel pitch or integer multiples of pixel pitch, or less than 1 pixel pitch Total number of emitting positions, or the total number of 2D images taken needed to construct the 3D image is the depth of the third axis divided by the resolution of the third axis.

In the case of moving in x and y dimensions, the total movement angle from emitting positions furthest apart is less than 0.1 or 0.1 or between 0.1 to 1 degree.

In case of moving in all three linear axes, x, y z, the total movement angle from emitting positions furthest apart long each of the axis, is less than 0.0008 degrees, or 0.0008 degree, or between 0.0008 to 0.5 degrees or 0.5 degrees to 1 degree.

For each 2D measurements, dual energy and spectral energy measurements may obtained by using x-ray source of broad spectrum with energy sensitive detectors, photon counting detectors, or photodiodes or spectral measurement assembly involving energy dispersive grating and spatially sensitive detectors. Material decomposition separate one or more component out of background of the subject image or background image of region of interest or an external spatial sensor or marker.

As 3D volume is resolved in x, y and z axis for the component and region of interest, the relative 6D or time sensitive 7D spatial position of the component to the background region of interest may be derived by comparing images constructed from first measurements and those of second or live measurements at a distinct time frame.

(6) 3D Functional Imaging

The 3D functional imaging step may incorporate any of the 2D functional imaging techniques described above.

(7) Actual and synthesized image of selected regions in 3D, multiple dimension image including multiple sliced 2D image in 3D, 2D, 1D and point region and their presentation with or without varies high resolution and low resolution image background The processor can provide a multi-axis representation at various resolutions or have 2D images combined with multiple dimension representation for both the 2D and 3D images for the various components, the region of interest, and/or the subject.

When such a 3D imaging method is implemented in x-ray microscopy or x-ray microscopy combined with x-ray absorptiometry, the x-ray optics may be modified to extend field of the view, and/or optimized in terms of its intended function and effect with x-ray coming out of varying emitting positions. The modification and/or optimization can ensure each projected 2D image measured at varying x-ray emitting positions from the source is comparable in terms of image quality, accuracy, sensitivity, and signal to noise ratio.

The x-ray apparatus disclosed herein can include x-ray absorptiometry at two or more energies, x-ray microscopy of transmission, diffraction, fluorescence, and/or interferometry. X-ray optics required for the above techniques can therefore be moved into the location for investigation of the region of interest 4 such as illustrated in FIGS. 12A-12C with the x-ray full field imaging detector present, or moved out of the field of the view. The x-ray optics can be placed with the x-ray full field imaging assembly as such apparatus are not in the beam path of x-ray full field imaging, for example, downstream of the full field x-ray detector.

For example, in the case of x-ray absorptiometry, the x-ray optics can include grating and spatial sensitive detectors and other related optics to disperse the projected x-ray beam passing through the region of interest and the full field x-ray imaging detector into different energy or wavelength levels and measure signals at various energy levels and/or at different spatially variant locations.

Using three-dimensional (3D) microscopy to produce an image of a subject using x-ray optics and a non-rotational method, the method can include a number of steps as described above, some of which are optional, such as calibration, acquiring 2D images from at least two different x-ray source locations relative to the subject, processing to product 3D images from 2D images, processing of the 3D images, and outputting the acquired information.

The method can provide a rapid, high-resolution 3D imaging involving x-ray optics as in for example x-ray microscopy and full field x-ray imaging. Each 2D x-ray microscopy image can be formed by images combined by those formed of multiple microbeams or sometimes, what is referred to as structured beam x-ray imaging. X-ray absorptiometry and x-ray spectroscopy can be combined with 2D or 3D x-ray microscopy. Preferably, measurements of multiple channels using x-ray absorptiometry or spectral x-ray measurements increase the field of view, can be combined with multibeam x-ray microscopy, especially when the x-ray source is polychromatic.

2D or 3D full field x-ray imaging combined with point, 1D, 2D or 3D x-ray absorptiometry and/or spectral x-ray measurements and 2D or 3D x-ray microscopy of single or multiple beams can be applied in structured x-ray microscopy imaging using multiple x-ray beams distributed spatially from each other.

The combined techniques can be used for tracking movement, physical property changes in morphology, dimension, conformation, shape, thickness and certain chemical characteristics and density, presence, interaction, location, flow dynamics, flow direction, kinetics of the components or region of the interest and the subject, in some cases, relative to each other, or in some cases, stand alone, in space (2D, 3D, or other multi dimensions) and time. The combined techniques can be used for observation and monitoring of x-ray detectable motion, event and physical phenomena, surgical guidance of human operated surgeries, robotics surgeries, biopsy and monitor or guidance or diagnosis remotely, in some instances, as in tele-medicine or in remote monitoring of manufacturing assembly line, inspection line and security applications. Each x-ray measurements and image may be time stamped for tracking and monitoring.

Accordingly, as shown in FIGS. 13B and 13C, an x-ray absorptiometry can be combined with 2D and 3D full field imaging, and/or 2D and 3D microscopy. The x-ray 3D microscopy apparatus and methods can be faster and lower in radiation than conventional 3D imaging modalities. Scatter removal methods, for example, when used with structural illumination configuration can performed in these apparatuses and may be combined with motion configuration used in 3D imaging to generate faster 3D images, especially of selected regions on the subject.

Optionally, 3D image acquisition and generation can also be based on scanning-beam digital x-ray SBDX. A scatter free technology can be applied to this method to derive an image with improved image quality.

The scanning-beam digital x-ray SBDX uses an electromagnetically scanned electron beam incident upon a large-area transmission style tungsten target. The electron beam can be raster scanned over a 2D array of source focal spot positions, for example, every $1/15$ s or at a different frequency. A multi-hole collimator can define a series of narrow overlapping x-ray beams convergent upon a 2D detector. The geometric relationship among the narrow beam projections can be constrained by the fixed geometry of the SBDX collimator and the fixed detector position. A typical SBDX system geometry can be as follows:

Source-detector-distance (SDD): about 1500 mm
Source-axis-distance (SAD): about 450 mm
Focal spot positions: about 71×71 mm
Focal spot pitch: about 2.3×2.3 mm
Native detector array: about 320×160 mm
Native detector element pitch: about 0.33 mm
Detector bin mode: about 2×2 mm SBDX has an inherent tomosynthesis capability due to the use of inverse geometry beam scanning. A live display analogous to conventional fluoroscopy can be generated using a GPU-based real-time image reconstructor. Each displayed 2D image frame can be generated through a two-stage reconstruction procedure. At the first stage, a shift-and-add digital tomosynthesis can be performed to generate a stack of, for example, 32 single-plane images with, for example, a 5 mm plane spacing. The pixel centers for the stack of tomosynthesis images can be defined such that a fixed pixel position (for example, row 100, column 100) in the stack corresponds to a ray originating at the detector center. At the second stage, a gradient filtering procedure can be applied to each of the single-plane images to identify local regions of high sharpness and contrast. The final 2D "composite" image can be formed by selecting, for each pixel position, the pixel value from the single-plane image with highest contrast and sharpness. Due to the geometry of the tomosynthesis pixel centers and the compositing procedure, the final composite image can be viewed as an inverted "virtual" cone-beam projection of the in-focus subjects in the subject volume. A virtual SBDX projection can originate at the center of the detector and fall on the source plane. The pitch of the virtual detector elements at the source plane can be, for example 0.23 mm based on the set geometry.

Examples of 3D Imaging Using K-edge Filter

An x-ray measurement apparatus 90 capable of determining qualitative 3D x-ray images of a region of interest in a subject 2 is illustrated in FIG. 9, which incorporates any of the features of the apparatus 10 in FIG. 1A. The relative spatial position of the x-ray source and/or the x-ray emitting position and/or the x-ray radiation are movable relative to the subject. The x-ray source and/or x-ray emitting position and/or x-ray radiation can be configured to move in dimensions same or similar to the resolution desired for the z axis, for example, less than one pixel pitch, or at one pixel pitch or multiples of pixel pitches of the detector, between two consecutive measurements and/or the distance between the most adjacent x-ray sources. The x-ray source and/or x-ray emitting position relative to the subject can move into positions defined as "first positions" in a 2D plane (which may be parallel to the detector) or a position in 6D space through linear movement or arc movement.

The processor of the x-ray measurement apparatus 90 can be configured to resolve the detected x-ray radiation into a three dimensional image by solving a system of linear equations.

Movements in a six-degree of freedom, each by one pixel or one voxel or in a unit of resolution desired for the depth, each generating a different set of illumination path through the unknown volume and introducing a one or very small number of unknowns, can lead to a number of 2D measurements based on which a complete 3D volume unknowns may be resolved.

If the pixel pitch dimension is pp per one pixel (um), the x-ray source to detector distance is SID (um), the thickness of the region or component of the interest or the subject is P (um), the total volume traveled, or the total area traveled, or the total traveled is PP.

The number of pixels or smallest unit resolved in the 3D dimension along the thickness NP is NP=P/PP. The number of data points or x-ray emitting position DP is DP=P/PP. The number of images taken NI is NI=P/PP.

The minimized total angle in which the emitting source is located to provide the smallest number of unknowns and complete 3D images in case of a 2D only area (the travel of the emitting x-ray source position) is TA=ARCTAN (square root of DP×unit of smallest revolving volume in 3D imaging/SID), or TA=ARCTAN (square root of DP×PP/SID). The minimized total angle in case of the x-ray emitting positions being in a 3D space is TA=ARCTAN (cubic root of DP×PP/SID).

When the x-ray source and/or x-ray emitting position relative to the subject moves into positions defined as "first positions", the number of newly introduced unknowns can be reduced by reducing magnitude of each movement and a total movement area or total movement space. Movements between the first positions or the selection of the first positions can be such that the measurement generated on the detector may resolve at least one or more unit of unknowns in the third axis.

The measurement of newly introduced unknowns may be derived by additional scans in the newly introduced regions. X-ray beams can selectively generated or transmitted using collimator illuminating only the newly introduced regions. The new x-ray emitting location can be defined as "second positions." The second positions may be in the same pixel pitch steps, but the center of the steps may be different from the first positions, or be moved in a distance other than distances between first positions.

The measurement of newly introduced unknowns may also be derived by recording of detector measurements in the projected paths of the illuminated newly introduced regions on the detector. For example, every time the x-ray emitting position is moved by one pixel pitch on an x-y plane, at least one additional pixel cell, or a line of pixels with a pixel width of one pixel can be taken into account in deriving information required for multiple dimensional imaging of the region of interest. As shown in FIG. 9, the original x-y area on the detector that receives signals from all projection paths passing through the region of interest or the subject 2 can include an m×n matrix of pixel cells. The newly introduced regions, the detector region right below the region of interest on the detector, can now include a (m+1)×n matrix of pixel cells for x-ray measurement when the x-ray emitting position is now moved to its next adjacent position relative to the original position for 3D image reconstruction of the region of interest.

The additional measurements from the added pixel regions can be used to solve additional linear equations involving the newly introduced voxels. The number of unknown units along the axis perpendicular to the detector may not have changed so the total number of linear equation is now (m+1)×n×P, where P is the depth in the z-axis. The calculation assumes that the x-ray source moves P positions where each unit of P is X, and for simplification purpose, Xa or Xb is the resolution of the pixel, or the pixel pitch of the detector. Xc is the resolution of the depth of sample needed to be resolved. The resolution of m or unit measurement of m is Xa, and in general, it is the pixel pitch that is the same as Xb, the unit measure of n. In this case, Xa=Xb=Xc. Then the total area on the detector to be measured is (m+√P)×(n+√P) for the region of interest. However, it is preferred that one additional pixel at a time or one additional pixel line can be added at a time. Such additional measurements can be taken into account so that the minimum number of pixel or cells can be used in order to solve the unknown voxels in the regions of interest. Not all of the total area, which is calculated as (m+√P)×(n+√P), may be utilized for the measurements needed to solve the linear equations.

There are instances when Xc is not the same as Xa, which means that the unit of P is not the resolution of the pixel pitch. When Xc is greater than Xa, as the x-ray emitting location moves to its most immediate adjacent x-ray emitting location from the original position, if Xc=2Xa, then m+2 will be read, or in another words a total of (m+2)×n pixels will be read. Alternatively, due to the small number of new unknowns introduced, the total number of x-ray images measured may not be affected by the newly introduced unknowns.

When the x-ray source is moving relative to the subject in the 2D, or 3D or 6D space, such as in an arc or a straight line, such movements may be translated to be equivalent to a movement on a 2D plane, which may be parallel to the detector, by calculation, calibration, and/or predetermined measurements, or by using additional hardware such as mechanical mechanisms such as a motorized mover, electric, or magnetics, or electro-optical mechanisms, electromagnetic mechanisms, or x-ray optics, including but not limited to mirrors, beam splitters, total internal reflection capillary tubes, MEM, gratings and crystals, or any combinations thereof.

When multiple regions of interest are distributed spatially in the subject 2, the regions may be scanned simultaneously, in a synchronized manner but with different frame rates, or not synchronized. The multiple regions may be measured with the same resolution or different resolutions.

For a source-image distance (SID) of around 100 cm, the furthest distance of x-ray emitting position is 7 mm from the initial x-ray emitting position, with a sample having a depth of 25 cm in the Z-direction, perpendicular to the detector, a maximum of 0.4 degree of a scan angle may be required to reach a resolution of 100 um. Other combinations of parameters are provided in the table below.

| Movement Region | Depth of Region of Interest P = 25 cm, SID = 100 cm Resolution in Depth vs Resolution on the X and Y plane parallel to the detector Resolution (um) Xc | Xc ≠ Xa 500 | Xc = Xa or Xc ≠ Xa 100 | Xc = Xa 1 |
|---|---|---|---|---|
| 2D | Furthest distance from two emitting positions (mm) if the emitting position is scanned in two dimensions, Df | 15.7 | 7 | 0.7 |
| 2D | Angle of total movement (degree) = arctan (Df/SID) | 0.9 | 0.4 | 0.3 |
| 2D | Total emitting positions (P/Xc) | =2500/5 | 2500 | =250000 |
| 2D | Total emitting coordinate on each axis ( square root of total emitting positions) | 23 | 50 | 500 |
| 3D | Emitting Positions moves in three axis perpendicular, x y z | | | |
| 3D | Furthest distance from the original position (mm) if scan in three dimensions, along each axis Df | 4 | 1.4 | 0.063 |
| 3D | Total Emitting Positions (Total number of images) (P/Xc) | =2500/5 | 2500 | =250000 |
| 3D | total emitting position along each axis ( cubic root of the total emitting positions) | 8 | 14 | 63 |
| 3D | Total scan angle (degree) = arctan ( Df/SID) | =0.23 | 0.08 | 0.0036 |

For material decomposition using single and/or dual or multiple energy measurements and analysis or spectral imaging described herein, in complete 3D imaging, other multiple dimensional imaging, and/or tracking (or surgical guidance), the following modalities can be used:

3D (as described herein or using any other 3D method of utilizing flat panel detectors);

2D imaging of the selected region of interest;

1D measurement, for example, using two or more pixels along a linear spatial position on the detector; and/or Point or small region measurements, for example, one or more spatially distributed groups of region with one or more pixels on the detector.

For tracking, a first set of measurements or data points or 2D images or multiple dimension images, or complete 3D images can be acquired prior to tracking. Alternatively, such first data set may be derived from conventional CT, quantitative tomography, 3D imaging method of the present disclosure, or other modalities, such as MRI, SPECT, PET, Optical imaging or measurements, spectroscopy, Photoacoustic Imaging, and/or Acoustic Measurements. One or more the first set of measurements can directly used or material decomposed to a set of data information describing an x-ray measurable characteristics and substances, and compared with the original images or first images or synthesized images from first images of region of interest, to track components or substances in the region of interest or the imaged subject itself in six dimensions.

As shown in FIG. 10, a coded k-edge aperture 15 may be used for fast energy and/or spectral sensitive measurement, preferably in sensing and tracking measurements using 2D or space distributed 1D or space distributed point measurements when there is minimal or no scatter interference. Filters can be placed in the aperture 15 between the x-ray source 12 and the subject 2 or placed between the subject 2 and the detector 14. The aperture 15 can be combined with an x-ray collimator 17, with two or more x-ray transmissive regions. The collimator 17 can be placed between the x-ray source 12 and the K-edge coded aperture 15. The collimator 17 may be moved, or the position of one or more apertures on the collimator 17 may be adjusted by moving the collimator 17 with an actuator, by using an anode which has an adjustable x-ray emission location, and/or by moving or rotating or programmed controlling, such as in a field emission nanotube x-ray source or a metal liquid jet source.

The coded aperture 15 can be a K-edge coded aperture. The K-edge can refer to an x-ray absorption edge. When the incoming x-ray beam has more energy than the K-shell-binding energy of an atom, there can be a sharp increase in the x-ray attenuation coefficient. A pixelated K-edge coded aperture structure 15 can be a structure that has a filtering aspect and a pixelated coding aspect. The filtering aspect and the pixelated coding aspect can be performed by a single structure including a plurality of apertures having at least one K-edge filter incorporated therein. Alternatively, the pixelated K-edge coded aperture structure can include a first structure for example, a patterned structure for pixelating the X-ray beam(s), and a second structure, for example, a K-edge filter structure for filtering of the X-ray beam(s) that is separate from the first structure. One or more kedge filters in sequence may be placed in the same beam path.

The x-ray beams can include quasi monochromatic beams or monochromatic beam at each pixel. The beams can be collected by a detector, which can be, for example, an energy sensitive detector, a pixelated energy sensitive detector, a detector with one or more energy sensitive pixels cells or photon counting cells, a spectroscopic detector, or a spectrometer.

When Xa or Xc is large enough to have both bone and soft tissue in 3D imaging of a region of interest, the x-ray apparatus 90 can better image the partial volume regions of the subject or the border region of two materials or substances, for example, at the interface of bone and soft tissue. After a first run of scan, a 3D image can be constructed. Due to functional imaging and material decomposition, the thickness of each tissue can be estimated from 2D images. However, as 3D measurements are established, the measurement can be further improved. If the results are still not satisfactory, higher resolution measurements of the selected region can be made to further improve the results. In this case, the m×n region can be limited to a region of interest much smaller than that of the subject. The detector used may have a higher resolution. A detector of the same or a much smaller form factor, and/or having a smaller pixel pitch or higher resolution can replace the flat panel detector 14, or be placed downstream the flat panel detector 14 or upstream of the detector 14 and downstream of the subject. Additionally or alternatively, spectrometer or energy sensitive detectors or spectral measurement assembly module and/or x-ray detector of much faster frame rate or photodiodes, photo diode arrays, photon counting detectors may be placed upstream or downstream of the detector for spectral measurements and fast image acquisitions.

Measurements which give rise to images of the region of interest can be made under the conditions of energy perturbation, chemically perturbation, mechanically or electromagnetically or electrically perturbation, pressure/force perturbation, ultrasound/acoustic perturbation, magnetic perturbation, and/or gated measurements.

The imaging methods disclosed herein can include adding a time stamp to each x-ray measurement, including 3D images, 2D images, 1D images, and/or point or region measurements. The time information may be acquired from the computer program that can read the time on the computer, or from a server apparatus, or from a separate time apparatus that is synchronized with time standards provided by organizations such as NIST in real time. Date and Time labels and/or DICOM labels can be added on the measurements itself and/or stored in a database. In addition, for non-medical applications, image labels similar to DICOM labels, including identification number, part name, description, and/or the like, may be used. Such information may be kept in a database with key identifiers and searchable key words, or one or more identifiers or one or more keys. In addition, such date, time, and/or identifier labels can be stamped on to the image derived from x-ray measurements using a software. Optionally, serial images of multiple dimensions may be constructed from the 3D, 2D, 1D, and/or points measurements of spectral or single energy measurements at different times and displayed in time as if playing a video.

Such images, especially those with DICOM image labels or DICOM-like image labels can be sent to a picture archiving and communication (PAC) system to be viewed and analyzed by a software, for example, remotely. Viewing of such images in 3D, 2D, 1D, and/or point or region measurements may be in real time via a server with wireless communication protocols, such as the Internet, WiFi, Bluetooth, or intranet. In addition, a data file including compressed images or image set of one or more studies may be organized into two subsets of data files, one including a small file with one or more preselected images or measurements or selected data or report relevant to the measurement, and the second including the complete data set. As the data file is transferred via a network to be viewed, the first subset is transferred first and may be available to be viewed or previewed immediately by the viewer prior to the complete data set transfer, while the second subset or the rest of the complete data set is transferred as the next step. Such preview data may be available for viewing as a stored file, linked to the complete file.

RIS. EMS, PAC. Viewer, X-ray Modality Acquisition and Viewer System

A modality acquisition and viewer system of the present disclosure can include the hardware and software described herein. The system may be standalone or connected to a RIS server via intranet or internet or special remote connection network. The modality acquisition and viewing system may be connected to a remote viewer or a PAC system. A PAC system may capture patient information from EMS, or the EMS may update the RIS server and so does the modality viewer and acquisition system.

Quantitative Analysis & Material Decomposition

Current x-ray imaging does not have the capability of obtaining a 2D projection x-ray image at the same time measurement of density information in the region of interest in a specific component or tissue. Accordingly, multiple x-ray images have to be taken at various times. In some applications, the CT scanner, MRI, Bone Scan, and General X-ray images have to all be taken in order to form accurate and timely diagnosis.

Relative density and images of area of interest within one component compared to the rest of the component, and/or relative density and image of a different component in the area of interest adjacent or relevant to that of the first component, may form indicative information for disease diagnosis and/or material composition characterization or identification. The ability of monitoring such information in time using a 2D x-ray apparatus may improve efficiency in early diagnosis of diseases. The quantitative 2D flat panel x-ray system disclosed herein can replace CT Scanners and be applicable to all disease types diagnosable with conventional CT scanners. In addition, the 2D x-ray apparatus disclosed herein can provide motion-based and/or fluid flow-based characterization in real time, enabling bio-fluid based disease diagnosis and monitoring, and/or other treatment-related activities.

The 2D x-ray apparatus disclosed herein can also provide a combined quantitative and image analysis of individual materials in a subject, in time and/or space. The apparatus can correlate the image, densitometry, and/or composite analysis (such as using artificial intelligence software) within a single material of the subject having two or more materials. The 2D x-ray apparatus disclosed herein can also separate three or more materials, which may be overlapping to a certain extent, of different atomic z numbers or x-ray measurable or differentiable properties such as in cases of visualizing blood vessel and/or nerve tissues separately from bone and/or other software tissues in surgical guidance, and/or or separating tissues (such as diseased tissues or tumors) which are labeled with antibodies conjugated with various contrast agents or materials of x-ray differentiable properties.

Example applications of the apparatus disclosed herein can include cancer diagnosis (localization of suspended cancer cells, stem cells, rare cells and foreign subjects), circulatory system diseases and conditions (such as coronary artery disease (atherosclerosis), blood vessel aneurysms, and blood clots), neurological disorders including spinal conditions, herniated discs, epilepsy, encephalitis, spinal stenosis (narrowing of the spinal canal), a blood clot or intracranial bleeding in patients with stroke, kidney and bladder stones, abscesses: inflammatory diseases (such as ulcerative colitis and sinusitis), muscle disorders, and/or injuries to the head, skeletal system, and/or internal organs. For example, for a pulmonary embolism or blood clot in the lungs, a spiral CT may be required to see details of various tissues in order for diagnosis. However, using the method disclosed herein with 2D flat panel, a much lower level of radiation is needed in order to achieve the detail and quantitative analysis information need for diagnosis. Other parameters provided by the apparatuses for diagnosis of various diseases can include, for example, dimension of vascular features, presence of clots, irregularities, micro-calcifications, special substances or cysts, fractures (such as stress fracture, when callus formation may happen near the fracture, affecting both bone measurement as well as tissue surrounding it), shin splint (with a density variation atypical in the area of injury compared normal bone density and its uniformity in unaffected bone areas and health tissue), diagnosis, treatment, and long term monitoring in pain management, increase of density within a region, loss of tissue content, addition of tissue fragments, specific microstructure, derivation of composition and changes due to density measurement and images, especially in cases where high resolution and accuracies and quantification measurements are required, such as requiring a CT scanner, bone scanner, MRI and/or densitometer.

The results can be used for surgical guidance, such for minimum invasive surgeries, radiation therapy, and biopsy, especially in cases requiring normally a CT scanner, bone scanner, MRI and/or densitometer. Example applications can also include treatment and surgical planning and guidance, therapeutic and treatment response, and/or post-treatment monitoring of other organs, kidney, limbs, eyes (for example, implant placement) in the body.

For material characterization and identification in industrial settings, such as in cargo inspection, security x-ray and automated x-ray inspection, where CT scanner may otherwise be required, a system based on the 2D flat panel disclosed herein may be sufficient for quantitative analysis of presence, location, characterization, and/or identification of a material or substance embedded in the subject in industrial applications such as cargo inspection, security x-ray and/or automated x-ray inspection. The results can be used for identification and characterization of components, materials, substances failure analysis, and parts inspections, especially in cases where normally a CT scanner would have to be used.

The quantitative and high resolution images can be comparable to that of CT. The details and quantitative information that can be revealed by the 2D flat panel image, optionally with scatter removed, can include, for example, separated tissue images and quantitative measurements correlating dimension, density, and/or images.

Images and quantitative measurements of individual components inside the subject can be separated, analyzed based on parameters such as dimension, composition, thickness, microstructure, shape, morphology, one or more areas of the same component, relative positions, location and/or other parameters. The measurements can be standalone, and/or compared to the rest of the subject and its relative location, position and/or other measurements, or to other area or areas of the same component in terms of density, and relative movement, relative position, dimension, composition, thickness, shape, morphology, microstructure, addition or loss of content, in high resolution and in real time and/or between time period, in 2D and/or multiple dimensional space.

Figure 11:
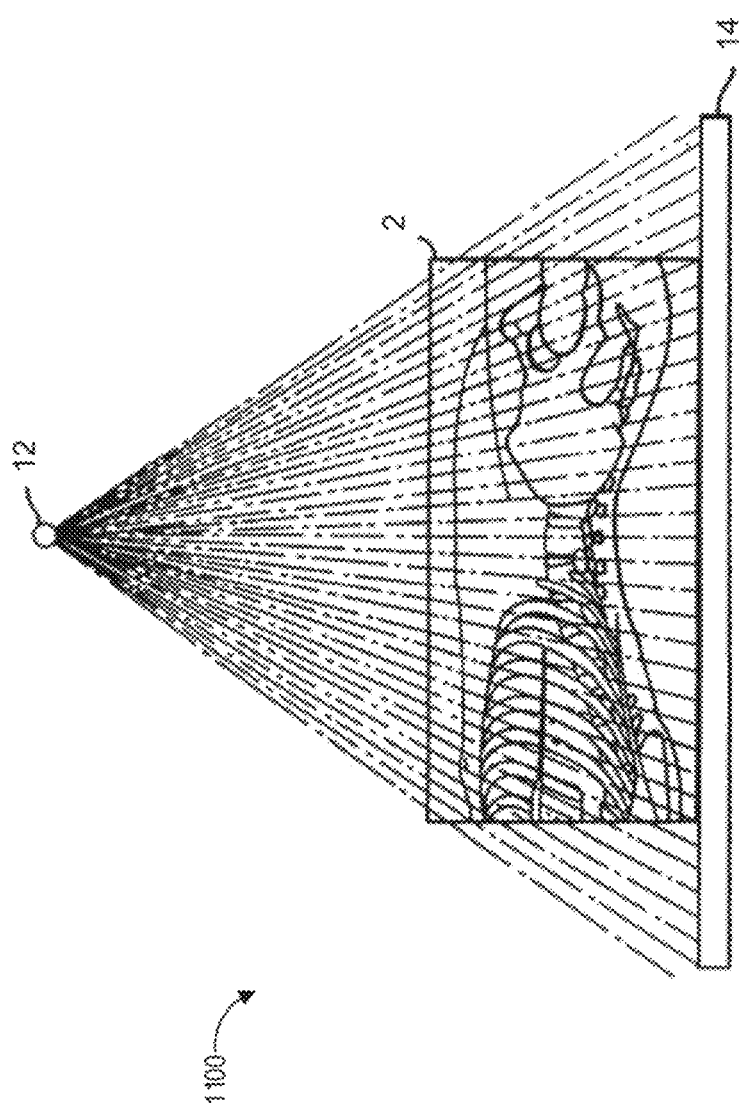
FIG. 11 illustrates schematically an example 2D x-ray imaging apparatus configured to provide quantitative measurements.

As shown in FIG. 11, which incorporates any features of the apparatus 10 of FIG. 1, a 2D x-ray apparatus 1100 can include an x-ray source 12 and a 2D x-ray detector or detector assembly 14.

The subject 2 can be inorganic material or a mixture of organic and inorganic material. The subject 2 can be a subject having three or more composites with various atomic z numbers. Examples of the subject can include a human body portion or organ containing molecular labels specific to the tissues or suspected diseased tissues. The subject can also be an industrial subject or an item to be inspected and characterized.

The subject 2 can located between the x-ray source 12 and the x-ray detector or detector assembly 14. The x-ray source 12 can emit x-rays with controllable energies. The x-ray source 12 can emit consecutive pulses for each imaging operation. The x-ray source 12 or a source module can assist in the removal of scatter by emitting beams at a faster pulse rate or by emitting beams of specific designs, for example, the thin beams as disclosed herein or otherwise.

The pulse can be various energy levels to achieve a higher level of scatter removal and/or densitometry and images of separate materials in the subject. A high-energy pulse with an average energy level H can be emitted, followed by a medium-energy pulse at an average energy level M, and a low-energy pulse at an average energy level L. Each pulse can have a single, essentially unchanged energy spectrum. The x-ray detector 14 can be any 2D digital x-ray detector that converts a 2D x-ray image information into a set of digital data suitable for being transmitted to a computer. The x-ray detector 14 can be a conventional detector, or an x-ray detector assembly, with or without the capability of removing scatter interference.

A conventional 2D (area) x-ray detector can receive certain amount of random-scattered x-rays mixed in its output signals. Optionally, scatter removal can be done using any combinations of hardware, x-ray source, detector and/or algorithms, or as disclosed herein. The apparatus can also optionally use a three-layer detector structure described in U.S. Pat. Nos. 5,648,997 and 5,771,269 for eliminating scatter interference. If the x-ray detector 14 receives a sufficiently small amount of scatter interference, under certain circumstances, a qualitatively correct, yet quantitatively inaccurate imaging result can still be obtained. To what an extent the scatter interference in acceptable is case-dependent, and can be decided by case-specific analysis.

The apparatus 1100 can include a mover to move the x-ray source 12 relative to the subject 2, and/or a mover to move the x-ray source 12 as well as the detector 14 relative to the subject 2. Optionally, the subject can move voluntarily, such as in the case of a living organism or animal, or an inanimate subject with internal robotics to move one or more components or the entirety of the subject.

The images produced using the apparatus 1100 can be collocated with images using other modalities, such as with PET or Optical Imaging, MRI, and/or Ultrasound or Acoustic or Photoacoustic Imaging method. The images produced can include X-ray Particle Image Velocimetry for measuring a flow using particles, for example, microbubbles, as tracers for investigation of hemodynamic characteristics and/or circulatory vascular diseases. The flow analysis can be used for deep tissue liquid flow measurements as the overlapping tissues and scatter can reduce the visibility and quantification capabilities when using the 2D x-ray detector.

The apparatus can be used for Stereoscopic Particle Image Velocimetry (PIV), which utilizes two detector panels with separate view angles to exact a z-axis displacement, or a 3D acquisition of a 2D flat panel based imaging method, which is faster in acquiring multiple dimension representation than a CT scanner and can be fast enough to acquire velocity of flow in a 3D space. PIV can be combined with separation of tissues and measurement in time for velocity measurements. The apparatus can be used for holographic using an interferogram-based method.

The apparatus can apply a spectral data decomposition method to produce 3D composition images including bone mass density image b (x, y), soft tissue image s (x, y), and/or a third material mass density image p (x, y) or molecular labeled tissue mass density image p (x, y). The method can also include analysis of the relative compositions, densities, and/or image information of regions of interest in an individual component as well as that of components relative to other components of a subject in position, density, and/or image (including morphology as well as dimensions of image, such as a tumor size or disease tissue size).

The apparatus including an x-ray source with a single, dual, or triple-energy or multiple energy can take one or more 2D images of a subject from a different location and/or at different times. The 2D x-ray detector, upon receiving the x-rays from the x-ray source, can convert the image information contained in the transmitted x-rays into electric signals to be sent to a computer or processor, such as the processor shown in FIG. 1.

The x-ray imaging apparatus can include an x-ray source configured to emit x-rays of an energy spectra having an average energy in the range of from approximately 15 KeV to 200 KeV or 500 Kev in industrial applications.

The apparatus 1100 can be portable, for example using low kw x-ray generator or nanotube based cold cathode x-ray source, such as being suitable for use in the field setting and can be packaged into a carryon bag. Such an apparatus can be battery-operated.

A diffraction grating (see FIG. 15E) or beam splitting after x-ray source can be added to the apparatus 1100 to produce an interferogram of the scattered and/or primary x-rays for measuring the velocity of blood and other bio-fluid in diagnosis of diseases. PIV can be combined with separation of tissues and measurement in time for velocity measurements.

Surgical Guidance Examples

Conventional 2D imaging method based on 2D flat panel is of a qualitative nature, but not of sufficient quantitative nature due to scatter. As a result, even though a spatial structure may be used as a framework to match 2D image with a 3D quantitative image from a3D CT scanner, the matching may not be accurate. Reliable real time positioning cannot be achieved. Although stereo x-ray imaging may be achieved with at least two x-ray sources and two independent detectors for each of the two sources, such a setup can result in high radiation level and still not as accurate in matching due to the nature of 2D image, which is qualitative, while 3D CT scanner produces quantitative images.

Due to inaccuracies in matching, especially when the patient moves, a portable 3D CT scanner may be used in the operating room or a 3D CT scan needs to be repeated during surgery for tracking of the surgical tools, implants, and/or others. This also results in a much higher radiation level. Similar situations can take place during post-treatment monitoring.

Repeated use of 3D CT scanner is not only a safety concern due to radiation level, but also costly and inefficient. Further, a CT scanner is not suitable for monitoring fluidic properties or flow characteristics due to the time required to complete a CT imaging and construction.

The 2D x-ray apparatus disclosed herein can improve the accuracy and efficacy and safety and speed of diagnosis, and treatments including surgical treatments, post treatment monitoring, and more particularly to tracking the location of a target region that is displaced during the treatment due to respiratory and other patient motions, or the location and dynamic physiological and physical characteristics of target of interest, target area for implant, for example, heart valve, deformed area in spine, implant, stent, cancer cell, cellular matrix, molecules and cellular structures, tissues, flow dynamics of blood vessel and blood vessel, apparatus or energy treatment and therapy target such as radiofrequency (RF) ablation, laser surgery or lithoplasty or drug therapy targets, or positioning of biopsy needles, or imaging guidance or colocation with other high resolution imaging and electromagnetics or ultrasound, RF wave based techniques such as photoacoustic or nonlinear microscopy or optical biopsy including OCT, ultrasound or endoscopy, PET and MRI and Magnetic Particle based imaging techniques, spectroscopy and interferometry. The x-ray apparatus disclosed herein can also be used in industrial applications, for example, tracking robots and droids and manufacturing processes and analysis of industrial processes and/or hardware.

Methods for imaging and measure properties of one component or more component in a volumetric region using quantitative 2D x-ray images and other x-ray imaging methods based on quantitative 2D methods, such as interferograms, and other measurable properties, such as multiple energy spectral absorptiometry, and/or the like, can allow the images to provide quantifiable data, for instance, density, composition, flow properties and fluidic dynamics, dynamic properties, presence, absence, phase, and/or coherence. The imaging and/or measuring may be over extended period of time.

The 2D x-ray apparatus disclosed herein can produce 3D images using 2D detectors in real time for tracking using the following process. A plurality of first measurements can be produced to generate data points of 1D, 2D images or multiple dimensional volumetric images in a region of interest including an internal target. Such plurality of first measurements may be of dual or multiple energy measurements, generated through a single pulse having one, two, or more energy levels, each at distinct time durations or at the same time, or through dual or more pulses of various energy levels or tunable wavelength pulses. The first measurements may be 1D, 2D images of selected regions or one or set of x-ray thin beam-projected data points, spatially distributed from each other, or data sets of thin beam-projected data regions, or interferograms. To position, track, and characterize dynamic movements, the first measurements may be sampled one or more times during a dynamic movement cycle, or a time duration of dynamic movement, to track and characterize the movements of the component in region of interest in space, for example, in six degrees of freedom (6D) and the corresponding time period.

Live measurements of the region of interest can then be sampled during tracking. The live measurements may be of the same or at a faster or a lower frequency than that of the first measurements for dynamic movements. Each live measurement may include one or more 1D or 2D images, one or more data points or data regions resulting from the x-ray thin beam illumination or a set of measurements in 1D and data points and selected data regions.

The first and live measurements are quantitative images, some of region of interest which produces low or minimal scatter interference or optionally produced with scatter removed using any of the techniques disclosed herein. Each live measurement or decomposed data from each live measurement can be matched to one of first measurements, synthesized data set including those of extracted data point, or selected data regions, or selected 1D, 2D or multiple dimension or 3D or 4D or 6 D or 7D presentations of various energy level, or energy decomposed data point, 1D, 2D or multiple dimension images, 3D or 4D or 6D or 7D of various materials and components in the region of interest generated from multiple dimensional image volumetric data reconstructed by the plurality of first measurements from static position as well as during dynamic movement positions corresponding with time. The matching may include matches based on spatial structure, flow properties, relative distance between components and relative spatial positions and/or orientation in 6D orientation, composition, and/or density, temporal marker, and flow and fluidics dynamics and direction. In case of matching using one or more spectral or single energy measurements of one or more data points, or data regions of a component, or 1D linear image via illumination path passing through the region of interest, speed may be improved significantly and radiation level to one specific area or total radiation level may be dramatically reduced especially when such measurements are of different illumination path generated each time.

The apparatus may include a miniature x-ray source that can be put inside an internal volume or cavity produce all or some of first and live measurements. Retrofit kits can also be used to modify existing x-ray radiography systems to perform tracking as described herein. The apparatus and methods can be offered to qualified hospital and clinics, surgical center, imaging center and managed care organizations with a zero upfront charge. The customers are charged each time an image is taken and/or only when such an image is utilized for diagnosis, pretreatment planning, treatment, monitoring and post treatment evaluation.

In the present disclosure, a "target" (see target 110 in FIG. 16) is the region to which treatment (e.g., surgical, or robotics, radiation, energy and drug) is to be directed, or in case of diagnosis, the region the diagnosis is to be based on. A "target" may be an implant or a region of a surgical tool. A "target" may be a selected region and its surround area in the region of interest by the computer or a user. A target can be embedded in a "region of interest" which refers to a region including adjacent regions surrounding a component of interest, which an x-ray beam may illuminate to produce the projected image. A region of interest may include one or more targets and their adjacent regions.

A "component" (see component 120 in FIG. 16) is the region within the target that may be identified by x-ray imaging and/or quantitative measurement by a set of defined quantifiable parameters and/or may be differentiated from a different component within the target based on this set of quantifiable parameters. A target may include one or more components.

A "thin beam", (see thin beam 400 in FIG. 17) disclosed herein is the x-ray beam with a field of view of that of integer multiples of pixels, or alternatively such a thin beam may produce a detectable signal on the active region of at least one pixel on the detector. Typically, a thin beam may be selected with a space of at least one pixel pitch between adjacent thin beams. When imaging and measuring properties of one component or more component in a volumetric region using x-ray thin beams, each time, the x-ray thin beams can illuminate different parts of components. One or more thin beams may illuminate multiple different components in region of interest to serve as a reference point or reference points for synthesize simulated data based on the measurements and for the positioning of components or region of interest or targets in 6D. Thin beam may refer to an x-ray beam which illuminates region of interest in a project path generating a signal on the detector, and the width of the signal projected on the detector may be in diameter dimension of 1 mm to around 10 mm, referred to as "minibeam": in diameter dimension between 1 um to 1 mm, refers to as "microbeam"; between 0.01 nm to 1 um, refers to as "nanobeam". Typically a x-ray thin beam generates x-ray measurements on the detector, with no or minimal scatter interference. Preferably, the projected path of the Thin Beam is calibrated in its spatial position and dimensions, relative to the x-ray emitting position and the detector, so that the signal is centered in middle of active area or in the middle of a pixel pitch on the detector, filled up at least one pixel pitch of a pixel area. If it is projected on to two or more pixels, similarly, the projected path is calibrated so that the Thin Beam projected fills the two or more pixel completely and no spilling over to the adjacent pixels.

A "first measurement" is the x-ray signal on a detector produced by illuminating the region of interest with an x-ray cone beam, fan beam or one or more x-ray thin beams.

A "first image" is 1D, 2D, 3D or 4D images and interferograms derived from measurements and images using 2D flat panel x-ray detectors, and x-ray full field imaging with a flat panel detector may be combined with x-ray microscopy, spectral measurements, spectral absorptiometry, or faster frame point, linear and small or large format 2D detectors, and/or energy sensitive detectors, silicon drift detectors, x-ray spectrometers, visible cameras when upstream scintillators to convert x-ray to visible light. The first image may be derived from or measured synchronously or at the same time frame from one or more of other imaging modalities, including CT scans, magnetic resonance imaging, and ultrasound and PET or optical imaging or optical spectroscopy or acoustic optical (photoacoustic), magnetic particle, other physical property measurement techniques and simulated data.

A "live measurement" A "live measurement" or sometimes refers to as "second measurement" in this disclosure is the x-ray signal on a detector produced by illuminating the region of interest with an x-ray cone beam, fan beam and/or one or more selected slice beams, or one or more x-ray thin beams during diagnostics, treatment, monitoring or tracking process. The "live measurement" can sample selected projected x-ray data on the detector in a time sensitive manner, and sometimes in real time. Live measurements of the component, target, region of interest, and the subject can be used to match the first measurements and/or first images or synthesized presentation in the forms of data points, data regions, 1D line image, 2D and multiple dimensional images, 3D and 4D or 6D or 7D images from multiple dimension images reconstructed from the data set of the first measurements and/or first images.

A "quantitative 2D image" is a 2D x-ray image that is a measurement of a region of interest, where 1) the region of interest is of a low scatter material, or the application requirement is such that measured x-ray image is from a detector of any kind that may be used for quantitative analysis, 2) the scatter and primary x-ray separation or differentiation methods and apparatus can be used, some of which are described herein to obtain an image which is very low in scatter, 3) other primary x-ray imaging methods were used, for example, those using ultrafast x-ray source, and detector pair or those with modulated primary x-ray imaging methods, and/or 4) the x-ray systems used have scatter removal with simulated scatter data or algorithms method which are sufficient enough for the quantification analysis in the application.

A "1D measurement" is a line image projected on the detector by one slice of an x-ray beam selected to illuminate a region of interest in a sliced fashion. The minimum width of the line image can be such that it may produce a signal on the detector in at least one pixel. The length of the line image can be more than one pixel. A typical line image can have a width of one or more pixel pitch and a length of the projected 1D measurements of the x-ray beam illuminating the region of interest with a selected 1D beam profile. The 1D measurement is a quantitative measurement and may be processed with the scatter removal to improve quantitative data available to further analysis. The 1D measurements may also include measurements of all pixels of sliced projected path, or two or more pixels distributed along the 1D projected slice on the detector, each pixel being separated from its immediate adjacent pixel measurements by at least one pixel.

A "data point" is a data point projected on the detector by one x-ray thin beam to illuminate a region of interest. The data point may include a signal collected from at least one pixel of the detector. The spatial position of the projected path and the pixel on the detector, namely "data point", collect the signal of the projected beam that may be predetermined or determined. It is preferred to select x-ray thin beams so that each beam projects to the center of a pixel on the detector or projects to a center of a group of pixels. The data point typically may have minimum scatter interference.

A "data region" is an x-ray thin beam projected to two or more connected pixels on the detector by one x-ray thin beam selected to illuminate region of interest. A data region can be of various shapes and dimensions. It is preferred to select x-ray thin beams so that each beam projects to the center of a group of pixels in the data region. The data region typically may have minimum scatter interference A "4D image" refer to a 3D or multiple dimension image with a relative or absolute time reference to other images or measurements of the same component or target or region of interest or the subject, or an external reference or sensor.

A "6D image" refers to a multiple dimensional image of a component or target or a region of interest or a subject which describes its x, y, z 3D volume as well as its spatial orientation in pitch, yaw and roll.

A "7D image" refers to an multiple dimensional image of a component or target or a region of interest or a subject which describes its 6D image with a relative or absolute time reference, especially relative to measurements at a time before and after this image or relative to other components, or region of interest, or target or the subject or an external reference or a sensor.

"Synthesized or simulated" image and/or data refer to deriving data from previous measurements or existing data or predefined property values. For example, for an x-ray data point of a component, when segment 1 of a bone tissue in one region may be have the similar densitometry measurement data as a different component of the same bone, segment 2, the dimensional data of segment 1 may be derived from a previous measurement of segment 2. The exact x-ray measurement and dimension of segment 1 and relative position to segment 2 may be derived from earlier measurements or a pre-existing database. 6D and 7 D positioning and tracking of the bone tissue, segment 1 and segment 2, may be extracted from the synthesized data. The two components also may be of different tissue type, or material types, but the relative position may be maintained. So long as there is at least one deterministic linear relationship from one property of one component of interest to a property of the second component, measurements of the thin beam projected data point on a second component may serve as a reference point for derivation of simulated properties therefore tracking and positioning of a first component, which is the component of interest.

"Spectral Measurements" refers to the method which generates x-ray measurements at two or more energy levels or two or more wavelength through the region of interest. Generated x-ray signals are generally measurements in dimensions of point, or 2D data region, or 1D line region or 2D images or multiple dimension images and 3D images. When such measurements are energy decomposed, different materials or components are quantitatively separated. Spectral measurements typically describe measurements in a low resolution imaging setting or of high spectral resolution, high number of wavelengths or energy levels and/or in small region or point or 1D line region. Spectral measurements may be done on a projected path only of a pixel pitch or close to a pixel pitch in dimension.

"Spectral Absorptiometry" refers to the method which generates x-ray measurements at two or more energy levels or two or more wavelength through the region of interest. Generated x-ray signals are generally measurements in dimensions of point, or 2D region, or 1 D line region or 2D images or multiple dimension images and 3D images. When such measurements are energy decomposed, different materials or components are quantitatively separated. Spectral Absorptiometry sometimes describes measurements of low spatial resolution. Spectral Absorptiometry sometimes describes measurements of low spatial resolution and high spectral resolution in 1D and 2D format. A typical resolution of spectral absorptiometry may be similar to that of scanning linear absorptiometry, such as DXA.

"Spectral Imaging" refers to methods generating x-ray images in 1D or 2D or 3D or higher dimensions, measured at more than one energy or wavelength levels in x-ray. Spectral imaging typically describes imaging methods which result in relatively high resolution spatially, relatively lower resolution than spectral measurements, relatively larger imaging area than those for "spectral measurements". Optionally, spatial and spectral resolution of highest performing systems using spectral imaging, or spectral absorptiometry or spectral measurement methods can be similar or the same. However, due to various practical considerations, each configuration can be different from one another in typical scenarios in the present disclosure.

"X-ray Thin Beam" refers to a x-ray beam which illuminates region of interest in a project path which generates a signal on the detector, and the width of the signal projected on the detector may be in diameter dimension of >mm, referred to as "minibeam": in diameter dimension between 1 um to 1 mm, refers to as "microbeam"; between 0.01 nm to 1 um, refers to as "thin beam". Typically a x-ray thin beam generates x-ray measurements on the detector, with no or minimal scatter interference. Preferably, the projected path of the Thin Beam is calibrated in its spatial position and dimensions, relative to the x-ray emitting position and the detector, so that the signal is centered in middle of active area or in the middle of a pixel pitch on the detector, filled up at least one pixel pitch of a pixel area. If it is projected on to two or more pixels, similarly, the projected path is calibrated so that the Thin Beam projected fills the two or more pixel completely and no spilling over to the adjacent pixels. Thin beams of x-ray for example, can be from 0.01 nm to 10 mm in diameter. When thin beam is integer multiples of mm in diameter, it may be called minibeams, or um in diameter, as in microbeams, and nm in diameter, as in thin beams. Thin beams can be far apart from its adjacent beam and illuminate the region of interest and produce individual projected images and measurement data points on the detector.

"Selected Region" in the region of interest refers to a smaller region than the region of interest where the user r the digital program in the processor selects based on results of the full field x-ray imaging or predetermined or randomly. Selected region may be illuminated selectively by combing a collimator or multiple collimator leaves combined to have selected transmission region downstream of the x-ray source. Or selected region is only illuminated by x-ray generated from an anode which has selective regions for emitting x-rays. Or selected region is illuminated when the x-ray source or the x-ray radiation rotates around each of the x, y z axis relative to the subject, or relative to the subject, moves in 3D space and/or combines with a collimator limiting area of x-ray beam output. Selected region may be used to track components and/or targets by illuminating at the same or different regions, each region being a portion of the component and/or target and/or region of interest.

A "flat panel" detector in the present disclosure refers to 2D detectors with dimension in at least one of the two dimensional axis to be 1 cm or higher. Typically such detectors are in xy dimensions of at least a few $cm^2$.

The tracking and static position measurement of component, target and the region of interest as described herein may use a movable x-ray source or multiple x-rays sources in the first measurements and live measurements. The measurements can be used to reconstruct multiple dimensional images for diagnosis, and to match, extracted data point, data region, 1D, 2D and 3D and 4D and 6D and 7D images from first measurements with live images produced from multiple dimensional images. When the miniature x-ray source(s) is (are) used, the source(s) and detector can be placed in close proximity to the target, for example, inside the human body's cavity to be used as the source for first measurements and live measurements. For example in dental or kidney or intestine, or internal organ or cavity measurements.

The apparatuses disclosed herein can report spatial data relevant to other parts of region of interest in the subject. For example, during spine surgery, the apparatus can report a distance from a surgical probe or robotics tool to a nerve and/or a blood vessel. Such data may provide an input signal to guide the surgical tool in an orthopedic or spine surgery and/or be display visually and/or audibly to warn operating apparatus and/or surgeons.

The apparatuses disclosed herein can provide faster matching. For example, an implant and/or tool which may have radiolucent markers or other types of markers. As such, a manufacturer may provide 3D representation of an implant size and design in x-ray images. Optionally, based on the material and design of the implant and/or tool, a 3D x-ray image may be simulated.

The apparatuses disclosed herein can provide relative illuminated position of thin beam in sequence. The apparatus disclosed herein can utilize one or more than one x-ray source or utilizing one or more than one x-ray emitting positions to provide real time multiple dimensional images of the subject, target, region of interest and component. The x-ray source or the x-ray emitting positions can be a fraction of pixel size, one pixel size, or an integer multiple of pixel size away from the adjacent x-ray source or the x-ray emitting position respectively. Alternatively, the emitting location of x-ray source may be designed to illuminate different adjacent region of target but still illuminate within the region of interest so that for a specific tissue area adjacent to the target, the radiation level is reduced and no new unknown pixels are introduced. The dataset derived from the first measurement can be used for quick lookup and matching. The apparatus disclosed herein can speed up improve measured data set from the x-ray thin beam with the first images and at the same time reduce radiation by shifting the location of the thin beam in a predicable fashion. Different regions of the component are illuminated sequentially, and with known spatial relative distance from each other. The matching of x-ray measured data to the stored data pool for the 3D volumetric region of the component can be carried out quickly.

Faster matching or looking up in the database of the first image set or reconstructed multiple dimension images or extracted 1D, 2D and 3D images can be also achieved by calibrating the geometry, the relative spatial relationship of x-ray beams from the x-ray source and detector to predict the approximate location and path of the x-ray thin beam or x-ray fan beam that will illuminate in the component and therefore limiting the scope of looking up in the database containing the first measurement data of the relevant region or extracted data from the first measurements or synthesized and simulated data or data generated from AI methods.

Faster matching may also be achieved by limiting the size of each component and therefore the database of possible thin beam paths or database of x-ray measurements in point, data region and 1D and 2D image of the component.

As each x-ray beam projected data point or pixel region carry quantitative data, matching may also be achieved by decomposing the projected data to derive the material type or composition of the component each beam illuminates. For example, an extracted image dataset for a unique anatomic part and its unique location and/or orientation may limit the database look up to a small number of dataset, or may limit and/or further reduce the overall volume of region of interest or target or component for live image imaging, therefore also potentially reducing the radiation dosage.

Optionally, each x-ray thin beam can be of a single energy, as extracted 2D image from three dimensional image constructed from first images may be constructed only of single energy (for example, a high single energy), which has a corresponding low energy in 2D image for the same projected path on the region of interest. As a result, one single energy live x-ray image may be sufficient to derive the location, density and other quantitative information of various material along the projected beam path. For example, bone and soft tissue compositions of a component or target and region of interest in the illuminated x-ray path may be extracted. Any methods of material decomposition and/or differentiation disclosed herein can be used. For instance, an implant or surgical tool or a component can be labeled with contrast agents.

K-edge measurements using filters, or sometimes kedge coded aperture between x-ray source and the subject can be included. In particular, when data point, data region, 1D and small 2D regions are measured using x-ray thin beam as the source, scatter interference is small. First and live measurements with kedge filter may be used. In addition, for region of interest with low scatter property, k-edge filter may also be used.

In some examples, tracking may be executed during diagnostics and inspection, prior to treatment, during treatment, and/or post-treatment. Prior to treatment, at least two 2D images can be measured, which can be from quantitative 2D images disclosed herein or data from other modalities including CT scans. Each 2D image may correspond to a time point in a dynamic motion cycle or process, such as respiratory cycle, or heart beat cycle or other motions relevant to the region of interest present in the subject. Each of the series of 2D images may be an actual 2D image or a combination of actual 2D image and computer-extracted 2D images. In order to extract 2D images for matching with live images, at least two quantitative 2D first images are taken. 2D synthesized images may then be extracted and processed from the actual 2D images. Each 2D image shows the position and/or orientation of the target.

During the time period when tracking is needed, one live quantitative x-ray image or multiple dimension x-ray images, or one or more projected thin beam data region, or two or more live thin beam projected data points may be measured at discrete time intervals during the dynamic movement. Multiple dimension quantitative x-ray images can be generated by at least one detector and at least two different x-ray emitting positions relative to the subject and the detector. Live quantitative x-ray image or thin beam projected data point may be generated by at last one detector and one x-ray emitting position from the x-ray source. Two or more x-ray sources and corresponding one or more detectors collecting x-ray projected images may be used to create multiple dimension images, or spectral images at various energy levels, or reduce radiation dosage for regions surrounding the target. The component may not be clearly visible in the x-ray measurement. However, tracking and 6D positioning of the component can be determined by comparing live measurements in time with first measurements or first images or extracted data point, 1D, 2D and 3D and 4D images from the reconstructed multiple dimension images of first measurements and images of data point, data region, 1D, 2D and multiple dimensions.

Based on the viewing angle associated with the best-matching projected image of component, target and region of interest, the exact angle or translational shift the subject was in when the live x-ray measurement was taken can also be determined. Both a translational/rotational shift of the subject (such as the patient's body) and the current physiological state relating to respiratory, cardiac, as well as other relevant physiological state involving movements of the subject may be inferred from the live x-ray measurements. No fiducial marker needs to be implanted for this procedure, which only requires x-ray projected measurements during treatment or tracking.

The first and live x-ray images and measurements can be made with two pulses, or three pulses or more pulses of an x-ray beam, each at a different energy level, or a tunable energy pulse source, or a pulse of multiple energy levels at the same time for material decomposition and optionally scatter removal of the target or the region of interest.

Alternatively, x-ray measurements may be taken at different energy levels during one or more pulses while an x-ray source generates a pulse with one or dual or three or more energy levels. The transition between energy levels can be gradual or instantaneous. Waveform and/or energy levels from one pulse may vary from the next. For example, a set of two pulses can have a first pulse with two different energy level generated by the generator and a second pulse with one energy level, which can be different from the two energy levels in the first pulse.

Optionally, energy levels from a first pulse can be of low energy levels from a second pulse may be of intermediate to high. Energy levels from a third pulse may be from high to intermediate. Energy levels from the fourth pulse may again be low.

The energy level of the pulse(s) for generating the first and live x-ray measurements can depend on what is required for the material decomposition and/or, scatter removal, of the target or the region of interest, and/or quantitative analysis of composition of unlabeled or contrast agent labeled regions.

Spatial positions of hardware of the apparatuses disclosed herein can be calibration for scatter removal, such as using methods disclosed herein, such as using a dual detector combination with a beam selector. Before live x-ray images are taken, relative positions of the beam selector and optionally with detector, to the source in the 3D space can be calibrated to ensure the scatter removal process and data acquired to be more accurate. Such calibration may be done in a per need basis. Calibration may also be done before each subject measurement if the detector and x-ray source are fixed in position. Calibration can be manual, light based, motorized, and/or based on other mechanical or visual methods. In some applications, such calibration may be optional.

Calibration can also be used to improve the speed of detector readout. If the x-ray source and detector are calibrated, for each time of x-ray sampling, only selected pixels on the detector need to be read corresponding to the specific illumination location.

The apparatuses can include a closed loop feedback system for reduced x-ray dosage. Based on the first image or the first set of first images acquired for the target in the region of interest, or the first image of the region of interest or first images at dual or multiple energy level, the x-ray beam radiation output level on the region of interest is adjusted and 5 x-ray beam is adjusted spatially to illuminate only region of interest or the target to minimize the input x-ray dosage for the subsequent first measurements and live measurements without comprising acquired data for the purpose of visualization and quantitative analysis. 10

Figure 16:
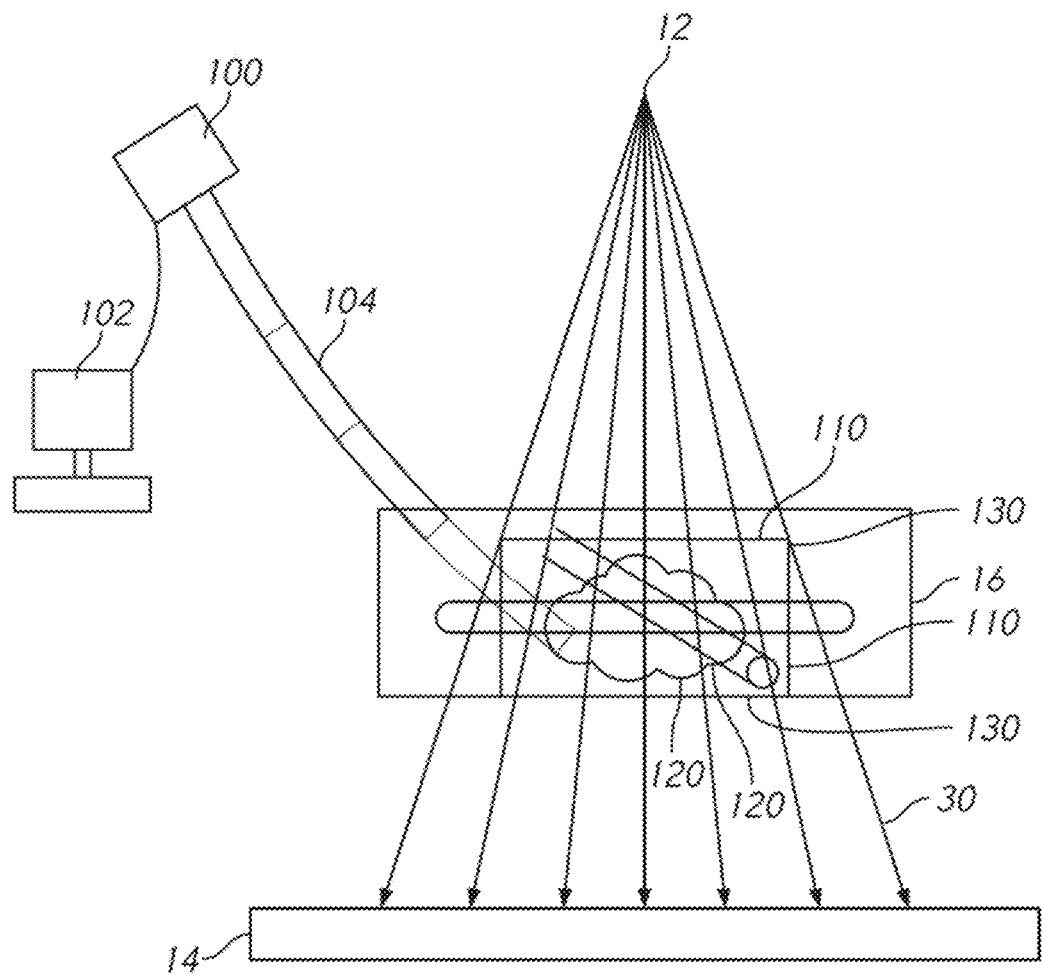
FIG. 16 illustrates schematically an example of an x-ray apparatus used in conjunction with a treatment apparatus, with a catheter guide wire and an implant in a minimally invasive surgery, imaged with a region of interest in a subject.

As shown in FIG. 16, an example computer-controlled energy treatment apparatus 100 can include a guide wire and catheter 104. The treatment apparatus 100 can be combined with an x-ray system disclosed herein to provide an image-based surgical guidance system.

An x-ray source 12 generates x-ray beam 30, which illuminates a component 120, contained in a target 130, which is in turn located in a region of interest 110, in a subject 16. The projected x-ray 30 forms an image on detector 14. A computing apparatus 102, which can include a processor (such as the processor in FIG. 1A), controls the energy treatment apparatus 100, to provide energy treatment. The catheter 104 can probe the subject 16, and to reach the component 120, internal to the target 110.

Figure 17:
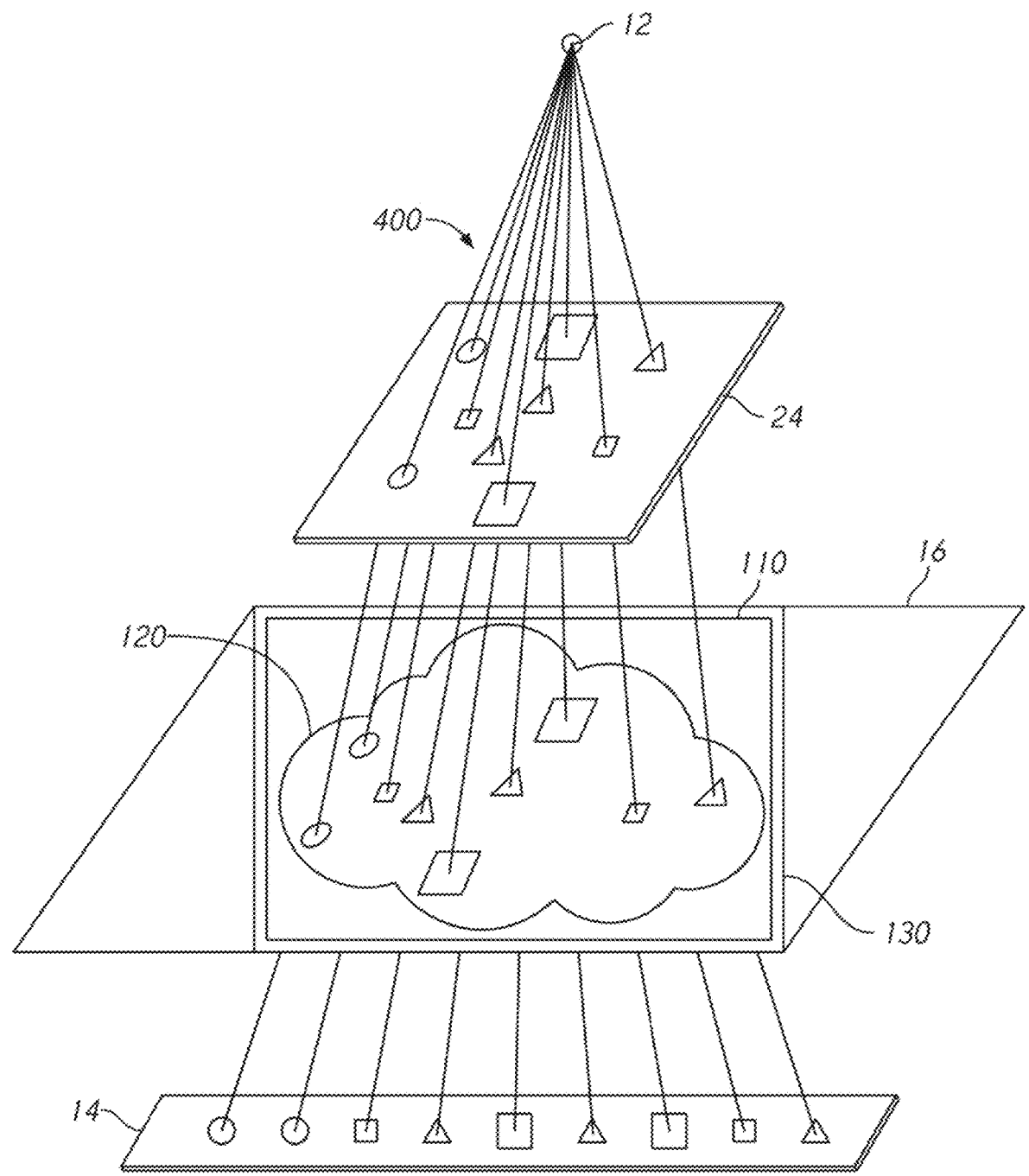
FIG. 17 illustrates schematically an example of x-ray thin beam apparatus for tracking and monitoring.
Figure 18:
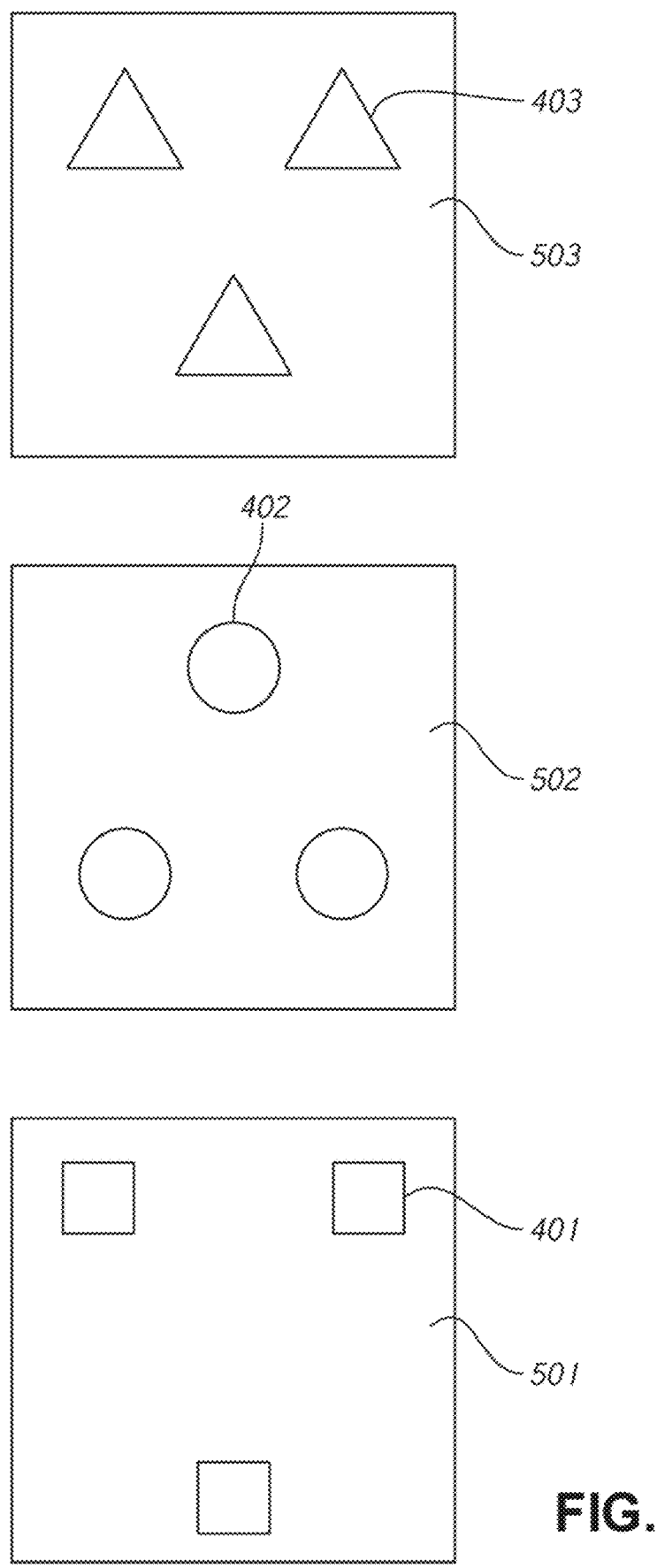
FIG. 18 illustrates schematically a top down view of different implementations of collimator 24 in FIG. 17, such as 501, 502, 503 in an x-ray apparatus where such collimators are placed in between x-ray source 12 and the subject 2.

The x-ray source 12 in FIG. 16 can provide an x-ray fan beam. In FIG. 17, the x-ray source 12 can provide multiple thin beams 400. A modulator (also referred to as a patterned mask, or a collimator) 24 can be used to selectively transmit x-ray thin beams 400, which can form detection regions on the detector 14. As shown in FIG. 18, these regions can be at locations designated as 401, 402, and 403 respectively on collimators 501, 502, and 503.

Optionally, a scanning x-ray source may scan over the collimator 24 to illuminate the target 110, at two or more regions, such as 401, 402, and 403, each at different times.

As shown above, multiple x-ray thin beams may be selected to illuminate the region of interest using a single x-ray source combined with a beam absorber or beam selector mask, such as the collimator 24 in FIG. 17 or FIG. 15B. Each of the beam may be detected by one or more pixels on the detector. The collimator 24 can allow certain areas transmissive to x-ray beam and the other regions to be completely opaque to x-ray.

Various positions and patterns of the collimator, such as any examples disclosed herein, can be used to select transmissive beam location at different times to minimize radiation dosage to tissue at a specific location. For example, in radiation therapy, it is common to take a 2D image every 10 seconds to update the location of the target. If each 2D image is replaced by one x-ray thin beam (or 1D x-ray sliced projected line, or a structured illumination by multiple x-ray thin beams), and/or each time, a different structure or a mask with different transmissive positions (or the mask having transmissive patterns that is in movement such as spinning (see FIG. 19) or moving in the 3D space), resulting in the x-ray thin beam illuminating at different regions of the target and surrounding regions compared to the next x-ray measurements the subsequent measurements throughout the imaging process, the total radiation dosage can be reduced or minimized for the illuminated regions.

In radiation therapy, the radiation therapy energy generator may be used as the source of x-ray.

As seen in FIG. 18, different collimator 501, 502, 503 can each be placed downstream from the x-ray source 12 to selectively transmit x-ray to illuminate different regions of the target to generate measurement data for first images and live images. Each data set can also be used to represent the x-ray data set of the same component measured at different times. Each of collimator may be placed in and out of the input x-ray path. The beam path for 401 is different than that of 402 and that of 403, therefore the tissue regions on each beam path is only illuminated once, or a limited number of times compared to the total sampling times. Optionally, only one beam path may be used so as to reduce the complexity of the system.

Figure 19:
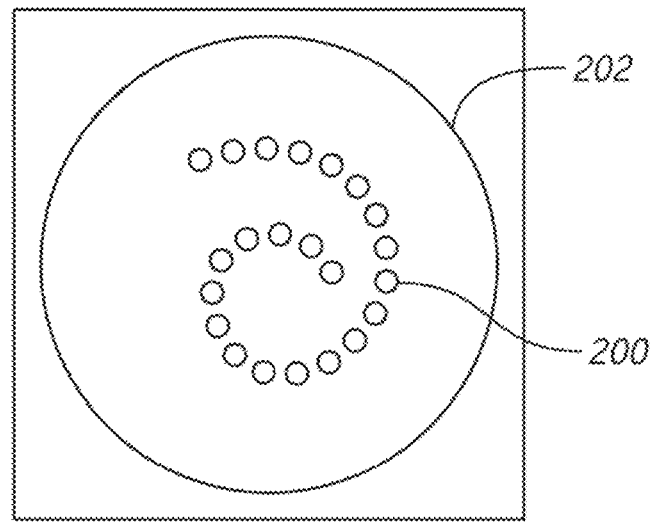
FIG. 19 illustrates schematically an implementation of collimator 24 in FIG. 17 in a spinning disk with regions of x-ray transmission.

FIG. 19 illustrates the collimator 202 being a spinning disk with regions of x-ray transmission 200. When x-ray measurements are taken at different times while the collimator 200 is spinning, the transmissive region can be at different positions during the spinning motion. The collimator 202 can be used to replace the collimator 24 in FIG. 17.

Figure 20:
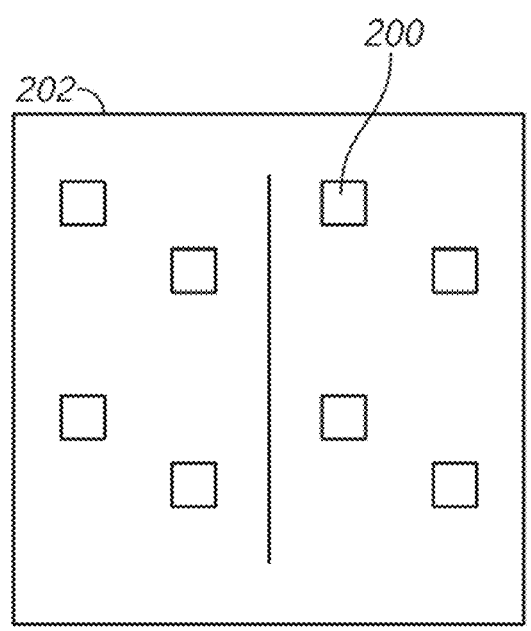
FIG. 20 illustrates schematically an example collimator 24 in the apparatus of FIG. 17, where the transmissive regions 200 form a pattern on a 2D plane.

In FIG. 20, a collimator 202 that can be used to replace the collimator 24 in FIG. 17 can have the transmissive region 200 forming a different pattern on a 2D plane. The collimator 202 may be moved by a mover in the 2D plane parallel to the detector or rotated along with the x-ray source, or moved in the third axis to reach the component or the target in different illumination paths to reduce radiation dosage to the target.

Figure 21:
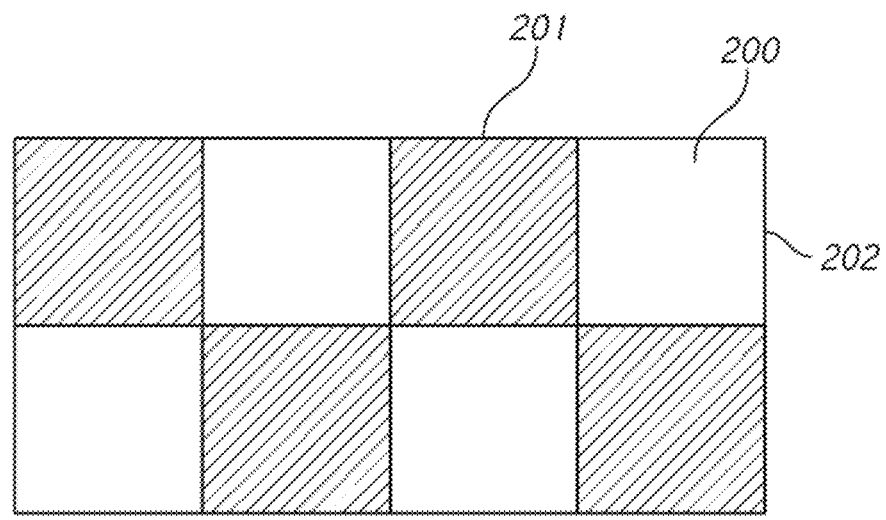
FIG. 21 illustrates schematically another example of collimator 24 for the apparatus of FIG. 17 with exemplary pattern and shapes for transmission and opaque regions.

FIG. 21 illustrates another example collimator 202, where the transmissive region 200 are in a checker board pattern with alternating x-ray absorbing region or x-ray opaque region 201. Such a collimator can be moved in the x and/or y position, each time at a pixel pitch of the region 201 or 200, so that the transmission and opaque regions are complementary each time x-ray measurements are sampled compared to the next time.

Figure 22:
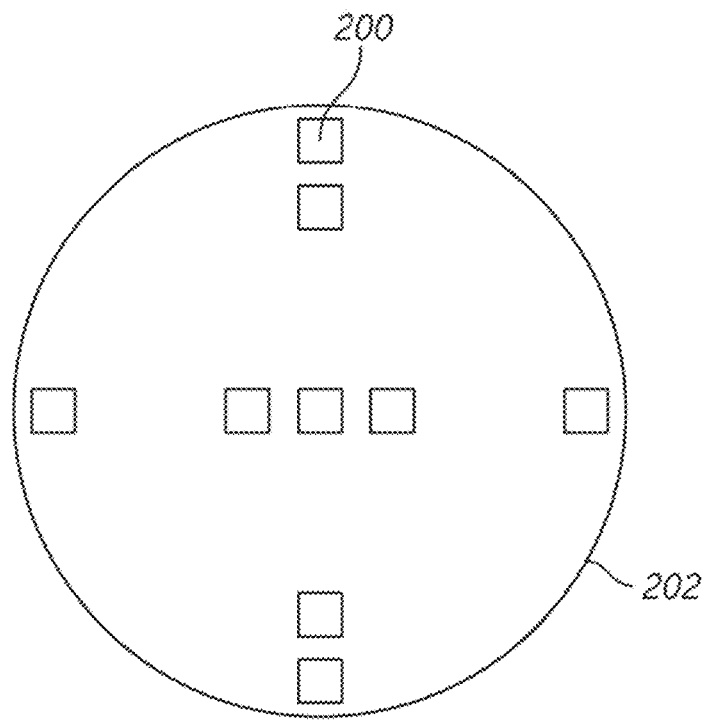
FIG. 22 illustrates schematically another example of collimator 24 for the apparatus of FIG. 17 with exemplary pattern and shapes for transmission and opaque regions . . .

FIG. 22 illustrates another example collimator 202 with transmissive regions 200. Such a collimator may be moved in x and/or y direction and/or may be spun in the 2D plane parallel to the detector.

Figure 23:
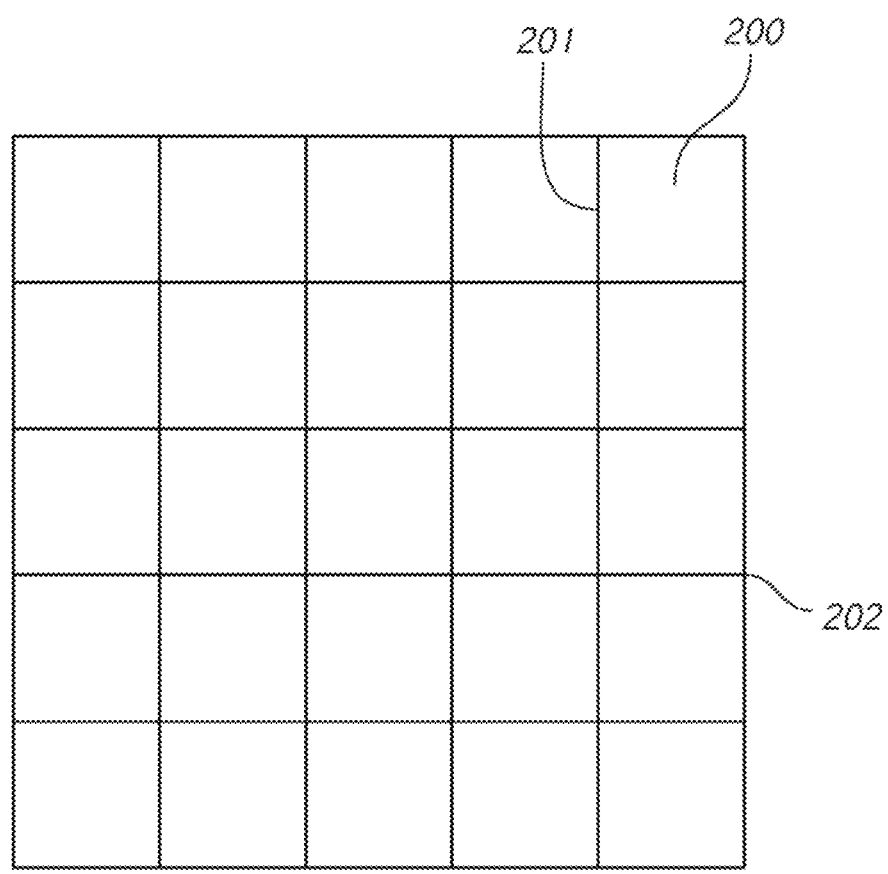
FIG. 23 illustrates schematically an example of collimator 24 in an x-ray apparatus illustrated in FIG. 17 with transmissive regions 200 interlaced with opaque region 201.
Figure 24:
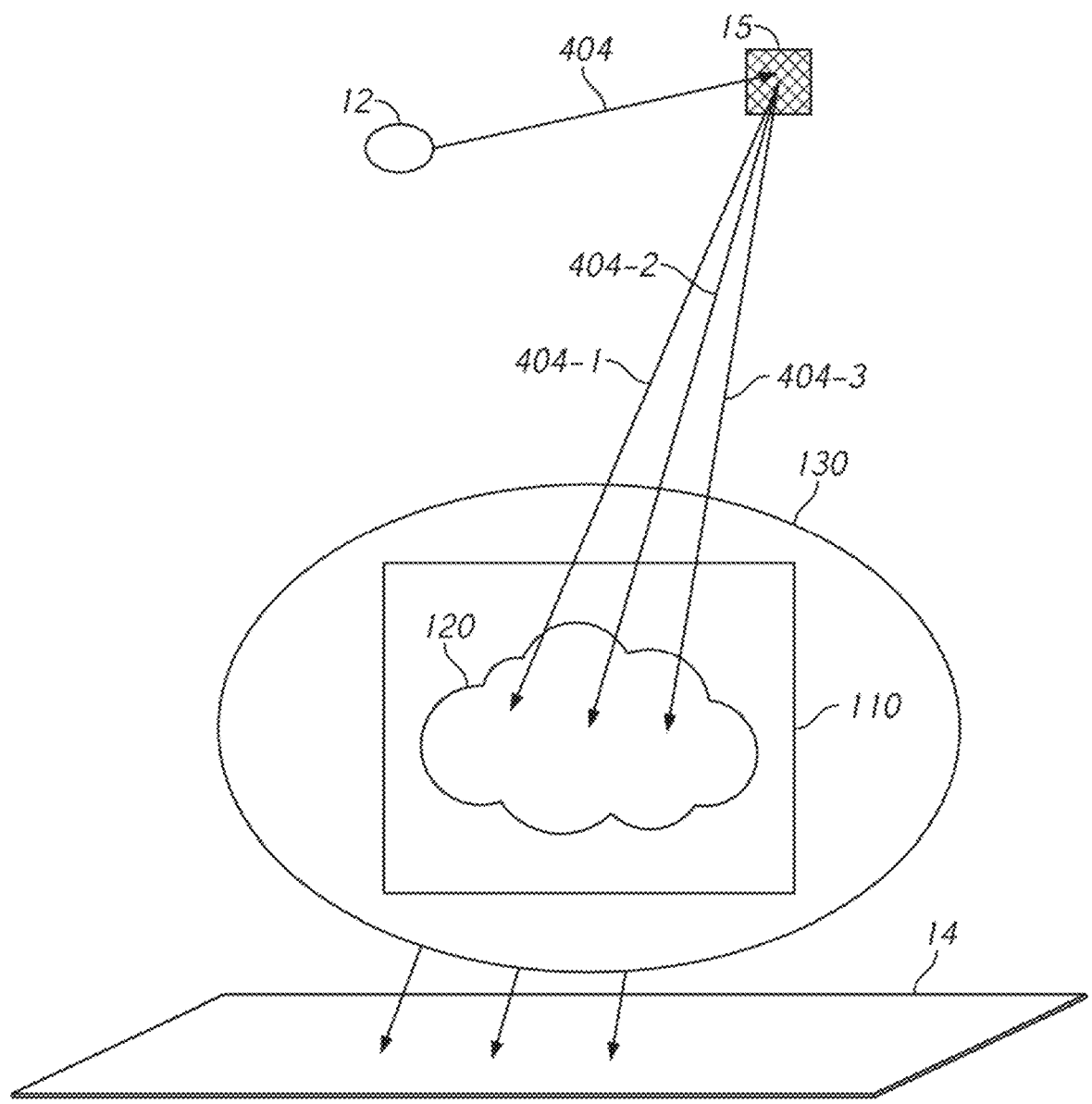
FIG. 24 illustrates schematically an example of combining an x-ray source and x-ray beam steering hardware for reduced radiation dosage to the tissues for any specific area.

FIG. 23 illustrates another example collimator 202, with transmissive region 200 interlaced with opaque region 201.

As described above, x-ray beams from an x-ray source may be scanned in a preprogrammed pattern during one or multiple frame of x-ray sampling. Alternatively, an X-ray source can simply illuminate the entire region 202 or selective regions of 202 to produce x-ray thin beams or selectively produce x-ray thin beams.

The selective opening of the collimator 24, 202 may selectively transmit an x-ray beam in a 3D space to illuminate the region of interest. Alternatively, one or more x-ray sources can be attached onto a 3D structure at different positions, or onto a beam steering apparatus, to steer the x-ray beam to scan the subject, as if the x-ray beams is coming into the region of interest from a varied 3D position.

FIG. 23 illustrates placement of an X-ray source 12 by a steering assembly 15 for reduced radiation level in the illuminated area for the same beam 404. The assembly 15 can include x-ray optics that may steer the x-ray beams 404-1, 404-2, and 404-3 toward the component 120 but each from a different angle in 3D. For example, the beam 404-1 can illuminate the component 120 at a first time point, the beam 404-2 at a second time and the beam 404-3 at a third time point. The assembly 15 can allow continued illumination at various areas on component 120 as needed so that the total radiation dosage to a specific area in the region of interest can be reduced and/or minimized for live measurements. The beam steering assembly 15 can be a refractive apparatus, and beams 404 from x-ray source 12 may be steered refractively. Alternatively, the beam 404s can each be an x-ray thin beam and the beam steering assembly can steer the beam 404 diffractively. The beam steering assembly 15 can be a MEM mirror or crystal or a diffractive grating (see also FIG. 15E) with beam stops or a tunable beam splitter 20 or x-ray guides such as capillary based total internal reflection based x-ray optics (see also FIG. 15D).

In FIGS. 26 and 27A-27C, respective target areas 110-$t1$, 110-$t2$, 110-$t3$ can be present in the region of interest 130 of the subject 16. As shown in FIGS. 26 and 27A-27C, two or more components 120-$c1$, 120-$c2$ and 120-$c3$ can also be in the region of interest 130. Multiple dimension images in 1D, 2D and 3D can be extracted from component images of components 120-C1 (for example, implanted heart valve), component 120-C2 (for example, cardiac tissue), and component 120-C3 (for example chest bone). Each component 120 may be differentiated by density, contrast label, spatial structure and shape, relative spatial position, composition, or movement characteristics, flow properties, flow characteristics, flow directions, fluidic dynamics, presence, visibility, or speed of movement or frequency of the movement, or any of such physical properties within a component, or any differentiable physical properties that may be analyzed by the first x-ray images, or simulated properties, or previously known properties or any combination of those properties.

Physical properties may include flow properties, which may be measured by speckle, frequency, phase contrast, in some instances, energy dispersive grating combined with spatially sensitive detectors spectral-absorptiometry, to monitor and measure changes in material composition and flow characteristics. Physical properties may include properties and structures which may be differentiated by an interferogram.

Simulated data may be based on preexisting data, for example, density of a tissue, such as bone density or movement of the various fragments of the known bone structure contained in the regions of interest, which may give rise to predictable strength properties of the bone, therefore properties of dynamic movement characteristics under different conditions such as breathing, heart pumping, or general movement, which may be simulated by software with pre-measured or extracted information from measurements done before. Simulated data may be derived, for example, for an implant or a surgical tool, which may have distinct composition and dynamic movement characteristics based on the material types and design of the implant. Its effect on the x-ray image can be determined before the live imaging step, based on virtual image generated from pre-existing data from measurements of the same type of implant or simulation of predicated value of implant. As described above, radiolucent marker may be used to label the implant before or as it is inserted in the region of the interest. In emergency situations, when the first images or complete set of first images of the subject 16 are not readily available or the subject imaged are in locations not accessible for complete first image constructions, such data can be simulated based on the data taken of animal or data validated based on statistics drawn from measured data of regions similar to component 120, target 110 or subject 16.

Previously known properties may include x-ray imaging and measurable properties such data of dimensions, spatial structures, shapes, density, and/or other relevant data used in the x-ray data and imaging analysis to locate and tract component 120, target 110 and the subject of interest 16. Previously known properties may be data from measurements of a different imaging/measurement technique using any of the following: energy or electromagnetic wave, including spectroscopy, MRI, ultrasound, optical imaging and analysis, PET, magnetic particle based imaging, photoacoustic, thermo- or optical-interferometry. Previously known properties may be computer or user input parameters and properties.

In robotics surgery, generally a virtual boundary is required outside of component, or target or region of interest, or alternatively a virtual boundary is required for an implant or surgical tool. Such boundaries exist to limit the movement and position of component, target, or region of interest to interact with an implant or surgical tool. All of the above-described properties may be used to differentiate components, target, and subject and set a virtual boundary for the computer to control the position, relative distance and the movement of the surgical tool or implant apparatuses.

The definition of geometry and therefore the boundary of component, or target or region of interest may be determined during diagnostics or treatment planning. Such information can be extracted from the first measurements and analyzed during diagnostics process, investigation and discovery process. A computer or a user may select such regions as region of interest for live measurements based on preexisting data and/or measured data from images acquired for diagnostics and planning. For example, smaller components, smaller targets may be defined for the heart tissue compared to a lung tissue due to its complexity in structure and its dynamic movement characteristics. As a result, a larger number of targets in a fixed 3D volume may be defined for the heart tissue compared to that of a normal lung tissue. During procedures of implant or treatment of a tissue or disease, only the selected number of components may be measured, and some may be at higher frequency than others in the same tissue or compared to other tissues.

Typical dynamic motions existing in a live human containing the subject 16. The motions can be of a set frequency, with a typical defined cycle or interval, or with a set pattern, for example, heartbeat, breathing, and/blood flow. The motions can be without a set frequency, but may behave with or without a pattern, and some may be at a set frequency when triggered by a normal physiological event, such as stomach movement during food digestion, or faster heart beat due to activities or emotional event. The motions can include voluntary motions, such as at joints, when multiple organs or segment of same organ may be in dynamic motion state. The motion can include involuntary motion, for example, a human moving or shifting his or her body under sedation, or while sleeping.

During imaging, a patient may experience any of those types of motion. A region of interest 130 may have dynamic motion characteristics specific to a condition, and each of its components 120 may have distinct dynamic characteristics, which may be captured by illuminating the component by an x-ray fan beam or selected one or more x-ray thin beam, and sampling measured data at different time intervals.

X-ray imaging can be combined with x-ray data measurement analysis in a hybrid imaging configuration. FIG. 25 illustrates an example flow diagram for hybrid measurements and colocation of quantitative x-ray images with non-x-ray imaging modalities in position and tracking of region of interest. Measured x-ray data of some of the first and live measurements may be derived from a microscopy or spectral absorptiometry system.

Much higher resolution imaging, for instance, resolving details in nm range and/or high resolution spectral quantitative analysis, may be achieved for selected field of view on the region of interest.

Additional details of the x-ray source will now be described. The-ray source may be of a conventional x-ray tube, or an x-ray source with multiple emitting positions, or capable of emitting x-rays from multiple emitting positions, or capable of steering the beam output, such as those with magnetic plates to deflect electron beam, or using various hardware methods to generate electronic beams, including cathodes such as conventional cathode, cooled cathode, light based, synchrotron and alike, crystal based, nanotube based cathodes, and/or anodes such as any conventional anode, liquid anode, or nanowire. The x-ray source can also be coupled with diffraction grating or collimators or beam splitters or tunable grating or beam selector or beam steering apparatus, including MEM, or crystal-based apparatus or total internal reflection based apparatus or waveguides. Any x-ray source with energy switching apparatuses can also be used.

An x-ray source can being placed inside a subject or be intra-cavity or miniature in size. For instance, the x-ray source may be carbon tube or crystal based, and may produce some or all of first image and live images. Such X-ray sources may be inserted into a cavity or internal volume of a subject 16 to illuminate the region of interest. For example, as the heart valve or stent implant is guided in to the location of the target, an x-ray source may be connected to the guided wire and/or place in a fixed position in relation to the implant position, in similar fashion as an endoscope with the exception that the detector is placed external to the subject. The x-ray source may be used with the same detector 14 as in FIG. 16 or a different detector. The x-ray source may be used with an x-ray optics assembly which may include a condenser lens and aperture to focus the x-ray and go through the region of interest. The transmitted x-ray can be collected and output to a detector. The x-ray of a monochromatic source can be any energy level (such as 0-70KeV or higher) for synchrotron and alike sources. A monochromatic source derived from conventional x-ray tubes can be any of the x-ray tube energy level, resulting from filtering and customization of anode target. The x-ray source can be an ultrafast x-ray source.

Alternatively, a waveguide with one or multiple channels may be used to connect the x-ray emitted from a convention source to the x-ray source having a liquid anode. The flow speed and spatial pattern of the liquid anode may be adjusted to tune generation of x-ray and amount of x-ray generated.

The detectors can be 2D or linear or point x-ray detector or energy sensitive detectors or a spectrometer module or multiple channel spectrometer module, each channel having an energy dispersive grating, and a spatially sensitive sensor array downstream from the subject or the 2D full field detector to measure energy characteristics of the line illuminated by the x-ray beam in the target contained in the region of interest.

A retrofit hardware assemblies and software can incorporate the x-ray tracking features disclosed herein to modify existing hardware and software to be suitable for the specific application, such as generating x-ray at 20KeV-1000KeV to surgical guidance, or in the MeV range for radiation therapy. A retrofit kit may include any one or more of the following: a calibration kit including both hardware and software, software to calibrate for the imaging methods disclosed herein, hardware and software to modify x-ray source and x-ray source control to switch from different energies, one or more additional x-ray sources as described herein including to replace existing x-ray source with new x-ray sources and/or to create more x-ray emitting positions, x-ray detectors assemblies as described in the scatter removal and material decomposition herein to replace a rear flat panel detector, software for imaging process and/or acquisition, hardware for positioning or mover to move x-ray source or other parts of the x-ray system involved in the methods described herein: one or more collimators to modified output from the x-ray source beam for scatter removal or material decomposition imaging, a beam selector to modify existing dual or multiple layer detectors, a beam selector plus a detector to complete a dual detector scatter removal assembly if there is already an existing detector, one or more additional detector if there is already a beam selector or collimator and a detector, a tunable hardware such as MEM or crystal for beam steering or adjusting x-ray beam field of view and other output properties or selecting thin beam, an x-ray beam position steering apparatus or an electron beam steering apparatus, any additional hardware needed for spectral absorptiometry or x-ray microscopy, any additional hardware needed to include x-ray or non x-ray imaging modalities and technique and spectroscopy or light analysis system, such as optical spectroscopy, MRI, PET, Optical Mechanisms, Photo Acoustic, Ultrasound, Thermo imaging and analysis.

More details on the method of tracking will now be described. As shown in FIG. 25, hybrid measurements and colocation of quantitative x-ray images with non x-ray imaging modalities can be used for positioning and tracking of the region of interest. At Step 1, existing quantitative 2D and multiple dimensional x-ray imaging and material decomposed image database can be combined with images from other modalities-MRI, PET, Optical Imaging and/or analysis, spectroscopy, photoacoustic, ultrasound, and/or magnetic particle based imaging modalities, all of which can be stored as first measurements of static positions and 3D and 6D tracking data sets, which can be sufficient to characterize dynamic movements for the region of interest.

At Step 2, live measurements of region of interest by x-ray can be made along with any other imaging methods. At Step 3, colocation can be performed based on co-location of dyes, or first, secondary, tertiary or more order dyes, each for a different modality, or common dyes, for two or more modalities. Alternatively and/or additionally, colocation can be performed based on component images differentiable based on measurable properties, or relative spatial locations or visibilities of specific component. Alternatively and/or additionally, colocation can be performed based on images for each material type or distinct spatial structure or physical property, or matching of measurements of dynamic movement characteristics for components or target or regions of interest. Alternatively and/or additionally, colocation of imaging modalities can be performed based by any combinations of the above.

At Step 4, a processor of the x-ray apparatus can match live measurements of all modalities with the first measurements database, and determine 3D positioning, 4D and 6D tracking of components, targets, and/or the region of interest.

FIG. 28 illustrates an example flow diagram for multiple dimension dynamic movement characterization and tracking incorporating scatter removal. At Step 1, the processor can obtain the existing 3D complete imaging data for region of interest including the dataset with single, dual or spectral energy first measurements. The data can be obtained from 2D flat panel based multiple dimension imaging database, or CT scanner or MRI, or PET and/or other light based quantitative analysis and imaging system. Matching of live point, data region, 1D, 2D, 3D and/or 4D measurements with first measurements or synthetic data set will now be described in greater detail. Dual and multiple energy first measurements of the region of interest may be combined with different first measurements of same energy level taken at the same stage of motion cycle and at various times, and 2D images or 1D image or point data set may be extracted to form new data set.

At Step 2, the processor can calibrate the x-ray source and detector relative distance and position, and beam selector position, such as using the calibration methods disclosed herein (which may be on an as needed bases throughout the tracking process. Correlation of x-ray thin beam position and regions of pixels on detector correlating to the x-ray thin beam positions can be registered. In some cases, Step 2 may not be needed.

At Step 3, the processor can sample one or more 2D images of region of interest different x-ray source emitting positions to locate the region of interest, its component and targets of static position at the start of the first measurements for dynamic movement characterization.

At Step 4, the processor can sample the first measurements at various energy levels, for example, each time using one or more data regions projected by an x-ray thin beam or 2D imaging of region of interest at one energy level, for instance, high energy level, and using one or more selected thin beam at a different energy level, for instance, low energy level, at various times throughout the dynamic movement process. For time sensitive measurement for tracking and position, a first measurement can be sampled at one energy level or multiple energy level if the source is that of multiple energy source emitting multiple energy x-ray beams at the same time. Such a measurement may be done in one pulse of x-ray illumination on the region of interest. The x-ray to illuminate the region of interest may be of one or two thin beams or a set of thin beams, or 1D sliced x-ray beam or selected x-ray fan beam regions, depending on the application requirements. One or more live measurements can be taken by sampling the x-ray beam at different times. Each image can be compared against extracted or synthesized 2D or 3D or 4D images from multiple dimensional image reconstructed from the set of data derived from first measurements and first images.

At Step 5, the processor can extract energy decomposed images of distinct substances, materials and components and targets in the region of interest, and selected data region, 1D-7D presentations of component, targets and region of interest at distinct energy levels, which can be synthesized to complete the database to characterize the dynamic movement of component, target, and region of interest during the dynamic movement process.

Multiple images of region of interest and components and targets can be reconstructed and data point, 1D, 2D, 3D and 4D images of the region of interest, components, and targets can be extracted from first measurements. If multiple dimension images are reconstructed for first measurements taken at different times during a dynamic movement cycle or a relevant time frame to a dynamic movement, 6D images of components and targets may be extracted based on 3D images of reconstructed from first measurements, which vary in time.

At Step 6, the processor can take live measurements necessary for the tracking of components, targets, and/or the region of interest, throughout the treatment or tracking process. At each time of measurements, the processor can sample one or more data regions projected by an x-ray thin beam or 2D imaging of the region of interest at one energy level (such as high energy level), and optionally based on the application requirement, one or more selected thin beam projected data point measurement at a different energy level (such as low or medium level).

Optionally, at Step 7, for each live measurement, the processor can illuminate the selected different regions of the component and region of interest with x-ray thin beam to reduce radiation dosage. The processor can also optionally select and define subsequent regions to be illuminated by x-ray thin beams so that looking up of location of the such regions can be relatively easy to with the position database, for example, when the illuminated region is right next to the one before to limit the number of datasets needed to position the new measurement data.

At Step 8, with each live measurement, the processor can match the live measurements or extracted data based on live measurements or synthesized data from live measurements and extracted data to those from first measurement for the corresponding time interval and selected x-ray illuminated position, of the component, target, and region of interest. Components of the same region of interest may be located in the three dimensional space. Matching of the stored 3D-7D image with the first measurements can be performed to locate the region of interest by looking up and extract imaging data set based on location of the x-ray illumination on the region of interest and the expected projected image location on the detector. For example, if only one of the components moves in the region of interest and the rest are static, then one image at one energy level with one pulse, may give the same image and material decomposed data for other adjacent regions and other components. The change in measurements can indicate movement and location of the component, compared to that before the measurement.

Matching can be performed between live measurements at single energy level and that of extracted or synthesized data from images reconstructed from first measurements and first images of illuminated region of interest, and the first measurements may be at single, dual or multiple energy levels. The entire first measurements can be based on multiple dimensional imaging methods disclosed herein. A component, for example, a heart valve implant, may be differentiated based on the dual or multiple energy material decomposition method for a distinct substance.

Single, dual and multiple energy first measurements of the region of interest may be combined with different first measurements of same energy level taken at the same stage of motion cycle and at various times, and images and measurements of various dimensions may be extracted to form new data set.

Since material composition does not change, x-ray data for regions other than the moving component in the same illuminated path of the region of the interest may be generated for the specific energy level the measurement is taken under. The exact measurement of the moving component may be extracted.

The extracted data for the moving component can be matched with synthesized data from the stored database described above and the position and movement orientation 1D, 2D, 3D and 6D images of the moving component may be derived.

In a situation where the component of interest is a blood vessel, the movement of blood flow creates varied images of blood vessel, while the rest of the region of interest in the background is relatively static. Accordingly, it may be suitable to use one or a small number of thin beams to illuminate the blood vessel to monitor and characterize flow properties. In some cases, contrast agents such as microbubbles or nanobubbles may be used. In some cases, phase contrast x-ray imaging, an interferogram may be used to monitor dynamic blood flow in the blood vessel. When a pulse of multiple energy x-ray beam illuminates the component, a spectral measurements may be taken further characterize the changes in the moving component.

At Step 9, the processor can extract the images and data representing various dimensions of selected region on the component or targets or region of interest for each time live measurements that take place to track and position components, target, and region of interest in 7D space When locating a region of interest for quantitative data analysis of the first images, for example, in addition to tumor, a surrounding region with lesion or cellular matrix anomaly to normal tissues may be identified to further identify the tumor region during diagnosis and treatment. The computer and/or a user in a heart value implant may segmented heart tissues into several areas, some areas may move due to breathing, some area may move due to heart valve pumping, and some regions of the heart may move more than the other region. All areas can be characterized so that x-ray images of various regions can be taken to monitor the procedure of implant placement at various times.

Due to movement characteristics, the illumination pattern of an x-ray beam may be planned before the surgery. For example, for regions that only move due to breathing, very limited number of x-ray thin beams, for example, as little as one beam, may be sufficient to locate and position this region. For regions of cardiac tissue where it moves corresponding to the pumping of blood and/or other blood related dynamics, a denser number of x-ray thin beams may be used to monitor their movement dynamics. Optionally, an x-ray beam with a field of view covering the entire region may be preselected to illuminate this region for motion tracking.

Even though other region of the subject (for example, chest bones in heart imaging) may move with a different dynamic, such regions may be used as a reference point for relative position of the regions of interest in cardiac tissue at various identified areas. In addition, with dual or multiple energy material decomposition disclosed herein, regions where the heart valve may be placed may be visible without a contrast label for the tissue. If microbubbles or contrast agents are used to label blood vessels, the relative position and structure of region of cardiac tissue where an implant such as a heart valve implant, may be characterized with greater precision.

For dynamic characterization, matching can be performed between live thin beam measurements at single energy level and that of extracted data from 2D image reconstructed from first measurements of thin beam illuminated region of interest, and the first measurements may be at single, dual or multiple energy levels. The entire first measurements can be based on multiple dimensional imaging methods disclosed herein. A component, for example, a heart valve implant, may be differentiated based on the single, dual or multiple energy material decomposition method for a distinct substance.

Dual and multiple energy first measurements of the region of interest may be combined with different first measurements of same energy level taken at the same stage of motion cycle and at various times, measurements or data representation of various dimensions may be extracted to form new data set.

Since material composition does not change, x-ray data for regions other than the moving component in the same illuminated path of the region of the interest may be generated for the specific energy level the measurement is taken under. The exact measurement of the moving component may be extracted.

The extracted data for the moving component can be matched with synthesized data from the stored database described above and the position and movement orientation 1D, 2D, 3D and 6D images of the moving component may be derived.

In a situation where the component of interest is a blood vessel, the movement of blood creates varied images of blood vessel, while the rest of the region is static. Accordingly, it may be suitable to use one or a small number of thin beams to illuminate the blood vessel to monitor and characterize flow properties. In some cases, an interferogram may be used to monitor movement in the blood vessel. When a pulse of multiple energy x-ray beam illuminates the component, a spectra spectrometry measurement may be taken with energy sensitive detector or energy dispersive grating and spatially sensitive detector to further characterize the changes in the moving component.

As the complexity of the moving component, target and region of interest increases, the number of thin beams may be increased to illuminate one component, and/or the field of view of each thin beam may be expanded, and/or a 1D x-ray beam to illuminate a sliced region on the region of interest may be needed and/or one complete 2D image or interferogram for the region of interest may be required. For example, for a component that has more elastic strength characteristics, such as a component made of soft tissue, more thin beams may be needed for different segments on the component. In the case of cardiac movement monitoring, even more thin beams may be needed for movement of the specific segment of heart to be fully described and investigated.

The first measurements for the dynamic movement characterization can be at different times in a dynamic movement process or cycle. If several types of movements are involved in the region of interest during the tracking process, due to various physiological conditions, measurements at statistically meaningful time intervals may be needed. For example, cardiac motion may take place every second. Sampling at 1-30 frames per second may be required to monitor heart tissue movement throughout a heartbeat cycle.

Images of various dimensions, for example, from point to 7D, can be extracted based on a set of first measurements and synthetic data derived from the first measurements and data based on other imaging techniques. All the first measurements and extracted relevant imaging presentation data can be combined for different statistically significant time period throughout a dynamic movement process or cycle to compile a database for the characterization of the dynamic movement of components or target or of the region of interest.

The same processes can be used during the surgical procedure and/or for post-procedure evaluation. The data during and after the surgical procedure can be matched. Since volumetric imaging data from the first measurements show the internal targets from decomposed material quantitative analysis, matching the live measurements or the live projected data point or data region to the results from the volumetric data of first images can lead to tracking of 3D and 6D position of the component, target as well as region of interest.

The x-ray apparatus disclosed herein may be used in conjunction with one or more sensors (such as external position sensors) and/or one or more reference targets to track the position of the target region on a real-time basis. The signal from the sensor or position of the reference targets in x-ray images or other position measurement techniques, light or RF or magnetic or ultrasound or radioactive measurements can be correlated with the position of the target region. The correlation model can be produced by simultaneously taking an x-ray and reading the signal from the sensor and/or reading the x-ray measurements passing through the artificial target and then using the x-ray to identify the best-matching 3D image that shows the target position. Once the correlation is established, the position of the target region can be tracked real time continuously.

Contrast Agent Examples he present disclosure includes contrast agents and methods of use for 2D and 3D imaging of x-ray imaging as well as hybrid modality or colocation imaging, for example, with optical spectroscopy and imaging, photoacoustic, CT, PET, MRI, magnetic particle based imaging and ultrasound. In some instances, the modalities are collocated with the systems of the present disclosure by anatomic or temporal markers. In other cases, contrast agents for one or more other modalities may be used as contrast agents in the x-ray system of the present disclosure. In some cases, contrast agents for the x-ray measurements of the present disclosure may be covalently or non-covalently linked to the contrast agent and/or other related ligand used in the imaging, diagnostics, monitoring and treatment and surgical guidance, drug delivery and therapeutic procedures involving other modalities.

Contrast agents disclosed herein which in some cases are contrast agents which have been used with x-ray imaging and CT and x-ray measurement of prior art, and/or with other modalities, can be used with the x-ray measurement and imaging system of the present disclosure, namely two or more dimensions, three-dimensional quantitative digital x-ray imaging based on 2D flat panel detectors and, hybrid system which include more particularly, relates to single, dual or multiple-energy x-ray imaging of selected regions on a region of interest of in subjects or subjects having two or more multiple materials or components as disclosed herein, the dimension of selected regions may be in diameter of nm, or um, or mm or cm or higher range. When the dimension of the selected region is small, the spatial resolution or spectral resolution or frame rate of the sensor for x-ray measurement can be increased dramatically, especially in a hybrid system where a full field x-ray image is used to select the selected region. A digital programmer may select the region based on one or more criteria based on the imaging results of a full field x-ray image. Or a user may select region. The subject and/or materials in the subject may not be differentiable visually or quantitatively in an x-ray image when taken by a full field x-ray detector. However, a full field image may capture enough information of the region of interest to determine which region may be selected for further analysis and imaging. In cases where the interface region of two or more tissues or inhomogeneous region, higher resolution in spectral and spatial and/or time dependent measurements may be used to further resolve much smaller units of unknowns in selected regions Contrast agents disclosed herein can be used for imaging and quantitative analysis of each of the multiple tissues in an organism, an animal or human body and/or imaging and densitometry of a subject with two or more different materials or components in a synthetic subject or in an organic subject or mixture of both.

In cases where a human body structure of soft tissue and bone is overlapped by a different material, for example, plaster or fiberglass cast material, or implants or surgical tools for medical purposes, contrast agents are used to mix with or chemically bind to the material to enable visualization and differentiation. Bone can be better separated in an x-ray image from soft tissue and/or other tissues, tumors, cells, and/or inorganic or organic materials labeled with molecules or molecule complexes or derivatives of molecules of differentiable atomic z numbers and/or densities, or subjects or component with a different atomic z number and/or densities. In addition to different atomic z numbers, and density measurements, differentiable x-ray properties may also extends to volume of the material, movement characteristics in time and in space, shapes, pattern, spatial position, fluidic dynamics, energy triggered state of being, flow direction, temporal and anatomic markers. When the imaged subject includes one or more components of very small unit dimensions that are too small or to similar to be resolved by x-ray systems, using contrast agents disclosed herein can improve detection of those components.

The contrast agents disclosed herein can be organic, ionic, non-ionic, non-metal (therefore less toxic), or metal, intrinsic and/or endogenous to the subject, such as $Ca^{2+}$ or $Ca^{2+}$ binding peptide or protein, gaseous matter, air bubbles, or regions that are rich in cations. The benefit of using intrinsic molecules in a subject or derivative or conjugated complexes based on such intrinsic molecules, such as $Ca^{2+}$ (or also potassium and/or the like), is that they are relatively non-toxic within a certain range. In addition, since calcium or calcium conjugate images separated from the rest of images of the subject may be taken before and after the contrast agents bind the molecular labels, a dual-energy system can take images where bone and other calcium-based images are separated from the rest of the images to indicate where and how much calcium is present in the images taken. This application can be especially useful in identification and quantification of components that have sporadic appearances in the region of interest, such as rare cells, molecular events, implants, diseased tissue cells, foreign antigens, tracking and long term and/or chronical monitoring can be achieved without toxicity concerns.

For example, the following is a list of endogenous or intrinsic elements in a human body:
  Quantity elements—Na, Mg, K, Ca, P, S, Cl,
  Essential trace elements—Mn, Fe, Co, Ni, Cu, Zn, Mo, Se, I, Mo, Cr
  Function suggested from active handling in humans, but no specific identified biochemical functions—Li, V, Cr, B, F, Si, As Na, Mg, K, Ca, P, S, Cl are preferred, as they exist in quantities naturally. A relative large dosage of contrast agents including such elements may be administered, especially when in low frequencies, it may be relatively harmless.

Ligands bind to targets, such as a tumor with a marker, or a diseased tissue with identifiable features, may be conjugated with such endogenous elements and their derivatives, and then input in to the subject. In another example, such a ligand may be administered without being linked, but its composition allows for active domains or epitopes to bind to free ions of the element or molecules comprising such element. Such molecules may be endogenous or synthesized prior to being administered to the subject, via oral intake, injection or inhaling. Clusters and complex assembly of such element ions or molecules comprising such element and their derivatives may be formed at the targeted region. And such clusters and assembly may break down over time, or chemically, such as enzymatically such as protease or redox molecular complexes conjugated with ligands recognize epitopes or domains or other identifiable properties of the molecular assembly or via energy perturbation such as using ultrasound to break down microbubbles containing contrast agents and its conjugates. PH and/or temperature may play a role in assembly, binding and breaking down of such molecular complexes for x-ray measurements. For example, PH in a tumor region is high at 7.4 compared to PH of 7.0, a relative normal cellular matrix area. Temperature probe induced temperature differences, or anti-inflammatory response of immune system to bacterial infection can induce temperature trigger enzymatic or chemical reactions.

The contrast agents can optionally be iodine-based or an iodinated compound. Contrast agent that utilizes iodine typically includes water-soluble organic compounds based on their relatively low toxicity and their covalent bonding of iodine atoms. The iodinated compound can be aromatic or nonaromatic. The iodinated compound can include, one, two, three or more iodine atoms per molecule. Thus, in addition to iodine atoms, such contrast agents may include carbon, hydrogen, and may include nitrogen, oxygen and other atoms having relatively low atomic z numbers. A preferred class of contrast agents may include various esters and amides of iodinated aromatic compounds. The iodine-based contrast agent may include, but are not limited to, diatrizoate, iothalamate, metrizoate, iodipamide, ioxaglate, iohexol, iobitridol, iomeprol, iodixanol, iopamidol. Illustrative nonionic contrast agents, include but are not limited to, metrizamide, ioglunide, iopamidol, iopromide, iogulamide, ioversol, and non-ionic triiodinated compounds. The concentration of the iodine-based contrast agent may be from 30 mg/ml to 100 mg/ml.

The disclosure can also be practiced with poorly soluble contrast agents. The disclosure can be practiced with poorly soluble derivatives of iodomethane sulfonamides, iodinated aromatic glucoanilides, 2-ketogulonamides, reverse amides, peptides, carbamates, esters, glucoside and glucose derivatives, benzamide derivatives, isophthalamides, bis compounds, and/or bis-polyhydroxylated acylamides. Further, many of the molecules described herein can be in a monomeric form, and can also be prepared as dimers, trimers, or polymers.

The contrast agents can optionally be metal-based contrast agents. Metal-based contrast agents may include lanthanide-based, barium-based, tantalum-based, tungsten-based, gold-based, bismuth-based, gadolinium-based, and/or ytterbium-based. Specific examples of lanthanide-based contrast agents may include, but are not limited to, gadoversetamide, gadopentetate dimeglumine, gadobutrol, gadobenate dimeglumine, goadoterate meglumine, and gadoxetate disodium.

The contrast agent can optionally be a negative contrast agent. A negative contrast agent is a contrast agent that is less dense than the surrounding blood or tissues. A negative contrast agent is visible in the image as lighter, in that it will show a higher luminance intensity. Air, oxygen, and carbon dioxide are examples of negative contrast agents.

In accordance with the disclosure, contrast agents may be administered to a subject. The contrast agent may be administered in any one of a range of conventional manners, such as orally or intravenously. A contrast agent is administered to produce the desired contrast in the tissues on which the area is to be x-rayed.

In some aspects, the contrast agent may be administered at different time points. The contrast agent composition and interaction of contrast agent and subject of interest can be used to enable quantitative analysis and visualization and identification and long term tracking. Long-term tracking can include tracking of cells for months to years, such as for clinical trials, which can require long-term follow-up of tissue function or host survival. In another example, a contrast agent may be administered at close proximity to each other to trace the progression of a contrast agent.

Compared to conventional CT which may have a spatial resolution from 0.3 um to 500 um, in some instances, x-ray systems, or preferably, the hybrid system of the present disclosure have higher spatial resolution and spectral resolution for selected regions. For microscopic instruments, the diffraction-limited spatial resolution is proportional to the wavelength, and to the numerical aperture of either the objective or the object illumination source, whichever is smaller. The highest resolution of microscopy has been reported at 0.1 nm range by using unique objectives. Generally, zonal plate is used as an objective, the highest resolution achievable is in the range 100 nm.

For example, diffraction limited resolution of x-ray microscopy may be proportional to that of its shortest wavelength, in the range of 0.01 nm. Current x-ray systems may allow imaging to have a resolution in the range of 0.1 nm. If hardware or x-ray optics continues to develop, an objective which may be developed to x-ray measurement at its highest possible resolution, its diffraction limited resolution. This leads to possibly 10× to $10^8$× improvement in resolution when using the x-ray system disclosed in the present disclosure, compared to that of CT. X-ray spatial resolution of the x-ray system of the present enclosure may reach the x-ray diffraction limit for selected regions. Therefore molar sensitivity, for example, of contrast agent, improves proportionally accordingly, increase in resolution in 3D is $10^3$ to $10^9$ or even higher. The concentration of contrast agents in the subject of interest can be increased to about a range of $10^{-3}$ to $10^{-12}$ molar and everything in between. The amount of contrast agent administered can be, for example, from 0.1 mg/ml to 1000 mg/ml. Preferably, the amount of contrast agent administered is from 0.1 mg/ml to 100 mg/ml. Preferably, the amount of contrast agent administered is from 1 mg/ml to 1000 mg/ml.

Contrast agents can be introduced either through mixing or molecular binding with subject specific markers to visualize one or more components having matter(s) that would otherwise not be differentiable from the rest of subject in x-ray imaging or x-ray hybrid imaging with other imaging modalities. Molecular binding can include an induced molecular cascade method for molecular labeling and imaging in the imaging apparatuses as well as techniques disclosed herein to reach sensitivity of up to single cell detection.

Labeling each component by contrast agents can be achieved using one or more antigen specific molecular labels to bind a second or third material in the subject to be imaged. Such molecular labels can include atomic z number differentiating particle or differentiable imaging properties or molecule or modified version of such particle or molecule. The molecular label can be intrinsic or externally synthesized.

Antigen specific molecular labels can include matters with different atomic z numbers than that those in a human body. Examples of antigen molecular label can include, not limited to Au-(gold), Pt-(platinum), Ta-(Tantalum), Yb-(Ytterbium), and Bi-(Bismuth) based nanoparticles, graphene nanoparticle or graphene radiolabel composites, nanotube composites, iodinated or barium, gadolinium small molecule and other contrast agents, or such molecules being modified to prolong circulating time and increase stabilization, such as polymer based molecules, for example, polyethylene, glycol (PEG), for example to effectively prevent NPs from rapid uptake by scavenger cells, or stabilized with gum— Arabic (GA) matrix, or dendrimers, or branched polyethylenimine (PEI) with abundant surface Primary amines, or oligo amino acids, such as oligoarginine, naturally occurring peptides, such as glutathione or GSH, other surface ligands capable of conjugating with different nanoparticle or small molecule protein corona in blood that can determine the RES absorption and cellular uptake efficiency, or for example, albumin-capped Au nanostars. Any molecular labels that are used for pharmaceutical drug delivery can be used as molecular labels in the present disclosure. The contrast agents disclosed herein can be conjugated with drug delivery agent or drug agent or therapeutic adjacent for improve imaging signal intensity or level.

The contrast agents or contrast agent complexes can optionally be in nanospheres and vesicles for various imaging modalities. Various contrast agents can be modified and linked to each other to enable sensitivities for two more imaging modalities or colocation of imaging methods, such as photoacoustic imaging or PET or MRI, or Optical Coherence Tomography, or bioluminescent or fluorescent imaging or ultrasound imaging. The contrast agent or contrast agent complexes for each modality can be chemically linked to ensure colocation.

The contrast agent may be in the form of a hydrogel. The hydrogel has water, a contrast agent, and reactive hydrophilic polymers that form a crosslinked hydrogel after contact with the tissue. The hydrogel coast the tissue and forms a coating. The coating may have a free surface. The contrast agent disposed in the hydrogel allows for a user applying the hydrogel to observe the hydrogel and estimate its thickness and apply hydrogel until it reaches a predetermined thickness. The contrast agent can be a suspension of the nanoparticles described herein a hydrogel form. The hydrogel may include calcium ions or calcium ion derivatives or other endogenous elements in microspheres, particles, or microcapsules. In some examples, the hydrogel is sterile. Hydrogel may expand/or shrink and migrate to the targeted region, based on markers, temperature, pH or enzymatic reactions and other perturbation, which may then be measurable by x-ray.

In addition, further modification, such as micelles or nanomicelles, polymeric micelles, nanosuspensions, nanocapsules, nanoemulsions, or lapidified version of the molecules, or any combination of such can be used for creating the contrast agents or contrast agent complexes. Nanosuspensions may include colloidal dispersions of pure drug particles stabilized by surfactants. An example of such may include, e 6-ethyoxy-6-oxohexyl-3,5-diacetamido-2,4,6-triiodobenzoate. Nanoemulsions are stable nanostructures of one liquid material within an immiscible second liquid. For example, nanoemulsions may be made with a mixture of vegetable oil and other oils to form an oily core, stabilized with phospholipids, cholesterol, and PEGylated lipids. Example of such nanoemulsion may include, but are not limited to, lipid-soluble iodinated-based compounds, such as lipiodol, or polyiodinated triglycerides. Nanocapsules are stable nanoparticles comprising a crosslimked polymeric membrane enveloping a payload-material that is often insoluble/immiscible with the surrounding solvent. Nanoparticles may be formed by crosslinking a polymer around an oil by nanodroplets. In some examples, the size of the micelles, nanomicelles, nanosuspensions, or nanoemulsions may be from 20 to 200 nm.

Alternatively, contrast agents can be liposome-based molecules. Liposomes are amphiphilic phospholipid vesicles with a bilayer membrane structure similar to that of biological membranes and an internal aqueous phase. Their amphiphilic nature allows them to transport both hydrophilic contrast agent molecules entrapped within their aqueous interior and hydrophobic molecules dissolved in their membrane. For example, iodine or $Ca^{2+}$—loaded liposomes can be used to accumulate contrast signal and density, while ensuring non-toxicity, easy transportability, and accessibility to the site of interest. $Ca^{2+}$ or other contrast agent loaded liposomes or any other versions of cage, 2D, 3D structure based, or simply a cluster or aggregate contrast agent assembly can be used as contrast agents in the present disclosure. Liposome-based contrast agents can be obtained through the chemical grafting of the contrasting atoms onto the lipids. Liposme-based contrast agents size may be modified with PEG. In some examples, the liposome-based molecules may include iodine or an iodine-based molecule. In some examples, the concentration of the iodine in the liposome-based molecule may be from 30 mg I/ml to 100 mg I/ml.

Contrast agents can be in the form of polymeric nanoparticles. Examples of polymeric nanoparticles include dendrimers, nanocapsules, nanotubes, or polymer-coated nanoparticles. Specifically, nanoscale metal-organic frameworks (NMOFs) may maintain the features of both their bulk MOF analog and nanoparticle formulation which can also be used for imaging and drug delivery. Nanoparticles may include crystalline nano-suspension of iodinated compounds. In some examples, the first contrast agent or contrast agent complex has an effective particle size of less than 300 nm. In some examples, the nanoparticles are in a range from 30 to 50 nm in average size.

Contrast agents can optionally include a pharmaceutically acceptable carrier or stabilizer. For example, the contrast agent can be dispersed in an aqueous liquid which serves as the pharmaceutical acceptable carrier. Other suitable pharmaceutical carriers include liquid carriers mixed with aqueous and nonaqueous solvents, such as alcohol, gels, gases, and powders. Stabilizer may include surface stabilizers and viscosity modifiers. Pharmaceutically acceptable carriers may include, but are not limited to, saline, buffer solution, water, isotonic solution, bodily fluids, or mixtures thereof. The pharmaceutically acceptable carrier may further include the addition of cations selected from sodium, potassium, calcium, magnesium, iron, zinc, and may be in an amount from about 0.01 M to about 5 M.

Nanobodies and/or the like may be able to improve imaging signal proximity to the molecule or subject of interest. The imaging technology used for cell tracking can have single-cell sensitivity and/or permit quantification of exact cell numbers at any anatomic location. Single-cell sensitivity in in vivo or ex vivo imaging can be especially important in stem cell or tumor cell characterization and identifications because the pattern of migration of, for example, stem cells, even after local injection, is unknown, and there is a distinct possibility that single stem cells scattered diffusely throughout the body might be effective therapeutics for certain disease states.

For applications requiring localization accuracy, molecular labels such as a nanobody or peptide or small molecule or chemical probe or its derivatives may be preferred, although other types of molecular labels disclosed herein can also be used.

Regardless of the level of sensitivity finally achieved, quantification of cell number can be especially difficult when considering the effects of contrast agent dilution during cell division, the propensity of some contrast agents to be transferred to non-stem cells, and/or certain technical limitations (discussed below).

In medical imaging, intrinsic or endogenous molecules can be included as contrast agents, for example $Ca^{2+}$ or other alkaline earth metals, or indicators of events or state of components, such as cation rich regions or cation aggregates due to enzyme related activities or change in speed of movement, including but not limited to heartbeat, fluidic dynamic such as blood flow in microvessel or capillary, and/or state of physiological condition such as oxygenated state.

As disclosed above, the subject can be located between the x-ray source and the x-ray detector or detector assembly. Using a dual or multiple-energy data, in some cases, combined with k-edge method, two or more material composition 15 images can be obtained as disclosed herein. For example, during in vivo imaging, bone mass density image b, soft tissue image s and a plaster cast mass density image p (or molecular labeled tissue mass density image p) can be obtained. Furthermore, components of interest may be labeled by one or more contrast agent and labels, such as iodinated molecule and/or nanoparticle conjugated with one or more subject-specific marker(s).

Any of the x-ray apparatus examples disclosed herein can be suitable for use with contrast agents, for example, scatter removed 2D and 3D x-ray imaging systems and their hybrid systems as described herein, which allowing quantitative measurement, or such systems may be combined with optical imaging, MRI, Magnetic Particle Imaging and optical spectroscopy, or any other suitable modalities. Materials can be better visualized and identified and quantified in a multiple component subject by the use of contrast agents along with any of these imaging modalities. Contrast agents for the x-ray system of the present disclosure may be the same as those for other modalities. Alternatively, contrast agents for the x-ray system may be conjugated with contrast agents of other modalities for better visualization and colocalization. In addition, anatomical, temporal, or spatial markers of the component or the region of interest, or reference marker or fiducial markers may be served as a reference for colocation.

The present disclosure provides one or more molecular complexes, in which a molecule (molecular label) binds to the subject of interest and carries a contrast agent, and has the ability to be detected by x-ray imaging method for quantitative 2D and 3D imaging using 2D flat panel detectors. Such molecules or molecular complexes can be called "NanoXgen". To allowing selective labeling, a primary contrast agent for x-ray imaging, can be made when molecules with distinct atomic z numbers or differentiable x-ray measurable properties are conjugated with one or more molecules which can specifically bind the subject of interest (also referred to as molecular labels) to create a "primary NanoXgen," These aforementioned molecular labels can be an antibodies, peptides, nanobodies, chemical probes, small molecules, oligonucleotides and/or their derivatives. One or more contrast agents of similar properties can be conjugated in the primary NanoXgen. In addition, multiple contrast agents may be conjugated with the molecular labels. Such conjugation can occur at the target site and/or ex vivo. NanoXgen based contrast agent system may allow precise quantification of molecule or markers of interest and low concentration molecules or cells or a target site to be quantifiable or sometimes visualized, especially in the x-ray system of the present disclosure.

NanoXgen can enable quantitative imaging by binding to other target sites in the subject interest, therefore increasing the density of contrast agents associated with the subject of interest to be detectable by the x-ray imaging method, or by binding sequentially other NanoXgens, for example, sequentially, (such as secondary and/or tertiary NanoXgens). To render a cell or collection of cells visible by using a contrast agent, such as a conventional solid metal material, the volume of metal associated with the cell volume typically has to be equal to or greater than the inverse of its density. For example, it would take approximately one eighth of the cell volume in solid iron to generate a signal above the background signal during conventional CT scanning.

However, the present disclosure provides a system which allows contrast agent sensitivity to be comparable that of MRI $10^{-6}$ or PET $10^{-12}$. As a result, the volume of the contrast agents, for example a metal based contrast agent enables, may be much lower than ⅛th of the cell volume, $10x$-$10^{-9}x$ less in molar concentration, the sensitivity of x-ray measurements using the x-ray system in the present disclosure described herein. The amplification factor requirements are application based and need to be analyzed to determine how many steps of the molecular amplification cascade is needed or how many orders of nanoXgen are required to reach the sensitivity of the x-ray system. Accordingly, the signal level from the initial binding of the primary contrast agent specific to the subject of interest may need to be increased at a fast speed at or near the binding site for some applications, such as for even higher high resolution imaging involving activation and deactivation of contrast agents similar mechanisms described in super resolution imaging.

NanoXgens are molecules that can include at least two or three parts. The first part can contain a domain, which specifically binds to one or more epitopes on the subject of interest. The affinity of the domain for the epitope can be designed so that it can be dissociated from the epitope after a specific timeframe. The second part can be a contrast label or contrast agent, which is detectable by x-ray imaging and/or x-ray microscopy, and/or x-ray spectral measurements or x-ray spectral absorptiometry, and can include, for example, gold, silver, iodine, calcium, potassium, fluorescent dye, or a contrast agent recognizable by ultrasound or MRI or PET or CT or Optical Imaging or photoacoustic or ultrasound modalities.

The third, optional part can be a new or second epitope that is created upon the binding of the domain to the target of the subject of interest. This second epitope can specifically bind to other NanoXgens and can be created due to the bind of the domain, formed in part by the target of the subject, in part by the binding molecule (that is, the NanoXgen): or due to conformational change of the molecule when bound.

To amplify the imaging signal level, a set of NanoXgens with varied domains for binding of different epitopes on the subject of interest, and/or a multitude order of such NanoXgens that bind sequentially can be used. The imaging level thereby can reach high enough level to be detectable by one or more in vivo imaging modalities along with x-ray imaging described herein, such as optical imaging, optical spectroscopy, Photoacoustic Imaging, Ultrasound Imaging CT, PET, Magnetic Particle or MRI to identify and characterize a smallest unit of such a subject.

The subject of interest or region of interest can be a cell or virus or molecule that can bind to one variable domain of the antibody or any other molecular label. The subject of interest can be a first component. A drug delivery agent or a drug agent, may be the second component. The primary NanoXgen can be designed such when the target of the first component binds to one domain of the primary nanoXgen, the target on the second component binds to the second domain, which is different from the first domain on the primary NanoXgen. This sequential, cascading process can form an induced molecular amplification system (IMAS), which can amplify the image signal generated by the binding of the primary NanoXgen via the use of multiple orders of NanoXgens so as to detect a low amount of subject of interest present.

Figure 29A:
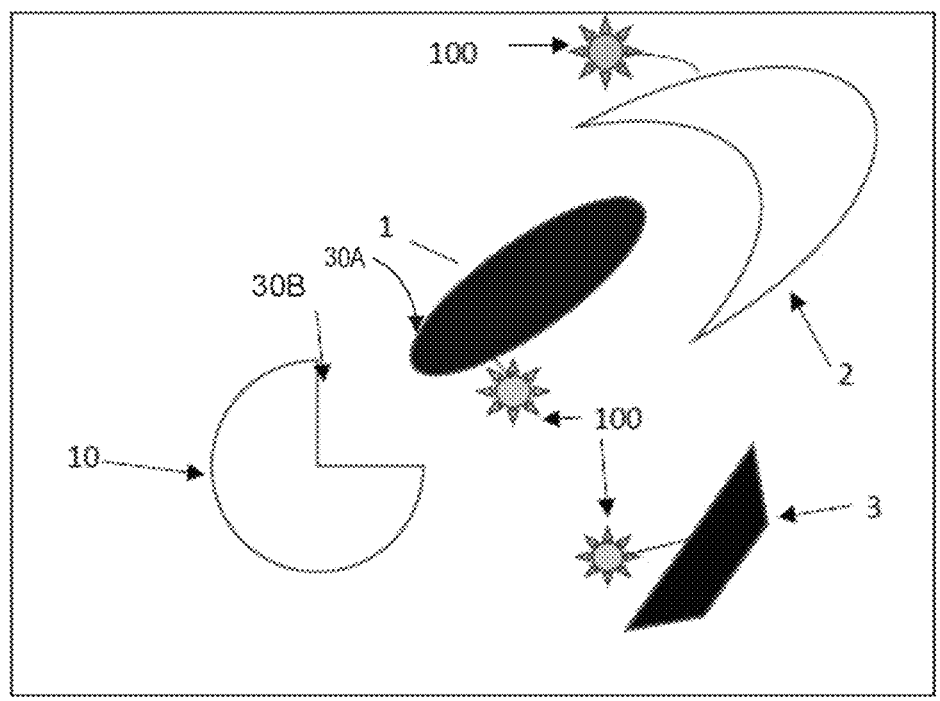
FIG. 29A illustrates example multi-order nanoXgens in their nascent states.
Figure 29B:
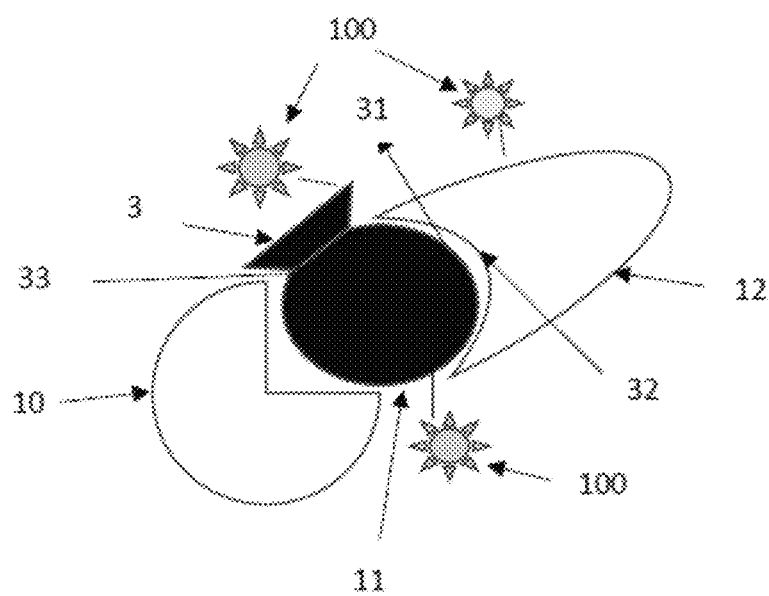
FIG. 29B illustrates the multi-order nanoXgens of FIG. 29A forming Primary, Secondary and Tertiary bindings of the target.

As shown in FIGS. 29A and 29B, the primary NanoXgen 1 can include contrast agent 100 and a domain 30A that can bind with an epitope 30B on a component 10 (such as a subject of interest) or component complex with another component. As shown in FIG. 29B, the binding triggers a molecular event, such as a change in the conformation of the bound molecular complex. The primary NanoXgen 1 changes into primary NanoXgen with a new conformation 11, with one or more epitopes 31 exposed for binding domain 32 of a second order NanoXgen (secondary nanoXgen) 2.

The secondary NanoXgen 2 can include a contrast agent 100 conjugated with a molecule containing the domain 32 that binds the newly exposed epitopes 31 created due to the primary NanoXgen 11's binding to the component or target 10 or target(s). The secondary NanoXgen 2 can include a contrast agent 100 which is the same or similar to that of the primary NanoXgen 1. As shown in FIGS. 29A and 29B, the binding between the domain 31 and the epitope 32 also can cause a conformation change of the secondary NanoXgen 2 to a new conformation 12.

If the contrast agents 100 in the bound secondary NanoXgen 12 and the primary NanoXgen 11 still do not reach the required sensitivity of the imaging system, a tertiary NanoXgen 3 can be used. The tertiary NanoXgen 3 can have binding specificity for one or more new epitopes 33 introduced as the result of binding by the secondary NanoXgen 12. The cascade can be designed to continue until the sum of the contrast agents on all bound NanoXgens reach the density required to be detected by the imaging modality such as the x-ray system disclosed herein.

Optionally, two or multiple epitopes on the targeted component can be used to bind a variety of different nanoXgens which are conjugated with the same or similar contrast agents, so that the total signal level is detectable by the preferred imaging modality or imaging modalities.

Optionally, the contrast agents conjugated with the binding molecules can be designed so that one contrast agent for one modality and a different contrast agent is sensitive for another imaging modality so that colocation of imaging modality signals can be achieved. For example, for contrast agents designed for other imaging modalities such as optical spectroscopy, CT or MRI, photoacoustics imaging or Ultrasound or Optical Imaging can be used as or conjugated with contrast agents in the same induced molecular amplification cascade.

Optionally, the secondary NanoXgen may bind to one or both of the primary nanoXgen and the subject of interest with low affinity. However, when the primary NanoXgen is bound to the subject of interest, the secondary NanoXgen may bind with higher affinity to both targets.

The cascading reaction is also illustrated in FIG. 30. In step 1, a domain on a primary NanoXgen binds epitope on subject of interest. In step 2, the binding causes a conformation change of the primary NanoXgen, resulting in a new 3D conformation of the primary NanoXgen. At step 3, after the conformation change, the primary NanoXgen forms a new epitope. At step 4, the new epitope binds with a secondary NanoXgen, inducing a conformation change of the secondary NanoXgen. At step 5, a complex can be formed by the primary NanoXgen binding the target and the secondary NanoXgen with the new conformation, thereby creating a third epitope involving the primary and secondary NanoXgens and the target. The third epitope can then bind to a tertiary NanoXgen. At step 6, all the contrast agents 100 in the three NanoXgens can label the subject or target, thereby amplifying the imaging contrast carried by the primary NanoXgen by about three time. The cascading steps can continue to additional NanoXgens until the imaging contrast reaches a sufficient intensity for the selected imaging modality.

The induced molecular amplification system may be designed so that each primary NanoXgen has a unique conformation or is attached to a barcode molecule such as a unique peptide or a single strand DNA, which only attracts a unique set of cascade molecular amplification system which has a distinct type of label (x-ray sensitive or can be detected by other imaging modalities including optical imaging, PET or MRI or ultrasound) at the site of interest. When the primary nanoXgen dissociates from its targets, it can trigger or not trigger the dissociation of all nanoXgens from their binding sites. Optionally, the primary NanoXgens can stay bound for a long period of time and the secondary NanoXgen can dissociate after the first measurement was made. Periodically, the cascade molecular amplification system can be administered to monitor the subject of interest.

NanoXgens disclosed herein also can allow for delivery of the contrast agent to be within nm distance from the target, therefore reduce localization error. In addition, such amplification system can occur in intracellular or extracellular environment depending on the location of the epitope on the subject of interest. NanoXgens can allow for site-directed labeling intracellularly for different organelles. For example, nanobody has been demonstrated to have delivered molecules previously not permeable to nucleolus to nucleolus.

Such an amplification system may be optional if the subject of interest has enough number of epitopes for various contrast agents to bind to directly to reach the density detectable by x-ray imaging or other imaging modalities.

Such amplification systems are designed so as not to trigger any major cellular events thereby changing the observant nature of imaging method, but only aims to increase the imaging signal level. The epitopes on the target bound by the primary NanoXgens can be selected to exclude those whose binding of primary nanoXgens can affect cellular physiological conditions, functions, mobility and/or vitality. The choice of location and the cell payload may also be minimized to maintain cell viability, functionality and mobility.

As described above, contrast agents used for detection and quantification of the subject of interest can already exist intrinsically or endogenously. that is, naturally occurring inside the biological body. For example, the subject of interest, such as a cell or a molecule, can bind to, nanoXgen, which has at least one domain can bind to $Ca^{2+}$ based contrast agents. Aggregation of such molecules conjugated with $Ca^{2+}$ can improve sensitivity to be detectable by x-ray imaging using the IMAS disclosed herein. When such contrast agent complexes dissociate from the subject of interest, contrast agents complexes can eventually disintegrate and depart from the site of interest, and release back in to the body without causing any toxicity.

The molecular composition of $Ca^{2+}$ binding NanoXgen can contain naturally occurring $Ca^{2+}$ binding protein domains, for example, in calmodulin. Calcium ions may be complexed by proteins through binding the carboxyl groups of glutamic acid or aspartic acid residues: through interacting with phosphorylated serine, tyrosine, or threonine residues: or by being chelated by $\gamma$-carboxylated amino acid residues. $Ca^{2+}$ or its derivatives, calcium carbonate or calcium biphosphate or hydroxyapatite (HA), which are naturally occurring in a human body, such as hydroxyapatite (HA), can be a contrast agent.

Figure 31:
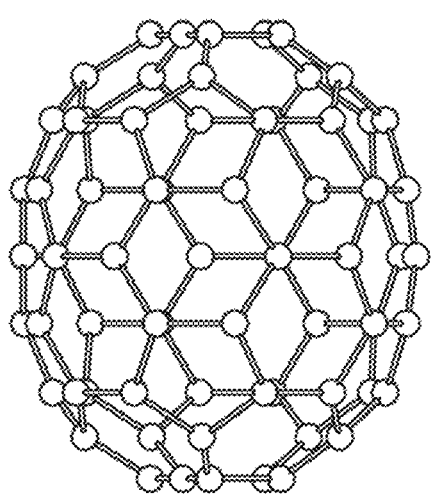
FIG. 31 illustrates an example self-assembled 3D enclosure structure or cages of various shape, for increased Ca++ density at the target.

As will be discussed below, the multi-order contrast agents can include repeat units of a set of three or more different NanoXgens. For example, small cage proteins can be used to self-assemble cage structures for trapping $Ca^{2+}$ and increase density of $Ca^{2+}$. The contrast agent can also be included in a self-assembled 3D structure or cage, such as a sphere (for example, similar to a bucky ball) or variation of such a structure shown in FIG. 31. FIG. 31 illustrates is an example structure of a Buckminister Fuller inspired type of ball structure including molecules such as small molecule, peptide, antibody or oligonucleotide fragments, or small cage proteins which allow the controlled binding and dissociation among one or more molecules to enable repeated units and patterns in multiple dimensions. Carbon or graphene based or other element structure can also be contemplated. Such a structure can enable influx and retention of $Ca^{2+}$ and its derivative molecules inside the structure. Alternatively, such a structure can have a meshed interior, interlaced with $Ca^{2+}$. Each basic unit for the formation of the cage or 3D structure can include repeating units of one or more cage forming molecules, some are small molecules, protein or oligonucleotides or combination of molecules. Upon closing of the structure, there can be an influx of $Ca^{2+}$ current (or any other intrinsic contrast agents) until the density of contrast agents reaches the desired level for visualization by the selected imaging modality.

Figure 32A:
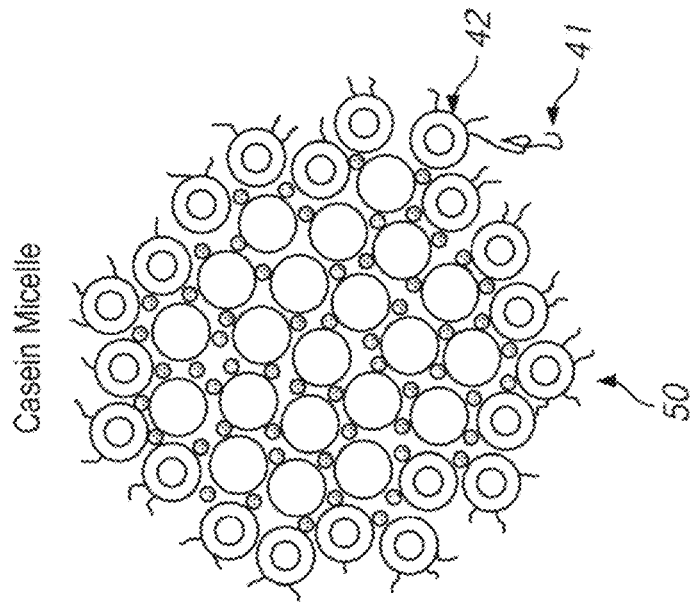
FIGS. 32A and 32B illustrate $Ca^{2+}$ micelle like structure.
Figure 32B:
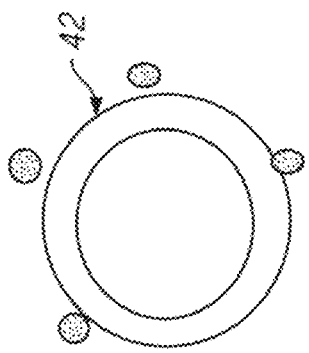

Alternatively, $Ca^{2+}$ can be interlaced in a 2D or 3D self-assembled mesh. One example shown in FIG. 32A is a structure similar to Casein micelle 50 with $Ca^{2+}$ or calcium containing nano-clusters or a casein submicelle 42 as shown in FIG. 32B. Such complexes can be designed to be formed adjacent to the target site, that is, close to the subject of interest.

To trigger the self-assembly process to form the casein micelle 50, a primary molecule 41, such as antibody, nanobody or small molecule binds can to the epitope of the target or the target marker. The conformation of the primary molecule can change, binding to a secondary molecule 42. As the secondary molecule is part of the micelle structure, a self-assembly process starts. After a designated time frame, such primary molecule 41 can dissociate and the assembly complex can break down, releasing $Ca^{2+}$ and other molecules.

The molecular binding based contrast agents disclosed herein has the advantage of rapid clearance and non-toxicity in addition to easy access to epitopes and colocation of detection point with the target interest.

When the contrast agent active part is intrinsic, such as $Ca^{2+}$, dual energy or K-edge types of imaging can be used to differentiate bone and soft tissue. If measurements are taken during and after the complex formation, the dynamic variability, namely visibility of the $Ca^{2+}$ rich points and/or its spatial locations indicate the presence of component of interest and quantitative measurement of the component can be obtained more accurately.

In addition, a target of interest can be tracked and identified over time, by a genetically engineered marker expressed on the cell or microorganism or molecule of interest, which binds primary NanoXgen, or by barcoding using a primary nanoXgen over time. The primary nanoXgen can stay connected to the target of interest. Alternatively, the primary nanoXgen can introduce a barcode, such as a DNA sequence or peptide, to the target of interest by bringing such a barcode to the binding site and using intrinsic catalytic function of primary nanoXgen or binding to another enzymatic protein to link such barcode permanently to the target of interest. Binding and dissociation of downstream nanoXgen specific for the primary nanoXgen or barcode tagged target can be carefully designed to allow monitoring over time.

The contrast agents disclosed herein can also be suitable when subject of interest include air, gas, for example, intraosseous gas and intradiscal gas, air gap in the lung, or presence of cation rich region in arthritis, or any x-ray detectable region which are differentiable from the rest of region of interest, such as those produced by enzyme activities, including aggregates of molecules in areas like the intracellular regions and the like. Time sensitive or triggered activity that can be monitored include, for example, an enzyme produced complex based on biotin-actin, or molecular event or chemical interaction, to measure and track internal events, such as, cellular apoptosis due to tumor growth or vascular growth, over a long term, year, day or hours. The contrast agents disclosed herein can also be suitable for monitoring in vivo liquid biopsy or molecular signaling pathway triggered by for example, presence of tumor, or cell apoptosis. Targets can be recognized by peptide or nanobody binding to the contrast agents or a molecule such as enzymes which may generate varied x-ray signals in the region of interest.

For example, in the case of energy therapeutics, such as RF ablation for renal denervation and cardiac ablation, as cell are affected, such as cell death related events occur, different chemicals are released. These chemicals trigger activity of enzymes tagged with target specific antibody, or peptide, or nanobody. For example, the target may be heart tissue or kidney tissue or specific regions of heart tissue or kidney. The enzyme activity may produce one or more x-ray measurable events, such as, cations, or formation of biotin and actin aggregates tagged with Cations or other molecular signature that can be detectable by x-ray. As a result, the effect of ablation may be quantified. Alternatively, the ablated tissue may produce cations rich regions or may be more rigid than live tissues. X-ray measurements may be able to detect the differences in flexibility and motion dynamics between live and dead tissues. Alternatively, ultrasound probes which can perturb the tissue region of interest while x-ray measurements are taken. Live and dead tissues respond differently and generate different x-ray measurements in temporally.

With the use of current photomultiplier (PMT) or photon counting detector or photodiode in dual, three energy or multiple energy x-ray imaging, any event including molecular, cellular or structural event, such as change in molecular composition, apoptosis triggered event, cellular interaction kinetics, molecule interaction kinetics such as protein and protein interaction can be measured by MRI or Optical Imaging or X-ray system of the present disclosure combined with none, one or more other modalities including optical imaging, spectroscopy, ultrasound MRI and PET.

Various parameters that can be monitored include measurement of physiological state, such as oxygenated state, change in state, movement characteristics, or previously measurable event by optical method, spectroscopy method, molecular interaction, flow dynamic and flow speed in vivo, which can trigger a change of state in vivo, can be measured by 2D or 3D x-ray quantitative method as described herein.

The formation of complexes or aggregates of contrast agents may be triggered by internal or endogenous chemical, electrical, electromagnetically, electrochemical, mechanical, acoustic event, magnetic mechanisms or any combinations thereof. The present disclosure includes the measurements of molecular, atomic, cellular and structural, or phenomena or movement or fluidic dynamics, which may be triggered by external force due to interaction with target or region of interest via chemical, electrical, electromagnetically, mechanical, electrochemical, magnetic, acoustic, or combination of two or more of these external force based events combined with internal events.

Events that can be monitored by the x-ray system of the present disclosure include fast events that characterizes kinetics of atomic and molecular, or nanostructure, microstructure, cellular and combinations of one or more events, femtosecond or picosecond laser triggered events, nonlinear event such as two photon microscopy or two photon x-ray trigger events, CARS, quantum kinetics events such as being measured by terahertz spectroscopy, or other events triggered by electromagnetic forces, or events such as surface plasmonic activities.

The measurements can include high spatial, spectral and time resolution measurements, for example up to sub nanometer resolution localization and sensitivity. Techniques similar to super resolution methods developed in vitro may be applied in vivo, in which different colors of active or static fluorescent dyes can be replaced by time sensitive changes measurable by x-ray. This x-ray measurement can include correlation of localization of the measured activity or region to that of the target region. The lasers used in super resolution imaging in in vitro imaging may be used or may be replaced by ultrafast lasers or ultrafast nonlinear event or x-ray produced nonlinear activity or any aforementioned internal activity or other chemical or external mechanical or electric force energy triggered activity.

Primary nanoXgens, secondary NanoXgen and/or tertiary nanoXgen can be administered orally, injected, inhaled, or otherwise as long as such agents may reach the target site. Intrinsic contrast agents, contrast agents are naturally part of the body, or live cell or organism, but may also be administered in this manner in some cases. Intrinsic molecules such as $Ca^{2+}$ from internal sources can also bind to other parts of nanoXgen after such particles or molecules or molecular complexes have entered the body or the imaged subject. After basic units of molecular labeling complexes as described herein is administered orally, intravenously, injected or inhaled, the entire labeling complex may be self-assembled at the target site to carry out its function.

Using a contrast agent described herein provides for a higher resolution in x-ray measurements. For example, a pico second x-ray source, may be combined with fast PMTs, or photon counting detectors, or photodiodes, or fast frame rate detectors, especially to image and measure selected regions of interest after the full field x-ray imaging or for suitable subject with user defined regions. In another example, using a conventional x-ray source including nanotube based x-ray source, 2D detector may be up to microseconds per image. resolution in time may be increased by at least 1 to $10^{12}$ folds. Further, spatial resolution may also be increased. For example, from 100 nm without using x-ray optics to 0.01 nm with or without x-ray optics, when using PMT, photon counting detectors, or photodiodes.

In the context of one or more parameter resolution improvements, the sensitivity of measurements has the potential to increase, too. For example, in the time measurements, absence or presence of an x-ray sensitive property can be monitored accurately. For example, as the thickness and density of various calcium rich components are measured, the growth and reduction of calcium component at various times may be monitored compared to conventional CTs. In addition, multiple x-ray sensitive properties may be measured at the same time and in the same region or relative region, to further increase sensitivity. For example, density measurements, thickness measurements of one or more tissues or substances in the region of interest may be used to derive facts or draw conclusions about a phenomenon, for example, whether there is a tumor or not. For example, in addition to contrast agents binding to tumor markers measurements, other indications, such as cation levels, and/or low pH induced molecular event, or cation doped contrast agents, may further increase sensitivity.

The present disclosure allows for a molar sensitivity may be increased to the levels of an MRI, PET, or ultrasound. The contrast agents, or contrast agent complexes, including contrast agents related ligands and linkers, may target or bind elements or markers in vivo and in vitro imaging and measurements of, such as MRI, PET, ultrasound and optical or acoustic optical or photoacoustic systems, and especially those with high x-ray absorption properties may now be used for x-ray measurements. In addition, due to high radiation level and time requirement, and low sensitivity, the use of endogenous element or molecule or their derivatives based contrast agents are limited in CT. However, with the present disclosure, 2D dual or multiple energy and spectral imaging systems, and multiple dimensional imaging and high spectral resolution measurements, especially for the selected region of interest, 3D imaging systems, endogenous high x-ray attenuating elements, such as calcium and calcium based contrast agents are now useful.

The molecular contrast agents disclosed herein can be combined with the combination of the 2D flat panel detector and the spectral material decomposition improved 2D and 3D imaging systems and methods disclosed herein. The improved x-ray imaging systems, such as with the addition of spectral absorptiometry on small area of region of interest and x-ray microscopy, as well as photon counting detectors or PMTs disclosed herein, can reduce the required concentration of contrast agents thereby reducing the toxicity (from a need of 60% cell contents being labeled by a heavy metal), for the contrast agents to be visible in the CT or 2D radiographs.

The present disclosure provides methods and systems to reduce the amount of heavy metal nanoparticles needed to measure and quantify in x-ray imaging, and using material decomposition, to separate out components for better visualization and quantification.

For example, endogenous elements, especially $Ca^{2+}$ and other naturally high quantity elements in the body are not toxic and can be used to: 1) Produce self assembled complexes from existing endogenous elements and derivatives.

2) Functionalize these elements, ally intake or inject into the body: As the sensitivity of the systems described herein is higher and radiation level is lower, before and after images and measurements can be taken. A slight increase in $Ca^{2+}$ quantitity at certain location can be measured with accuracy. Previously, it is not suitable to use CT to do so as the radiation level is high, and before and after photos using conventional CT are not practical.

3) Existing ligand developed for other nanoparticles, such as gold, bismuth and copper, can be used to functionalize $Ca^{2+}$ nanoparticles.

4) Calcium can be placed in graphene or microbubbles, nanobubbles so that both x-ray and ultrasound may be sensitive to the label.

5) Calcium like endogenous element can form complexes with existing nanoparticles, so that x-ray can detect these particles due to calcium presence, without having to need high concentration of other heavy metal nanoparticles at the target.

Additionaly, most of the endogeneous elements and its natural and synthersized derivatives may be used as contrast agents in different formats. For example, for calcium, the example can include the following:

Calcium biphosphate formed complexes: calcium phosphate is a family of materials and minerals containing $Ca^{2+}$ together with in organic phosphate anions. Some calcium phosphates contain oxide and hydroxide as well.

Calcium Carbonate (optional)

A hybrid drug delivery system (DDS) including tumor targeting ability such as hyaluronan and calcium carbonate (CC). For example, by taking advantage of the tumor-targeting ability of hyaluronan and the drug-loading property and x-ray image contrast of CC, the well-formed hyaluronan-CC nanoparticles can serve as a DDS targeting colorectal cancer with a decent drug loading content, which can be beneficial in the chemotherapy of colorectal cancer.

Calcium may be used in a hydrogel, which is known to expand and/or shrink, therefore having x-ray measurable properties such as variable density and dimensions, triggered by external conditions to be monitored such as changes in PH, temperature and enzymatic activities.

$Ca^{2+}$ derivatives in microsphere or particles or microcapsule,

Self assembled calcium complexes.

Binding or disintegration of nanocluster or cage system may be triggered by pH and temperature, contact or electromagnetic energy. Calcium conjugate proteins or their derivatives can aggregate or bind to high affinity active domains of target of interest. Given the appropriate condition in PH or temperature and molecular environment and matrix: or presence or absence of proteases, which interact with the calcium conjugate protein, leads to disintegration, or change in conformation, or releasing of calcium cations. X-ray measurements of both the calcium cation or bound calcium and their temporal presence or absence at the target site may be linked to specific cellular condition or activity or event such as necrosis or apoptosis, therefore can be monitored accordingly by x-ray measurement of the present disclosure. Calcium and its derivative molecule or molecular complexes may be integrated into microbubbles. Microbubbles disintegrated by enzymatical, redox activity or ultrasound energy disruption by an ultrasound probe or it may have a natural half-life.

Optionally, in presence of competitive ligand, metabolite contrast agent can be used in the x-ray system of the present disclosure to monitor metabolic activities previously not done in a x-ray system or CT. Examples of metabolite contrast agent are cavitand based nanoscale coordinate cages, reversible, tetradentate cavitrand, ligand and appropriate metal precursor.

Alternatively, the contrast agents disclosed herein can be used with conventional x-ray source including nanotube based x-ray source, light based ultrafast x-ray source, coupled with 2D detector, photon counting detector and photodiode and photo multiplier tubes, the image acquisition rate may be in microseconds or ps or fs. Time resolution for the selected region therefore may improve by at least 1 to $10^{12}$ folds. Spatial resolution increases, for example, 100 nm without using x-ray optics as published previously, to sub nm with x-ray optics, especially when using PMT, photon counting detectors, or photodiodes and objective lens designed for sub nm x-ray microscopy, Using the 3D imaging methods of the present disclosure, spatial resolution in all three axes may be improved by at least $1-10^9$ folds compared to conventional x-ray CT. Spectral resolution increases, instead of typically 1-12 energy levels by using spectral sensors, high resolution measurements with 0.01 nm spectral resolution or higher may be measured using photon counting detectors, PMTs, silicon drift detectors, sometimes coupled with energy dispersive gratings and spatially sensitive detectors, with the resolution in the subnm range. Multiple x-ray sensitive properties may be measured at the same time and in the same region or adjacent regions, to further increase sensitivity. For example, high spatial and spectral and time resolution measurements, of molecular complexes and molecular interactions and interaction kinetics which takes place in the ps, fs or ms range, for example, protein peptide binding kinetics of an active domain on a tumor receptor target which binds to an epitope of a contrast conjugated protein such as calcium or np conjugated protein ligand/or the target itself is a calcium binding protein, may be monitored by calcium concentration over time at the site of the target site or rapid disappearance of calcium signals. Each nanoXgen may have one or multiple binding sites for calcium based molecules such as calcium biophosphate or calcium carbonate or calcium ca++ free ion or calcium protein complexes.

The contrast agents disclosed herein can be used to derive facts or draw conclusions about a phenomenon, for example, other than contrast agents binding to tumor markers measurements, other indicators, such as cation levels, and low pH induced molecular event, or cation doped contrast agents, may further increase sensitivity.

Generally, MRI requires molar sensitivity of $10^{-3}$ to $10^{-5}$. Nuclear Medicine requires molar sensitivity of $10^{-12}$ to $10^{-10}$. Ultrasound detection of microbubbles requires molar sensitivity of about $10^{-12}$. Conventional CT requires molar sensitivity of about 0.1 or 0.01. With the systems disclosed herein, the molar sensitivity may be increased to the level of MRI, or PET or Ultrasound in some instances. Contrast agents and contrast agents related ligand and linker, and target or marker binding elements developed for in vivo and in vitro imaging, measurements and test such as MRI, PET, Ultrasound and Optical or Acoustic Optical or photoacoustic systems, especially those with high x-ray absorption properties may be used for x-ray measurements.

The contrast agent level can be adjusted according to the application. For organic and inorganic subjects which are not differentiating from each other by different atomic z, different atomic z materials or radiolabel such as iodine may be mixed in with the matter to be imaged to achieve the density required to be visualized in 2D. The proportion of the radio labeled needed to visualize these materials may need to (1) allow bone casting to solidify and achieve the rigidity and stability needed over time for the bone healing to occur and for other intended function of the cast: (2) allow quantification and visualization in x-ray imaging and therefore separation of cast image from the human organ and/or tissue image which are of bone or soft tissue.

To achieve the second objective, the following formula can be used to evaluate of density needed in the mixture for x-ray detector to sense the signal needed for imaging and quantification. X-ray transparency of a substance primarily depends on density. Theoretical and experimental studies show that when an x-ray beam transverses a medium, the beam intensity is reduced due to both absorption and deflection of photons by the medium, the degree of x-ray attenuation obeying the following equation: $I=I_0 e^{-\mu x}$, where I is the transmitted beam intensity, $I_o$ is the incident beam intensity, x is the thickness of the medium. The mass attenuation coefficient, $\mu$ expressed in $\mu=\rho Z^4/AE^3$, where p is the density, Z is the atomic number, A is the atomic mass, and E is the x-ray energy. Therefore x-ray attenuation is high with low energy x-rays and with materials of high atomic number.

Therefore, based on this formula, in bone casting material in medical imaging, or battery material or microchip material in industrial applications, two or more 2D images can be further extended to formed 2D layered images, or 3D images, the quantitative imaging data and differentiating material quantitative data, and density measurements of such materials.

For bone cement or casting materials or biofilms, mixing cement and casting material with contrast agents such as iodinated or other atomic z varying label molecules or their derivatives may achieve the radio density needed for x-ray detection. Alternatively, inorganic compound, namely iron sulfate, silver-coated micro-particles or 1-chloronaphtalene, holmium, hafnium, or even nanoparticles, other contrast agents can used for in vivo imaging.

Methods of mixing a plaster cast with the labels which can be identified by x-ray or hybrid imaging modalities include the following steps. 1. Mix the contrast agents with the plaster casting evenly. The contrast agents may be conjugated beforehand with a color pigment to ensure homogenized mixing by visual inspection. 2. Add water. For the fiber glass cast, the first step can include mixing the contrast agents with the resin evenly. The contrast agents may be conjugated or mixed with a pigment to ensure visualized verification of homogenization. In a second step, a catalyst can be added to cure the fiber glass.

Microbubbles as Contrast Agents for x-Ray Imaging of the Present Disclosure

Tracer suitable for introduction into a bloodstream of a subject can include micro-bubbles. The micro-bubbles can be visible in images registered using an ultrasound imaging system or x-ray imaging or phase contrast x-ray imaging system. The micro-bubbles can contain a contrast agent which is visible in images registered using a nuclear medical imaging system. The micro-bubbles can have a controlled fragility corresponding to a threshold of ultrasonic energy such that when an ultrasonic energy is applied to the micro-bubbles which exceeds the threshold, a rupture of the micro-bubbles occurs and the contrast agent is released from the micro-bubbles. Targeted microbubble can form by functionalizing ligands targeting biomarkers. Ultrasound energy generated by an ultrasound probe, for example, may disrupt such microbubbles. Or integrity of microbubbles may have a natural half life.

With the appropriate enzyme, pH, and temperature, contrast agents may aggregate and amplify or disintegrate.

Contrast Agents based on Invisibility such as crystal nanomaterials may be used as a quantification and identification tool.

Crystal nanomaterials with a functionalized surface, with certain density of, for example, calcium binding domains of calmodulin, Calretinin, S100B protein, or other ion binding proteins which has high affinity for calcium ion, or other element zinc ion, magnesium ion, or other type of metal ions, or their derivatives can be visible in x-ray measurement compared to the background. Once in a solution or cellular matrix, or in the region where certain targets has higher affinity to calcium ions and its derivatives, as or other type of metal ions or markers of the region have higher affinity for the crystal surface are present, ligands can be released into the environment and bind the target so that the crystal nanomaterials can become invisible.

Terminology

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising." "including," "having." and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Conjunctive language such as the phrase "at least one of X, Y, and Z." unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately." "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

Any methods disclosed herein need not be performed in the order recited. The methods disclosed herein include certain actions taken by a practitioner; however, they can also include any third-party instruction of those actions, either expressly or by implication. For example, actions such as "illuminating a subject" include "instructing illumination of a subject."

All of the methods and tasks described herein may be performed and fully automated by a computer system. The computer system may, in some cases, include multiple distinct computers or computing apparatuses (e.g., physical servers, workstations, storage arrays, cloud computing resources, etc.) that communicate and interoperate over a network to perform the described functions. Each such computing apparatus typically includes a processor (or multiple processors) that executes program instructions or modules stored in a memory or other non-transitory computer-readable storage medium or apparatus (e.g., solid state storage apparatuses, disk drives, etc.). The various functions disclosed herein may be embodied in such program instructions, and/or may be implemented in application-specific circuitry (e.g., ASICs or FPGAs) of the computer system. Where the computer system includes multiple computing apparatuses, these apparatuses may, but need not, be co-located. The results of the disclosed methods and tasks may be persistently stored by transforming physical storage apparatuses, such as solid state memory chips and/or magnetic disks, into a different state. In some embodiments, the computer system may be a cloud-based computing system whose processing resources are shared by multiple distinct business entities or other users.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. An x-ray measurement system comprising:
an x-ray source configured to emit one or more x-ray beams directed to an imaging subject; and
a two-dimensional (2D) x-ray detector downstream of the imaging subject, wherein a controller of the system is configured to obtain three-dimensional (3D) images of a region of interest in the subject by having a plurality of relative positions of x-ray emission to the region of interest, achieved by one or more of moving the region of interest or moving or steering x-ray emitting positions or having a plurality of the x-ray sources in at least two axes of the 3D space including positions in x-y-z axis, and obtaining 2D x-ray measurements; and
a non-transitory computer for storage medium containing software for reducing or removing scatter from the 2D x-ray measurements, such that data derived are used to create at least one 3D image of the region of interest,
wherein a distance between adjacent x-ray emitting positions or relative distance of the region of the interest between the moved positions is equal to approximately a resolution in a third axis, such that each of the adjacent x-ray emitting positions is configured to generate at least one or more different projection paths in the region of interest, and
wherein said distance is greater than zero and up to one pixel pitch.

2. The system of claim 1, wherein the non-transitory computer for storage medium contains software for performing measurement for at least one application of diagnostics, guidance of treatment and surgery, biopsy, pre-operation planning, inspection, tracking and/or monitoring of a subject.

3. The system of claim 1, wherein the x-ray source is configured to emit x-ray beams with controllable energy levels.

4. The system of claim 3, wherein the x-ray measurement system is configured to apply a spectral material decomposition method to produce the 3D image for at least one component and or to produce in 3D relative density of a component to that of other components or rest of the region of interest, wherein the x-ray source is configured to emit at least two consecutive x-ray beams with the controllable energy levels for each imaging operation to apply the spectral material decomposition method.

5. The system of claim 1, comprising a beam selector or beam absorption plates configured to selectively allow ray beams to reach predetermined locations of the x-ray detector and/or for scatter removal or reduction.

6. The system of claim 5, wherein the controller is configured to reduce or remove scatter in time domain, space domain, and/or frequency domain in the x-ray measurements and/or to use a software to perform interpolation to produce high resolution primary x-ray image.

7. The system of claim 1, comprising a second 2D x-ray detector.

8. The system of claim 1, wherein a material decomposition method is configured to separate components or materials, enabling 3D imaging for at least one component relative to that of other components or region of interest, and/or driving six-dimensional (6D) or seven-dimensional (7D) image for at least one component in space and time compared to that of background or an external spatial marker or sensor.

9. The system of claim 1, wherein a processor of the system is configured to receive and process a full view x-ray signal of the imaging subject from the x-ray detector and a higher spatial or spectral resolution signal of a region of interest within the imaging subject from x-ray microscopy, x-ray spectroscopy, or x-ray absorptiometry assembly.

10. The system of claim 1, wherein a detector or detector assembly comprises a flat panel detector and a smaller 2D detector or one-dimensional (1D) or point detector behind the flat panel detector.

11. The system of claim 1, wherein approximately a total number of emitting positions, or a number of 2D images taken to construct the 3D image is quantitatively related to a depth of the third axis of region of interest or thickness of a portion of region of interest and/or the resolution in the third axis.

12. The system of claim 1, wherein when moving or steering in x and y dimensions, a total movement angle from emitting positions that are furthest apart is between 0.1 to 1 degree.

13. The system of claim 1, wherein after the 2D images are taken, an equation system, m×n×p equations, with approximately m×n×p variables can be solved such that location of the x-ray source can produce an image of size m×n and there can be approximately p layers, wherein a linear equation system can be solvable by either an iterative method or a matrix method.

14. The system of claim 1, wherein a processor can use a conventional computing tomography imaging algorithm to derive 3D image based on combined data and solution of a linear equation.

15. The system of claim 1, wherein a material decomposition method is used for determining density, thickness, composition, x ray measurable properties of each component in the region of interest.

16. The system of claim 1, wherein the x-ray measurement system is configured to output a material decomposition analysis based at least in part on a database of x-ray measurement properties of different materials, each material comprising of substances with known density and or thickness; or based on, basis function spectral x-ray imaging method, and other methods and algorithms are used in spectral CT and dual or multiple, or spectral x-ray imaging, or those of prior art may also be used for material decomposition.

17. The system of claim 1, wherein each component in the region of interest may be differentiated by density, contrast label, spatial structure and shape, relative spatial position, composition, or movement characteristics, flow properties, flow characteristics, flow direction, fluidic dynamics, presence, visibility within a component, or any differentiable physical properties that may be analyzed by a first x-ray images, or simulated properties, or previously known properties or any combination of those properties.

18. The system of claim 1, wherein contrast label is a traditional or x ray contrast agent, or an endogenous element or selected from the group consisting of calcium, zinc, air, argon, nitrogen, carbon dioxide, nitrogen dioxide, methane, helium, oxygen, gadolinium, iron, magnesium, manganese, copper, chromium, gold, silver, thulium, and barium, sodium, potassium, phosphorous, sulfur, chlorine, iron, cobalt, nickel, copper, zinc, molybdenum, selenium, iodine, chromium, Au-(gold), Pt-(platinum), Ta-(Tantalum), Yb-(Ytterbium), and Bi-(Bismuth) based nanoparticles, graphene nanoparticle or graphene radiolabel composites, nanotube composites, iodinated or barium, gadolinium, hydrogel or negative contrast, selected from microbubble, nanobubble.

19. The system of claim 1, wherein the x-ray measurement system and or a non-transitory computer for storage medium for display is comprising a viewing or display software which includes a capability to display for an application needed for a user.

20. The system of claim 1, wherein the controller of the system is configured to obtain 3D images of the region of interest in the subject based on primary x-ray beams passing through the region of interest derived from at least one measurement and/or data derived from any with reduced or minimal scatter.

21. The system of claim 1, wherein a computer processor can perform data analysis of data derived using a method of visualization and/or quantitative data analysis performed previously on Computed Tomography (CT) scanner, Magnetic Resonance Imaging (MRI), Positive Emission Tomography (PET) and Single Photon Emission Computed Tomography SPECT and other existing quantitative tomography and imaging methods, which are much expensive and/or time-consuming than 2D radiography. The visualization and/or quantitative data analysis performed on the 2D x-ray imaging apparatuses disclosed herein can be done by running algorithms developed for diagnosis and identification and characterization using artificial intelligence, deep machine learning, artificial neural network, convolution neural network, and/or deep neural network.

22. The system of claim 1, wherein the 3D data derived may be used in applications selected from the following: cancer diagnosis (localization of suspended cancer cells, stem cells, rare cells and foreign subjects), circulatory system diseases and conditions (such as coronary artery disease (atherosclerosis), blood vessel aneurysms, and blood clots, neurological disorders including spinal conditions, herniated discs, epilepsy, encephalitis, spinal stenosis (narrowing of the spinal canal), a blood clot or intracranial bleeding in patients with stroke, kidney and bladder stones, abscesses; inflammatory diseases (such as ulcerative colitis and sinusitis), muscle disorders, and/or injuries to the head, skeletal system, and/or internal organs.

\* \* \* \* \*